(12) United States Patent
Ichihashi et al.

(10) Patent No.: US 9,935,273 B2
(45) Date of Patent: Apr. 3, 2018

(54) FLUORANTHENE DERIVATIVE, LIGHT-EMITTING DEVICE MATERIAL CONTAINING SAME, AND LIGHT-EMITTING DEVICE

(71) Applicant: TORAY INDUSTRIES, INC., Tokyo (JP)

(72) Inventors: Yasunori Ichihashi, Otsu (JP); Tsuyoshi Tominaga, Otsu (JP); Daisaku Tanaka, Otsu (JP); Takeshi Ikeda, Otsu (JP); Takeshi Arai, Otsu (JP); Atsushi Ikeda, Otsu (JP)

(73) Assignee: TORAY INDUSTRIES, INC., Tokyo (JP)

( * ) Notice: Subject to any disclaimer, the term of this patent is extended or adjusted under 35 U.S.C. 154(b) by 291 days.

(21) Appl. No.: 14/434,846

(22) PCT Filed: Oct. 4, 2013

(86) PCT No.: PCT/JP2013/077047
§ 371 (c)(1),
(2) Date: Apr. 10, 2015

(87) PCT Pub. No.: WO2014/057874
PCT Pub. Date: Apr. 17, 2014

(65) Prior Publication Data
US 2015/0280139 A1  Oct. 1, 2015

(30) Foreign Application Priority Data

Oct. 12, 2012 (JP) .................. 2012-226612

(51) Int. Cl.
| | |
|---|---|
| *H01L 51/00* | (2006.01) |
| *C07D 213/74* | (2006.01) |
| *C07C 255/58* | (2006.01) |
| *C07D 215/38* | (2006.01) |
| *C07D 401/04* | (2006.01) |
| *C09K 11/06* | (2006.01) |
| *H05B 33/10* | (2006.01) |
| *C07D 213/38* | (2006.01) |
| *C09B 57/00* | (2006.01) |
| *C09B 57/10* | (2006.01) |
| *H01L 51/50* | (2006.01) |
| *H01L 51/52* | (2006.01) |

(52) U.S. Cl.
CPC ........ *H01L 51/0072* (2013.01); *C07C 255/58* (2013.01); *C07D 213/38* (2013.01); *C07D 213/74* (2013.01); *C07D 215/38* (2013.01); *C07D 401/04* (2013.01); *C09B 57/001* (2013.01); *C09B 57/008* (2013.01); *C09B 57/10* (2013.01); *C09K 11/06* (2013.01); *H01L 51/006* (2013.01); *H01L 51/0052* (2013.01); *H01L 51/0054* (2013.01); *H01L 51/0055* (2013.01); *H01L 51/0058* (2013.01); *H01L 51/0059* (2013.01); *H01L 51/0061* (2013.01); *H01L 51/0067* (2013.01); *H01L 51/0077* (2013.01); *H01L 51/0085* (2013.01); *H05B 33/10* (2013.01); *C07C 2603/52* (2017.05); *C09K 2211/1007* (2013.01); *C09K 2211/1011* (2013.01); *C09K 2211/1014* (2013.01); *C09K 2211/1029* (2013.01); *C09K 2211/1044* (2013.01); *C09K 2211/1059* (2013.01); *C09K 2211/1088* (2013.01); *H01L 51/5012* (2013.01); *H01L 51/5056* (2013.01); *H01L 51/5072* (2013.01); *H01L 51/5088* (2013.01); *H01L 51/5206* (2013.01); *H01L 51/5221* (2013.01)

(58) Field of Classification Search
None
See application file for complete search history.

(56) References Cited

U.S. PATENT DOCUMENTS

| | | | | |
|---|---|---|---|---|
| 2008/0122344 | A1* | 5/2008 | Shin ................. | C07D 209/86 313/504 |
| 2009/0015144 | A1 | 1/2009 | Takashima et al. | |
| 2009/0256468 | A1 | 10/2009 | Kim et al. | |
| 2011/0279020 | A1* | 11/2011 | Inoue ................ | C07D 209/82 313/504 |
| 2012/0193619 | A1 | 8/2012 | Taka et al. | |
| 2013/0234118 | A1* | 9/2013 | Kwon ............... | H01L 51/006 257/40 |

FOREIGN PATENT DOCUMENTS

| | | |
|---|---|---|
| CN | 101186593 A | 5/2008 |
| CN | 101525334 A | 9/2009 |
| EP | 2108690 A1 | 10/2009 |
| EP | 2674418 A1 | 12/2013 |
| JP | 2005-272805 A | 10/2005 |
| JP | 2009-215559 A | 9/2009 |

(Continued)

OTHER PUBLICATIONS

Extended European Search Report for European Application No. 13844716.4, dated Aug. 22, 2016.
Chinese Office Action and Search Report for Chinese Application No. 201380052576.6, dated Jan. 19, 2016, with an English translation of the Office Action only.
El-Khouly et al., "Stabilization of the Charge-Separated States of Covalently Linked Zinc Porphyrin-Triphenylamine-[60]Fullerene," ChemPhysChem, vol. 11, 2010, pp. 1726-1734.
Partial Supplementary European Search Report for European Application No. 13844716.4, dated May 3, 2016.
Zhang et al., "Synthesis and properties of a new [60] fullerene-donor system containing dicyanovinyl groups," Materials Letters, vol. 64, 2010 (Available online Jul. 15, 2010), pp. 2244-2246.

*Primary Examiner* — Robert S Loewe
(74) *Attorney, Agent, or Firm* — Birch, Stewart, Kolasch & Birch, LLP

(57) ABSTRACT

The purpose of the present invention is to provide an organic thin-film luminescent element which exhibits improved luminous efficiency, drive voltage and durability life. This fluoranthene derivative is characterized by having a specific structure that contains a fluoranthene skeleton.

13 Claims, No Drawings

(56) References Cited

FOREIGN PATENT DOCUMENTS

WO    WO 2011/046166 A1    4/2011
WO    WO 2012/108388 A1    8/2012

* cited by examiner

FLUORANTHENE DERIVATIVE, LIGHT-EMITTING DEVICE MATERIAL CONTAINING SAME, AND LIGHT-EMITTING DEVICE

TECHNICAL FIELD

The present invention relates to a light-emitting device capable of converting electric energy into light, and a material to be used for the same. The present invention is capable of being used for areas such as display devices, flat-panel displays, backlight, lighting, interior design, labels, signboards, electrophotography machines, and light signal generators.

BACKGROUND ART

Researches on an organic thin-film light-emitting device in which electrons injected from a cathode and holes injected from an anode emit light when they are recombined in an organic fluorescent body held by both electrodes have been actively conducted in recent years. This light-emitting device is characteristic for high luminance light emission in the form of a thin type and under a low driving voltage, and multicolor light emission due to selection of a fluorescent material, and has been paid attention.

Such researches have undergone many studies for practical use since C. W. Tang et al. of Kodak Co., Ltd. showed that an organic thin-film device emits light at high luminance, and organic thin-film light-emitting devices have steadily come into practical use as they have been employed in main displays of mobile phones, and the like. However, there are still many technical problems and, especially, attainment of both increased efficiency and prolonged life of a device is one of the major problems.

For the organic thin-film light-emitting device, it is necessary to satisfy an improvement in luminous efficiency, a reduction in driving voltage and an improvement in durability. Particularly, realization of both luminous efficiency and durable life is a major problem. For example, materials having a fluoranthene skeleton and a nitrogen-containing heterocyclic ring have been developed for improving luminous efficiency and durable life (see, for example, Patent Documents 1 to 5)

PRIOR ART DOCUMENTS

Patent Documents

Patent Document 1: WO 2008059713
Patent Document 2: WO 2007100010
Patent Document 3: WO 2012108388 (particularly [Chemical Formula 38])
Patent Document 4: Japanese Patent Laid-open Publication No. 2009-215559
Patent Document 5: Japanese Patent Laid-open Publication No. 2009-215281

SUMMARY OF THE INVENTION

Problems to be Solved by the Invention

However, conventional technologies were difficult to reduce the driving voltage of a device sufficiently, and even if they had been able to reduce the driving voltage, the luminous efficiency and the durable life of a device were insufficient. Thus, technologies capable of realizing all of high luminous efficiency, low driving voltage and durable life have not been found yet.

An object of the present invention is to solve such problems with the conventional technologies and provide an organic thin-film light-emitting device that has improved all of luminous efficiency, driving voltage and durable life.

Solutions to the Problems

The present invention provides a fluoranthene derivative represented by the following general formula (1):

[Chemical Formula 1]

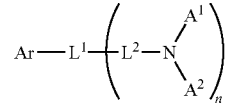

(1)

wherein Ar represents a group containing a fluoranthene skeleton; $L^1$ and $L^2$ each represent a single bond, a substituted or unsubstituted arylene group, or a substituted or unsubstituted heteroarylene group; $A^1$ and $A^2$ each represent a substituted or unsubstituted benzene ring having 6 to 40 carbon atoms, a substituted or unsubstituted fused aromatic hydrocarbon ring having 6 to 40 carbon atoms, a substituted or unsubstituted monocyclic aromatic heterocyclic ring having 1 to 40 carbon atoms, or a substituted or unsubstituted fused aromatic heterocyclic ring having 1 to 40 carbon atoms, with the proviso that at least one of atoms that form rings $A^1$ and $A^2$ is an electron-accepting nitrogen atom; $L^2$ and $A^2$ may form a ring when $L^2$ is a substituted or unsubstituted arylene group, and $A^2$ is a substituted or unsubstituted benzene ring having 6 to 40 carbon atoms, or a substituted or unsubstituted fused aromatic hydrocarbon ring having 6 to 40 carbon atoms; substituents that $L^1$, $L^2$, $A^1$ and $A^2$ optionally have are each selected from the group consisting of an alkyl group, a cycloalkyl group, a heterocyclic group, an alkenyl group, a cycloalkenyl group, an alkynyl group, an alkoxy group, an alkylthio group, an aryl ether group, an aryl thioether group, an aryl group, a heteroaryl group, a halogen, a cyano group, a carbonyl group, a carboxyl group, an oxycarbonyl group, a carbamoyl group and —P(=O)$R^1R^2$; $R^1$ and $R^2$ each represent an aryl group or a heteroaryl group; $R^1$ and $R^2$ may be fused to form a ring, with the proviso that when both $L^1$ and $L^2$ are single bonds, both $A^1$ and $A^2$ are not heteroaryl groups having two or more electron-accepting nitrogens, and when one of $L^1$ and $L^2$ is a single bond, the other one of $L^1$ and $L^2$ is not a heteroarylene group having two or more electron-accepting nitrogens; n is 1 or 2; and when n is 2, two $L^2$-N($A^1$)($A^2$)s may be the same or different, with the proviso that a carbazolylene group is not included as a heteroarylene group, and when n is 2 and $L^2$ is a single bond, $L^1$ is not an acene having three or more rings.

Effects of the Invention

According to the present invention, there can be provided an organic thin-film light-emitting device that realizes all of luminous efficiency, driving voltage and durable life.

EMBODIMENTS OF THE INVENTION

A fluoranthene derivative represented by the general formula (1) will be described.

[Chemical Formula 2]

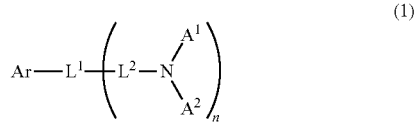

(1)

wherein Ar represents a group containing a fluoranthene skeleton; $L^1$ and $L^2$ each represent a single bond, a substituted or unsubstituted arylene group, or a substituted or unsubstituted heteroarylene group, with the proviso that an antracenylene group is not included as an arylene group, and a carbazolylene group is not included as a heteroarylene group; $A^1$ and $A^2$ each represent a substituted or unsubstituted benzene ring having 6 to 40 carbon atoms, a substituted or unsubstituted fused aromatic hydrocarbon ring having 6 to 40 carbon atoms, a substituted or unsubstituted monocyclic aromatic heterocyclic ring having 1 to 40 carbon atoms, or a substituted or unsubstituted fused aromatic heterocyclic ring having 1 to 40 carbon atoms, with the proviso that at least one of atoms that form rings $A^1$ and $A^2$ is an electron-accepting nitrogen atom; $L^2$ and $A^2$ may form a ring when $L^2$ is a substituted or unsubstituted arylene group, and $A^2$ is a substituted or unsubstituted benzene ring having 6 to 40 carbon atoms, or a substituted or unsubstituted fused aromatic hydrocarbon ring having 6 to 40 carbon atoms; substituents that $L^1$, $L^2$, $A^1$ and $A^2$ optionally have are each selected from the group consisting of an alkyl group, a cycloalkyl group, a heterocyclic group, an alkenyl group, a cycloalkenyl group, an alkynyl group, an alkoxy group, an alkylthio group, an aryl ether group, an aryl thioether group, an aryl group, a heteroaryl group, a halogen, a cyano group, a carbonyl group, a carboxyl group, an oxycarbonyl group, carbamoyl group and —P(=O)$R^1R^2$; $R^1$ and $R^2$ each represent an aryl group or a heteroaryl group; $R^1$ and $R^2$ may be fused to form a ring, with the proviso that when both $L^1$ and $L^2$ are single bonds, both $A^1$ and $A^2$ are not heteroaryl groups having two or more electron-accepting nitrogens, and when one of $L^1$ and $L^2$ is a single bond, the other one of $L^1$ and $L^2$ is not a heteroarylene group having two or more electron-accepting nitrogens; n is 1 or 2; and when n is 2, two $L^2$-N($A^1$)($A^2$)s may be the same or different.

In all the groups described above, hydrogen may be heavy hydrogen. For example, the substituted or unsubstituted arylene group having 6 to 40 carbon atoms has 6 to 40 carbon atoms including carbon atoms contained in the substituent with which the arylene group is substituted, and the same applies to other substituents that define the number of carbon atoms.

As substituents associated with the term "substituted or unsubstituted", the above-mentioned alkyl group, cycloalkyl group, heterocyclic group, alkenyl group, cycloalkenyl group, alkynyl group, alkoxy group, alkylthio group, aryl ether group, aryl thioether group, aryl group, heteroaryl group, halogen, cyano group, carbonyl group, carboxyl group, oxycarbonyl group and carbamoyl group are preferable, and further specific substituents mentioned as preferable substituents in the descriptions of the substituents are preferable. These substituents may be further substituted with the substituents described above.

The term "unsubstituted" associated with the term "substituted or unsubstituted" means that a group is substituted with a hydrogen atom.

The same applies to the term "substituted or unsubstituted" for the compounds described below or substructures thereof.

The alkyl group denotes a saturated aliphatic hydrocarbon group, such as a methyl group, an ethyl group, a n-propyl group, an isopropyl group, a n-butyl group, a sec-butyl group, and a tert-butyl group, and it may or may not have a substituent. When the alkyl group is substituted, the additional substituent is not particularly limited, examples may include an alkyl group, an aryl group and a heteroaryl group, and the same holds true in the descriptions below. The number of carbon atoms in the alkyl group is not particularly limited, but from the viewpoints of easy availability and cost, it is preferably within the range of 1 or more and 20 or less, more preferably 1 or more and 8 or less.

The cycloalkyl group denotes a saturated alicyclic hydrocarbon group, such as a cyclopropyl group, a cyclohexyl group, a norbornyl group, and an adamantyl group, and this may or may not have a substituent. The number of carbon atoms in the alkyl group moiety is not particularly limited, but is preferably within the range of 3 or more and 20 or less.

The heterocyclic group denotes an aliphatic ring having an atom other than carbon in the ring, such as a pyran ring, a piperidine ring, and a cyclic amide, and this may or may not have a substituent. The number of carbon atoms in the heterocyclic group is not particularly limited, but is preferably within the range of 2 or more and 20 or less.

The alkenyl group denotes an unsaturated aliphatic hydrocarbon group containing a double bond, such as a vinyl group, an allyl group, and a butadienyl group, and this may or may not have a substituent. The number of carbon atoms in the alkenyl group is not particularly limited, but is preferably within the range of 2 or more and 20 or less.

The cycloalkenyl group denotes an unsaturated alicyclic hydrocarbon group containing a double bond, such as a cyclopentenyl group, a cyclopentadienyl group, and a cyclohexenyl group, and this may or may not have a substituent.

The alkynyl group denotes an unsaturated aliphatic hydrocarbon group containing a triple bond, such as an ethynyl group, and this may or may not have a substituent. The number of carbon atoms in the alkynyl group is not particularly limited, but is preferably within the range of 2 or more and 20 or less.

The alkoxy group denotes a functional group with an aliphatic hydrocarbon group bonded via an ether bond, such as a methoxy group, an ethoxy group, and a propoxy group, and this aliphatic hydrocarbon group may or may not have a substituent. The number of carbon atoms in the alkoxy group is not particularly limited, but is preferably within the range of 1 or more and 20 or less.

The alkylthio group denotes a group in which an oxygen atom of an ether bond in an alkoxy group is substituted with a sulfur atom. The hydrocarbon group of the alkylthio group may or may not have a substituent. The number of carbon atoms in the alkylthio group is not particularly limited, but is preferably within the range of 1 or more and 20 or less.

The aryl ether group denotes a functional group with an aromatic hydrocarbon group bonded via an ether bond, such as a phenoxy group, and the aromatic hydrocarbon group may or may not have a substituent. The number of carbon atoms in the aryl ether group is not particularly limited, but is preferably within the range of 6 or more and 40 or less.

The aryl thioether group denotes a group in which an oxygen atom of an ether bond in an aryl ether group is substituted with a sulfur atom. The aromatic hydrocarbon group in the aryl ether group may or may not have a substituent. The number of carbon atoms in the aryl ether group is not particularly limited, but is preferably within the range of 6 or more and 40 or less.

The aryl group denotes an aromatic hydrocarbon group, such as a phenyl group, a naphthyl group, a biphenyl group, a phenanthryl group, a terphenyl group, a pyrenyl group, and a fluoranthenyl group. The aryl group may or may not have a substituent. The number of carbon atoms in the aryl group is not particularly limited, but is preferably within the range of 6 or more and 40 or less.

The heteroaryl group denotes a cyclic aromatic group having one or a plurality of atoms other than carbon in the ring, such as a furanyl group, a thiophenyl group, a pyridyl group, a quinolinyl group, an isoquinolinyl group, a pyrazinyl group, a pyrimidyl group, a naphthyridyl group, a benzofuranyl group, a benzothiophenyl group, an indolyl group, a dibenzofuranyl group, a dibenzothiophenyl group and a carbazolyl group, and this may be unsubstituted or substituted. The number of carbon atoms in the heteroaryl group is not particularly limited, but is preferably within the range of 2 or more and 30 or less.

The halogen denotes an atom selected from fluorine, chlorine, bromine, and iodine.

The carbonyl group, the carboxyl group, the oxycarbonyl group, the carbamoyl group and the phosphine oxide group may or may not have a substituent. Here, examples of the substituent include an alkyl group, a cycloalkyl group, an aryl group and a heteroaryl group, and these substituents may be further substituted.

The arylene group denotes a divalent or trivalent group derived from an aromatic hydrocarbon group such as a phenyl group, a naphthyl group, and a biphenyl group, and this may or may not have a substituent.

When the $L^1$ and $L^2$ in the general formula (1) is an arylene group, the number of nucleus carbon atoms is preferably within the range of 6 or more and 12 or less. Specific examples of the arylene group include a 1,4-phenylene group, a 1,3-phenylene group, a 1,2-phenylene group, a 4,4'-biphenylylene group, a 4,3'-biphenylylene group, a 3,3'-biphenylylene group, a 1,4-naphthylene group, a 1,5-naphthylene group, a 2,5-naphthylene group, a 2,6-naphthylene group and a 2,7-naphthylene group. A 1,4-phenylene group and a 1,3-phenylene group are more preferable.

The heteroarylene group denotes a divalent or trivalent group derived from an aromatic group having one or a plurality of atoms other than carbon in the ring, such as a pyridyl group, a quinolinyl group, a pyrimidinyl group, a pyrazinyl group, a naphthyridyl group, a dibenzofuranyl group, and a dibenzothiophenyl group, and this may or may not have a substituent. The number of carbon atoms in the heteroarylene group is not particularly limited, but is preferably within the range of 2 to 30.

Examples of the fused aromatic hydrocarbon ring include a naphthalene ring, an azulene ring, an anthracene ring, a phenanthrene ring, a pyrene ring, a chrysene ring, a naphthacene ring, a triphenylene ring, an acenaphthene ring, a coronene ring, a fluorene ring, a fluoranthene ring, a naphthacene ring, a pentacene ring, a perylene ring, a pentaphene ring, a picene ring, a pyranthrene ring and an anthraanthrene ring. Further, the fused aromatic hydrocarbon ring may have a substituent.

Examples of, the monocyclic aromatic heterocyclic ring include a furan ring, a thiophene ring, a pyridine ring, a pyridazine ring, a pyrimidine ring, a pyrazine ring, a triazine ring, an oxadiazole ring, a triazole ring, an imidazole ring, a pyrazole ring and a thiazole ring. Further, the monocyclic aromatic heterocyclic ring may have a substituent.

Examples of the fused aromatic heterocyclic ring include a quinoline ring, an isoquinoline ring, a quinoxaline ring, a benzimidazole ring, an indole ring, a benzimidazole ring, a benzothiazole ring, a benzoxazole ring, a quinoxaline ring, a quinazoline ring, a phthalazine ring, a carbazole ring, a carboline ring and a diazacarbazole ring (a ring in which one of carbon atoms of a hydrocarbon ring that forms a carboline ring is further substituted with a nitrogen atom). Further, the fused aromatic heterocyclic ring may have a substituent.

The fluoranthene derivative of the present invention has one or two groups represented by $L^2\text{-}N(A^1)(A^2)$, and accordingly crystallinity is reduced and the glass transition temperature is increased, so that stability of the film is improved.

The fluoranthene derivative of the present invention has a fluoranthene skeleton. The fluoranthene skeleton has a five-membered ring structure of $5\pi$ electron system. When given one electron (when reduced), the five-membered ring structure of $5\pi$ electron system turns to a $6\pi$ electron system, so that aromatic stabilization occurs (Huckel's rule). Thus, the five-membered ring structure of $5\pi$ electron system shows high electron affinity, and the fluoranthene skeleton according to the present invention also has high electron affinity. Since anthracene and pyrene, generally famous fused ring aromatic skeletons, do not have a five-membered ring structure of $5\pi$ electron system, there is no increase in electron affinity resulting from aromatic stabilization due to reduction, and such a phenomenon is a nature specific to a skeleton having a five-membered ring structure of $5\pi$ electron system.

Thus, when the fluoranthene derivative of the present invention is used for the light-emitting device, e.g., used for an electron transporting layer, proper electron injection property from the electrode is exhibited, so that the driving voltage of the light-emitting device can be reduced. As a result, luminous efficiency of the light-emitting device can be improved. The light-emitting device material also contributes to an increase in life.

The fluoranthene skeleton has high flatness, so that molecules are well superimposed on one another, and therefore high charge transporting property is achieved. Thus, when the fluoranthene derivative of the present invention is used for any of the layers that form the light-emitting device, electrons generated from the cathode and holes generated from the anode can be efficiently transported, and therefore the driving voltage of the device can be reduced. As a result, luminous efficiency of the light-emitting device can be improved. The light-emitting device material also contributes to an increase in life.

The fluoranthene skeleton has high stability to charges, so that reduction by electrons and oxidation by holes can be smoothly repeatedly performed. When the fluoranthene derivative of the present invention is used for the light-emitting device, life can be improved.

The group containing a fluoranthene skeleton is a group having a fluoranthene skeleton in the molecular structure, and may or may not have a substituent. Adjacent substituents may form a ring, and the size of the ring formed by the adjacent substituents is not particularly limited, but a five-membered ring or a six-membered ring is preferable from the viewpoint of stability of a molecular structure. The ring formed may be an aliphatic ring or an aromatic ring. The ring formed by adjacent substituents may further have a substituent, or may be further fused. The ring formed may contain a hetero atom other than a carbon atom. Particularly, it is preferred that the ring is formed by only carbon and hydrogen because electrochemical stability is increased, leading to improvement of durability of the device. The number of carbon atoms in the group containing a fluoranthene skeleton is not particularly limited, but is preferably within the range of 16 or more and 40 or less. Specific examples include a fluoranthenyl group, a benzofluoranthenyl group, a benzoaceanthrylenyl group, a benzoacephenanthrenyl group, an indenofluoranthenyl group and an acenaphthofluoranthenyl group.

In $L^2$-$N(A^1)(A^2)$ in the fluoranthene derivative of the present invention, at least one of atoms that form $A^1$ and $A^2$ is electron-accepting nitrogen. In substituents represented by $A^1$ and $A^2$, a group containing electron-accepting nitrogen may be bonded directly to N, or a group containing electron-accepting nitrogen may be substituted via coupling group. Specifically, $A^1$ may be a benzene ring, and $A^2$ may be a benzene ring substituted with a pyridyl group. Here, the electron-accepting nitrogen denotes a nitrogen atom which forms a multiple bond with an adjoining atom. Since nitrogen atoms have high electronegativity, the multiple bond has an electron-accepting nature. For this reason, $L^2$-$N(A^1)(A^2)$ having electron-accepting nitrogen has high electron affinity. Thus, when the fluoranthene derivative represented by the general formula (1) in the present invention is used for the emissive layer or the electron transporting layer, a proper electron injection property from the electrode is exhibited, so that the driving voltage of the light-emitting device can be reduced. As a result, luminous efficiency of the light-emitting device can be improved. The light-emitting device material also contributes to an increase in life.

$L^2$-$N(A^1)(A^2)$ has electron-donating nitrogen. Here, the electron-donating nitrogen denotes a nitrogen atom in which all the bonds with adjacent atoms are single bonds. In $L^2$-$N(A^1)(A^2)$, the nitrogen atom bonded to $A^1$ and $A^2$ corresponds to the electron-donating nitrogen. The electron denoting nitrogen has high stability to holes, so that oxidation by holes can be smoothly repeatedly performed. When the fluoranthene derivative represented by the general formula (1) according to the present invention is used for the hole transporting layer, life can be improved.

When the fluoranthene derivative represented by the general formula (1) has a $L^2$-$N(A^1)(A^2)$ group, the electronic conduction level is low. Thus, when the fluoranthene derivative represented by the general formula (1) in the present invention is used for the electron transporting layer, the energy barrier between the electron transporting layer and the emissive layer decreases, and therefore electron injection from the electron transporting layer to the emissive layer can be enhanced, so that the driving voltage of the light-emitting device can be reduced.

Further, when the fluoranthene derivative represented by the general formula (1) has a $L^2$-$N(A^1)(A^2)$ group, sublimability and deposition stability are improved, crystallinity is reduced, and stability of the film due to a high glass transition temperature is improved. Thus, when the fluoranthene derivative of the present invention is used for the light-emitting device, life can be improved.

From the above, the fluoranthene derivative of the present invention has in the molecule a fluoranthene skeleton and $L^2$-$N(A^1)(A^2)$, and therefore has high electron injection/transporting properties, electrochemical stability, proper sublimability, proper deposition stability, proper film quality and a high glass transition temperature. Thus, when the fluoranthene derivative of the present invention is used for any of the layers that form the light-emitting device, an organic thin-film light-emitting device having all of high luminous efficiency, low driving voltage and durable life can be provided.

In the case where $L^2$ and $A^2$ form a ring when $L^2$ is a substituted or unsubstituted arylene group, and $A^2$ is a substituted or unsubstituted benzene ring having 6 to 40 carbon atoms, or a substituted or unsubstituted fused aromatic hydrocarbon ring having 6 to 40 carbon atoms, a fused polycyclic structure is formed using $L^2$, $A^2$ and nitrogen atoms therebetween. For example, when $L^2$ is a phenylene group, and $A^2$ is a phenyl group, the fused polycyclic structure is a carbazole skeleton. For example, when $L^2$ is a naphthylene group, and $A^2$ is a phenyl group, the fused polycyclic structure is a benzocarbazole skeleton.

When both $L^1$ and $L^2$ are single bonds, both $A^1$ and $A^2$ are not heteroaryl groups having two or more electron-accepting nitrogens. Specific examples of the heteroaryl group having two or more electron-accepting nitrogens include groups such as those of pyrazine, pyrimidine and triazine. When both $L^1$ and $L^2$ are single bonds, the electronic state of —$N(A^1)(A^2)$ directly affects a fluoranthene skeleton. Here, when both $A^1$ and $A^2$ are substituents having two or more electron-accepting nitrogens, the effect of electron-accepting property excessively increases, so that the electronic conduction level of the material becomes high. Thus, when this material is used for the electron transporting layer, for example, the energy barrier between the electron transporting layer and the emissive layer increases, and therefore the driving voltage of the light-emitting device cannot be reduced.

Accordingly, even when both $L^1$ and $L^2$ are not single bonds, it is preferred that both $A^1$ and $A^2$ are not substituents having two or more electron-accepting nitrogens.

When one of $L^1$ and $L^2$ is a single bond, the other one of $L^1$ and $L^2$ is not a heteroarylene group having two or more electron-accepting nitrogens. Specific examples of the heteroarylene group having two or more electron-accepting nitrogens include groups such as those of pyrazinylene, pyrimidinylene and triazinylene. When one of $L^1$ and $L^2$ is a single bond, the electronic state of the other one of $L^1$ and $L^2$ directly affects a fluoranthene skeleton. Here, when the other one of $L^1$ and $L^2$ is a heteroarylene group having two or more electron-accepting nitrogens, the effect of electron-accepting property excessively increases, so that the electronic conduction level becomes high. Thus, when this material is used for the electron transporting layer, for example, the energy barrier between the electron transporting layer and the emissive layer increases, and therefore the driving voltage of the light-emitting device cannot be reduced.

Accordingly, even when one of $L^1$ and $L^2$ is not a single bond, it is preferred that both $L^1$ and $L^2$ are not substituents having two or more electron-accepting nitrogens.

A carbazolylene group is not included as a heteroarylene group. When the heteroarylene group is a carbazolylene group, two groups having electron-donating nitrogen in the molecule are directly bonded to each other, so that the electronic conduction level becomes considerably low. When this material is used for the electron transporting layer, for example, the energy barrier between the electrode and the electron transporting layer increases, and therefore the driving voltage of the light-emitting device cannot be reduced. It is to be noted that when n is 2, two groups having electron-donating nitrogen are bonded to each other via a coupling group, and therefore a proper electronic conduction level is achieved, so that the voltage can be reduced.

When n is 2 and $L^2$ is a single bond, $L^1$ is not an acene having three or more rings. The acene is a group having a structure in which a plurality of benzene rings are linearly fused, and specific examples of the acene having three or more rings include groups such as those of anthracene, tetracene and pentacene. When n is 2 and $L^2$ is a single bond, an acene having three or more rings is directly substituted with two amine nitrogens when $L^1$ is an acene having three or more rings. The acene having three or more rings has a long absorption wavelength, and when the acene is directly substituted with two amine nitrogens, the absorption wavelength becomes longer, so that the acene intensely absorbs visible light. When this material is used for, for example, light emitting device, the compound itself intensely absorbs light emitted at the emissive layer, and therefore luminous efficiency cannot be improved. Accordingly, not only in the case where n is 2 and $L^2$ is a single bond, but also in other cases, it is preferred that $L^1$ is not an acene having three or more rings.

Preferably, one form of Ar is represented by the following general formula (2). When Ar is represented by the general formula (2), conjugation is moderately expanded. Consequently, the compound is electrochemically stable, and the charge transporting property is further improved.

[Chemical Formula 3]

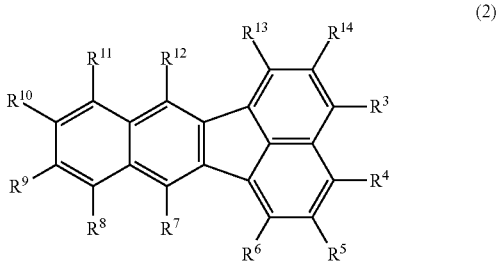

(2)

In the formula, $R^3$ to $R^{14}$ may be the same or different, and are each selected from the group consisting of hydrogen, an alkyl group, a cycloalkyl group, a heterocyclic group, an alkenyl group, a cycloalkenyl group, an alkynyl group, an alkoxy group, an alkylthio group, an aryl ether group, an aryl thioether group, an aryl group, a heteroaryl group, halogen, a carbonyl group, a carboxyl group, an oxycarbonyl group and a carbamoyl group; and $R^3$ to $R^{14}$ may form a ring by adjacent substituents, with the proviso that the group is coupled to $L^1$ at the position of any one of $R^3$ to $R^{14}$.

Preferably, $R^3$ to $R^{14}$ in the general formula (2) are each selected from the group consisting of hydrogen, an alkyl group, a cycloalkyl group, an aryl group, a heteroaryl group and halogen among the groups described above. When $R^3$ to $R^{14}$ are each hydrogen, an alkyl group, a cycloalkyl group, an aryl group, a heteroaryl group or a halogen, the glass transition temperature is increased, and thin-film stability is improved. When thin-film stability is improved, degeneration of the film is suppressed even when the light-emitting device is driven for a long period of time, and therefore durability is improved. Since the substituent is hard to be decomposed under a high temperature, heat resistance is improved. When heat resistance is improved, decomposition of the material during preparation of the device can be suppressed, and therefore durability is improved. Further, when the substituent is an aryl group or a heteroaryl group, conjugation is expanded, so that electrochemical stability becomes higher, and charge transporting property is improved.

In this form, it is preferred that the fluoranthene derivative represented by the general formula (1) is represented by the following general formula (3). The fluoranthene derivative represented by the general formula (3) is substituted at position 3 of a benzofluoranthene skeleton with a substituent containing $L^2\text{-}N(A^1)(A^2)$. In a benzofluoranthene derivative, when the benzofluoranthene skeleton is substituted at position 3 with an aromatic substituent, the electronic state thereof is significantly changed, so that conjugation is efficiently expanded, resulting in improvement of charge transporting property. As a result, the light-emitting device can be driven at a lower voltage, so that luminous efficiency can be further improved. Further, since conjugation is expanded, stability to a charge is further improved. As a result, when the fluoranthene derivative represented by the general formula (3) according to the present invention is used for the light-emitting device, life can be further improved.

[Chemical Formula 3]

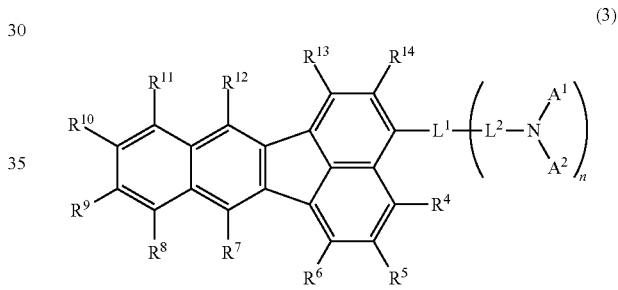

(3)

In the general formula (3), $R^4$ to $R^{14}$ may be the same or different, and are each selected from the group consisting of hydrogen, an alkyl group, a cycloalkyl group, a heterocyclic group, an alkenyl group, a cycloalkenyl group, an alkynyl group, an alkoxy group, an alkylthio group, an aryl ether group, an aryl thioether group, an aryl group, a heteroaryl group, halogen, a carbonyl group, a carboxyl group, an oxycarbonyl group and a carbamoyl group; $R^4$ to $R^{14}$ may form a ring by adjacent substituents; and $L^1$, $L^2$, $A^1$, $A^2$ and n are the same as in the general formula (1).

Preferably, $R^4$ to $R^{14}$ in the general formula (3) are each selected from the group consisting of hydrogen, an alkyl group, a cycloalkyl group, an aryl group, a heteroaryl group and halogen among the groups described above. When $R^4$ to $R^{14}$ are each hydrogen, an alkyl group, a cycloalkyl group, an aryl group, a heteroaryl group or a halogen, the glass transition temperature is increased, and thin-film stability is improved. Since the substituent is hard to be decomposed under a high temperature, heat resistance is improved. Further, when the substituent is an aryl group or a heteroaryl group, conjugation is expanded, so that electrochemical stability becomes higher, and charge transporting property is improved.

Preferably, another form of Ar is represented by the following general formula (4). When Ar is represented by the general formula (4), conjugation is moderately expanded. Consequently, the compound is electrochemically stable, and the charge transporting property is further improved.

[Chemical Formula 5]

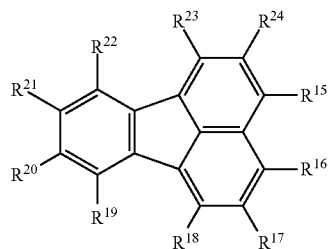

(4)

In the formula, $R^{15}$ to $R^{24}$ may be the same or different, and are each selected from the group consisting of hydrogen, an alkyl group, a cycloalkyl group; a heterocyclic group, an alkenyl group, a cycloalkenyl group, an alkynyl group, an alkoxy group, an alkylthio group, an aryl ether group, an aryl thioether group, an aryl group, a heteroaryl group, halogen, a carbonyl group, a carboxyl group, an oxycarbonyl group and a carbamoyl group; and $R^{15}$ to $R^{24}$ may form a ring by adjacent substituents, with the proviso that the group is coupled to $L^1$ at the position of any one of $R^{15}$ to $R^{24}$.

Preferably, $R^{15}$ to $R^{24}$ in the general formula (4) are each selected from the group consisting of hydrogen, an alkyl group, a cycloalkyl group, an aryl group, a heteroaryl group and halogen among the groups described above. When $R^{15}$ to $R^{24}$ are each hydrogen, an alkyl group, a cycloalkyl group, an aryl group, a heteroaryl group or a halogen, the glass transition temperature is increased, and thin-film stability is improved. When thin-film stability is improved, degeneration of the film is suppressed even when the light-emitting device is driven for a long period of time, and therefore durability is improved. Since the substituent is hard to be decomposed under a high temperature, heat resistance is improved. When heat resistance is improved, decomposition of the material during preparation of the device can be suppressed, and therefore durability is improved. Further, when the substituent is an aryl group or a heteroaryl group, conjugation is expanded, so that electrochemical stability becomes higher, and charge transporting property is improved.

In this form, it is preferred that the fluoranthene derivative represented by the general formula (1) is represented by the following general formula (5). The fluoranthene derivative represented by the general formula (5) is substituted at position 3 of the fluoranthene skeleton with a substituent containing $L^2$-$N(A^1)(A^2)$. In a fluoranthene derivative, when the fluoranthene skeleton is substituted at position 3 with an aromatic substituent, the electronic state thereof is significantly changed, so that conjugation is efficiently expanded, resulting in improvement of charge transporting property. As a result, the light-emitting device can be driven at a lower voltage, so that luminous efficiency can be further improved. Further, since conjugation is expanded, stability to a charge is further improved. As a result, when the fluoranthene derivative represented by the general formula (5) according to the present invention is used for the light-emitting device, life can be further improved.

[Chemical Formula 6]

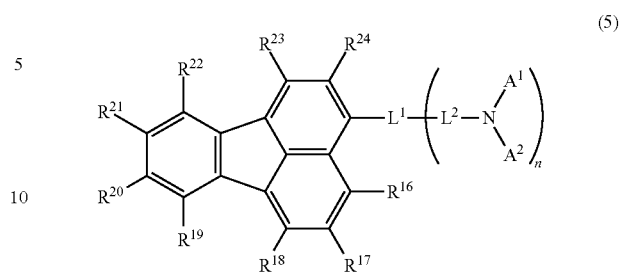

(5)

$R^{16}$ to $R^{24}$ may be the same or different, and are each selected from the group consisting of hydrogen, an alkyl group, a cycloalkyl group, a heterocyclic group, an alkenyl group, a cycloalkenyl group, an alkynyl group, an alkoxy group, an alkylthio group, an aryl ether group, an aryl thioether group, an aryl group, a heteroaryl group, halogen, a carbonyl group, a carboxyl group, an oxycarbonyl group and a carbamoyl group; $R^{16}$ to $R^{24}$ may form a ring by adjacent substituents, $L^1$, $L^2$, $A^1$, $A^2$ and n are the same as in the general formula (1).

Preferably, $R^{16}$ to $R^{24}$ in the general formula (5) are each selected from the group consisting of hydrogen, an alkyl group, a cycloalkyl group, an aryl group, a heteroaryl group and halogen among the groups described above. When $R^{16}$ to $R^{24}$ are each hydrogen, an alkyl group, a cycloalkyl group, an aryl group, a heteroaryl group or a halogen, the glass transition temperature is increased, and thin-film stability is improved. Since the substituent is hard to be decomposed under a high temperature, heat resistance is improved. Further, when the substituent is an aryl group or a heteroaryl group, conjugation is expanded, so that electrochemical stability becomes higher, and charge transporting property is improved.

When $L^2$-$N(A^1)(A^2)$ has the above-mentioned structure, the electron-donating property of electron-donating nitrogen is enhanced, and therefore the electronic conduction level can be made low. Thus, when the fluoranthene derivative represented by the general formula (1) in the present invention is used for the electron transporting layer, the energy barrier between the electron transporting layer and the emissive layer decreases, and therefore electron injection from the electron transporting layer to the emissive layer can be enhanced, so that the driving voltage of the light-emitting device can be further reduced.

Preferably, another form of $L^2$-$N(A^1)(A^2)$ has a structure represented by any one of the following general formulae (6) to (9), and this commonly applies to all the forms of the fluoranthene derivative represented by the general formula (1). When $L^2$-$N(A^1)(A^2)$ has a structure represented by any one of the following general formulae (6) to (9), moderate electron-donating property of electron-donating nitrogen can be maintained, and the electron conduction level can be made low. Thus, when the fluoranthene derivative represented by the general formula (1) in the present invention is used for the electron transporting layer, the energy barrier between the electron transporting layer and the emissive layer decreases, and therefore electron injection from the electron transporting layer to the emissive layer can be enhanced, so that the driving voltage of the light-emitting device can be reduced. When $L^2$-$N(A^1)(A^2)$ is any one of the general formulae (6) to (9), the glass transition temperature increases, so that thin-film stability is further improved. When thin-film stability is improved, degeneration of the film is suppressed even when the light-emitting device is driven for a long period of time, and therefore durability is further improved. Since the substituent is hard to be decomposed under a high temperature, heat resistance is further improved. When heat resistance is improved, decomposition of the material during preparation of the device can be suppressed, and therefore durability is further improved.

[Chemical Formula 7]

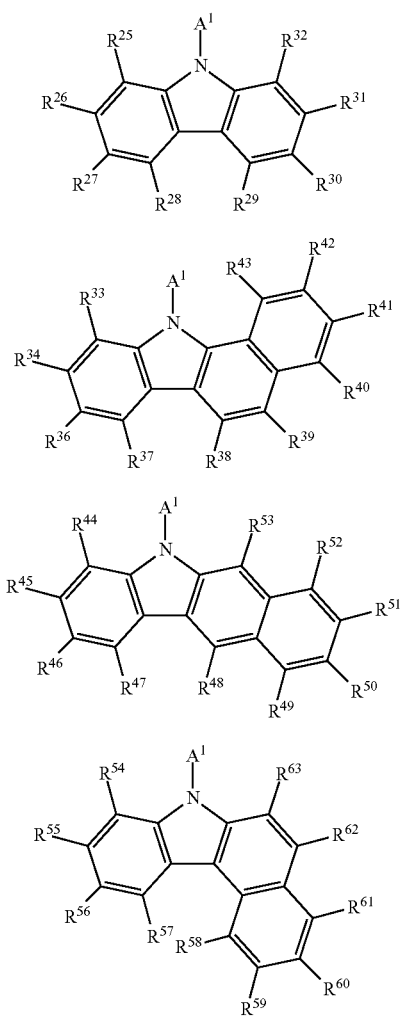

$A^1$ is a substituted or unsubstituted monocyclic aromatic heterocyclic ring having 1 to 40 carbon atoms, or a substituted or unsubstituted fused aromatic heterocyclic ring having 1 to 40 carbon atoms, with the proviso that at least one of atoms that form $A^1$ is an electron-accepting nitrogen atom; $R^{25}$ to $R^{63}$ may be the same or different, and are each selected from the group consisting of hydrogen, an alkyl group, a cycloalkyl group, a heterocyclic group, an alkenyl group, a cycloalkenyl group, an alkynyl group, an alkoxy group, an alkylthio group, an aryl ether group, an aryl thioether group, an aryl group, a heteroaryl group, halogen, a carbonyl group, a carboxyl group, an oxycarbonyl group and a carbamoyl group; and $R^{25}$ to $R^{63}$ may form a ring by adjacent substituents, with the proviso that the group is coupled to $L^1$ at the position of any one of $R^{25}$ to $R^{63}$. More preferably, the fluoranthene skeleton is coupled to $L^1$ at the position of any one of $R^{25}$ to $R^{28}$ in the general formula (6), at the position of any one of $R^{33}$ to $R^{37}$ or $R^{39}$ in the general formula (7), at the position of any one of $R^{44}$ to $R^{47}$ in the general formula (8), and at the position of any one of $R^{54}$ to $R^{57}$ in the general formula (9).

n is preferably 1, and this commonly applies to all the forms of the fluoranthene derivative represented by the general formula (1). When n is 1, sublimability and deposition stability are improved.

$R^7$ and $R^{12}$ in the general formulae (2) and (3) are each preferably a substituted or unsubstituted aryl group. When $R^7$ and $R^{12}$ are each a substituted or unsubstituted aryl group, overlap of π conjugation planes between molecules can be moderately avoided. When $R^7$ and $R^{12}$ are each an aryl group, heat resistance is further improved. As a result, without impairing high charge transporting property of the benzofluoranthene compound, improvement of sublimability, improvement of deposition stability, reduction of crystallinity and improvement of thin-film stability due to a high glass transition temperature can be realized.

$R^7$ and $R^{12}$ in the general formulae (2) and (3) are each more preferably a substituted or unsubstituted phenyl group. When $R^7$ and $R^{12}$ are each a substituted or unsubstituted phenyl group, overlap of π conjugation planes between molecules can be moderately avoided. Since the molecular weight becomes moderate, sublimability and deposition stability are further improved.

Preferably, $A^1$ has a structure represented by any one of the following general formulae (10) to (12), and this commonly applies to all the forms of the fluoranthene derivative represented by the general formula (1). When $A^1$ has a structure represented by any of the following general formulae (10) to (12), high electron mobility and high electron-accepting property are achieved, so that the driving voltage of the light-emitting device can be further reduced. As a result, luminous efficiency of the light-emitting device can be further improved. The life of the light-emitting device is further increased.

[Chemical Formula 8]

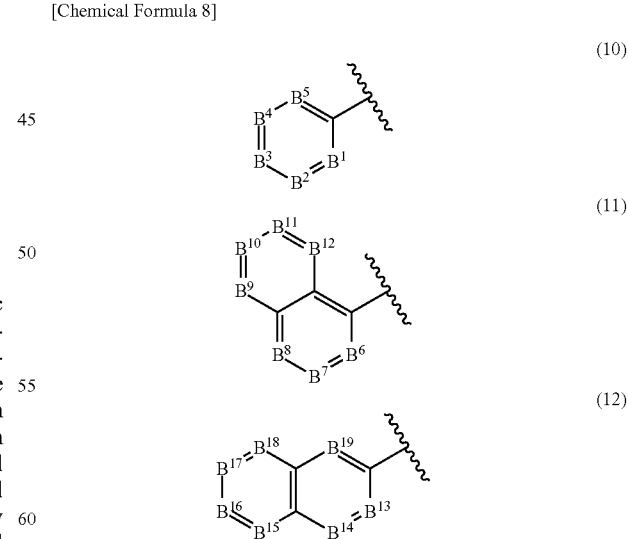

$B^1$ to $B^{19}$ each represent CH, a substituted carbon atom or a nitrogen atom, with the proviso that when $B^1$ to $B^{19}$ do not contain nitrogen atoms, $A^2$ is a substituted or unsubstituted monocyclic aromatic heterocyclic ring containing electron-accepting nitrogen, or a substituted or unsubstituted fused aromatic heterocyclic ring containing electron-accepting nitrogen, and when $L^2$-$N(A^1)(A^2)$ has a structure represented by any one of the general formulae (6) to (9), any one of $B^1$ to $B^{19}$ is a nitrogen atom; and a substituent that $B^1$ to $B^{19}$ optionally have is the same as in the general formula (1).

Preferably, $A^2$ has a structure represented by any one of the following general formulae (13) to (15), and this commonly applies to all the forms of the fluoranthene derivative represented by the general formula (1). When ring B is a structure represented by any of the following general formulae (13) to (15), high carrier mobility and high electron-accepting property are achieved. As a result, low-voltage driving of the light-emitting device becomes, possible, so that luminous efficiency can be improved. Sublimability and deposition stability are further improved, crystallinity is further reduced, and stability of the film due to a high glass transition temperature is improved.

[Chemical Formula 9]

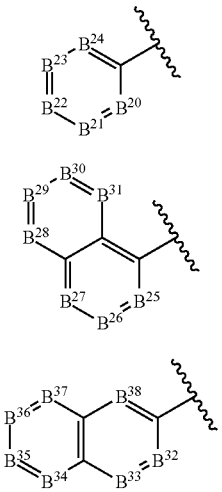

(13)

(14)

(15)

$B^{20}$ to $B^{38}$ each represent CH, a substituted carbon atom or a nitrogen atom, with the proviso that when the $B^1$ to $B^{19}$ do not contain nitrogen atoms, at least one of $B^{20}$ to $B^{38}$ is a nitrogen atom, and when $L^2$-$N(A^1)(A^2)$ has a structure represented by any one of the general formulae (6) to (9), $B^{20}$ to $B^{38}$ do not contain nitrogen atoms; and a substituent that $B^{20}$ to $B^{38}$ optionally have is the same as in the general formula (1).

In the general formula (1), substituents of $L^1$, $L^2$, $A^1$ and $A^2$ are each preferably an aryl group. When substituents of $L^2$, $A^1$ and $A^2$ are each an aryl group, improvement of sublimability, improvement of deposition stability, reduction of crystallinity and improvement of thin-film stability due to a high glass transition temperature can be realized. The aryl group is not particularly limited, and specific examples thereof include a phenyl group, a naphthyl group, a biphenyl group, a phenanthryl group, a terphenyl group, a pyrenyl group, and a fluoranthenyl group.

In the general formula (1), substituents of $L^1$, $L^2$, $A^1$ and $A^2$ are each further preferably a group containing a fluoranthene skeleton. That is, the structure of the general formula (1) is preferably a structure of the following general formula (16) or the following general formula (17). When the structure of the general formula (1) is a structure of the following general formula (16) or the following general formula (17), the fluoranthene derivative has two fluoranthene skeletons having high electron affinity, so that high carrier mobility and high electron-accepting property are achieved. As a result, further low-voltage driving of the light-emitting device becomes possible, so that luminous efficiency can be improved. Improvement of sublimability, improvement of deposition stability, reduction of crystallinity and improvement of stability of the film due to a high glass transition temperature are realized.

[Chemical Formula 10]

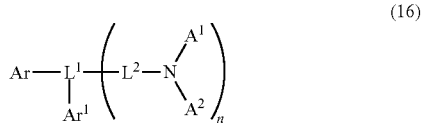

(16)

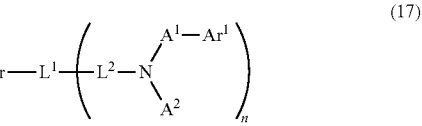

(17)

In the formula, $Ar^1$ represents a group containing a fluoranthene skeleton; and Ar, $L^1$, $L^2$, $A^1$, $A^2$ and n are the same as in the general formula (1), with the proviso that in the general formula (16), L is not a single bond.

$Ar^1$ in the general formula (16) or the general formula (17) is more preferably a substituted or unsubstituted fluoranthenyl group. When $Ar^1$ is a substituted or unsubstituted fluoranthenyl group, high carrier mobility and high electron-accepting property are achieved. Since the molecular weight becomes moderate, sublimability and deposition stability are further improved.

Further preferably, n is 1 and $L^2$ is a single bond in the general formula (16) or the general formula (17).

The group represented by $L^2$-$N(A^1)(A^2)$ is not particularly limited, and specific examples include those of the following formulae.

[Chemical Formula 11]

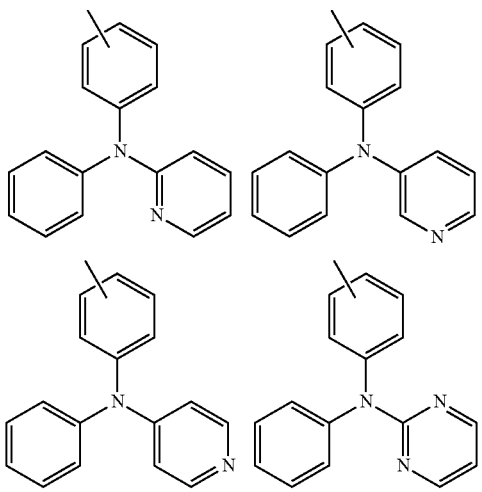

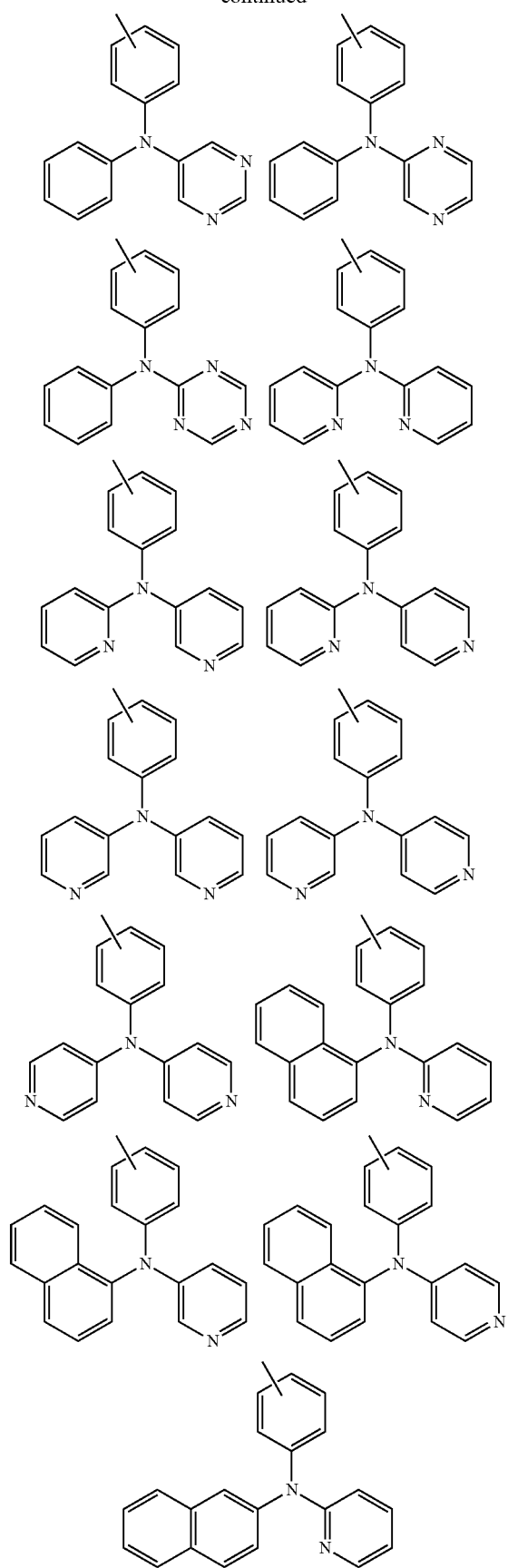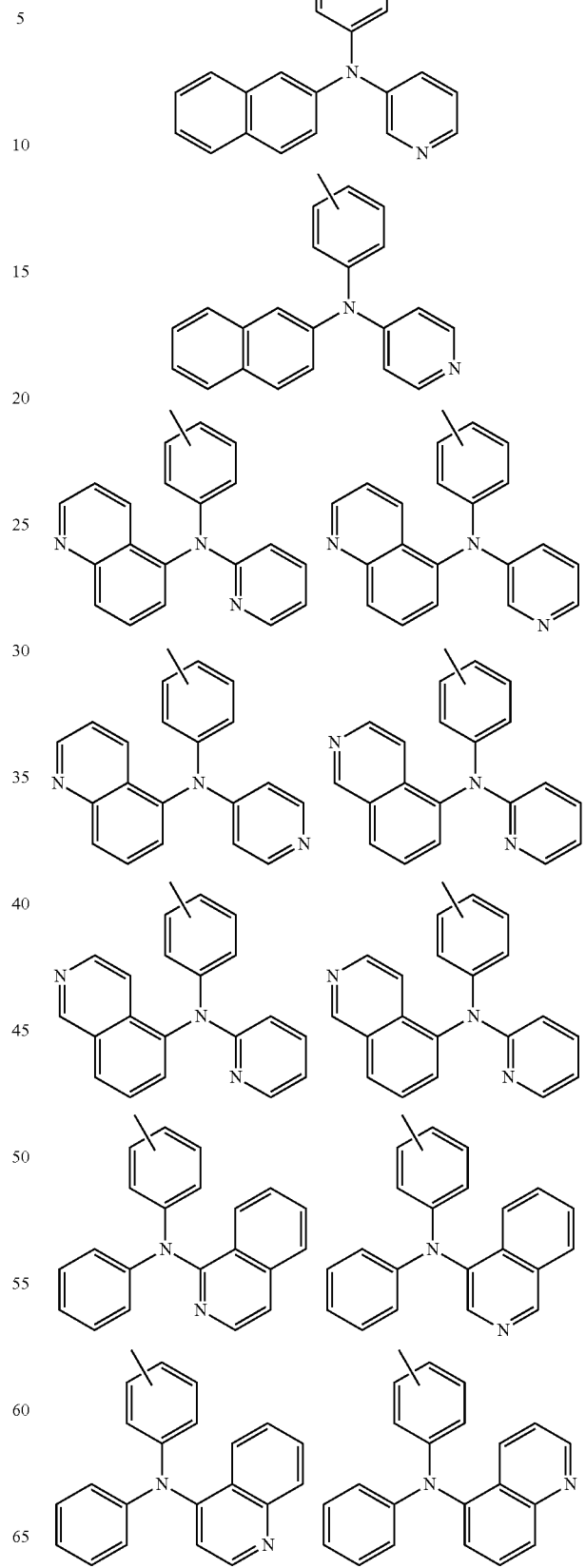

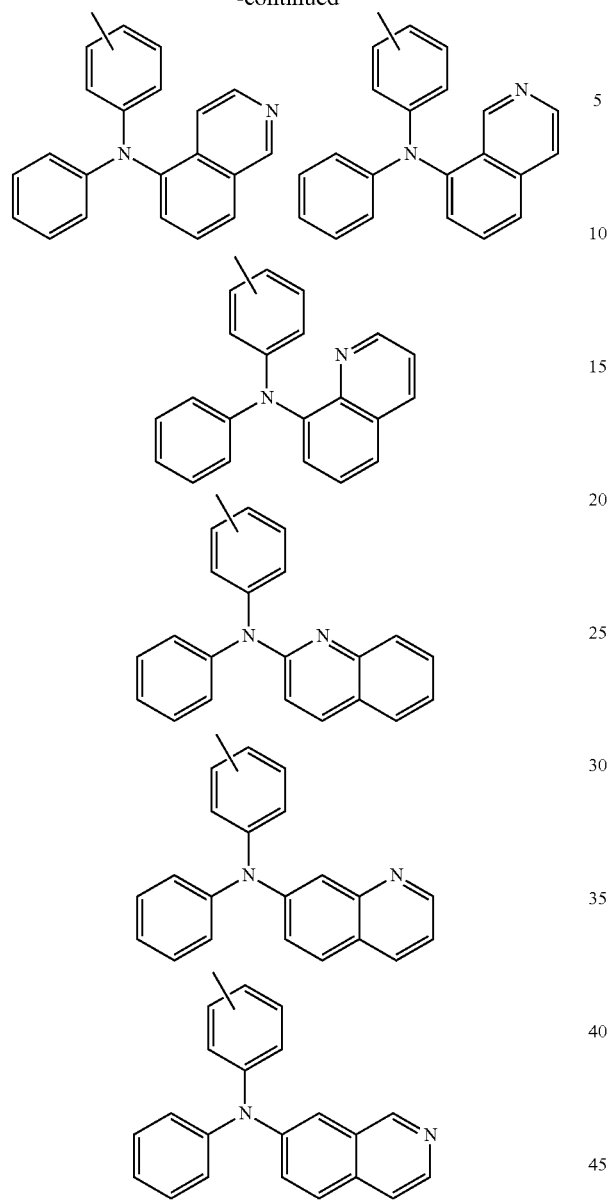
[Chemical Formula 12]
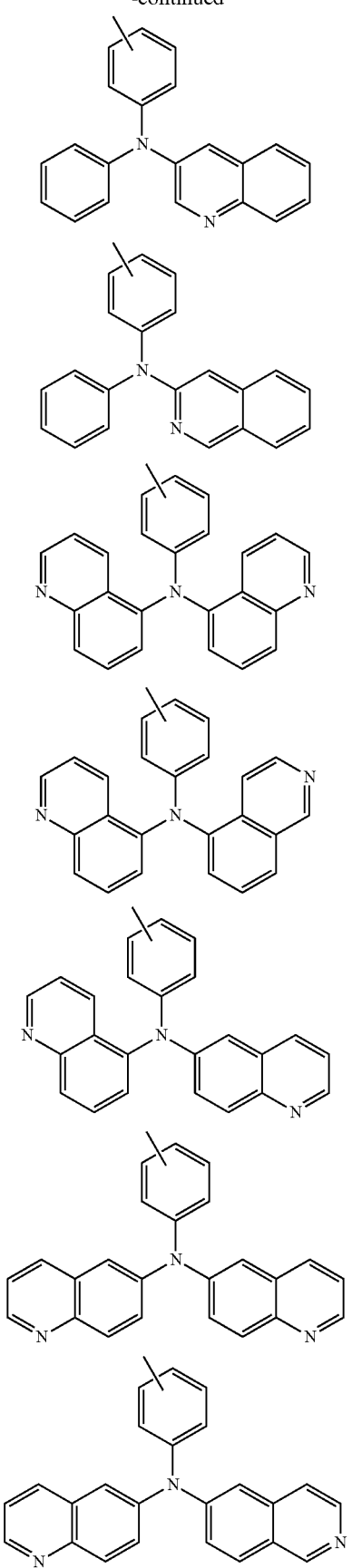

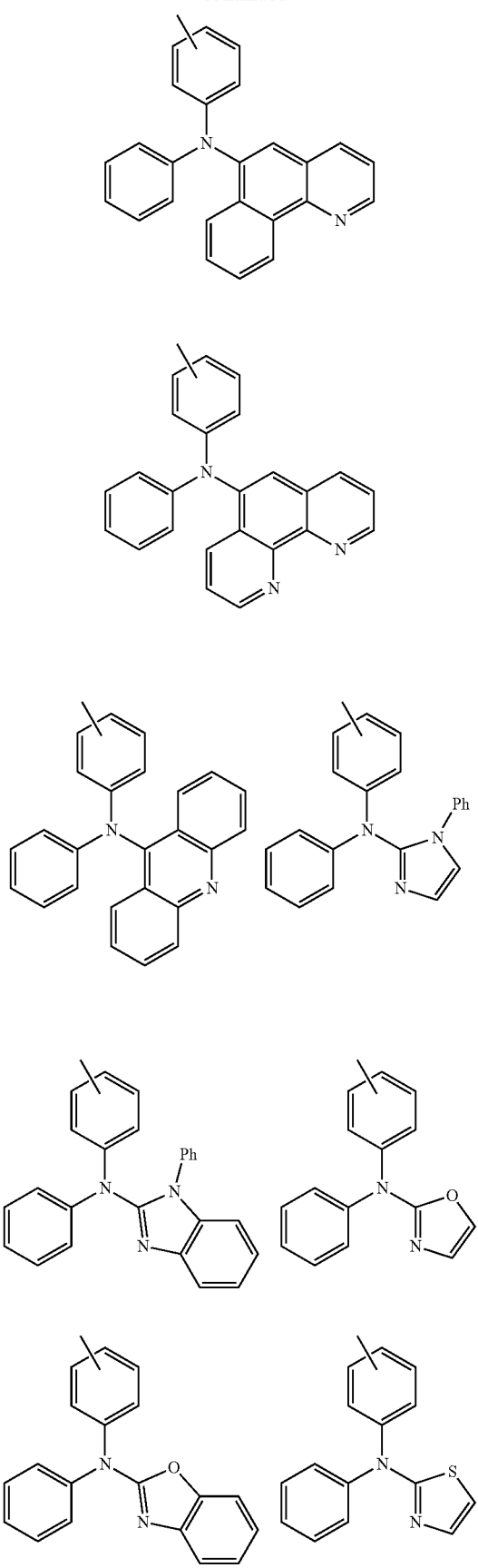
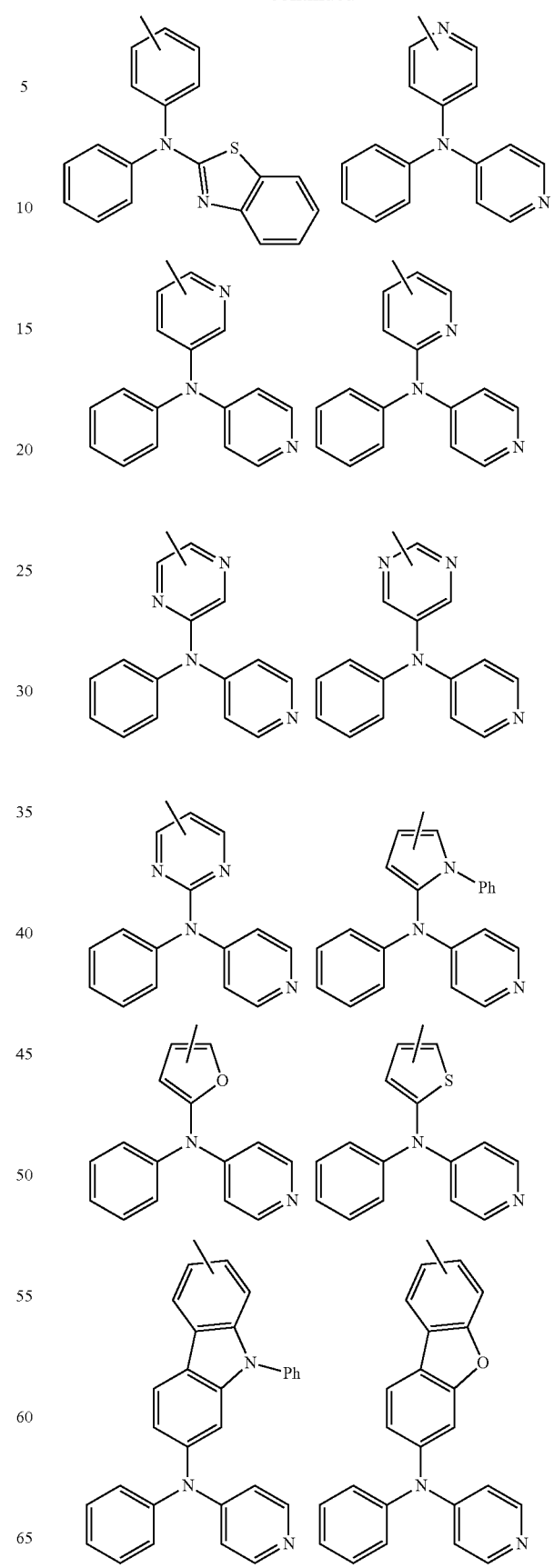

23
-continued
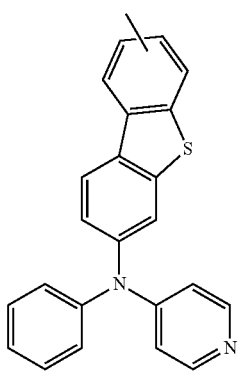
24
-continued
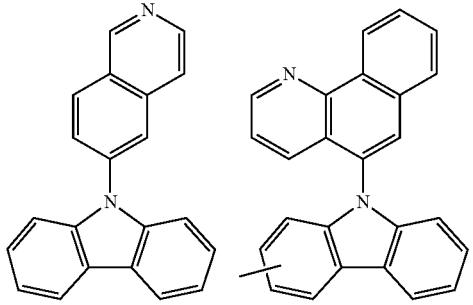
[Chemical Formula 13]
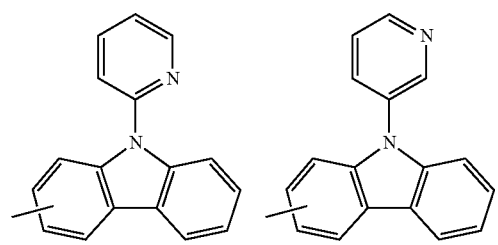
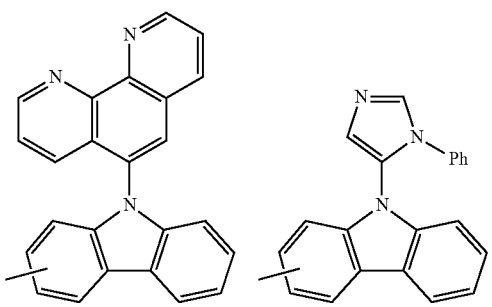
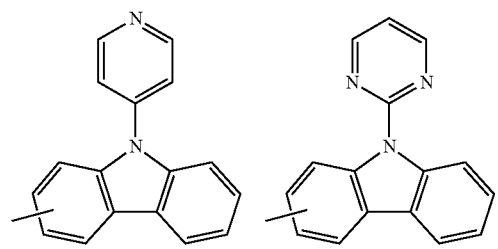
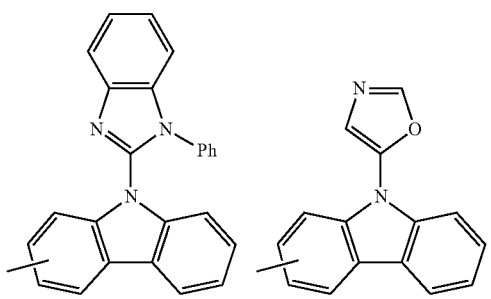
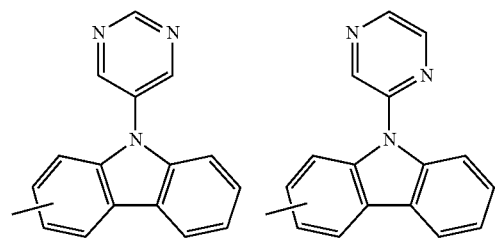
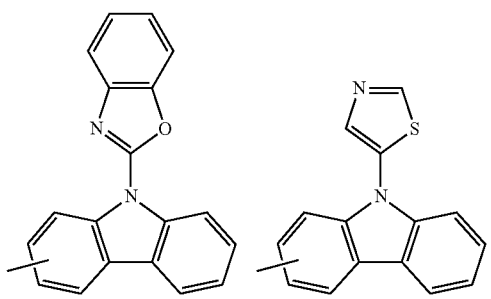
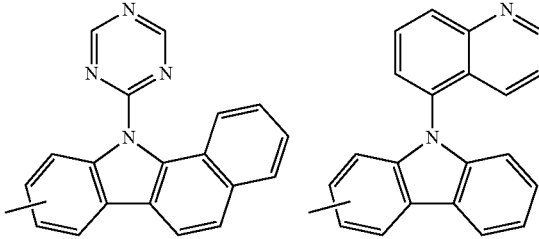
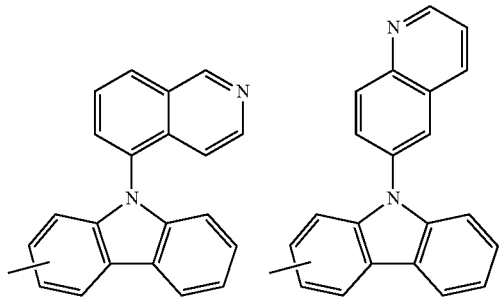
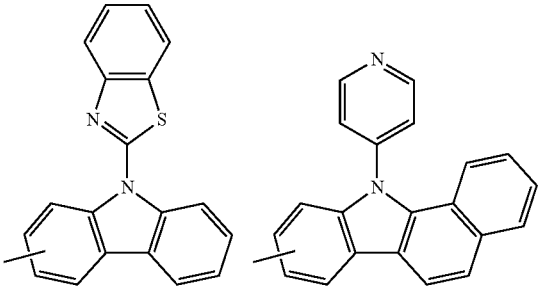

-continued
[Chemical Formula 14]
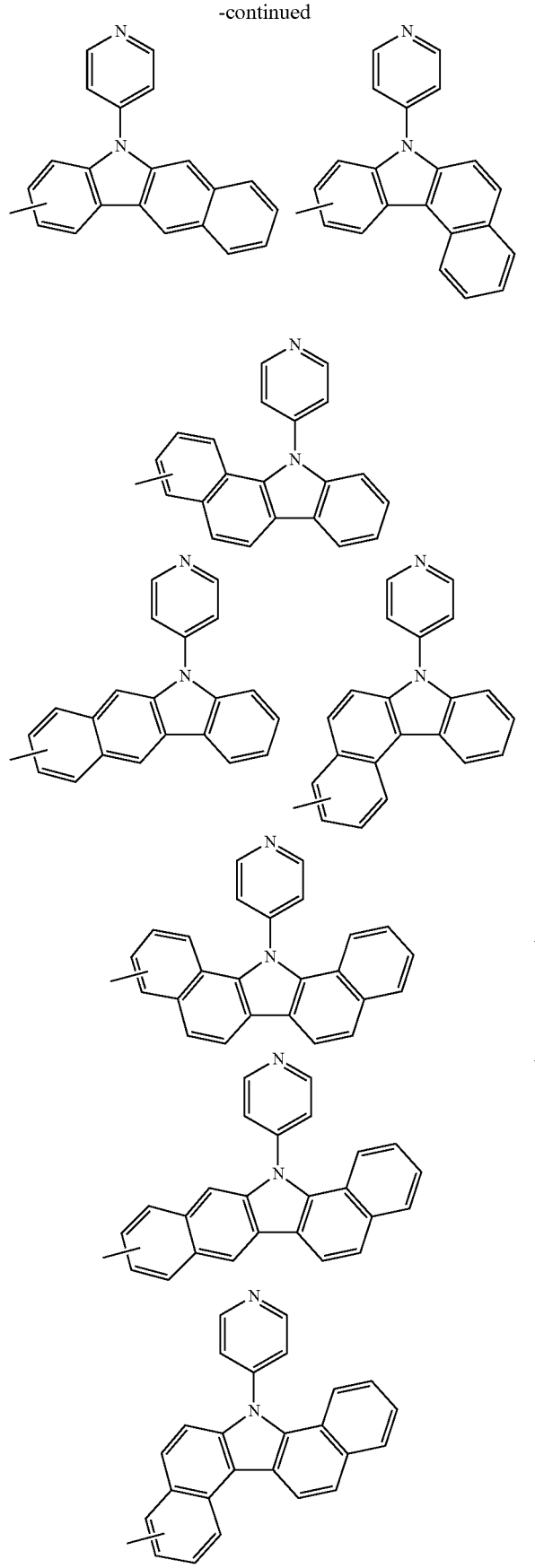
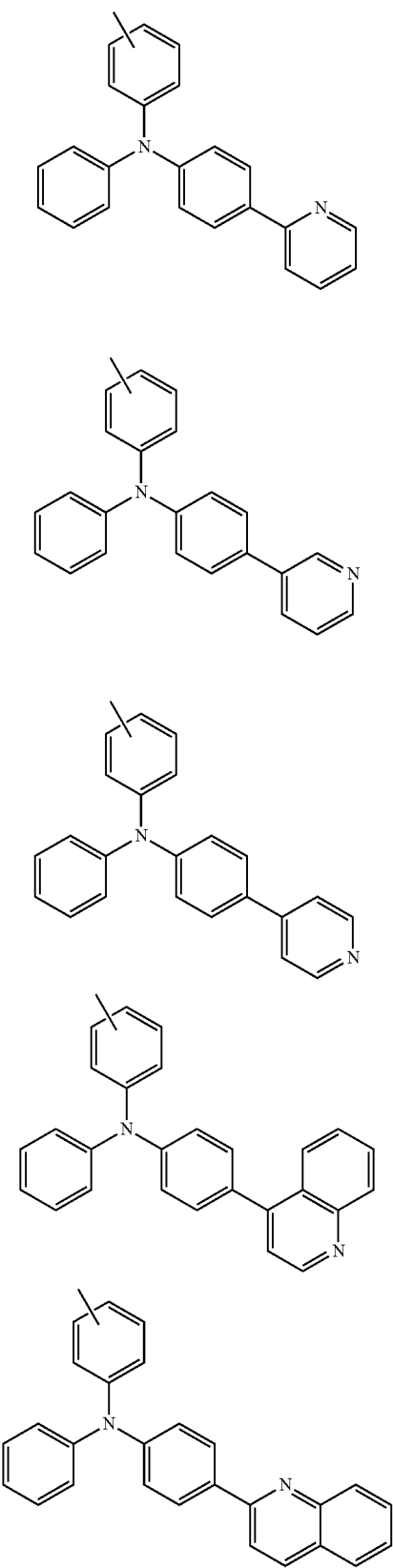

27
-continued
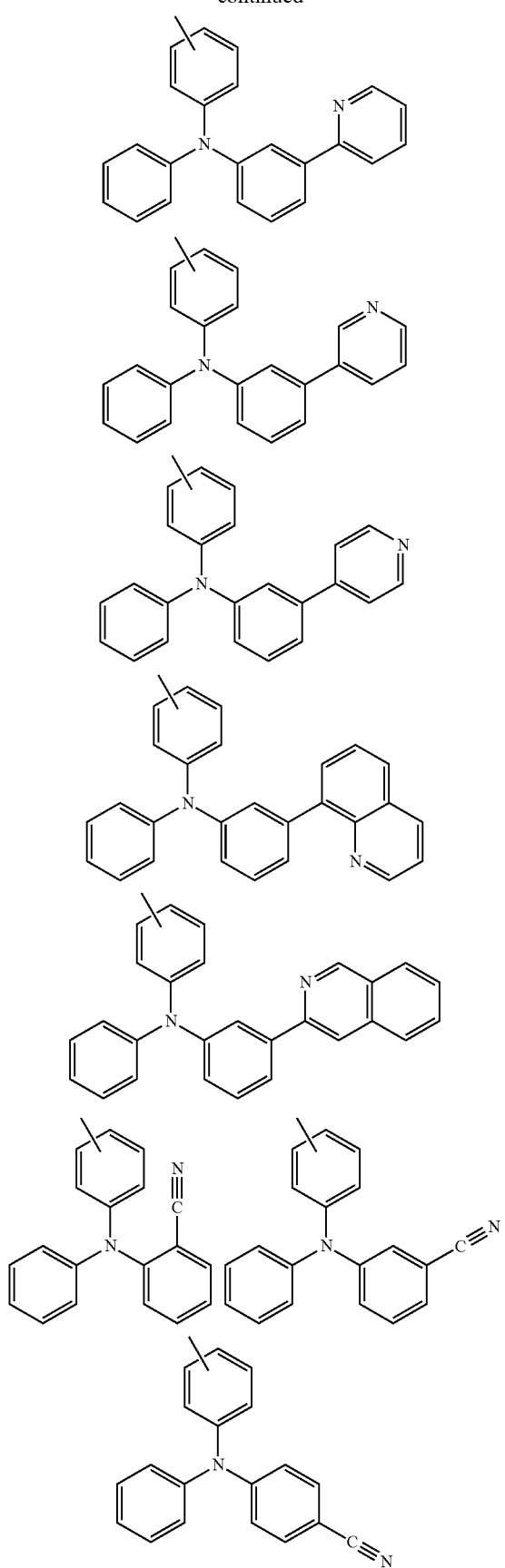
28
-continued
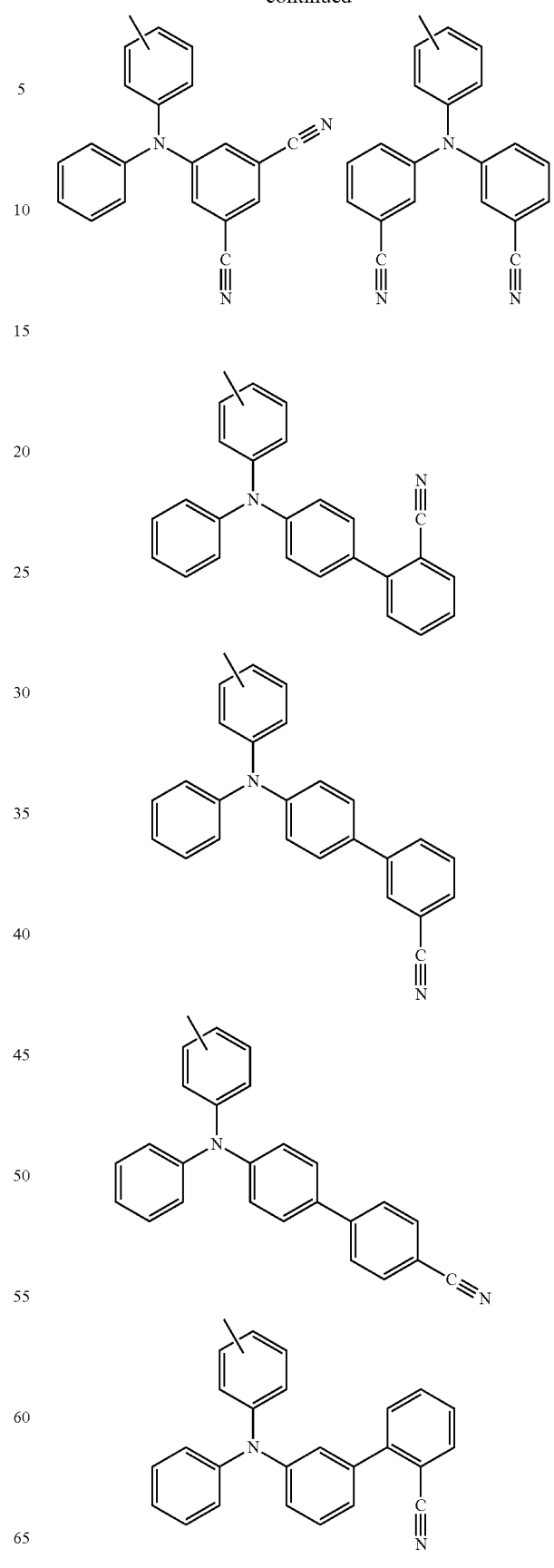

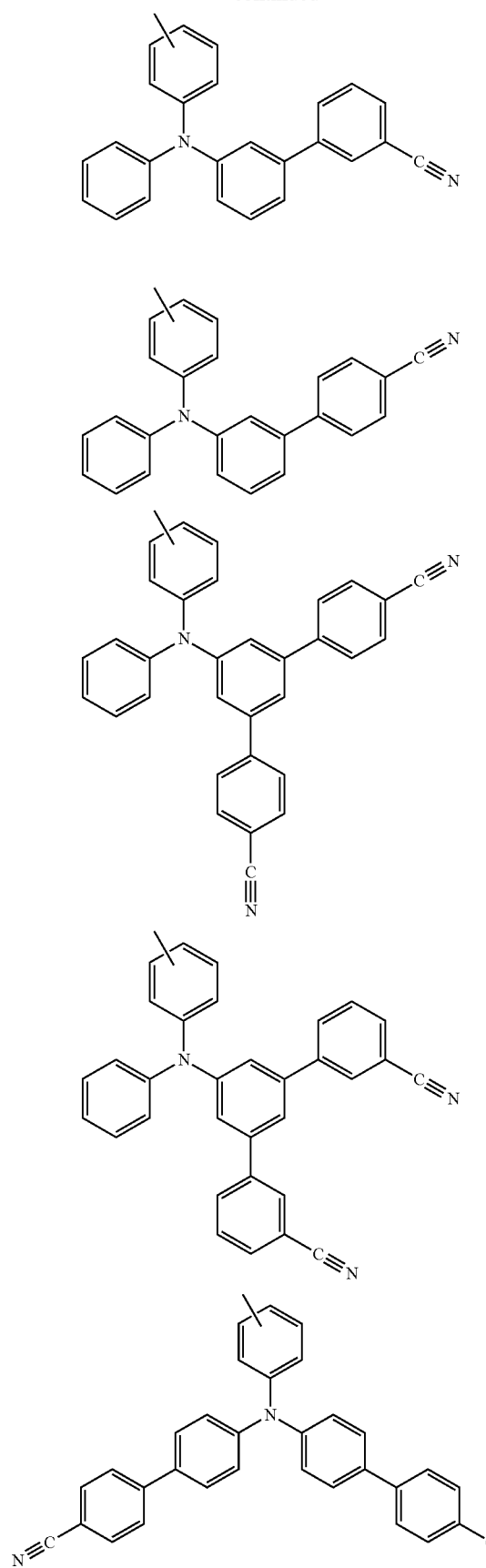

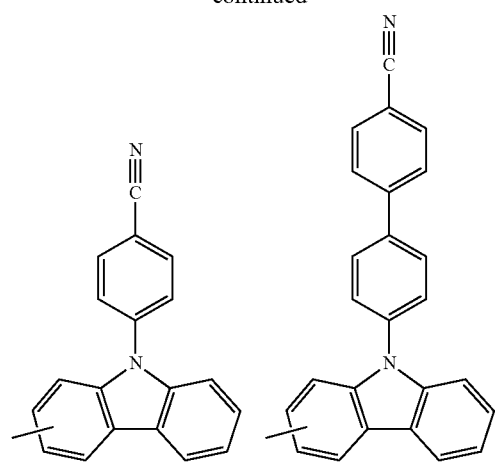
[Chemical Formula 15]
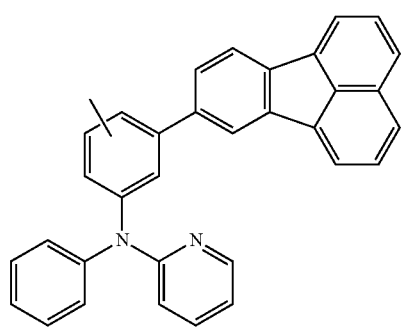
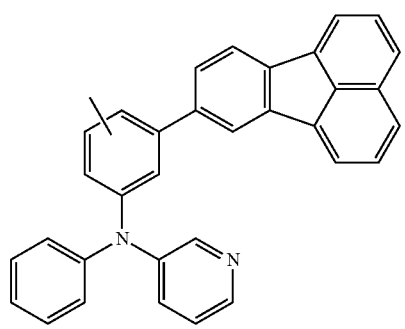
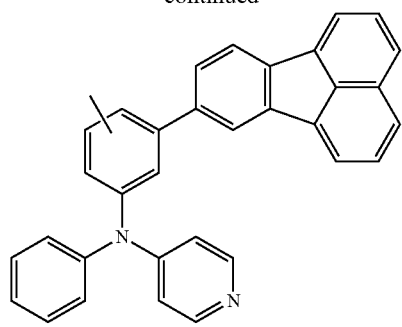
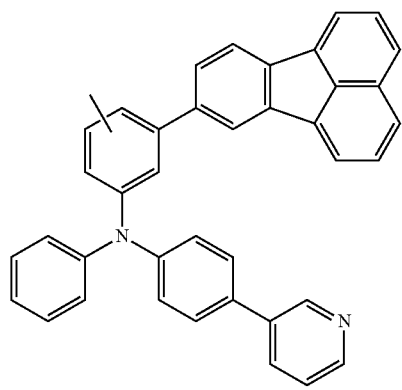
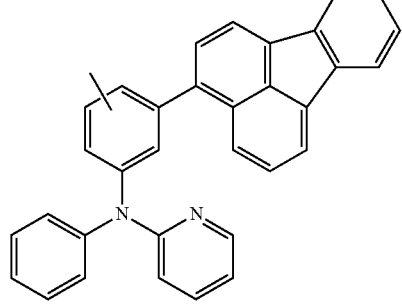

33
-continued
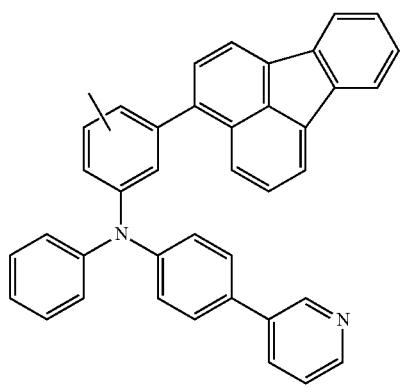
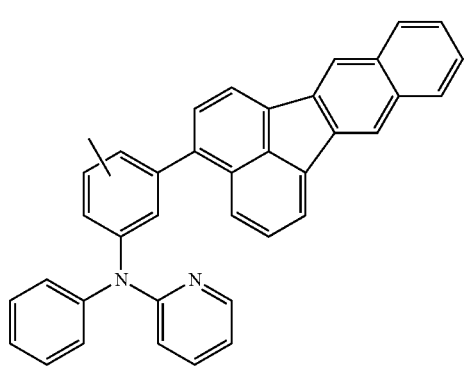
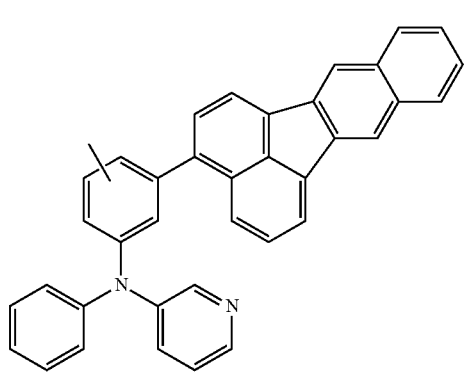
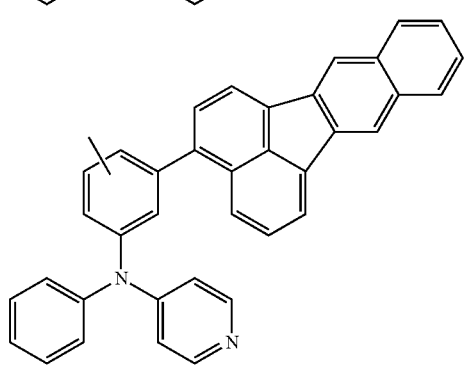
34
-continued
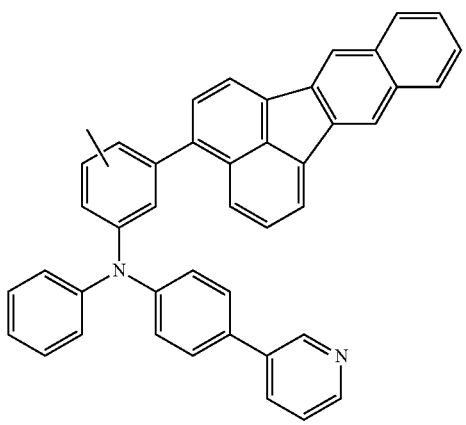
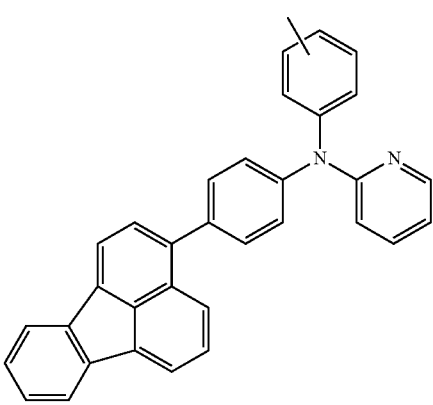
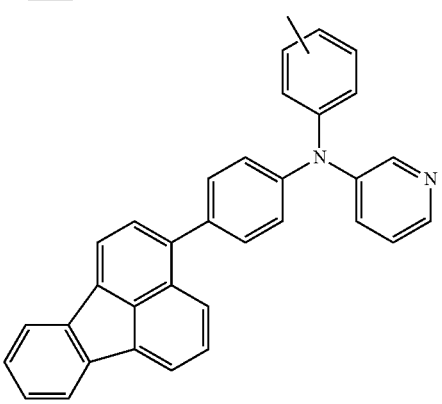
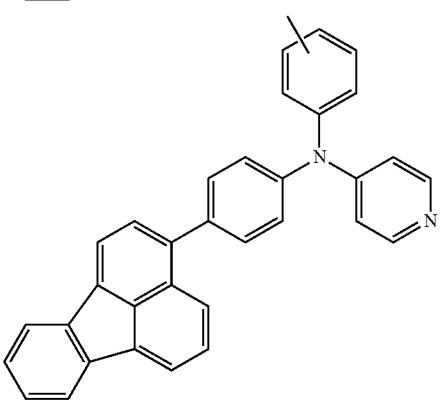

-continued
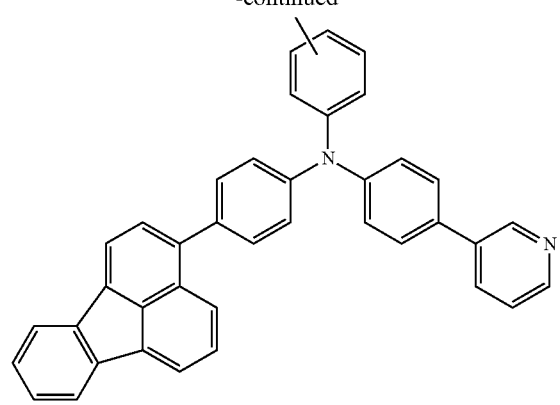
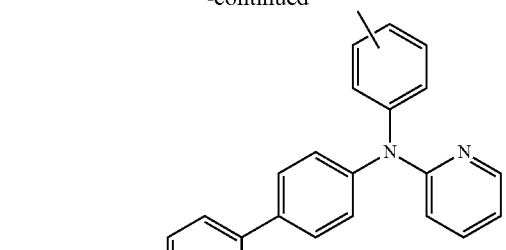
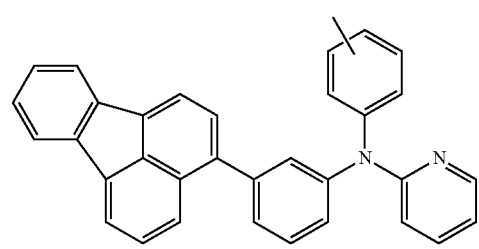
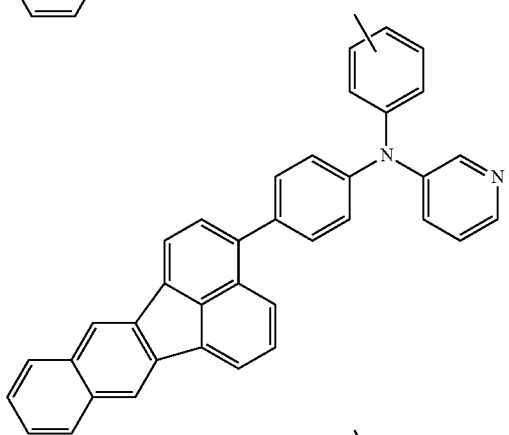
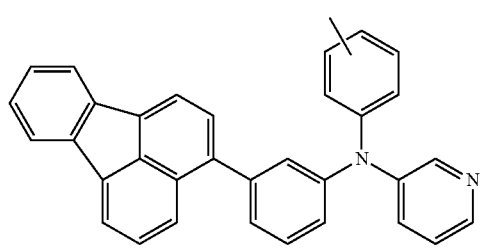
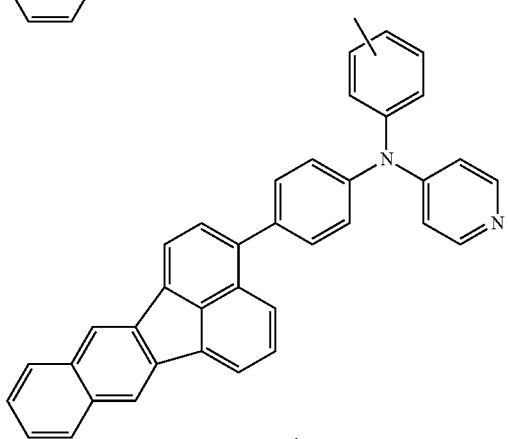
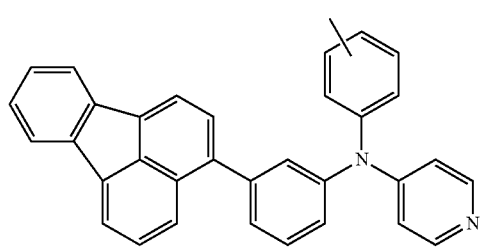
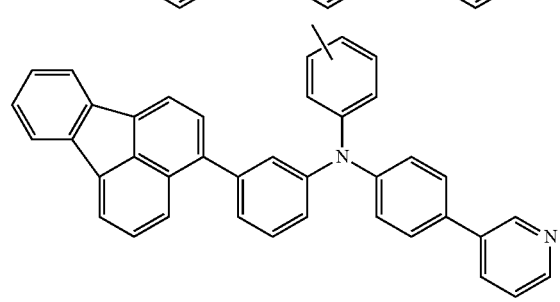
The fluoranthene derivative represented by the general formula (1) is not particularly limited, and specific examples include those of the following formulae.

[Chemical Formula 16]
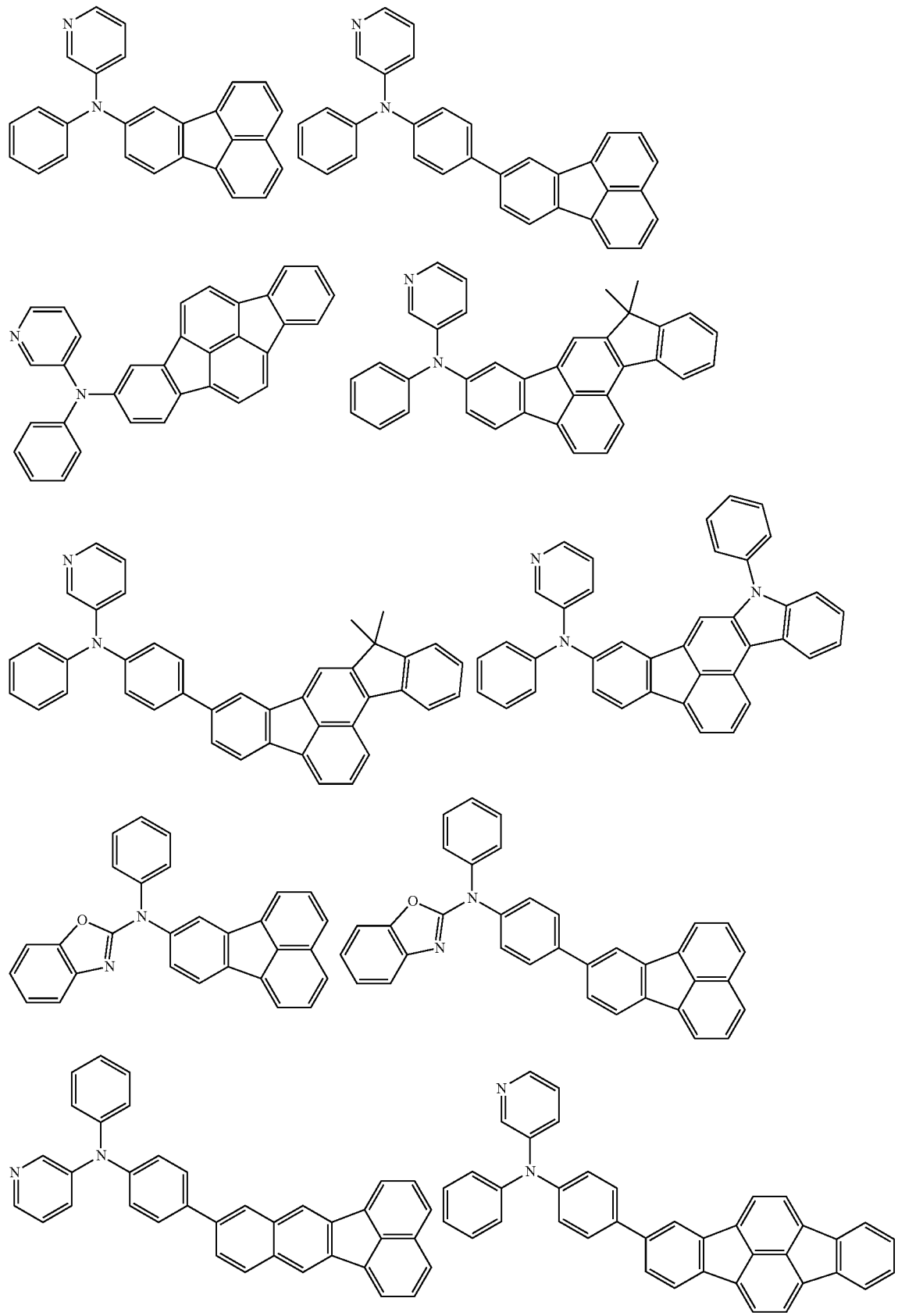

-continued
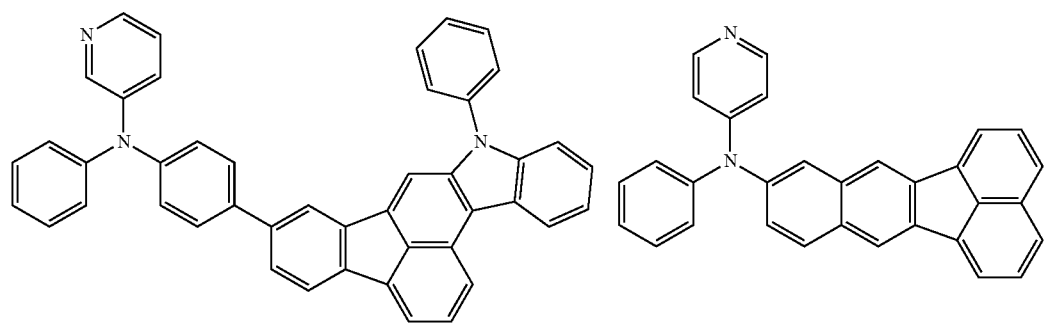
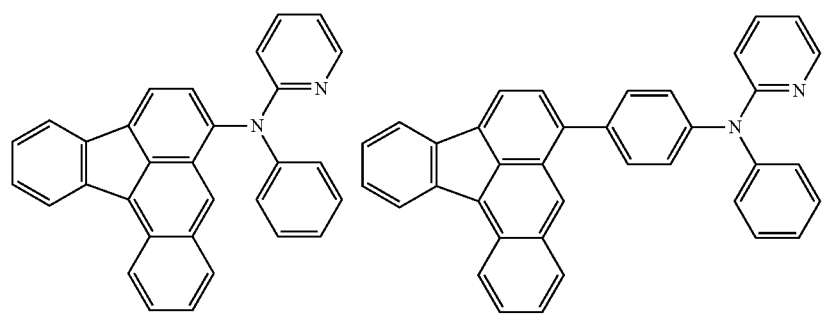
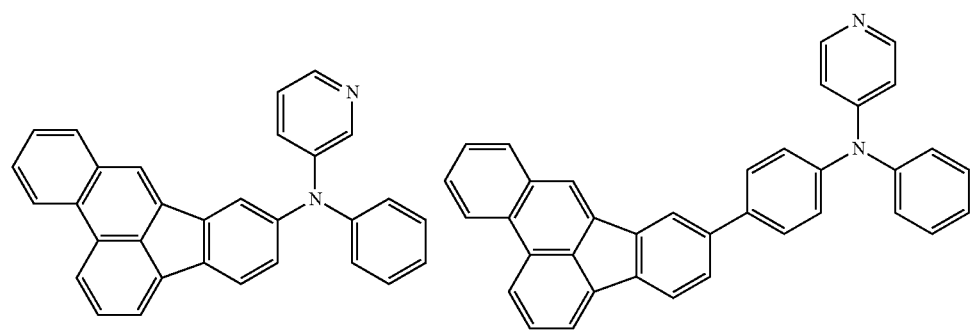
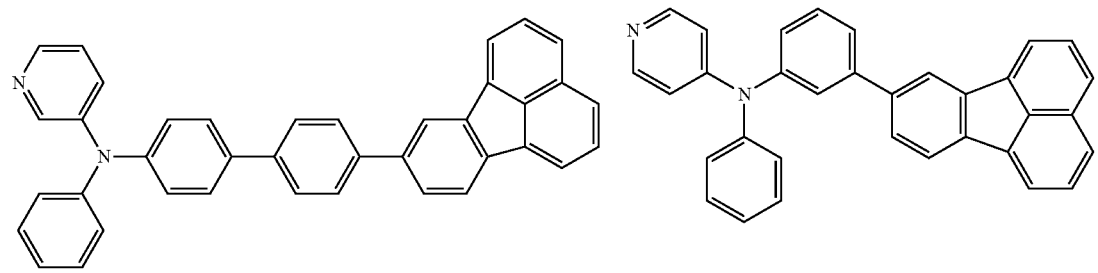
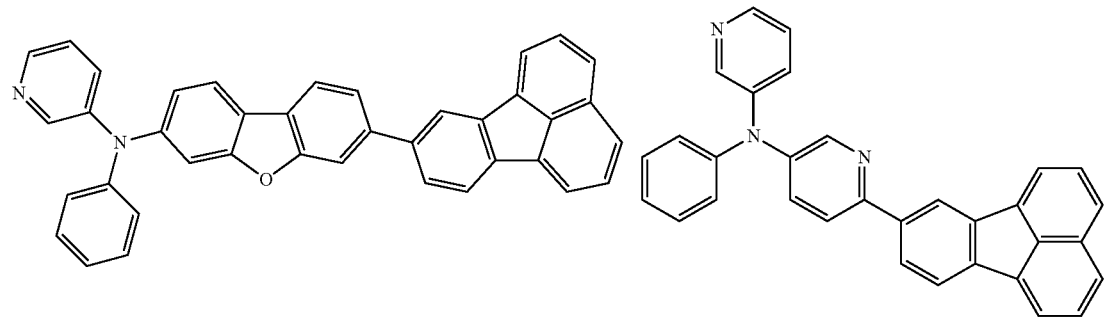

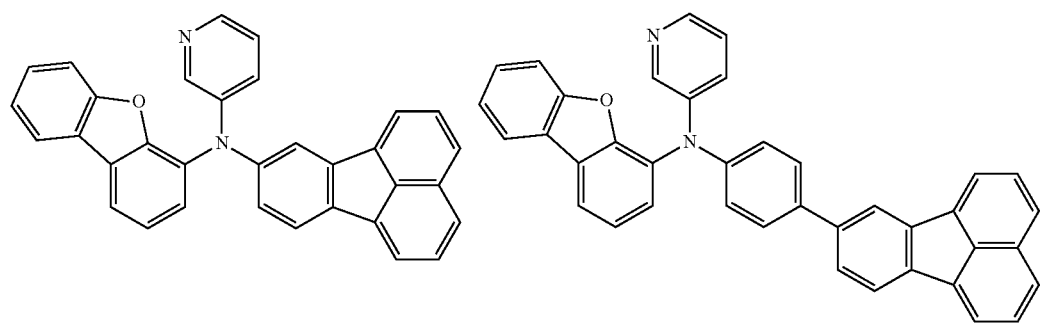
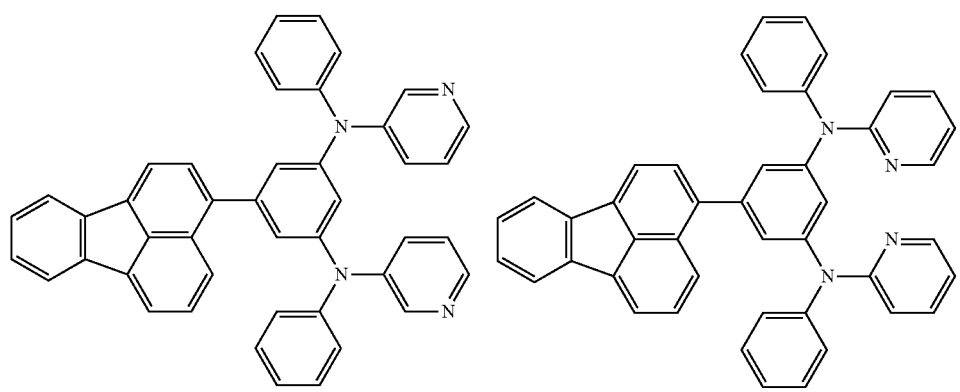
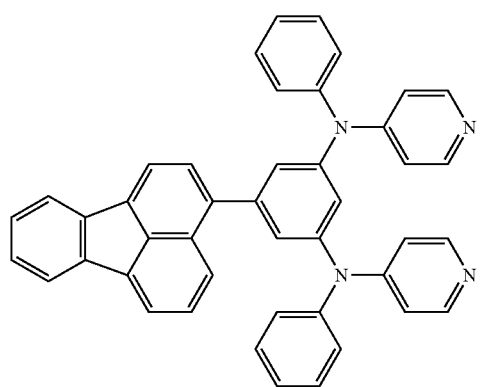
[Chemical Formula 17]
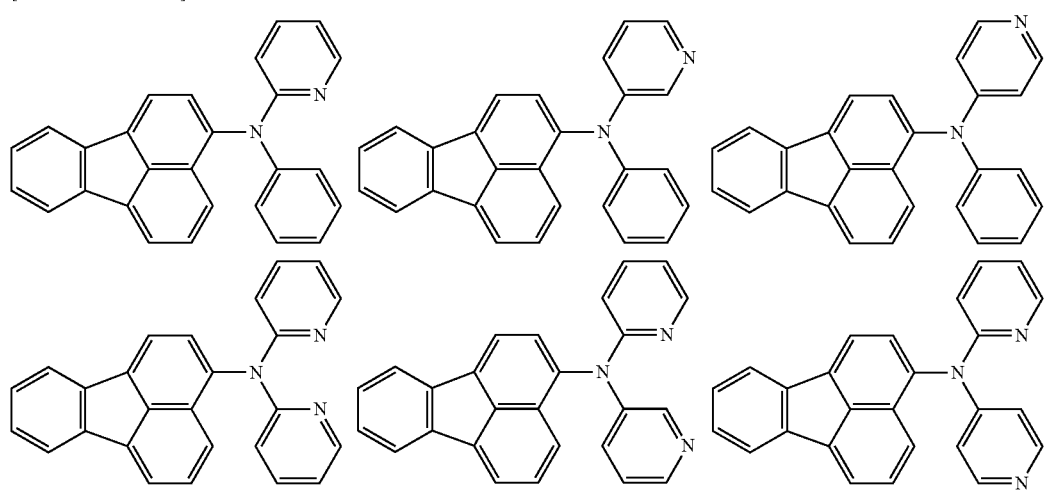

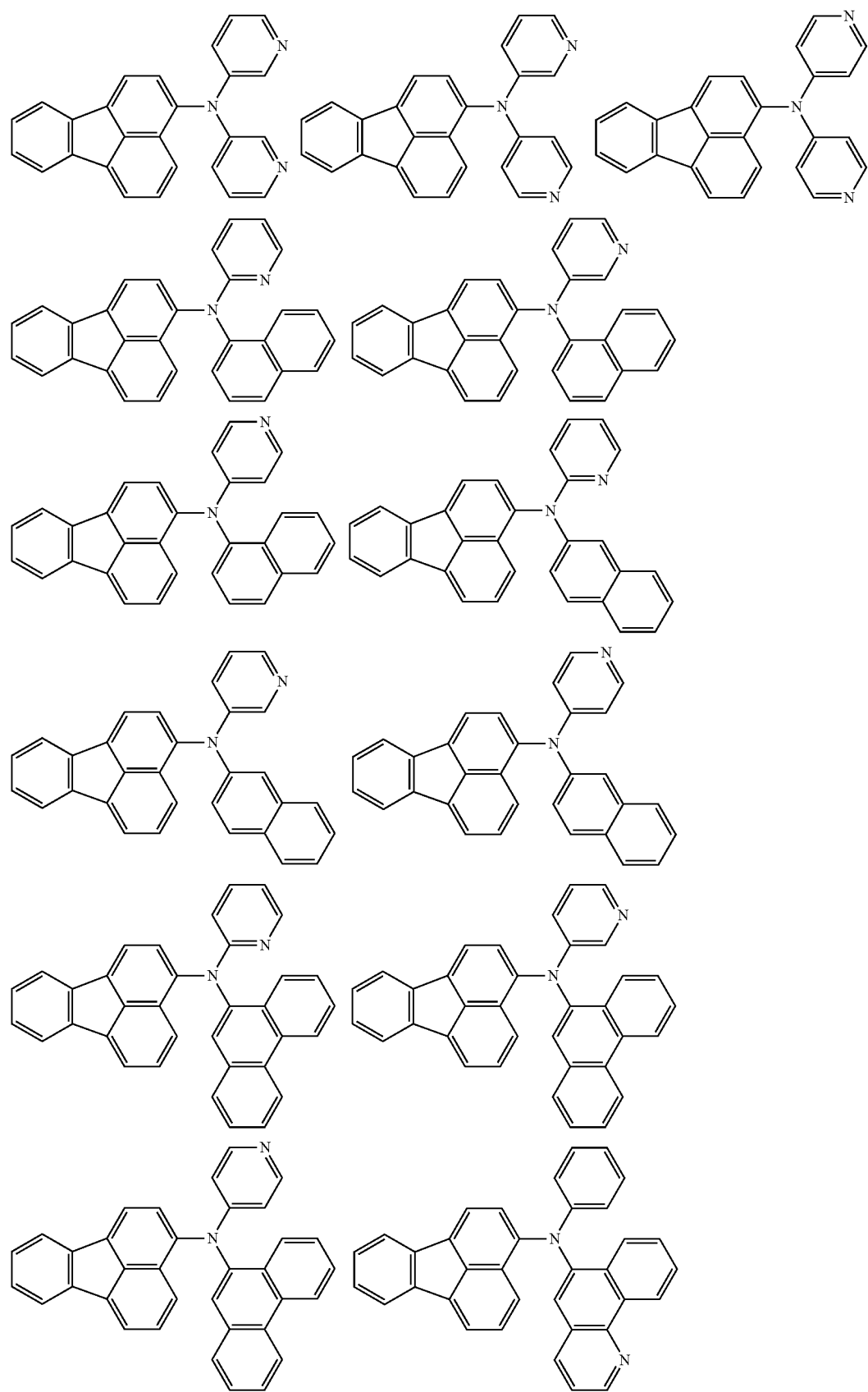

-continued
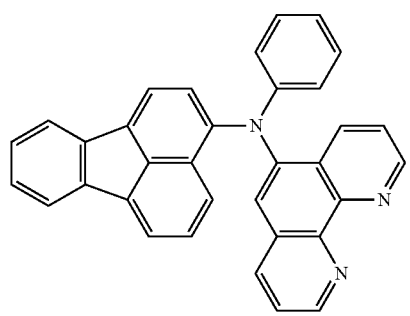
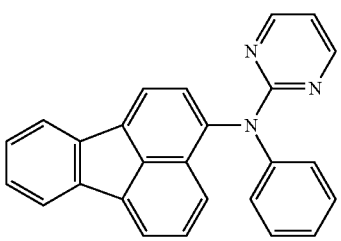
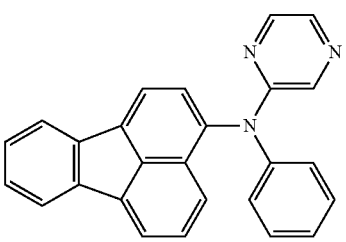
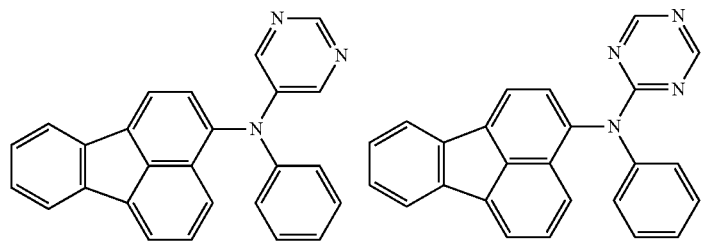
[Chemical Formula 18]
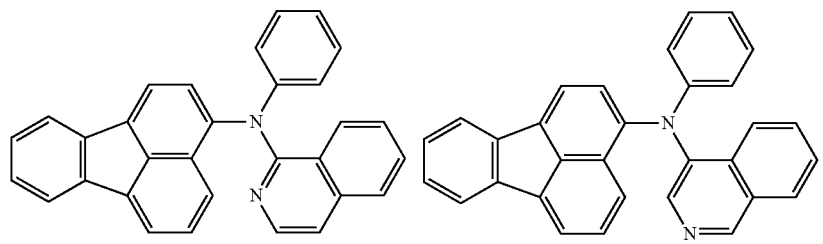
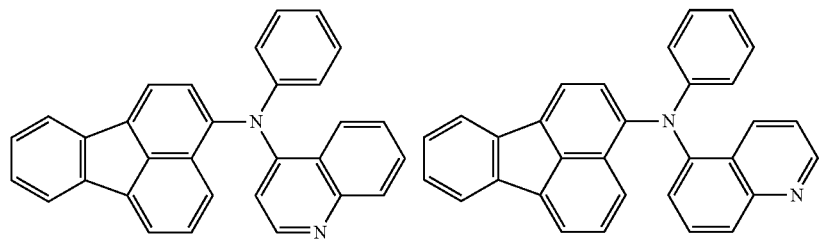
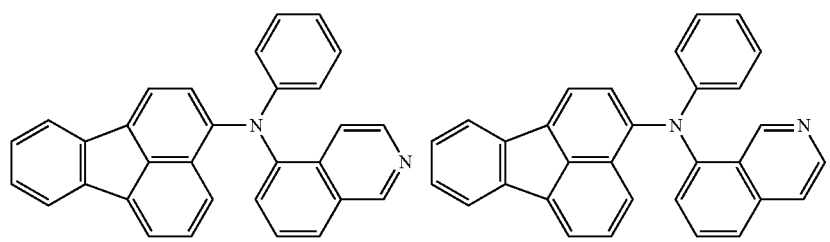
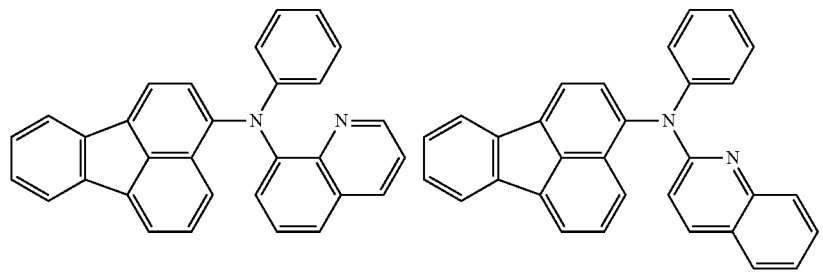

-continued
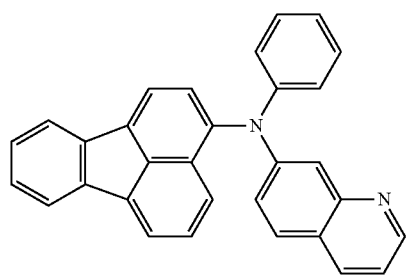 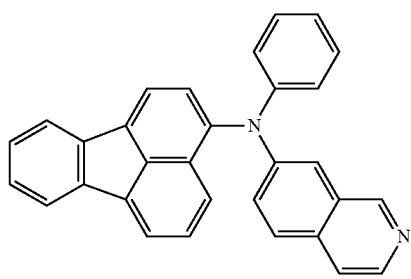
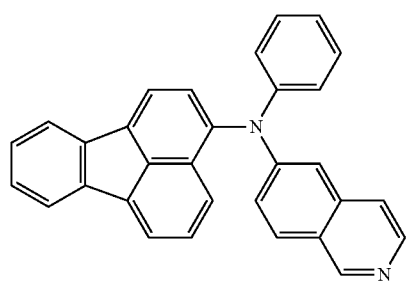 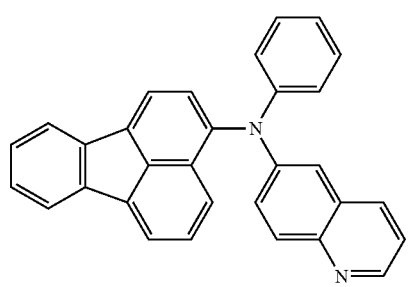
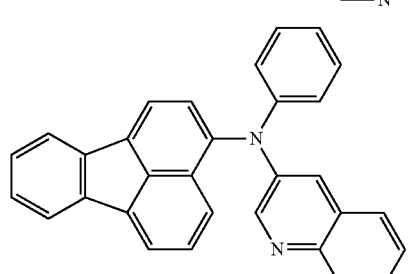 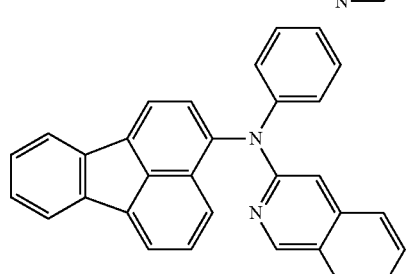 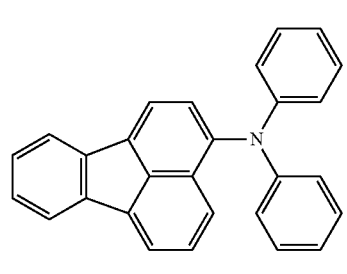
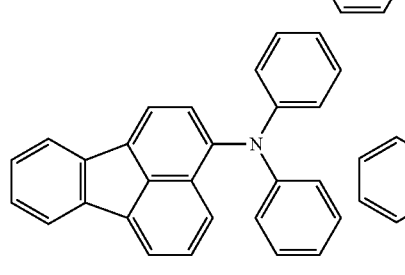 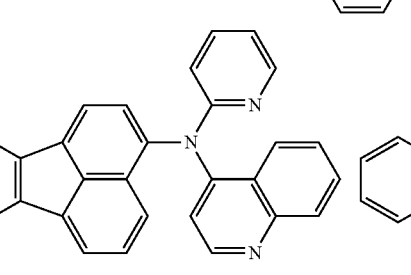 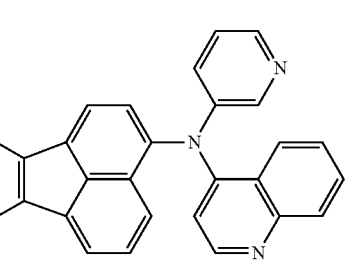
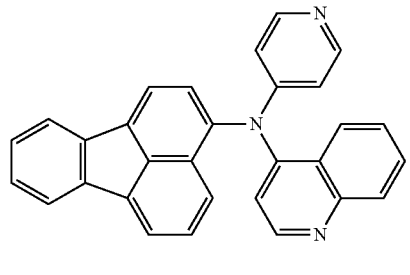 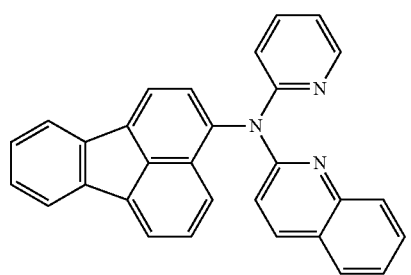
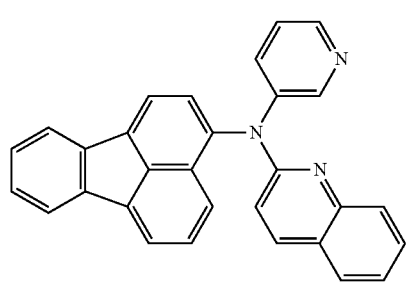 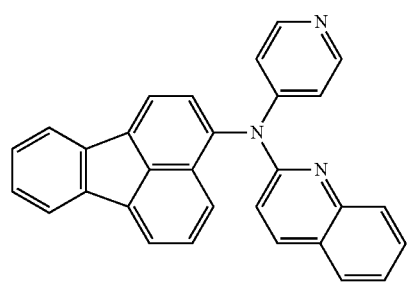

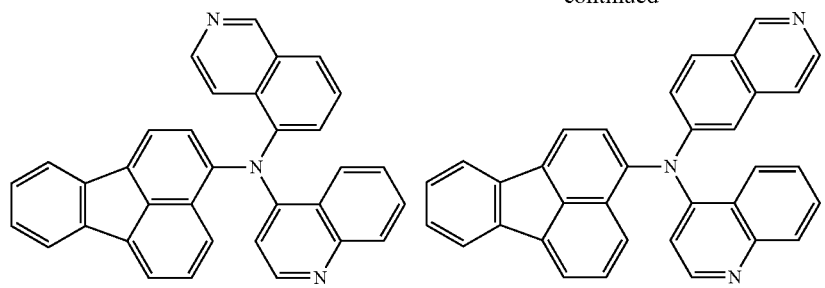
[Chemical Formula 19]
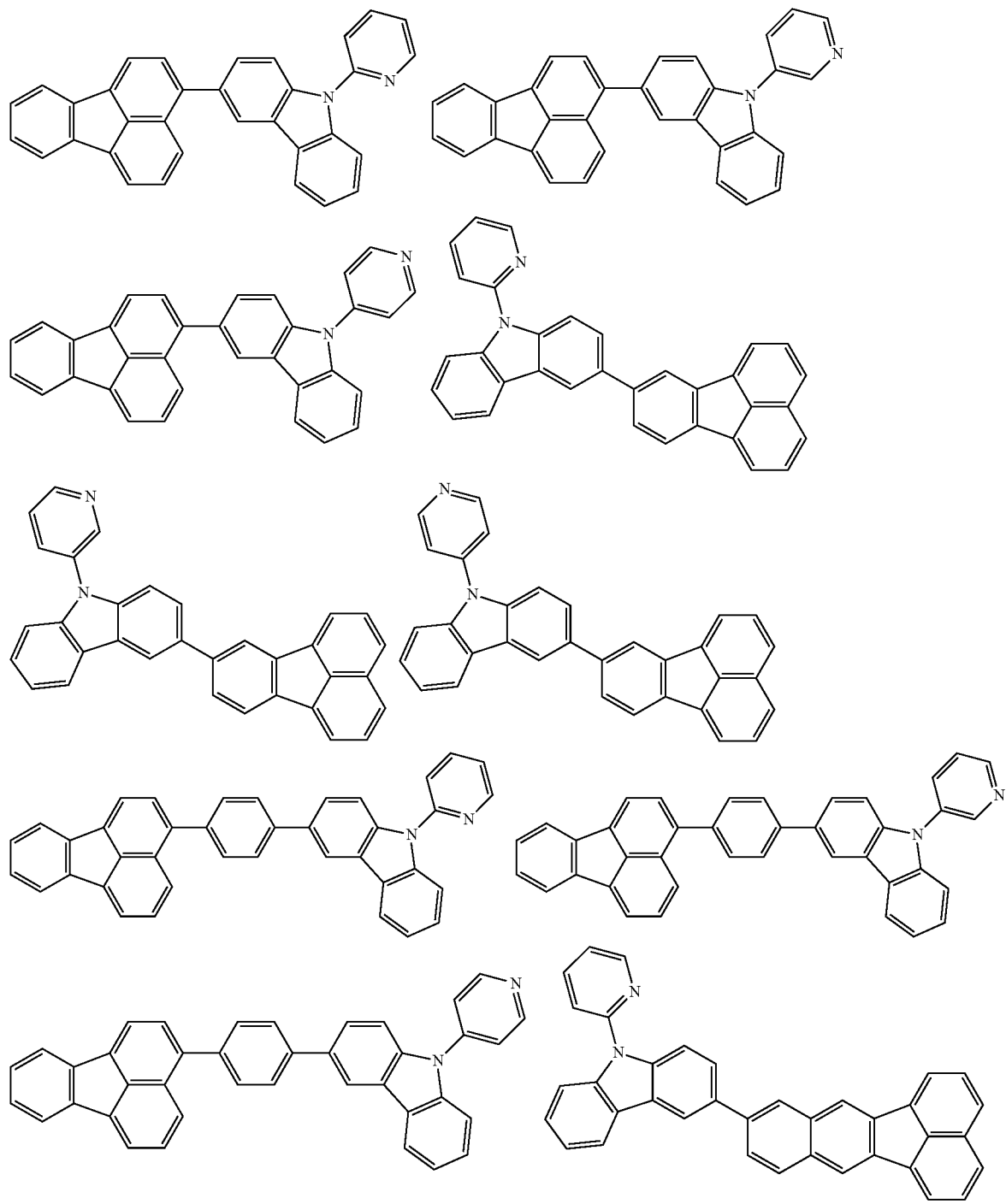

-continued
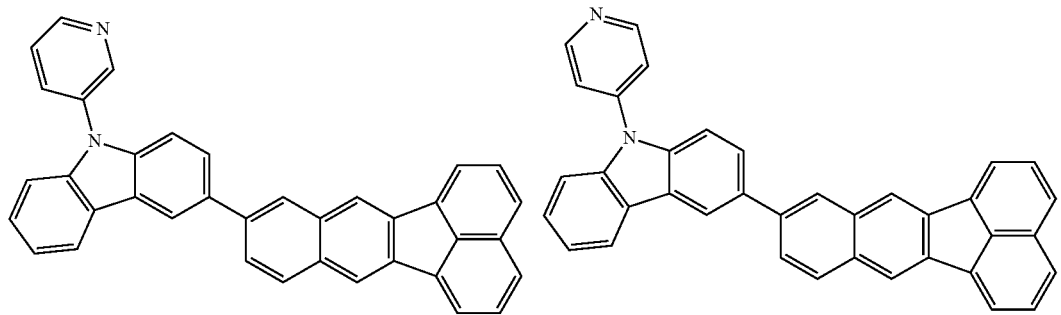
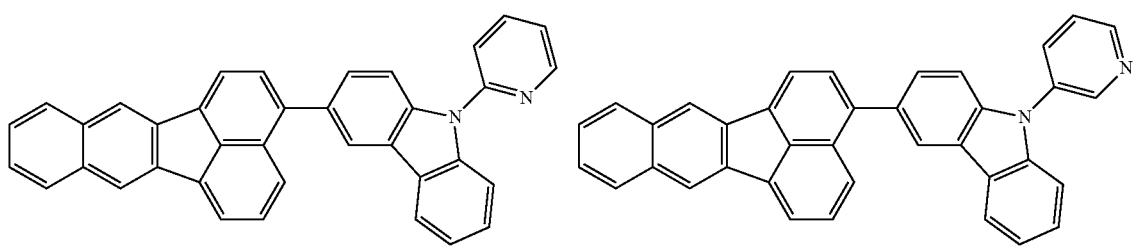
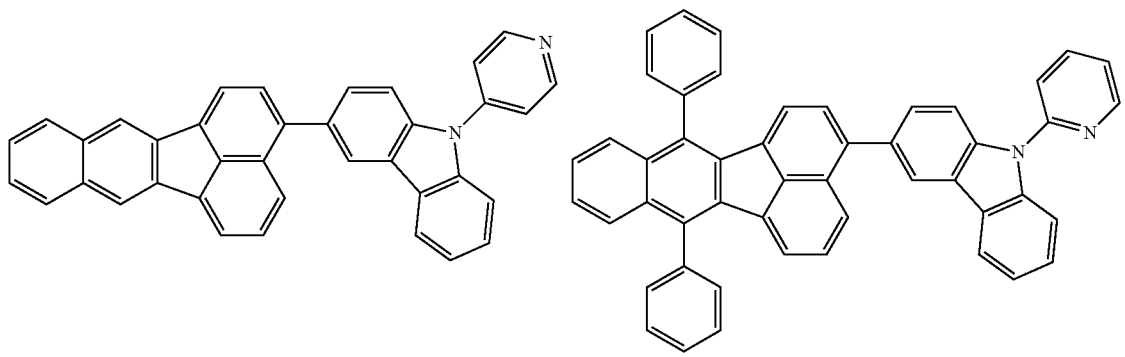
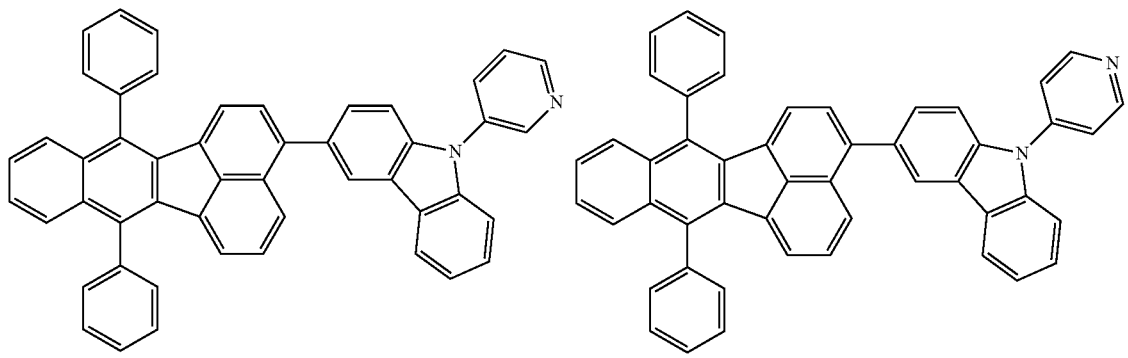
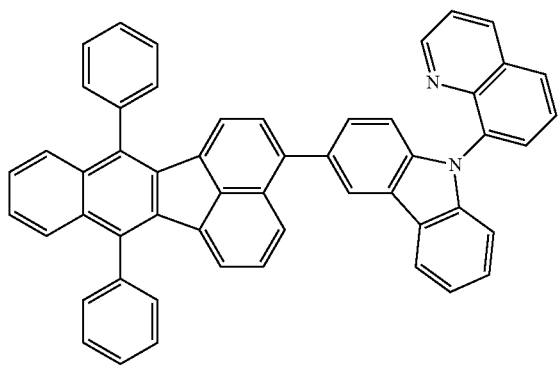

-continued
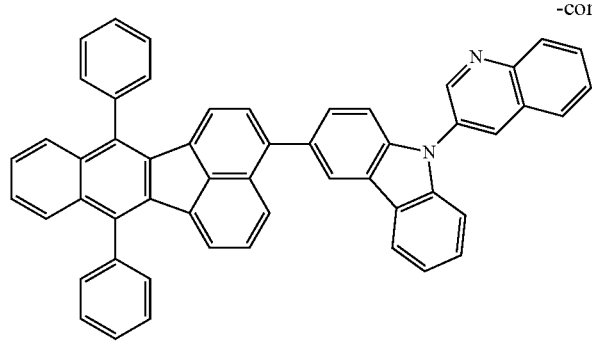
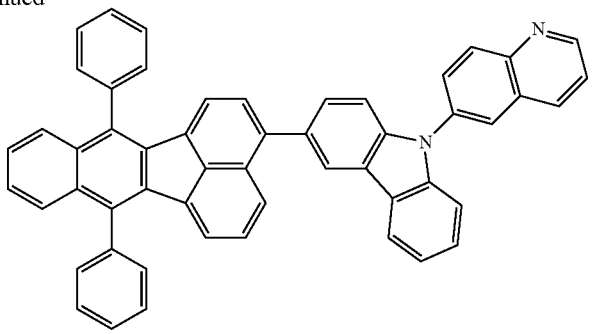
[Chemical Formula 20]
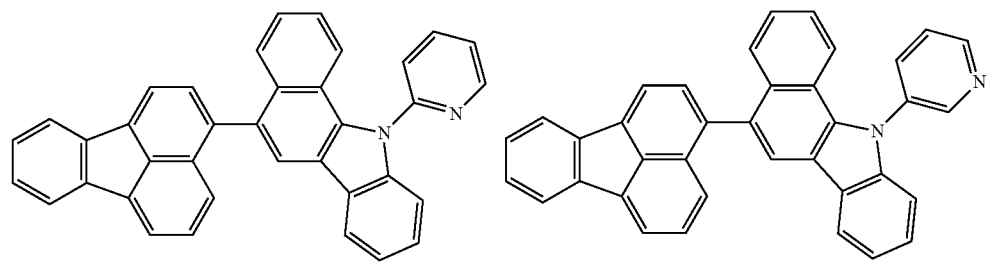
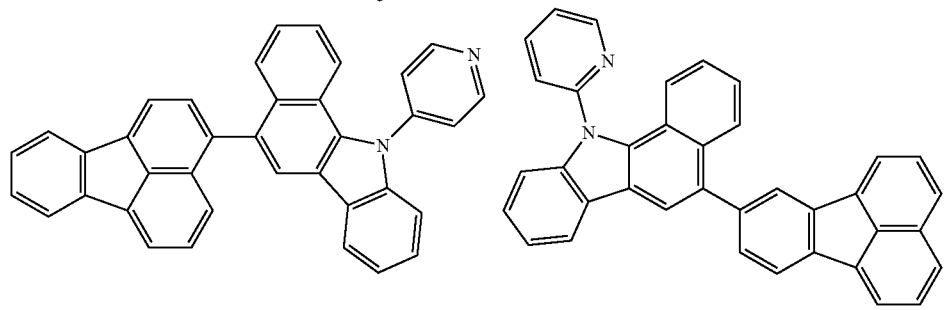
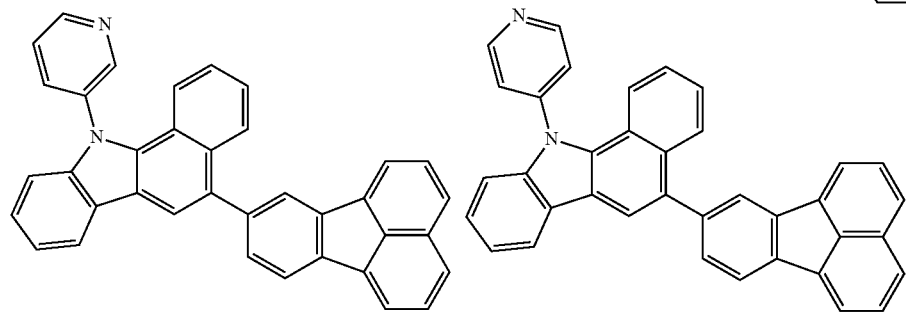
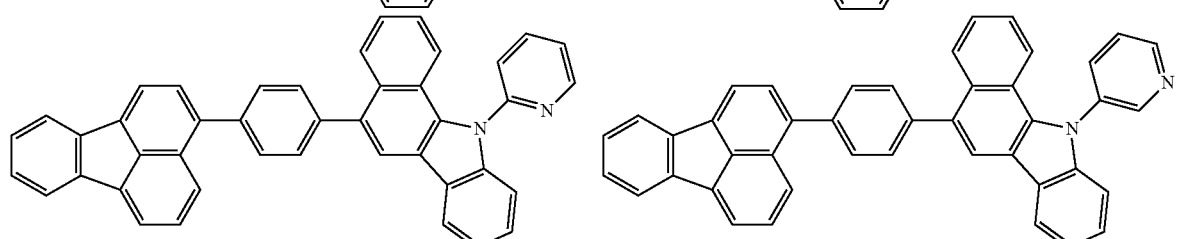
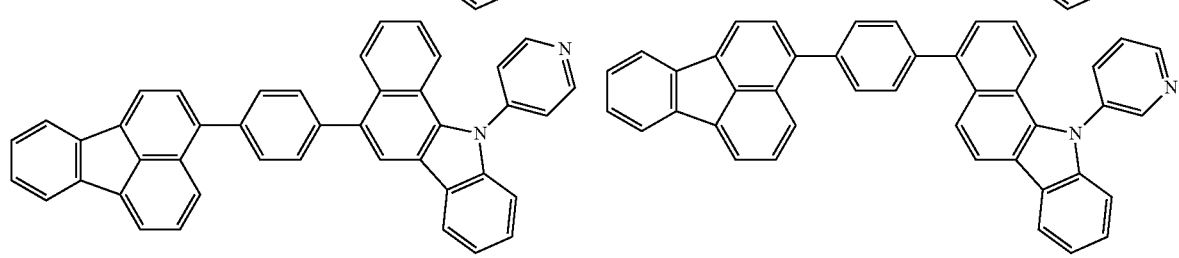

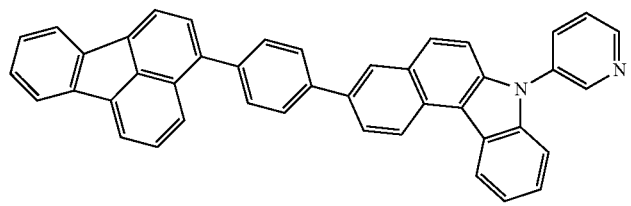
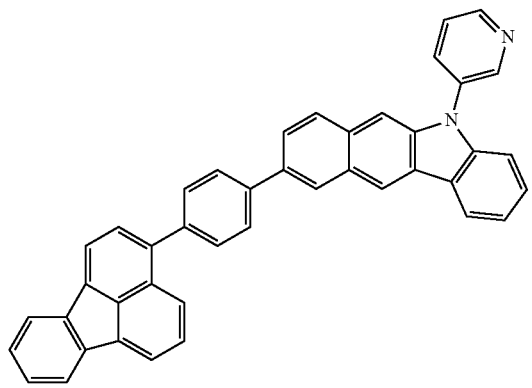
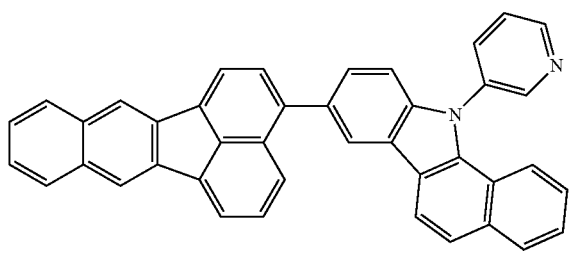
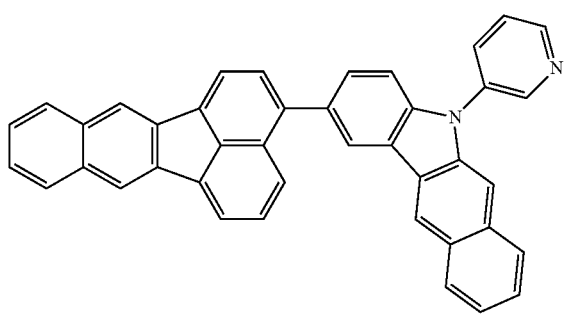
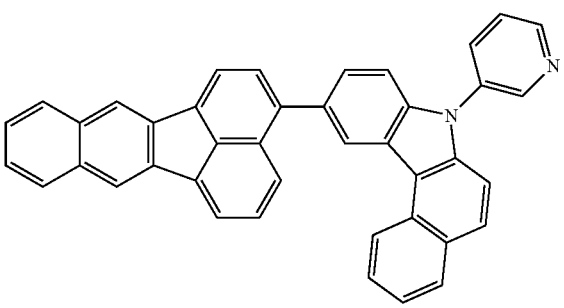
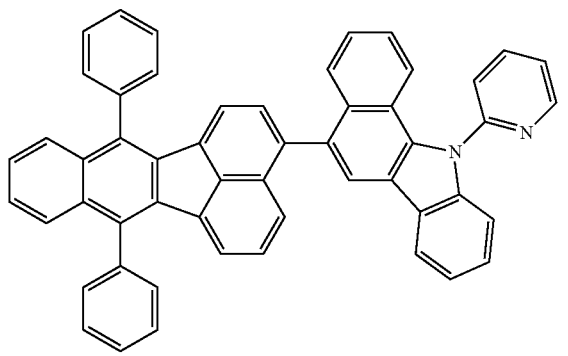
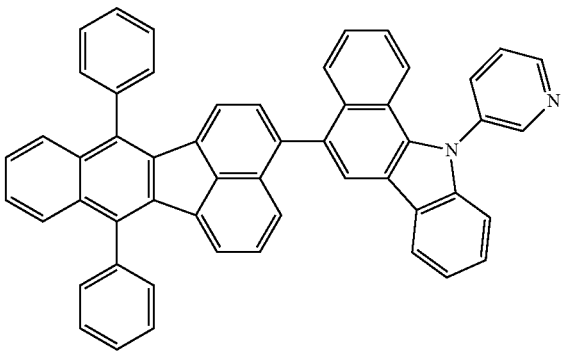
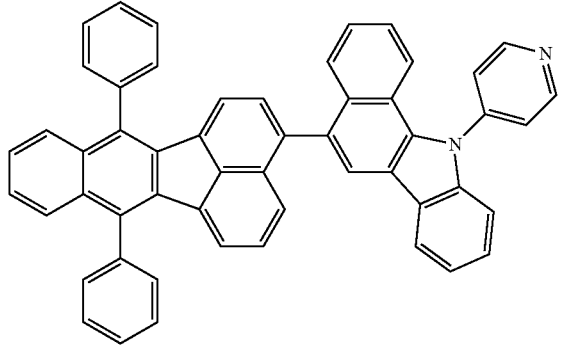
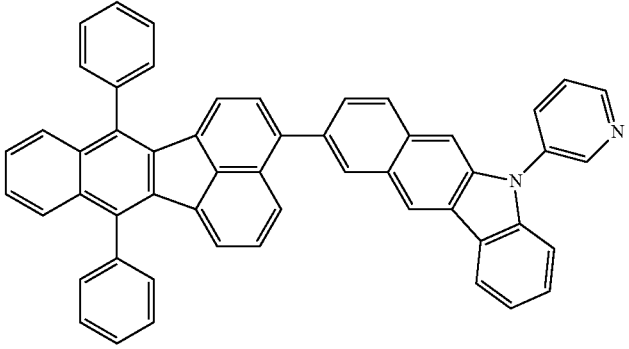

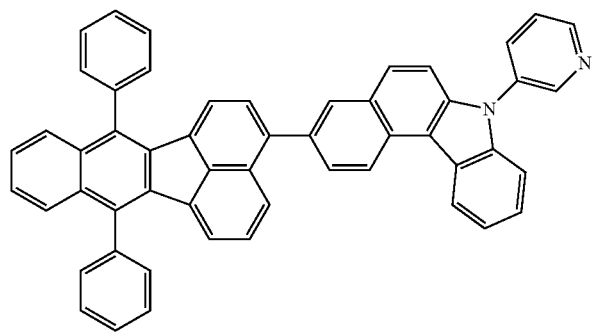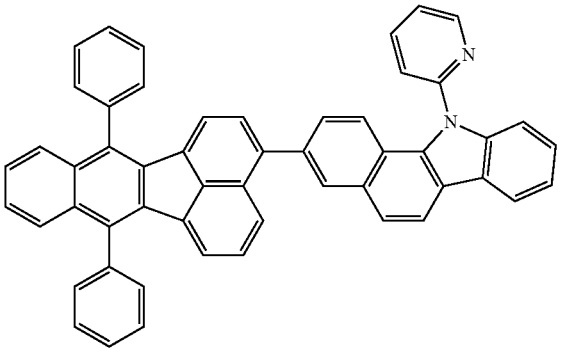
[Chemical Formula 21]
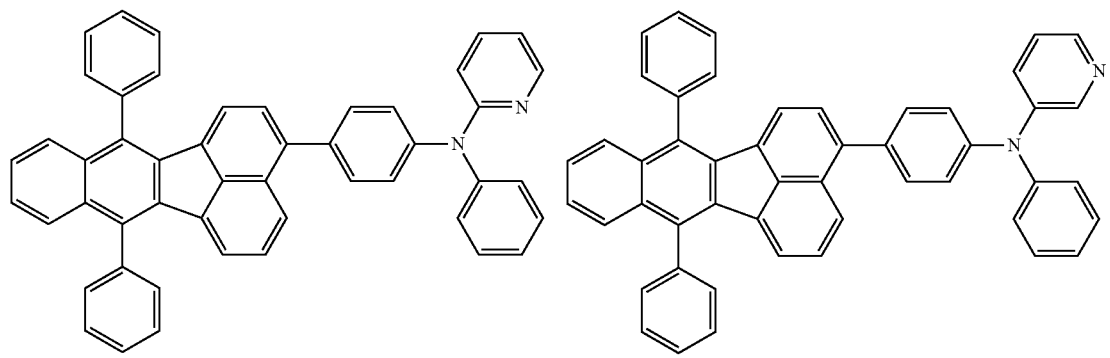
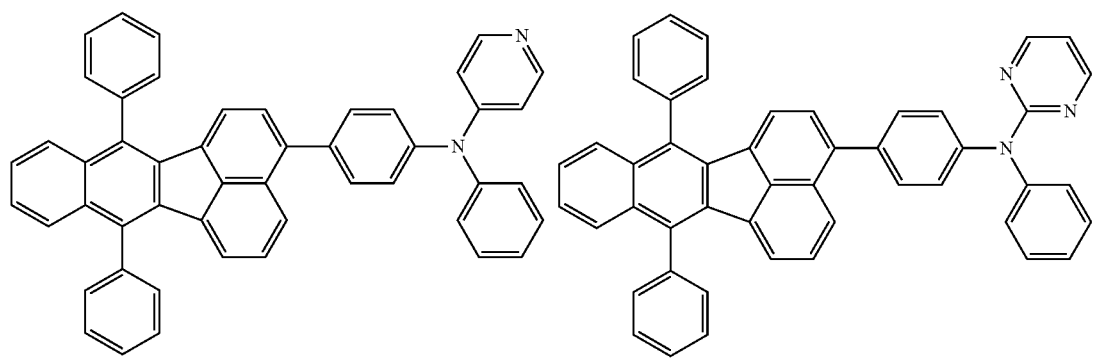
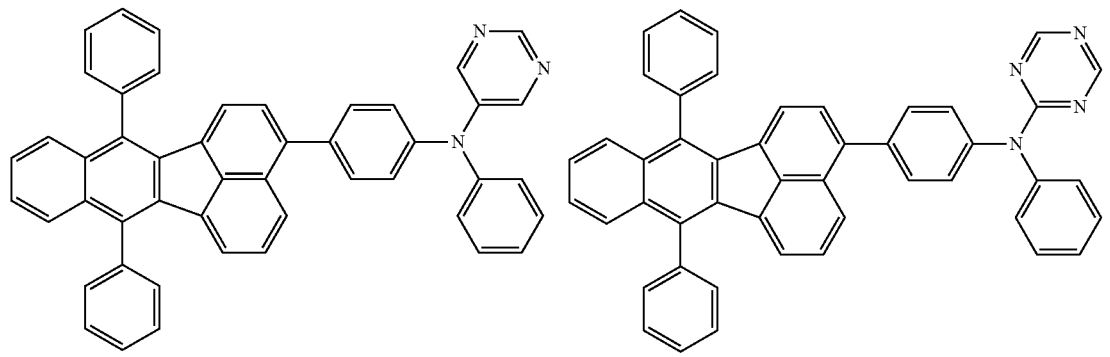

-continued
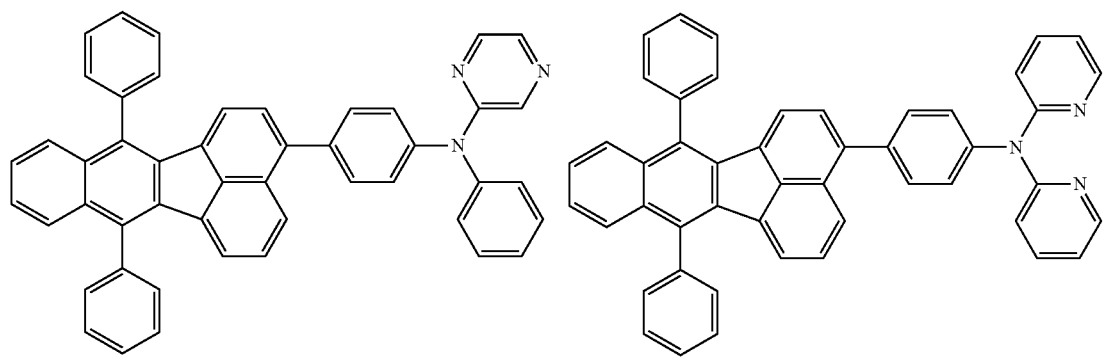
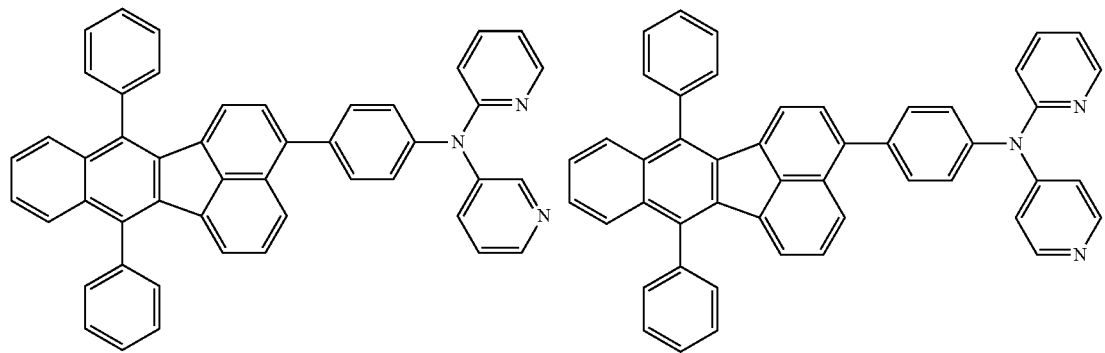
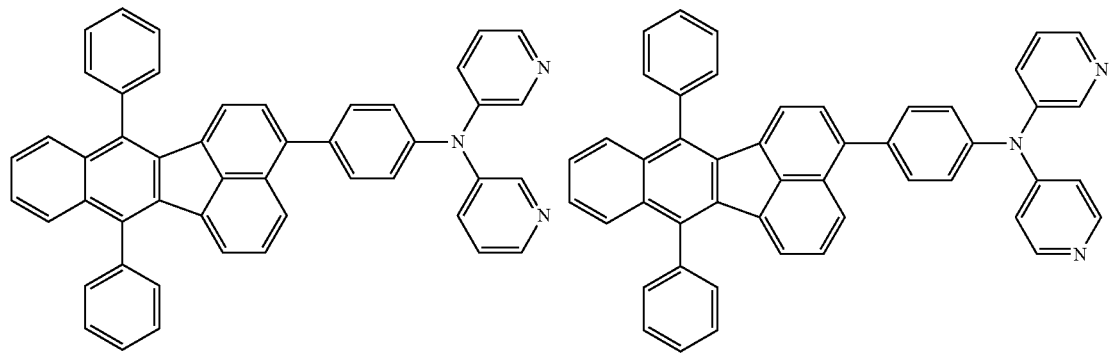
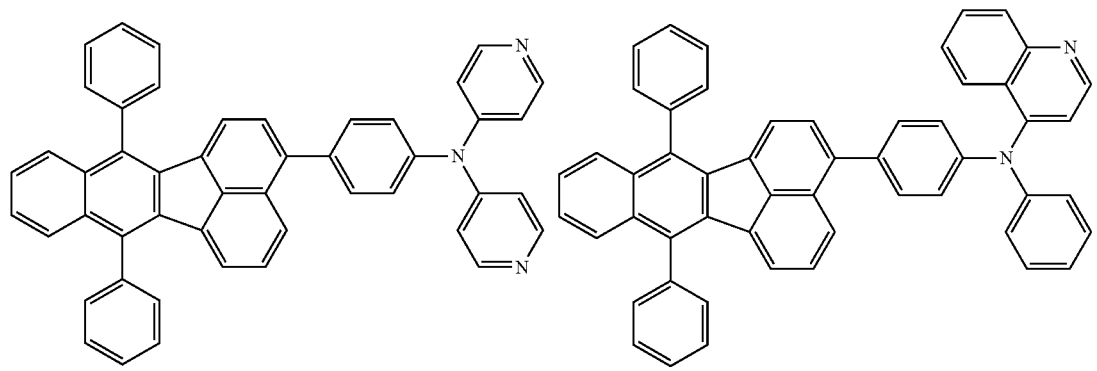

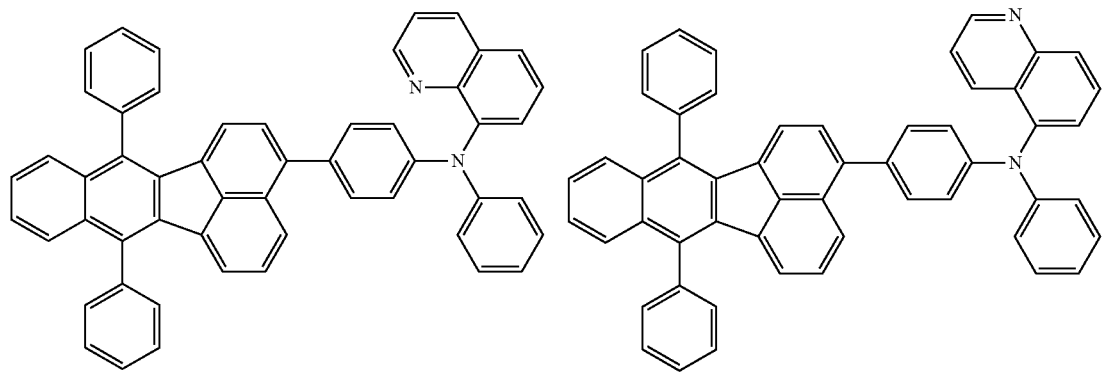
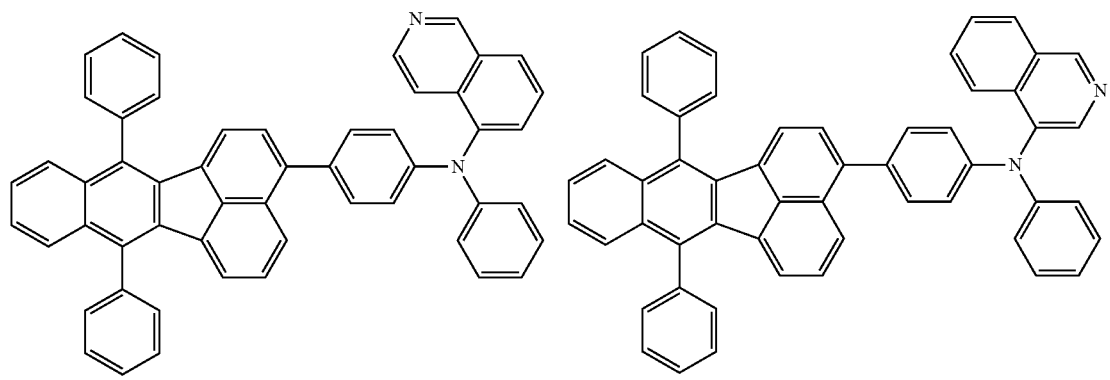
[Chemical Formula 22]
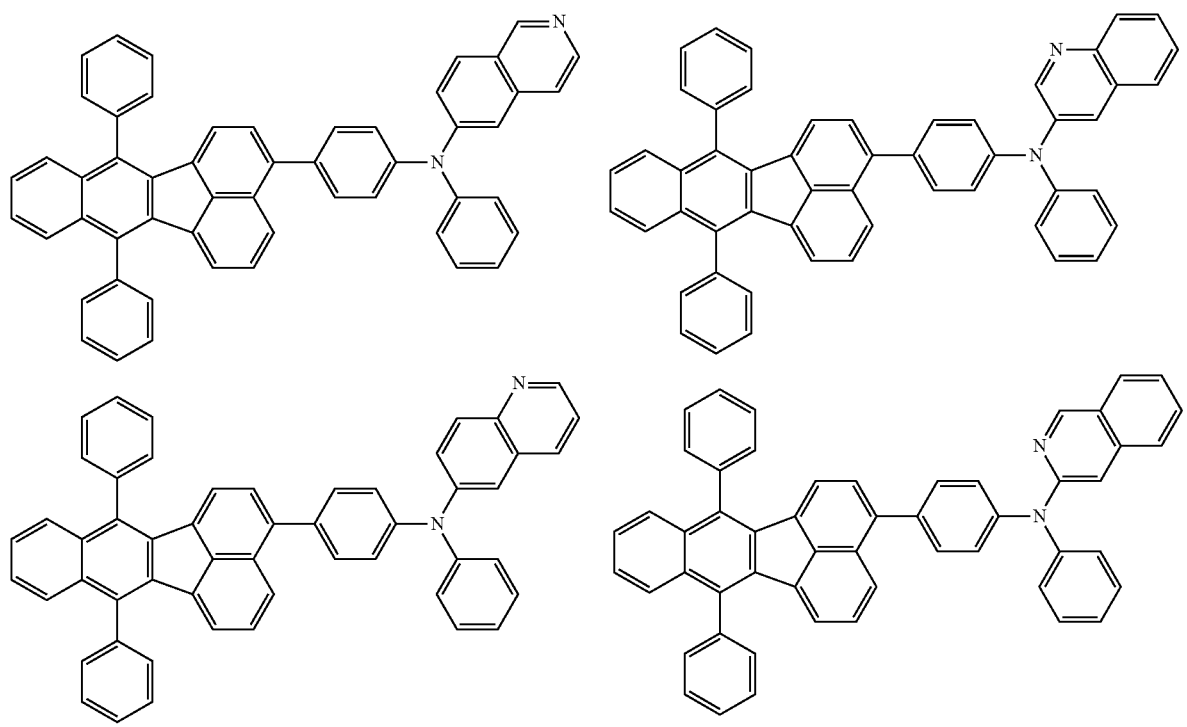

-continued
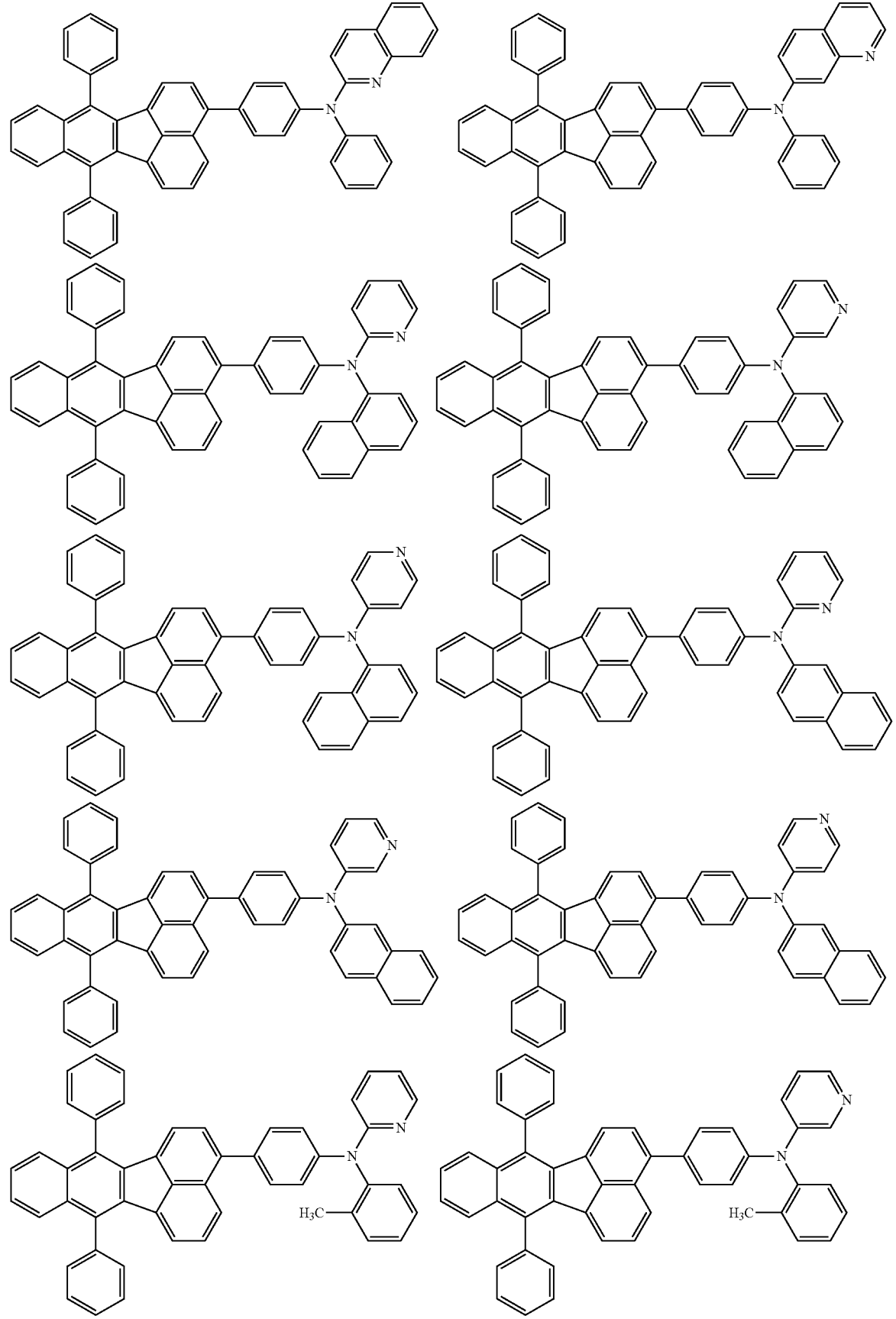

-continued
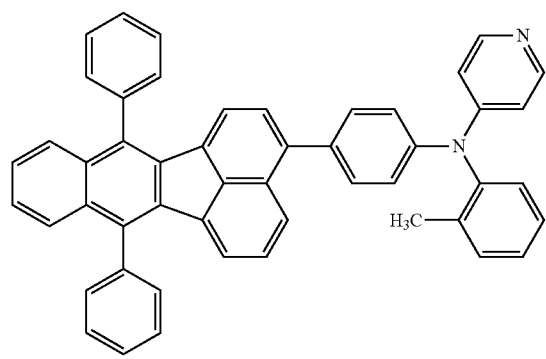
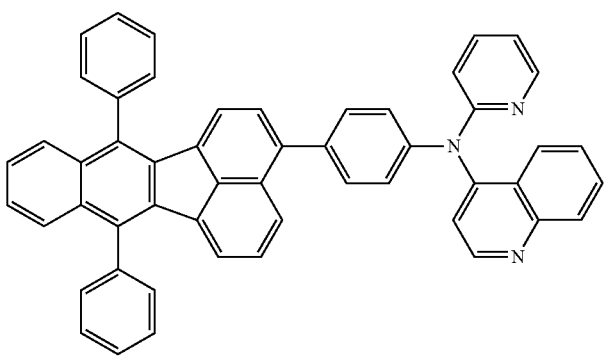
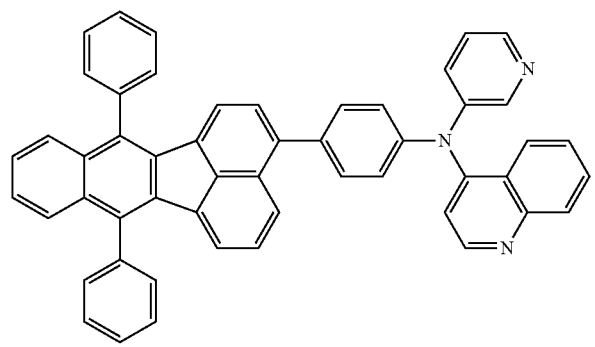
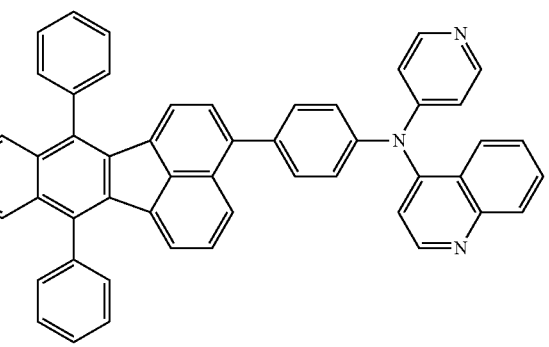
[Chemical Formula 23]
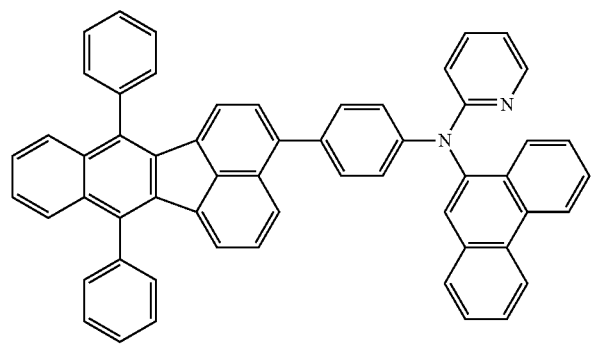
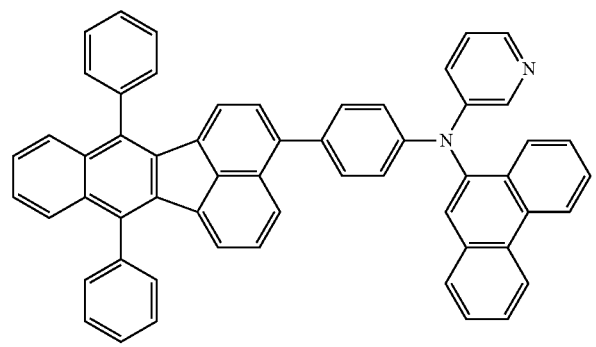
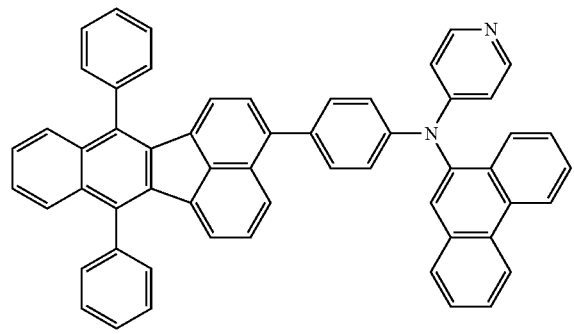
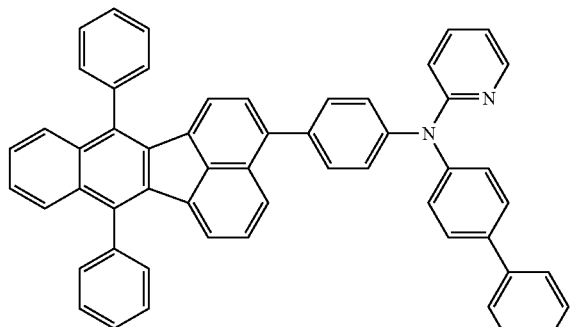

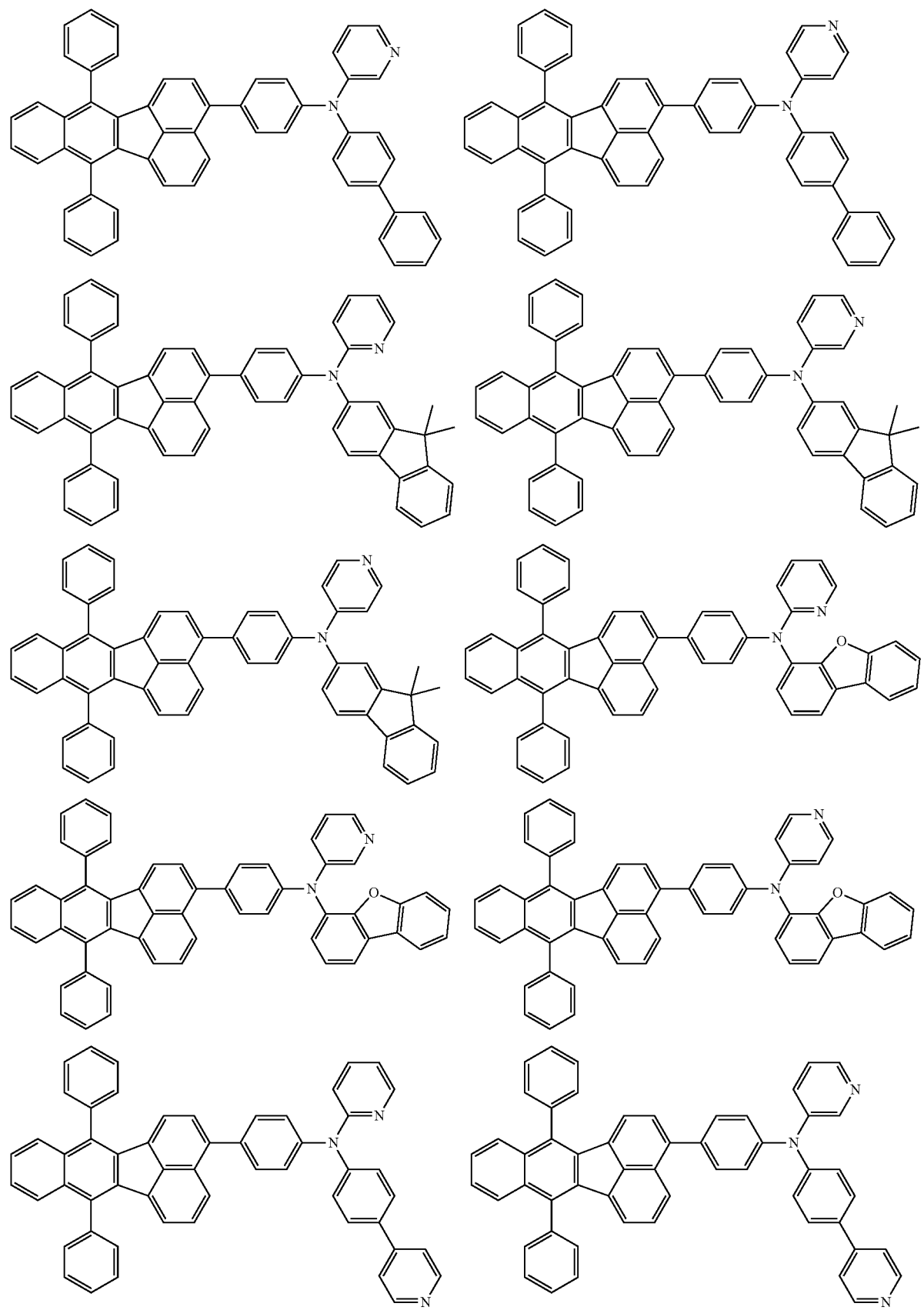

-continued
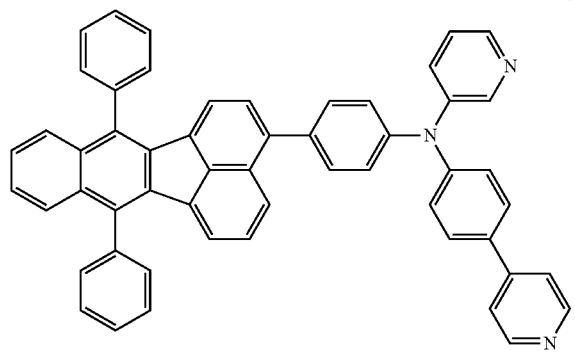
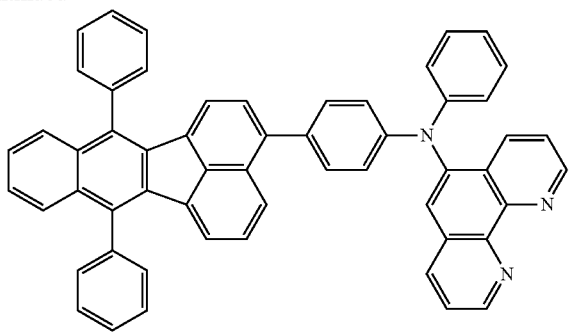
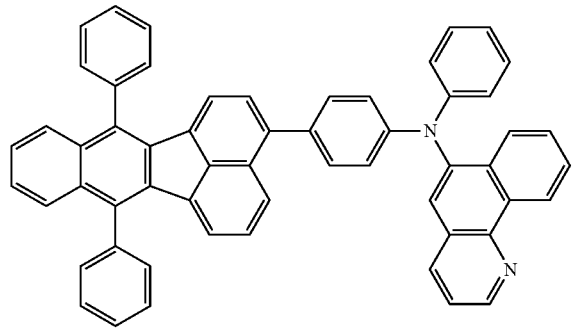
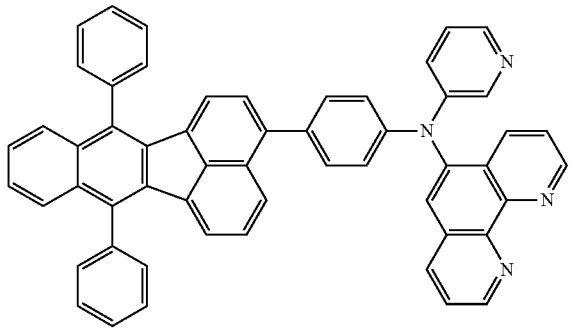
[Chemical Formula 24]
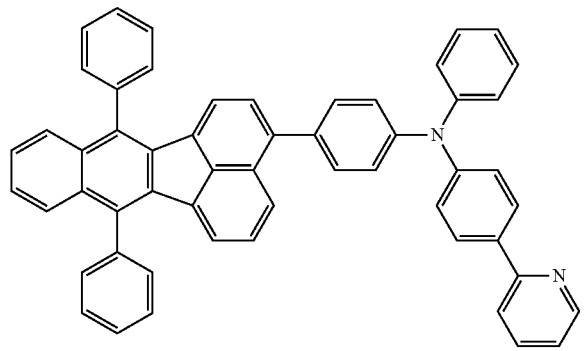
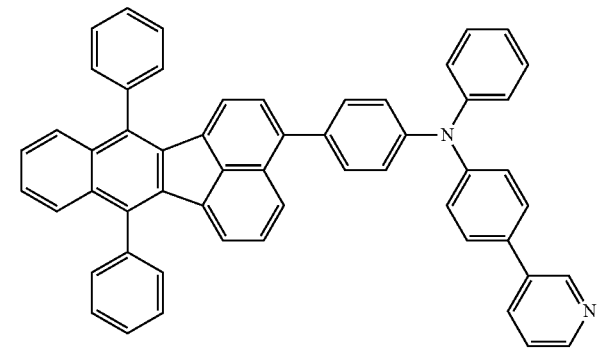
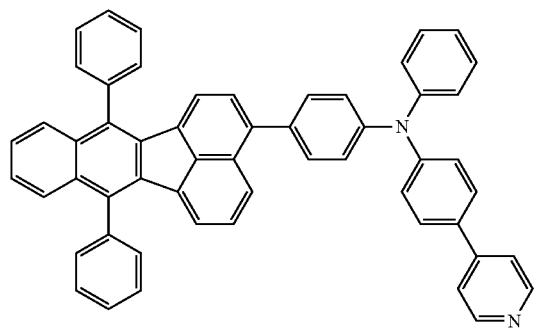
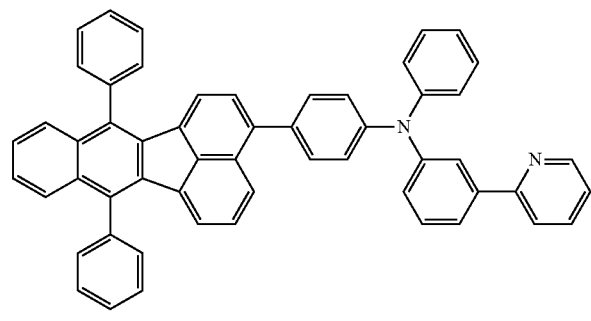
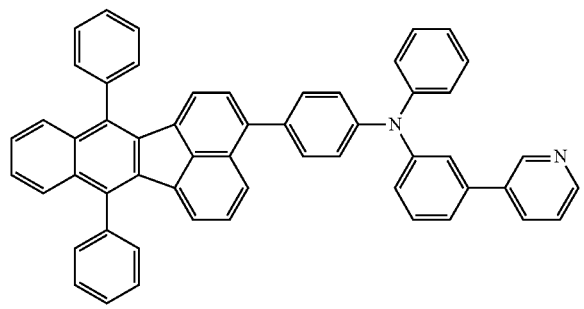
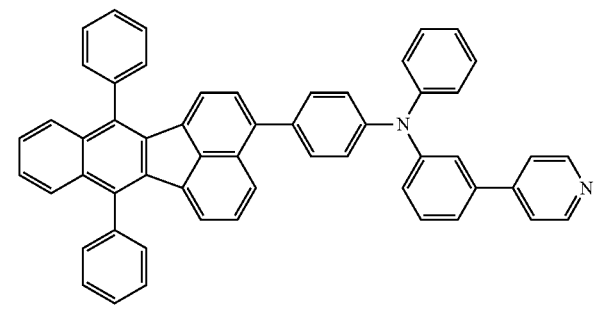

-continued
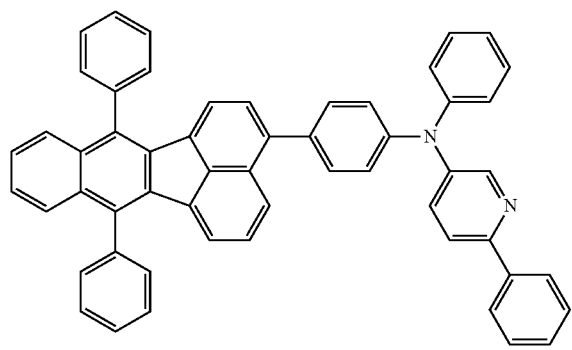
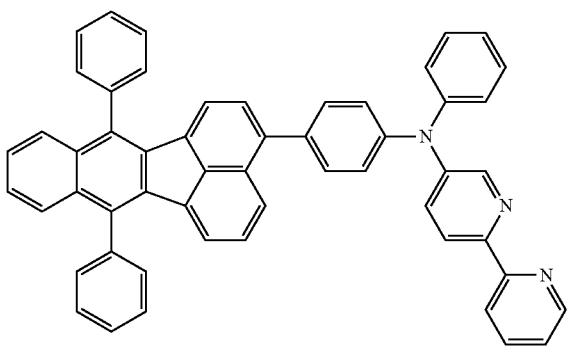
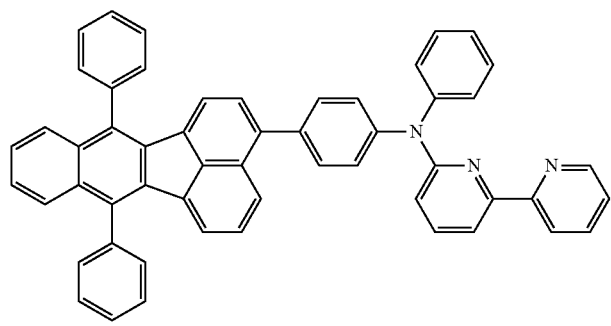
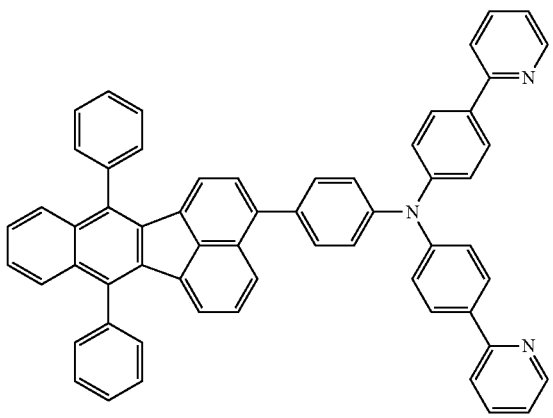
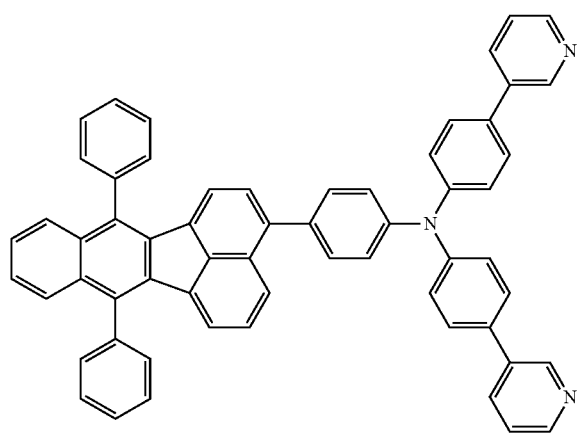
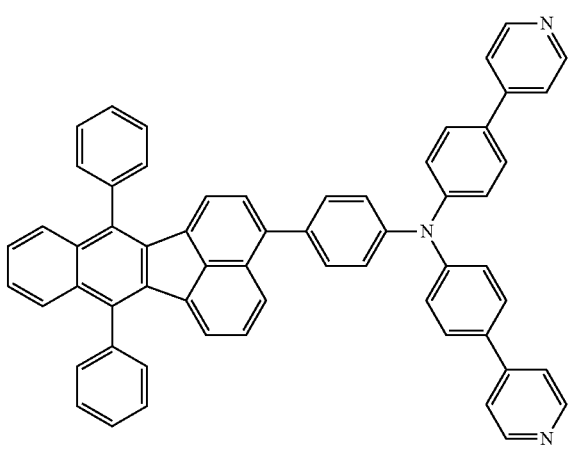
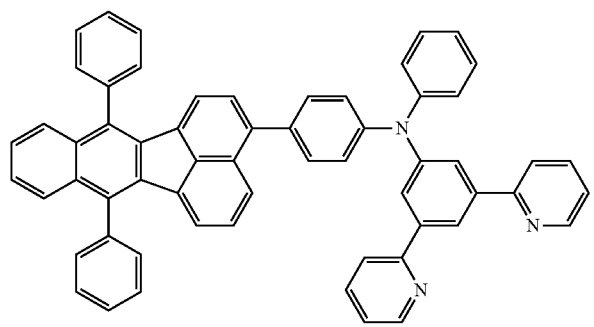
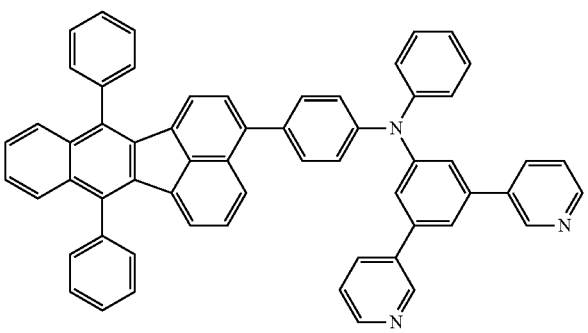

-continued
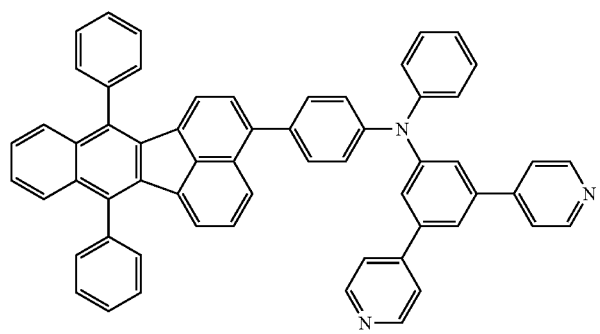
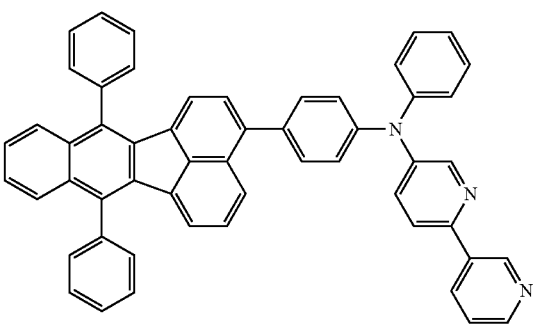
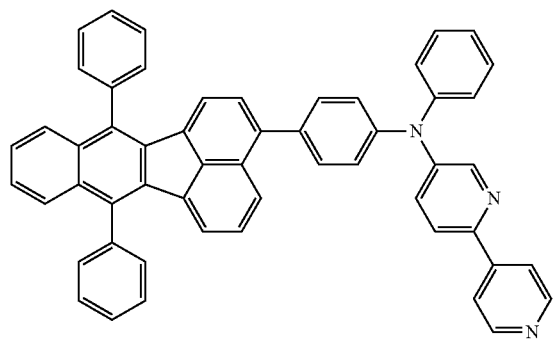
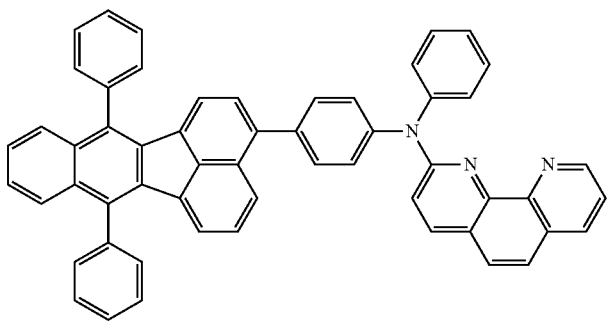
[Chemical Formula 25]
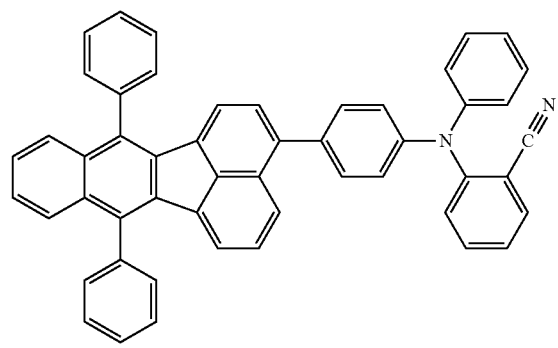
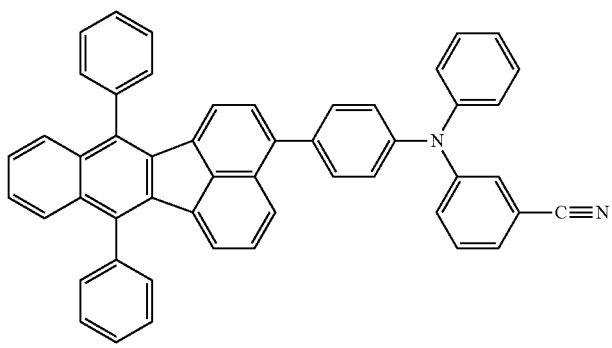
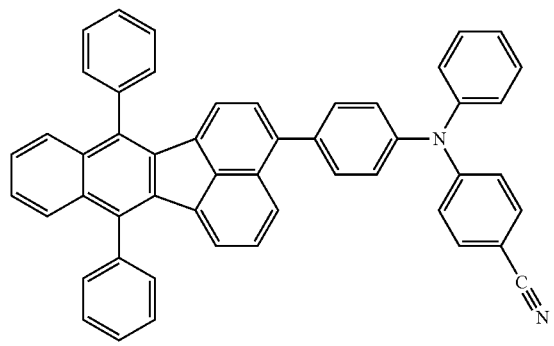
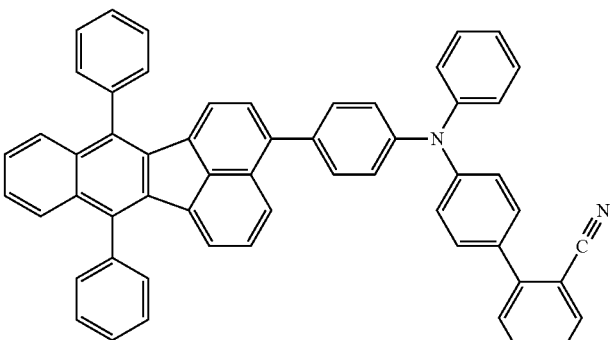

-continued
| 75 | 76 |
|---|---|
| 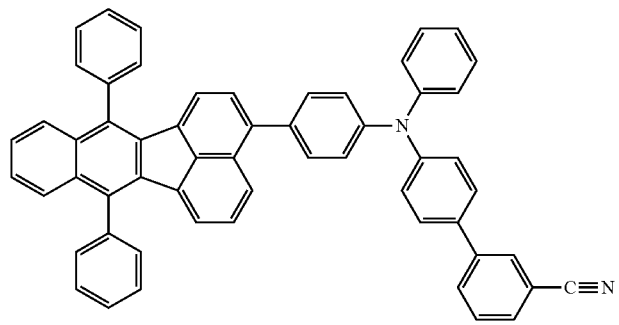 | 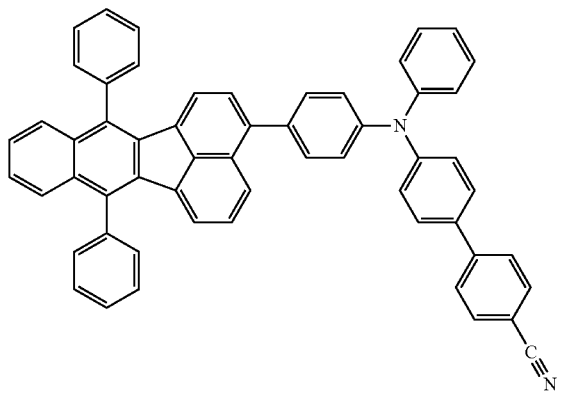 |
| 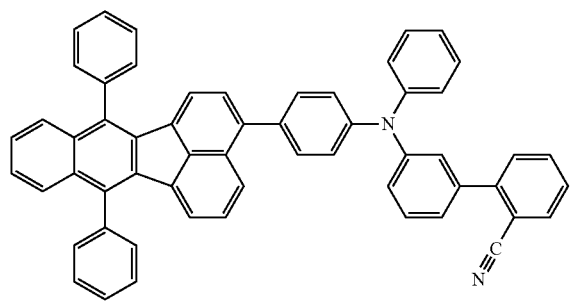 | 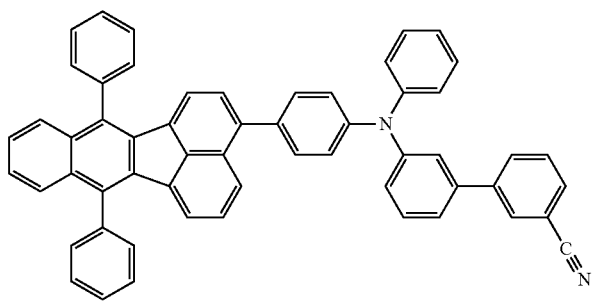 |
| 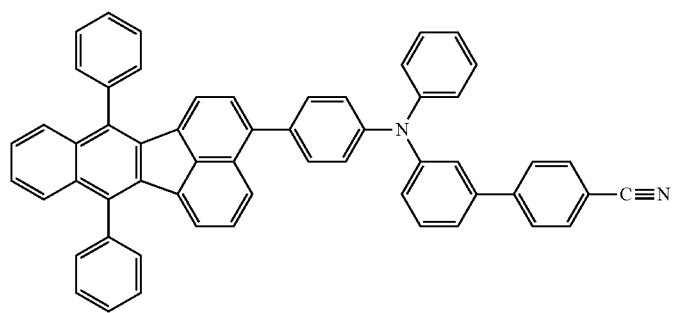 | 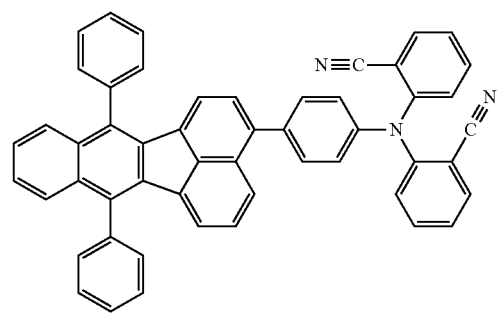 |
| 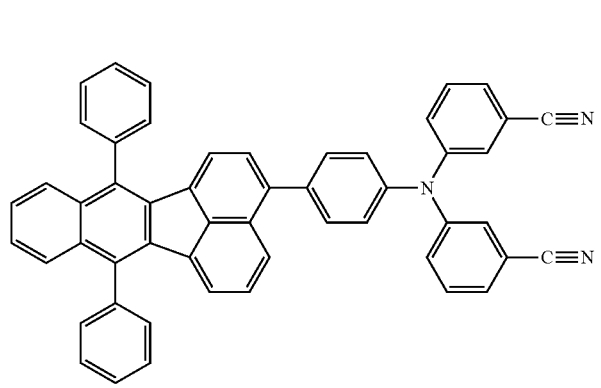 | 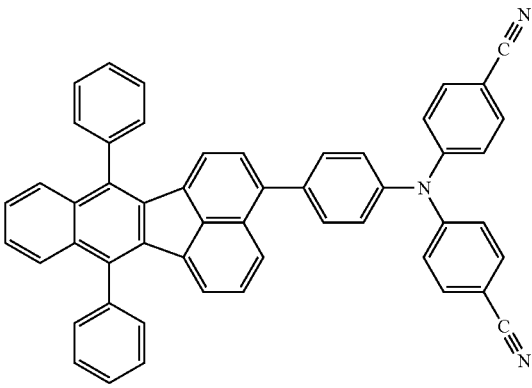 |

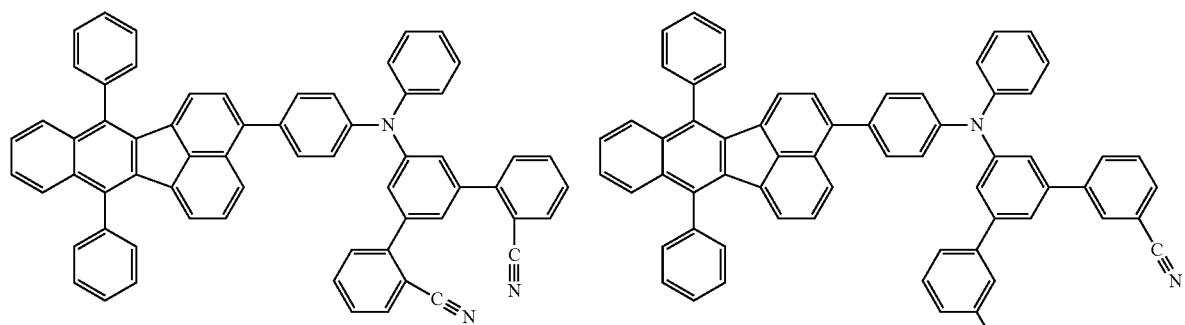
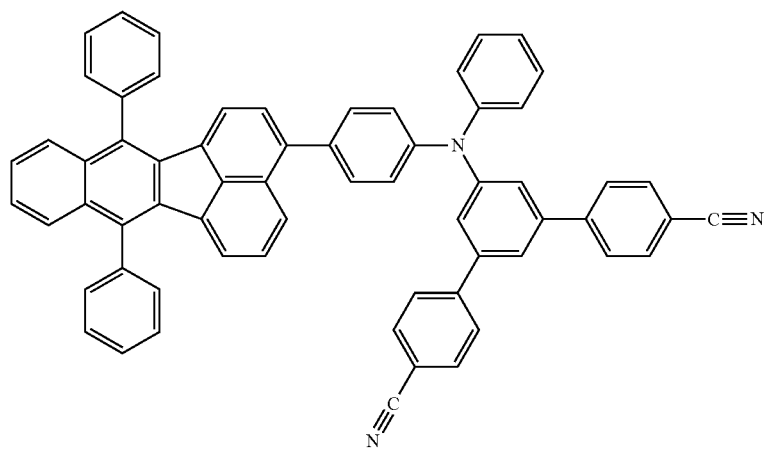
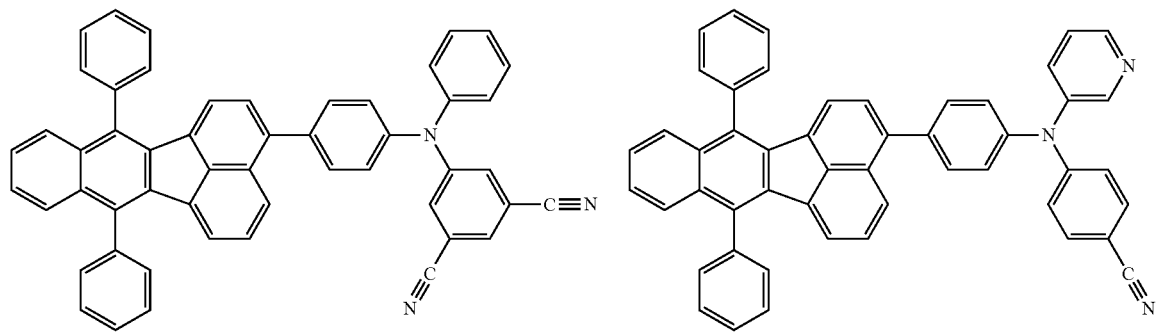
[Chemical Formula 26]
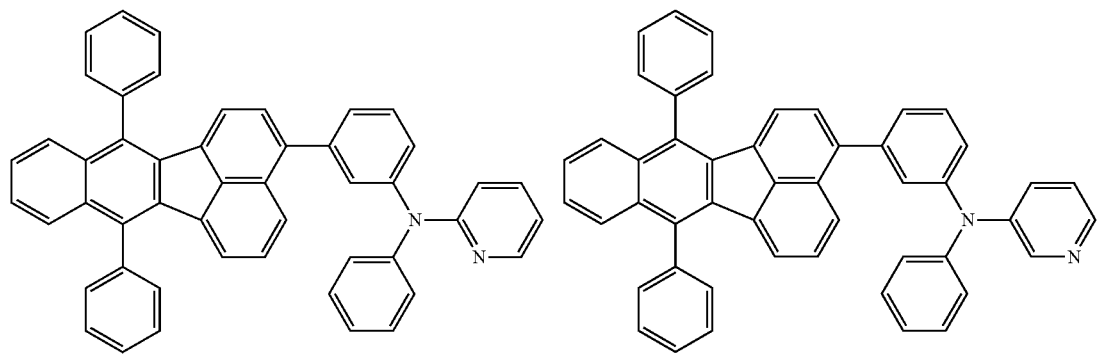

-continued
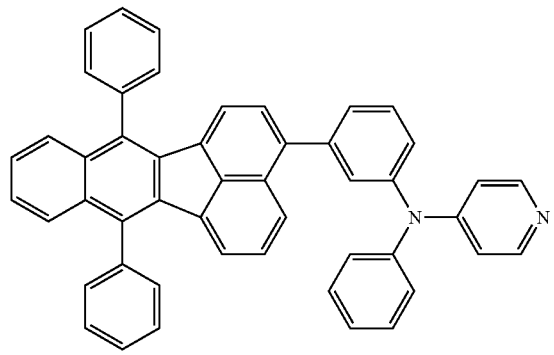
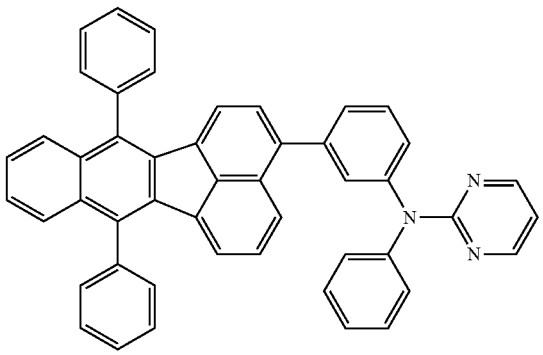
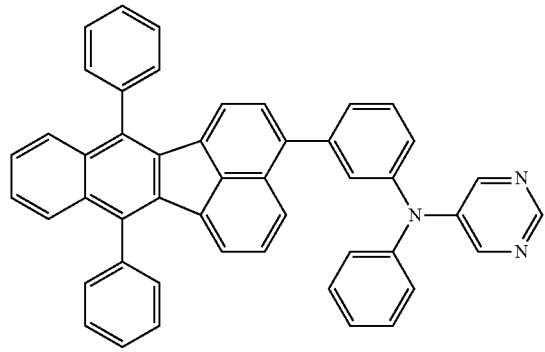
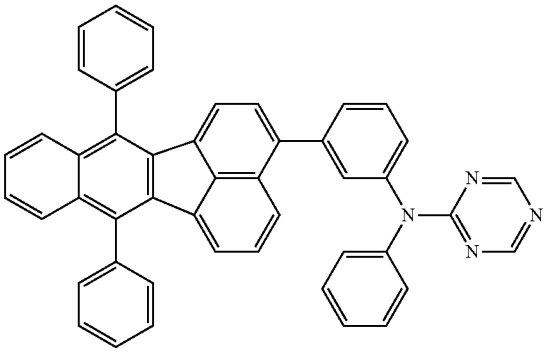
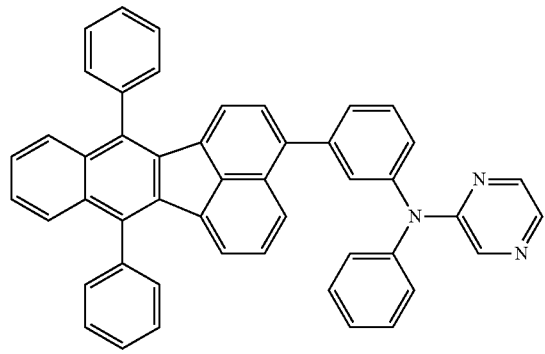
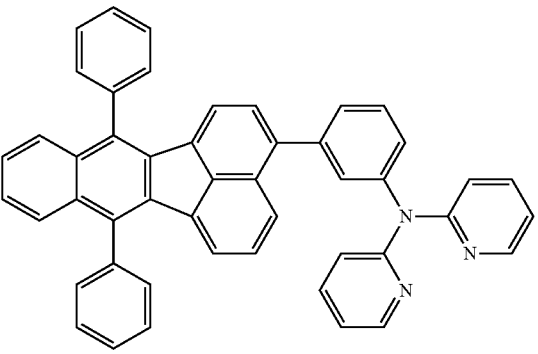
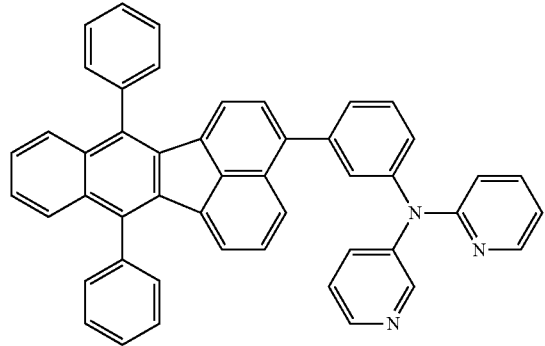
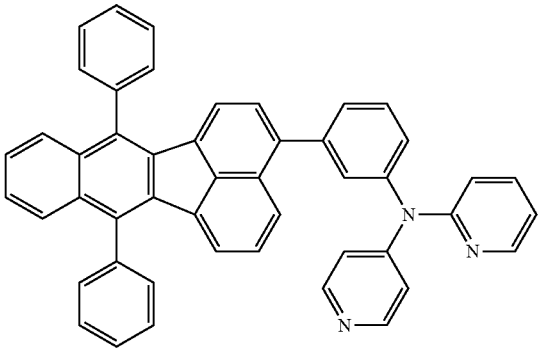

81                                  82
-continued
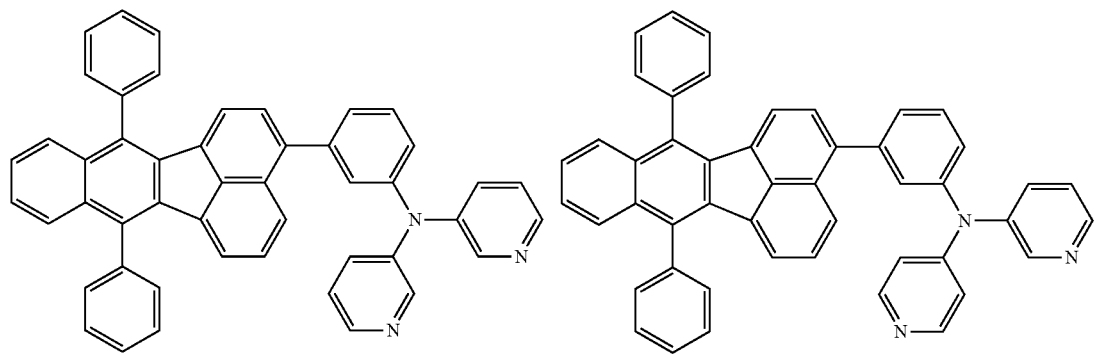
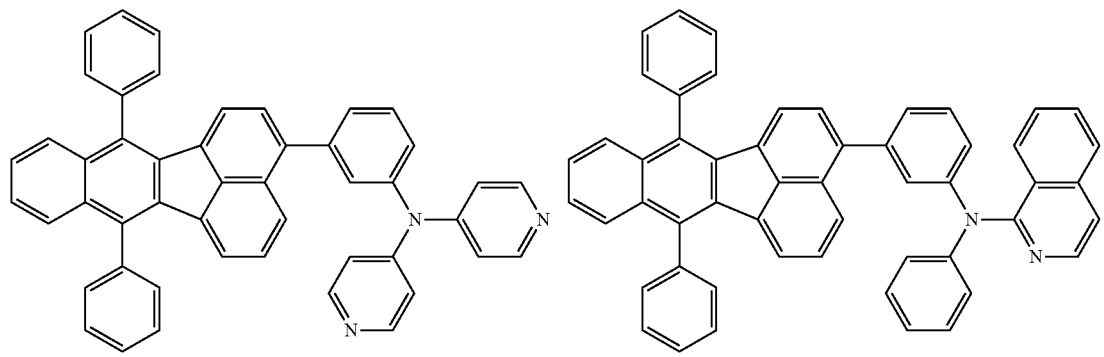
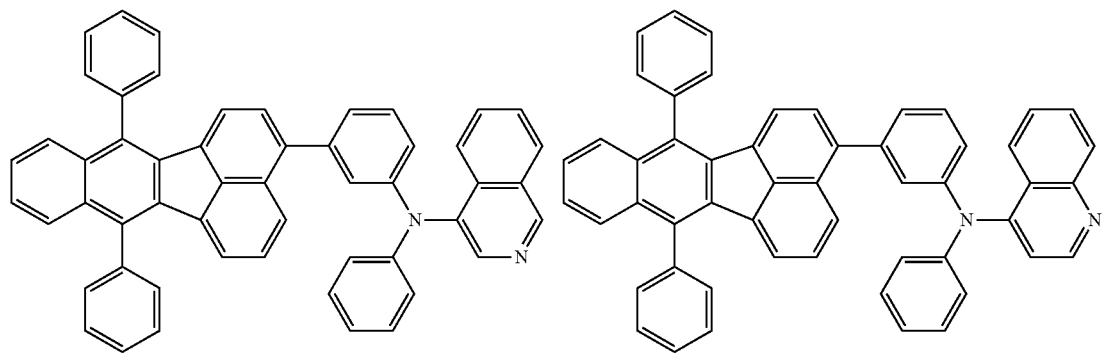
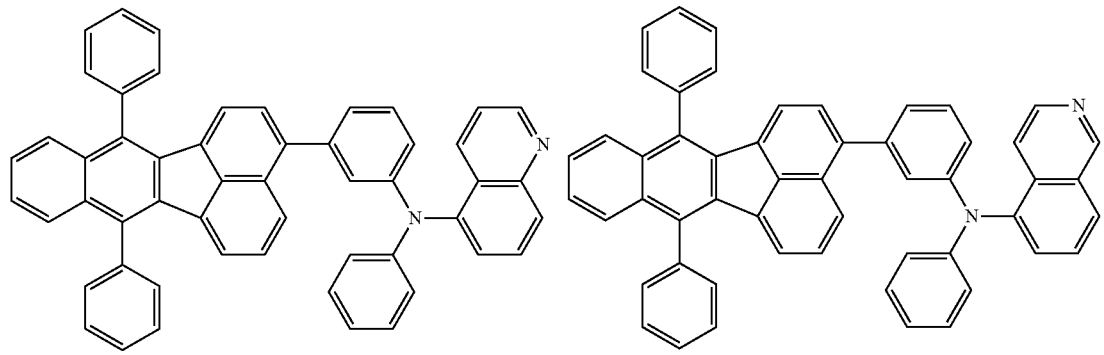

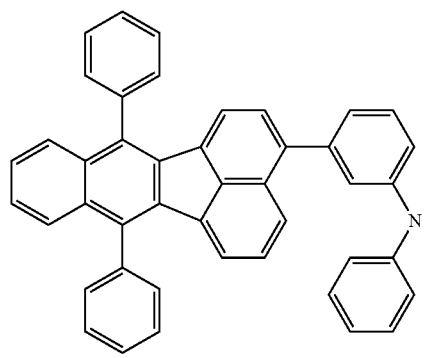
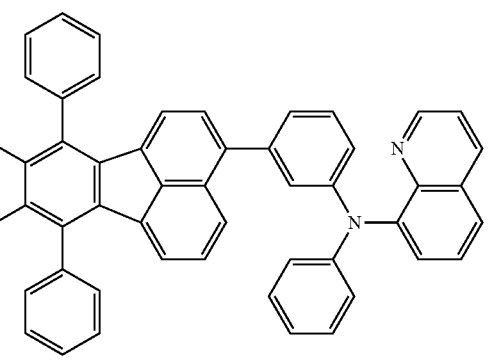
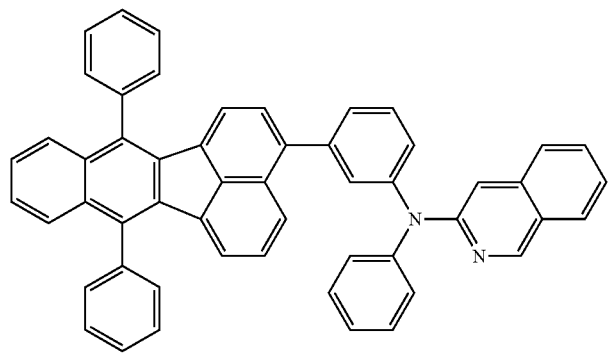
[Chemical Formula 27]
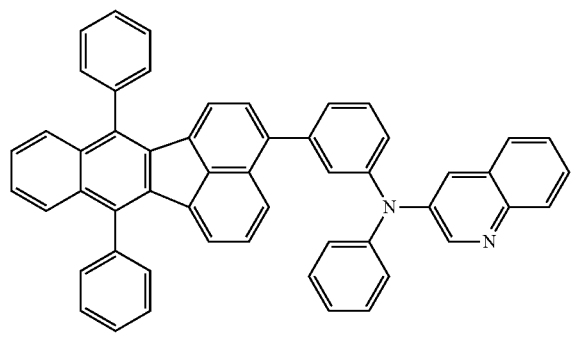
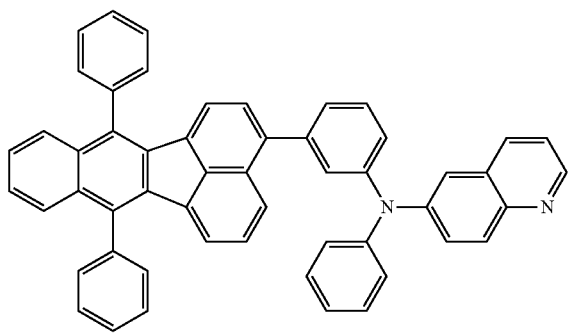
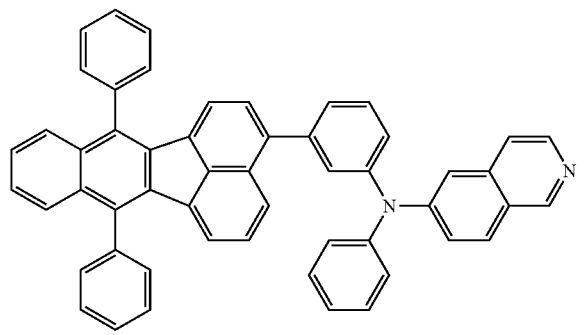
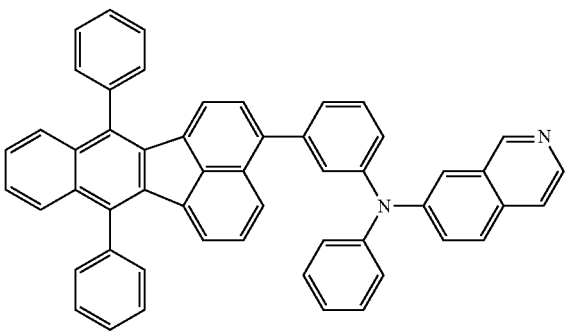

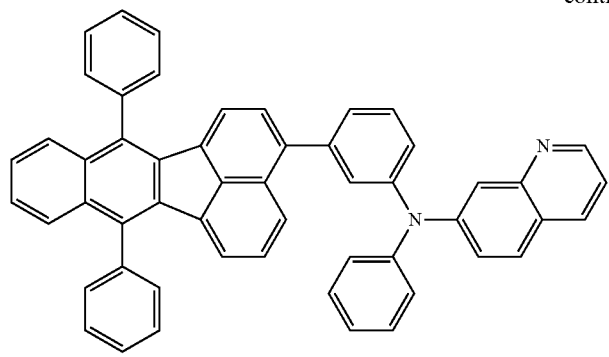
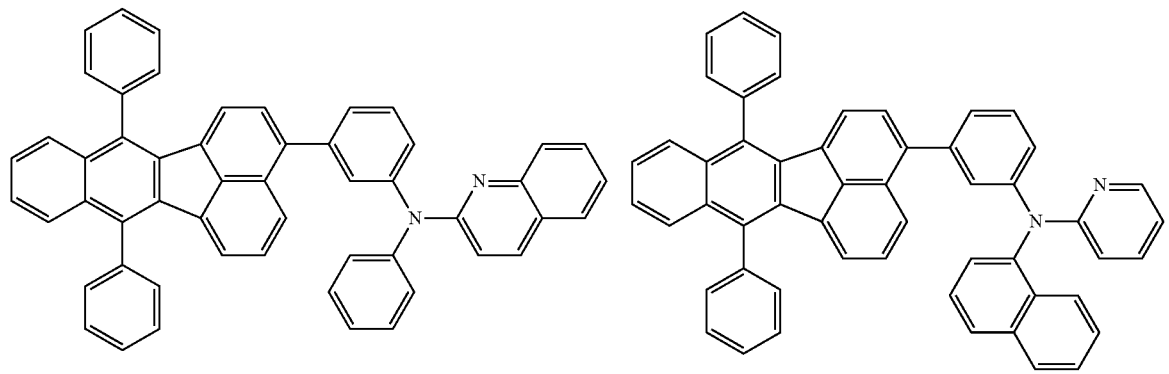
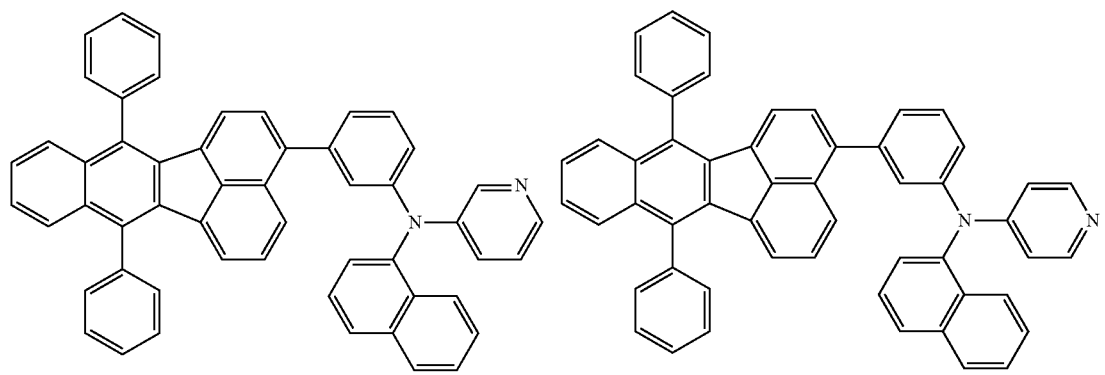
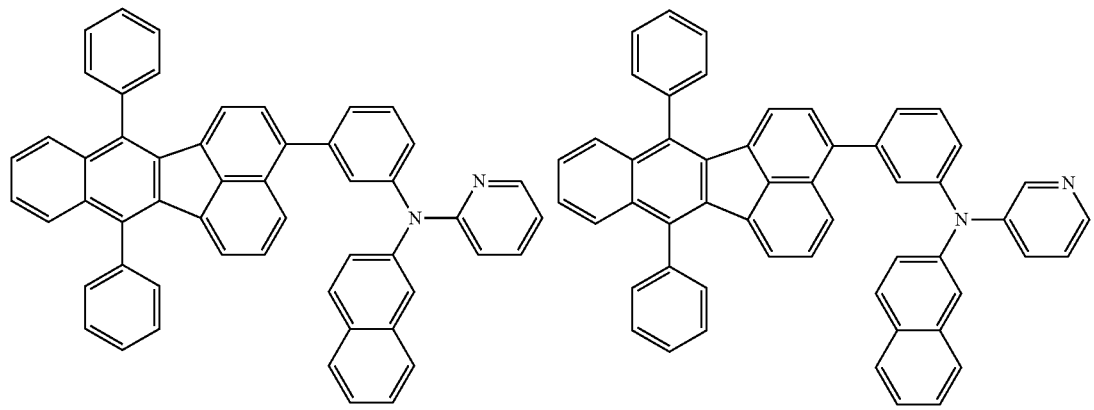

-continued
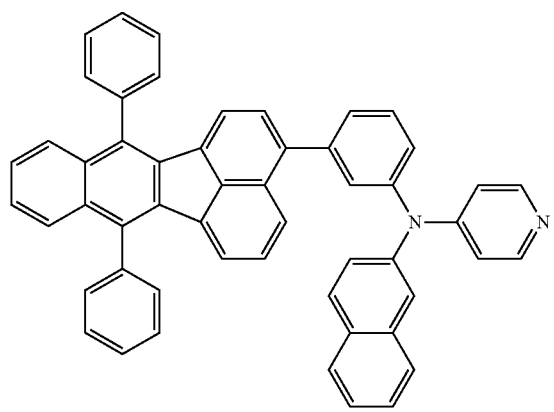
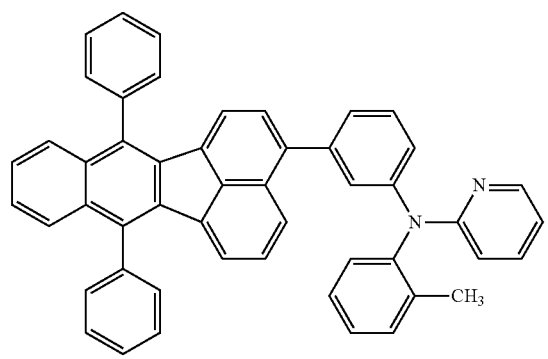
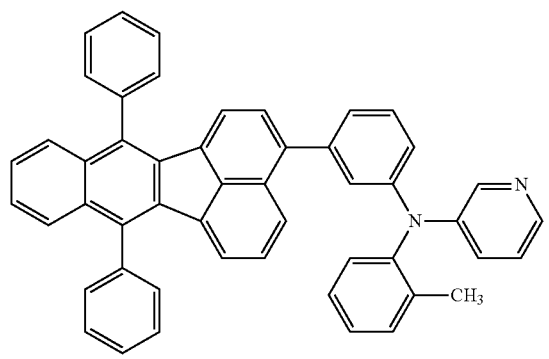
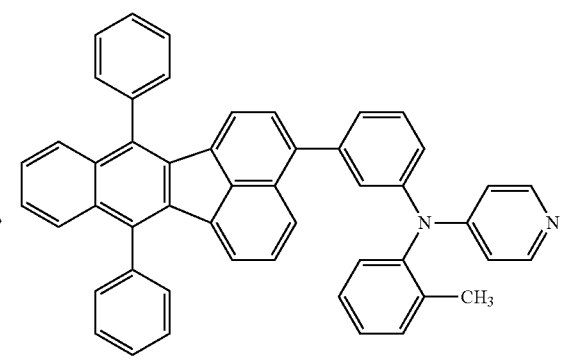
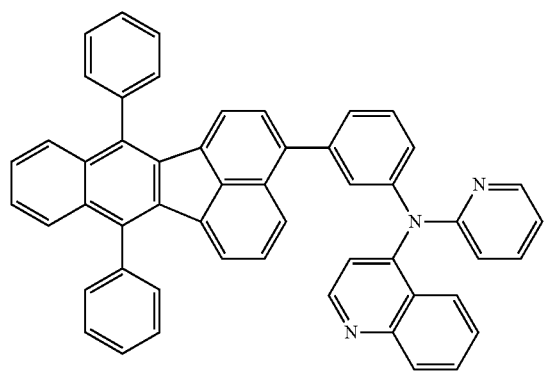
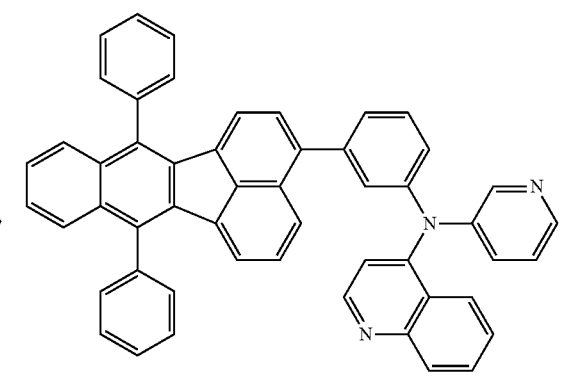
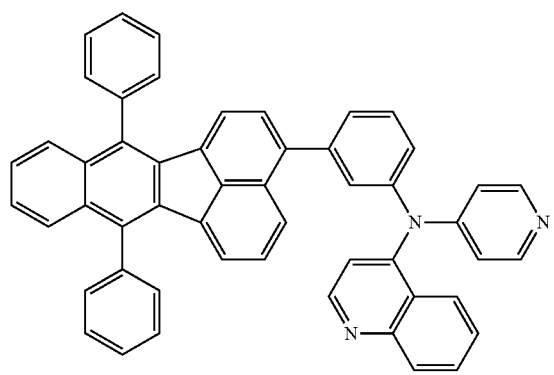
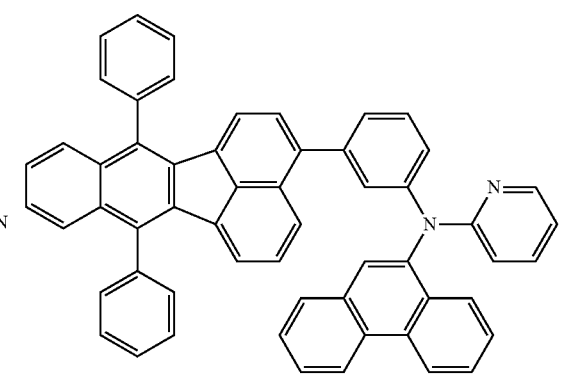

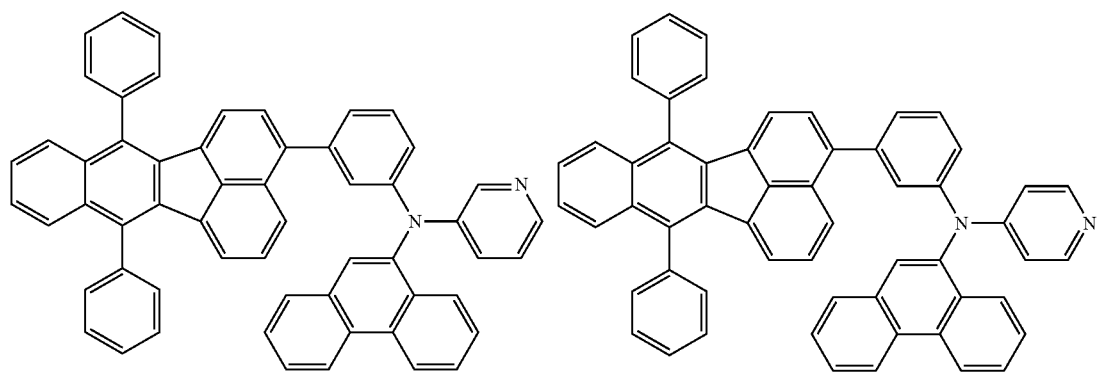
[Chemical Formula 28]
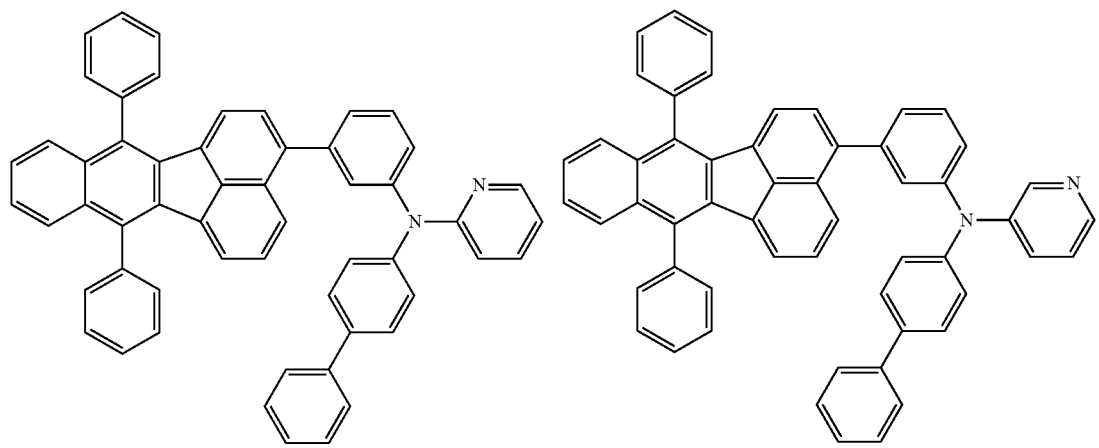
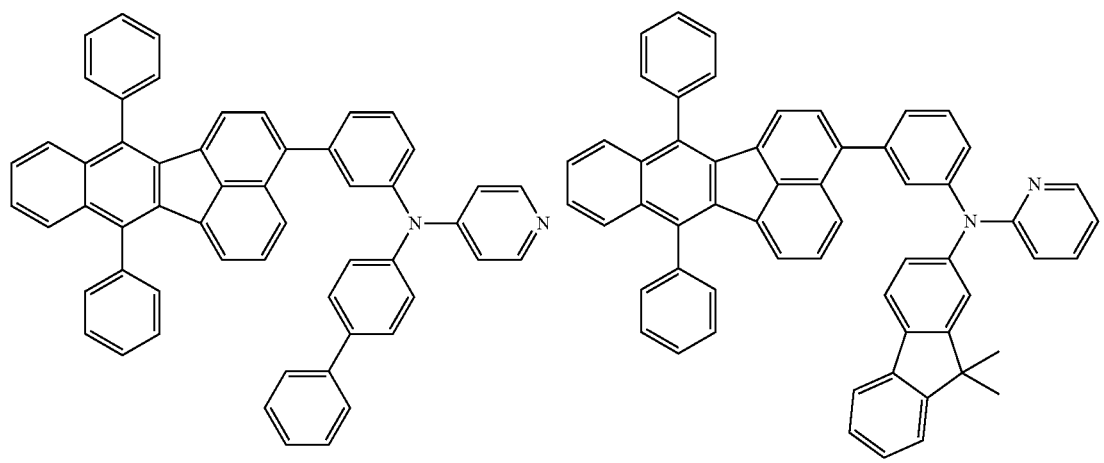

91 92
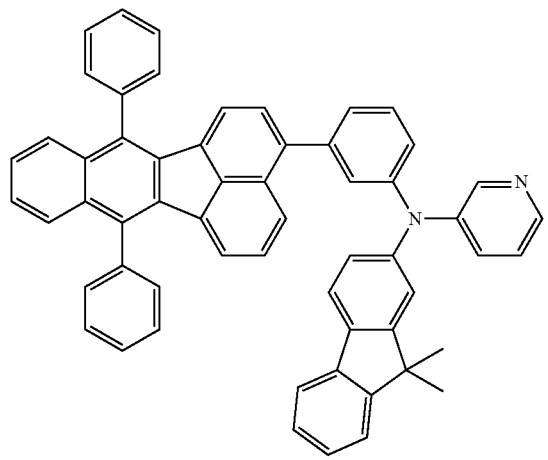
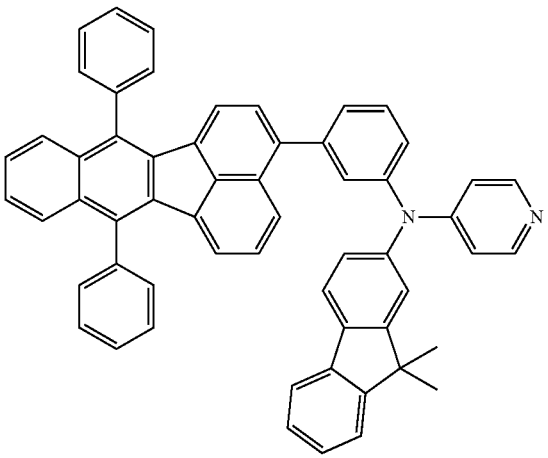
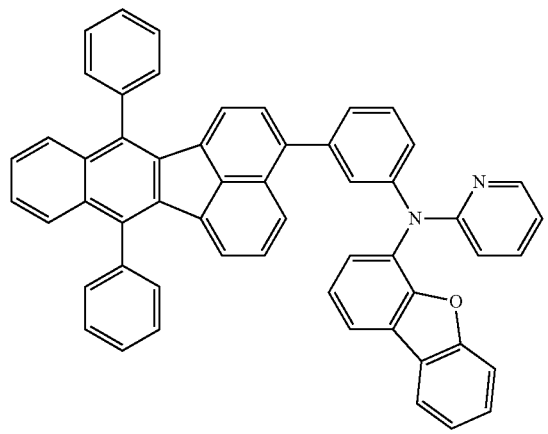
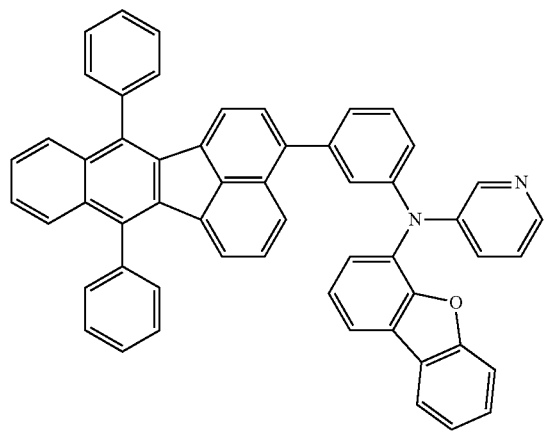
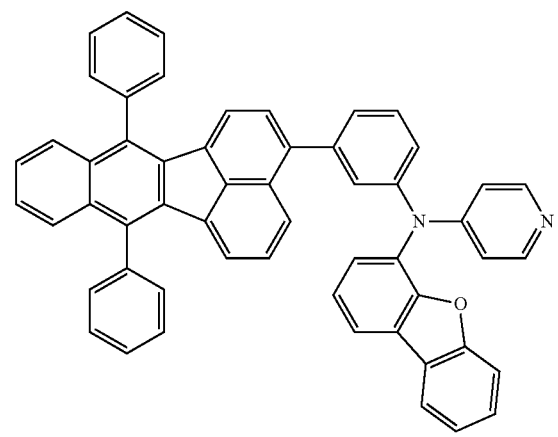

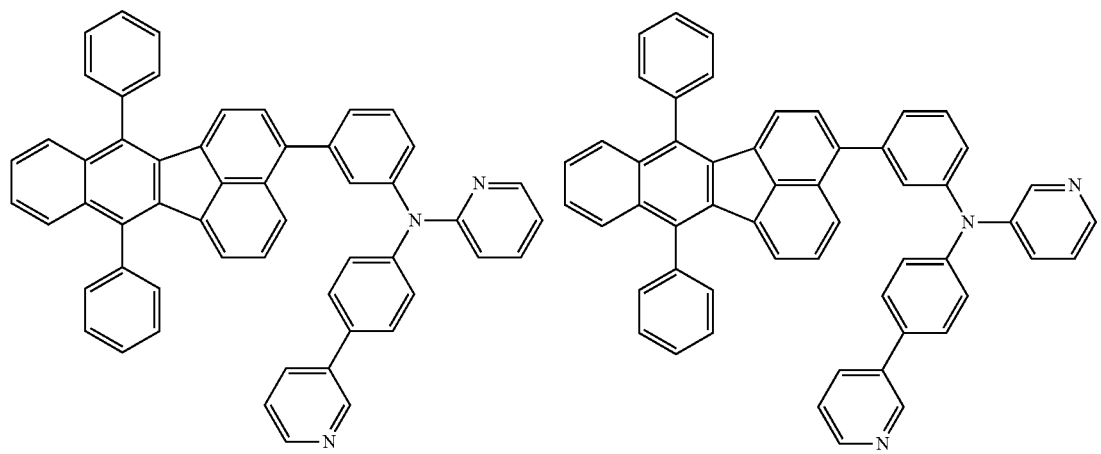
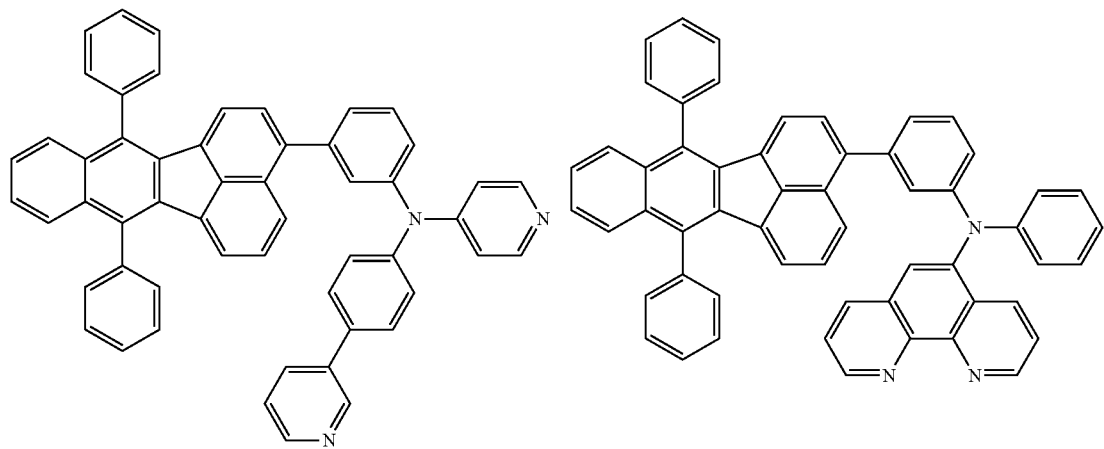
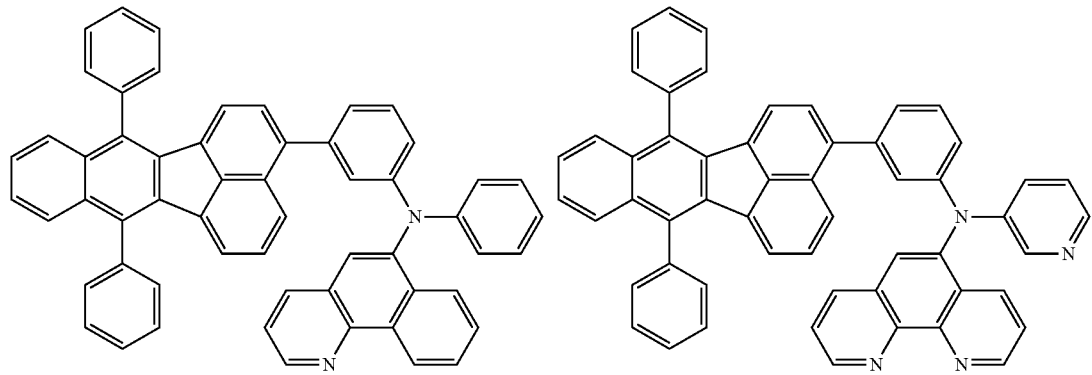

[Chemical Formula 29]
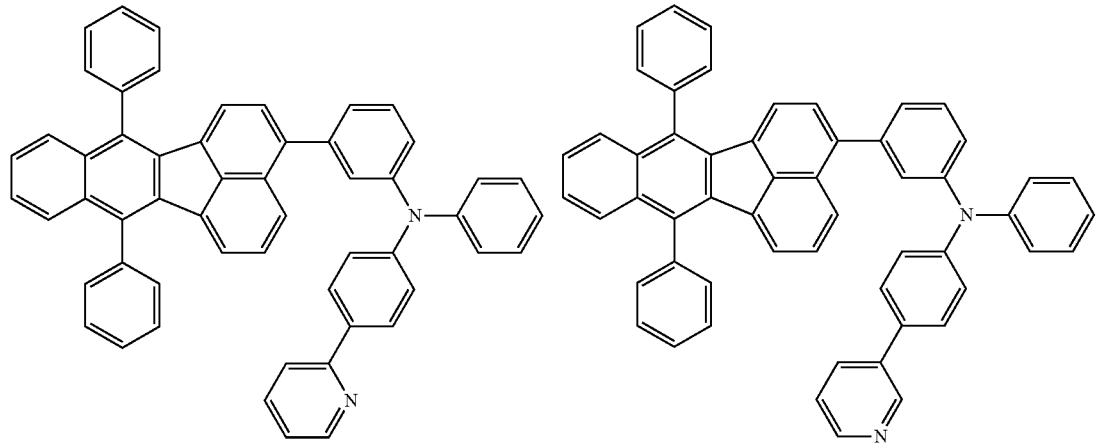
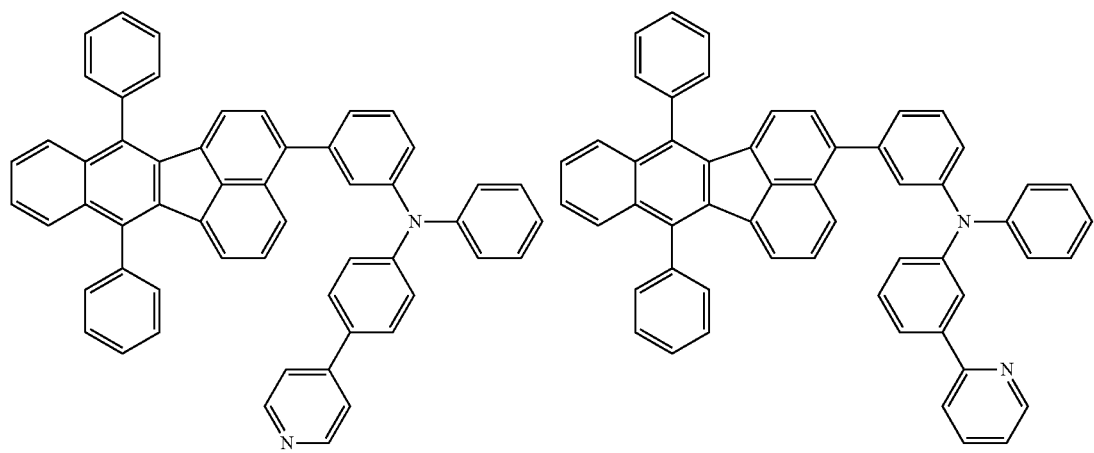
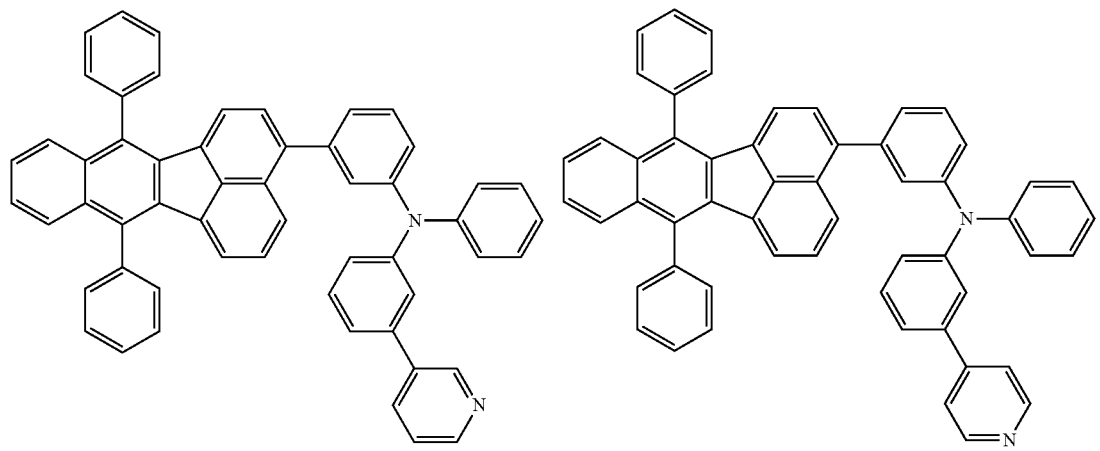

97
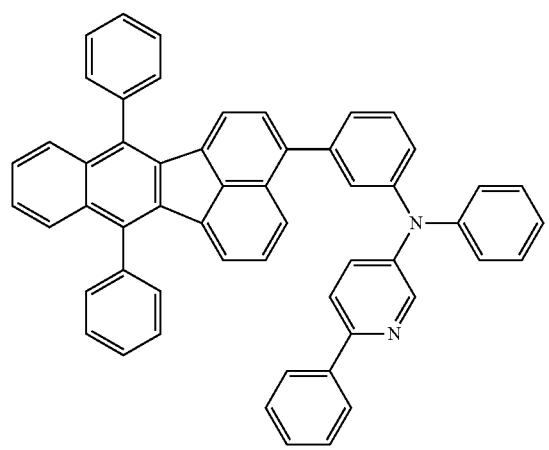
98
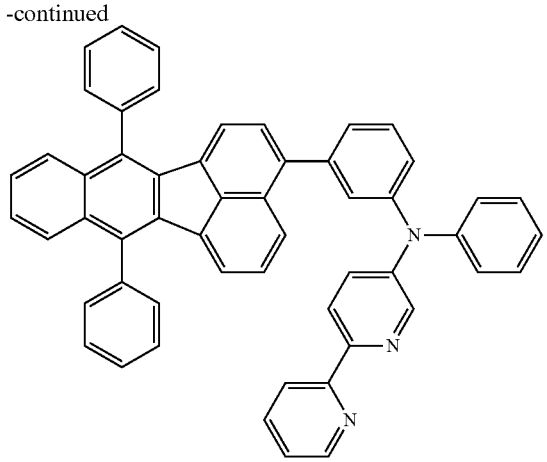
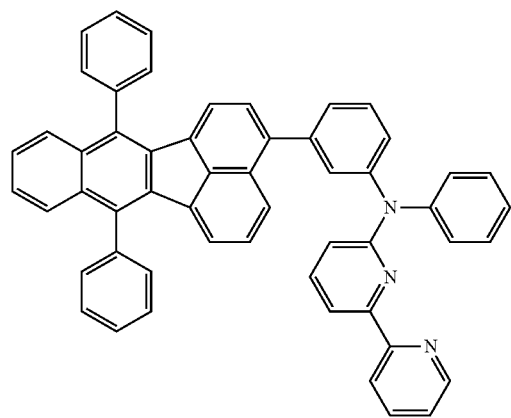
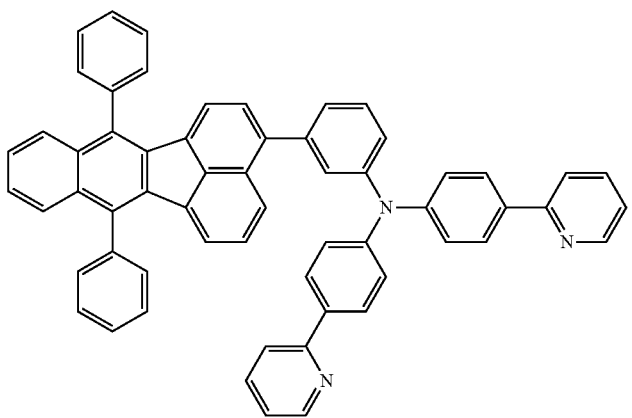
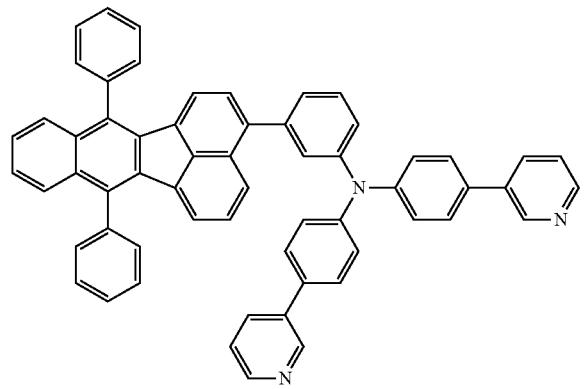
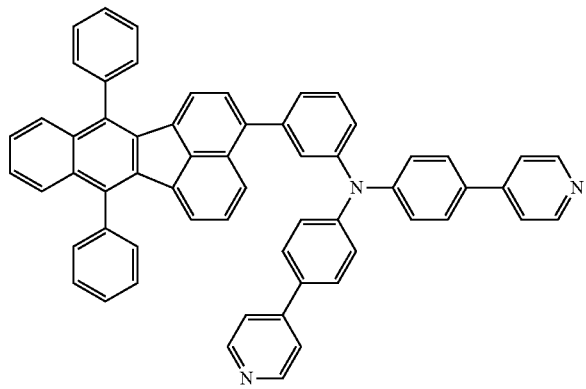

-continued
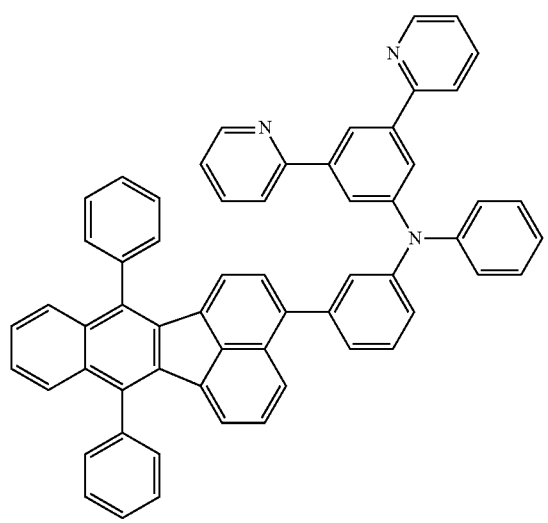
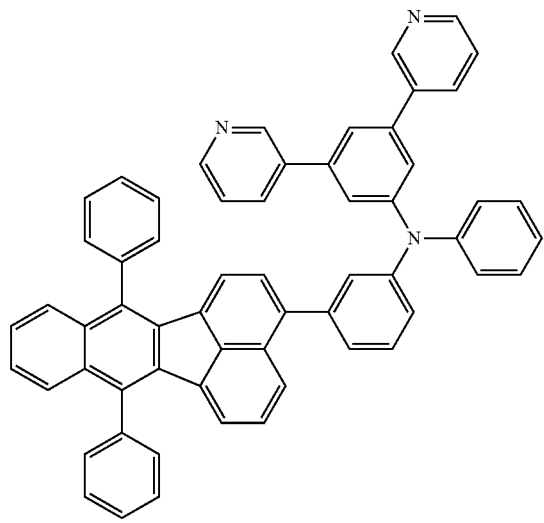
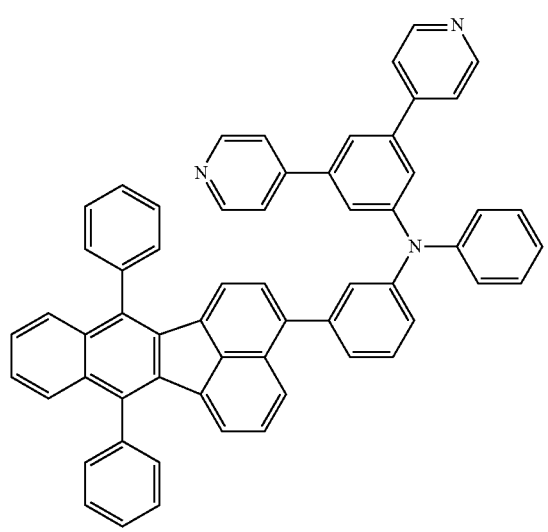
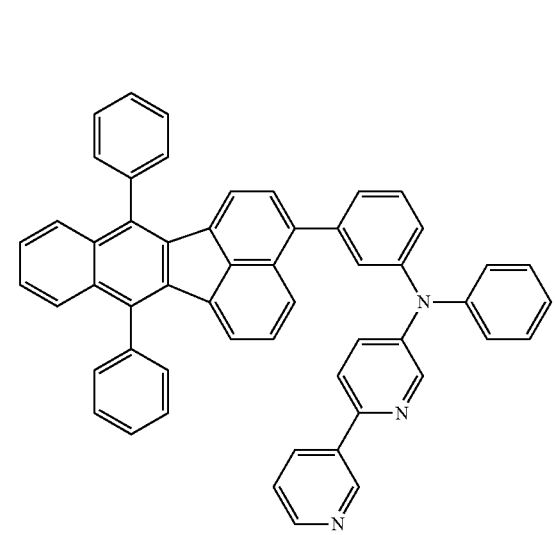
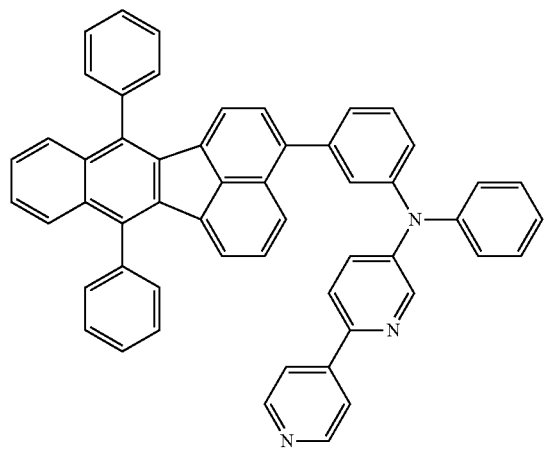
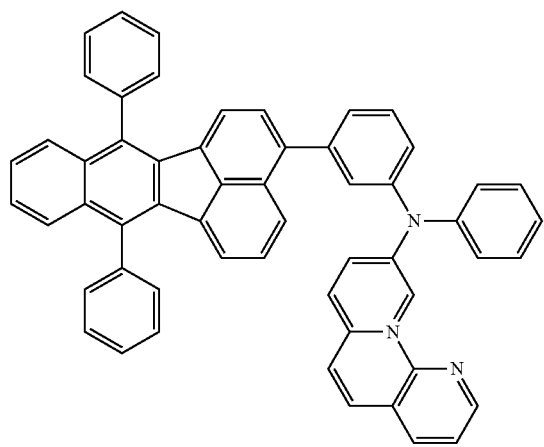

[Chemical Formula 30]
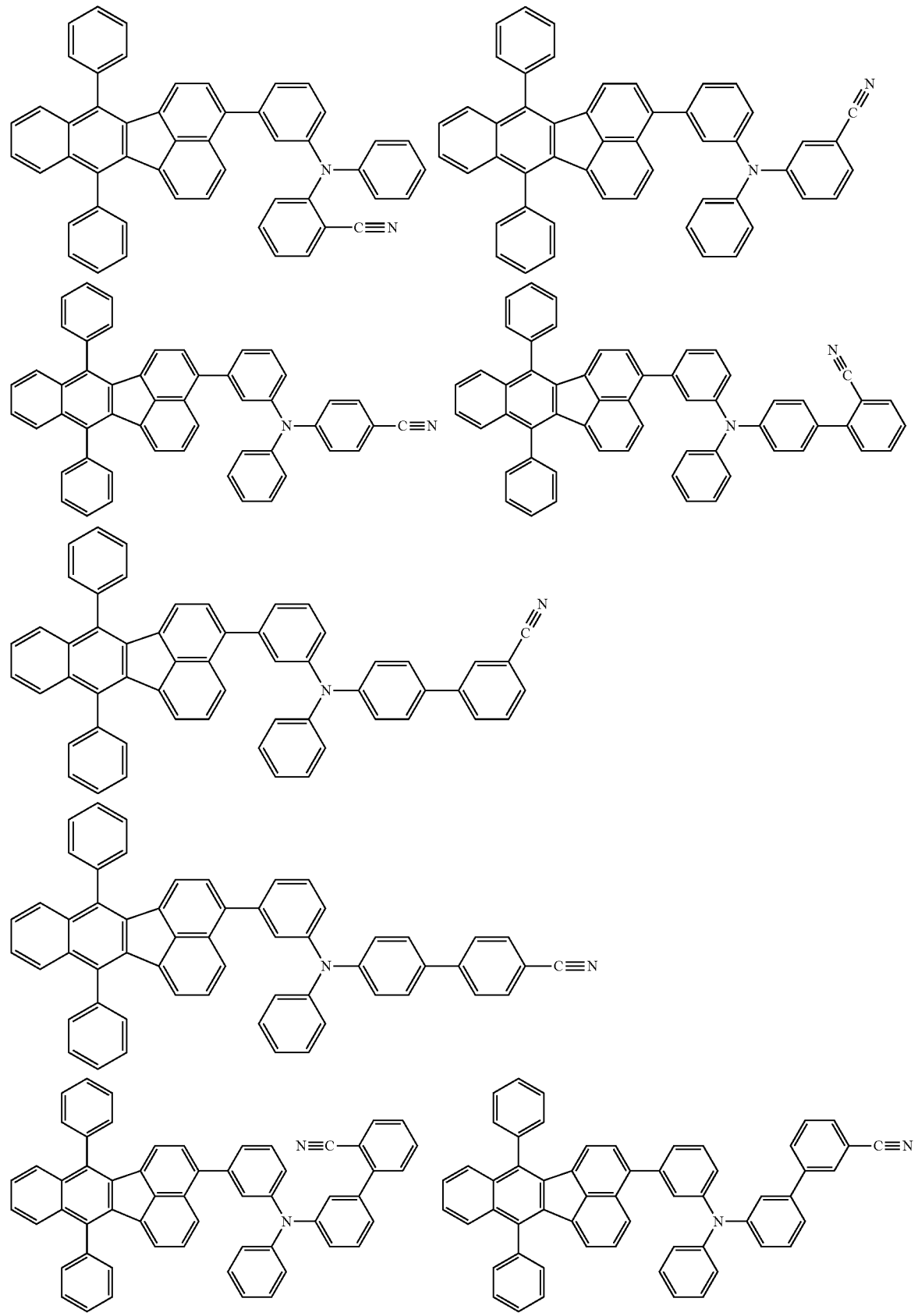

-continued
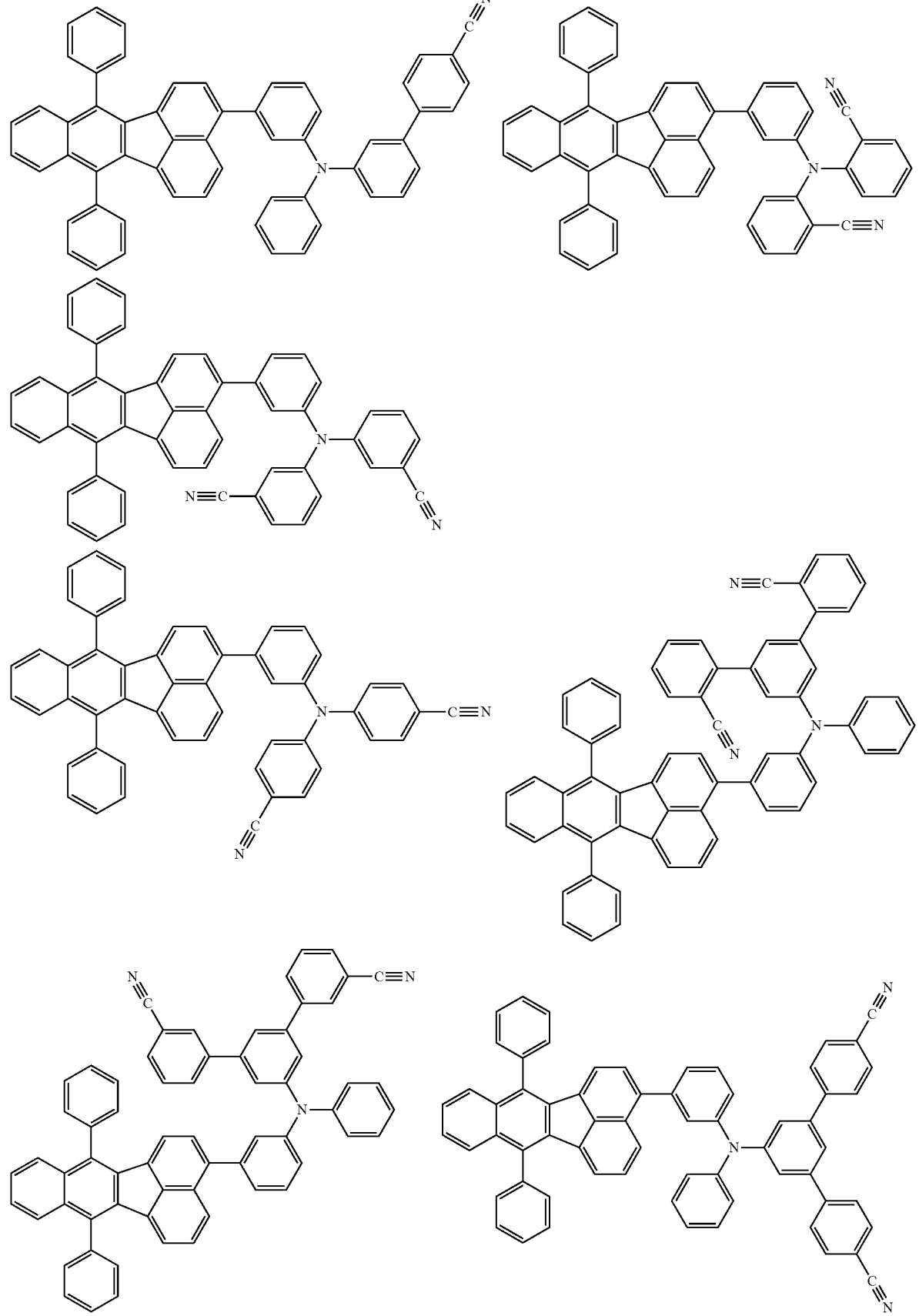

-continued
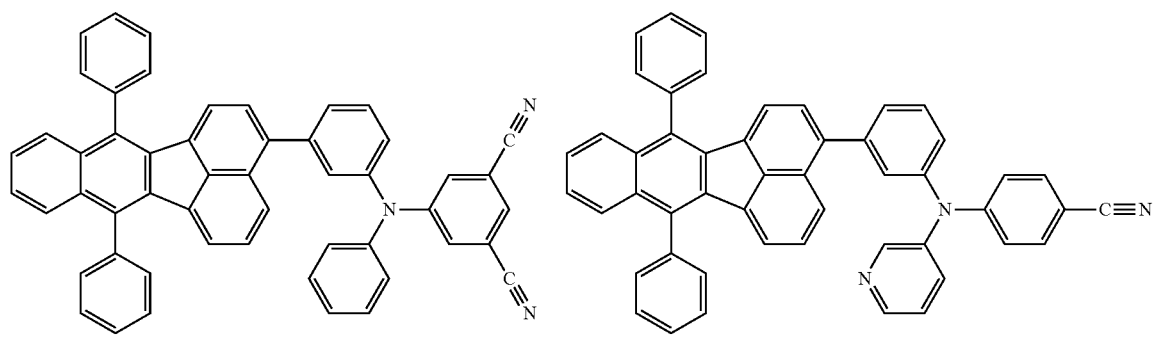
[Chemical Formula 31]
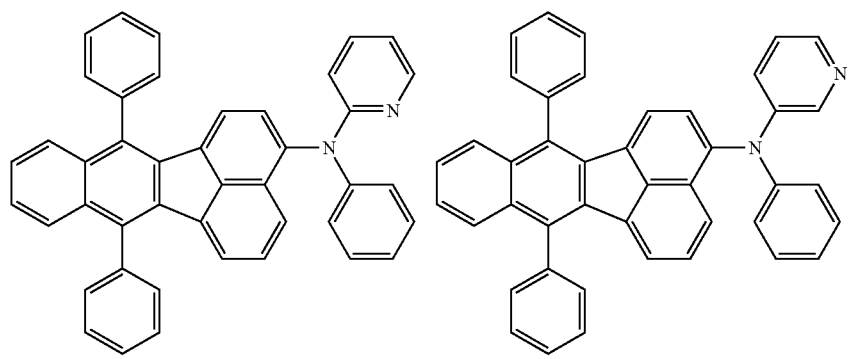
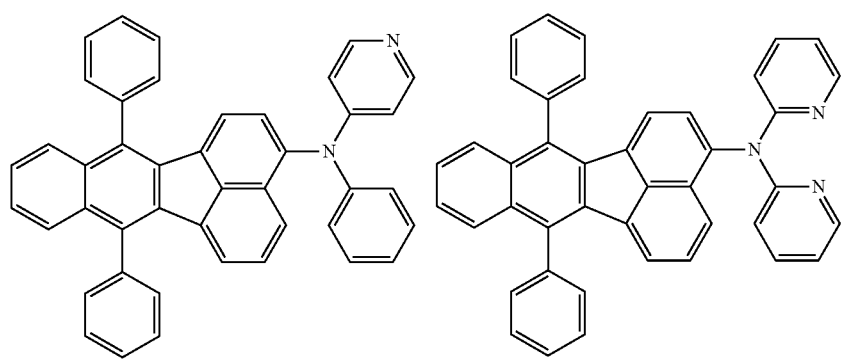
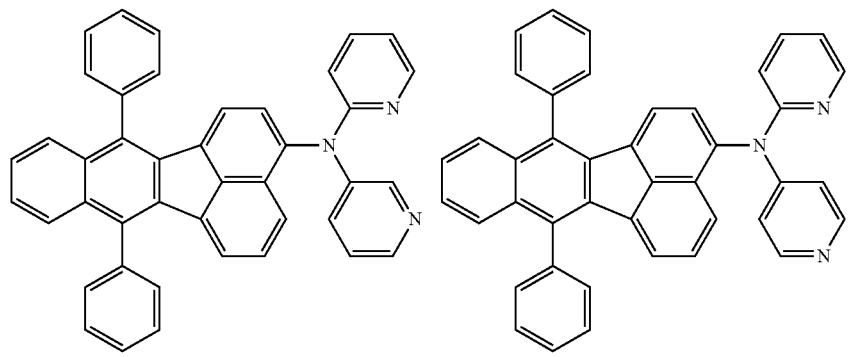

-continued
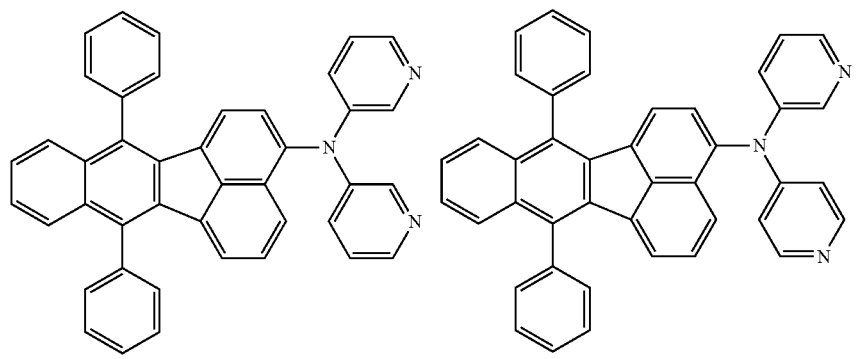
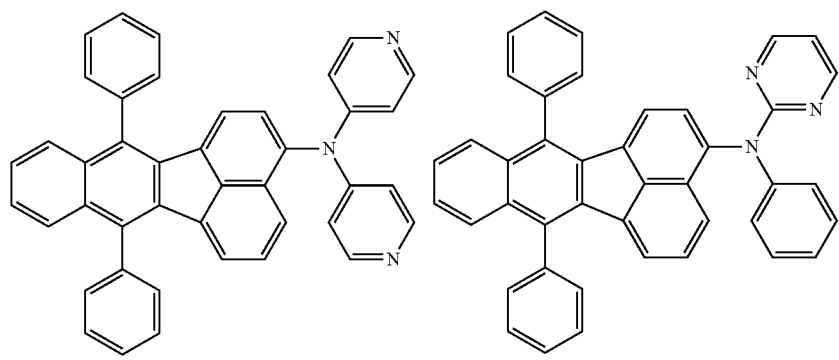
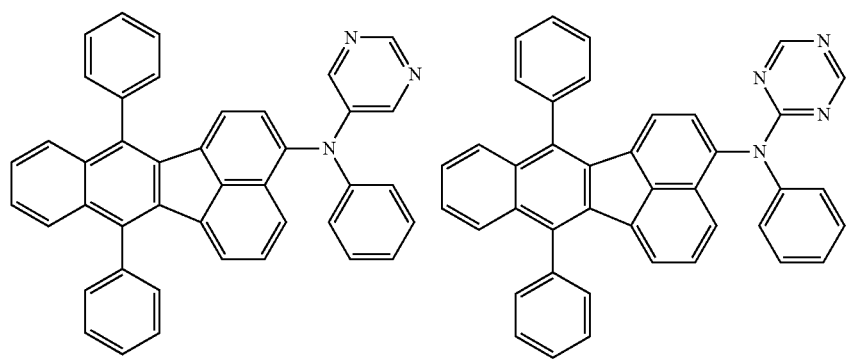
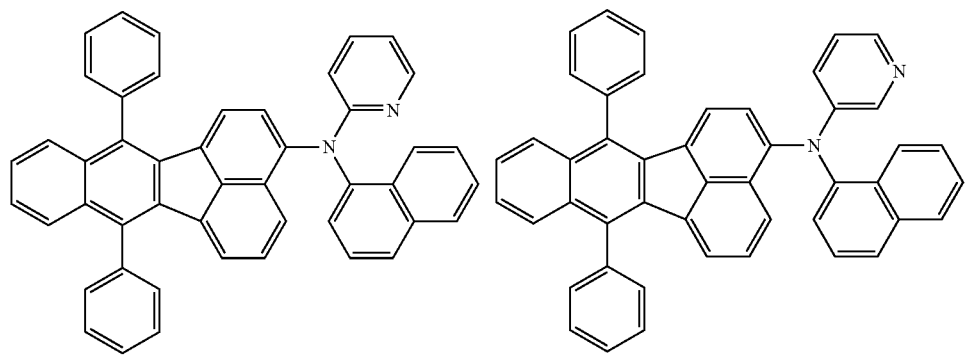

-continued
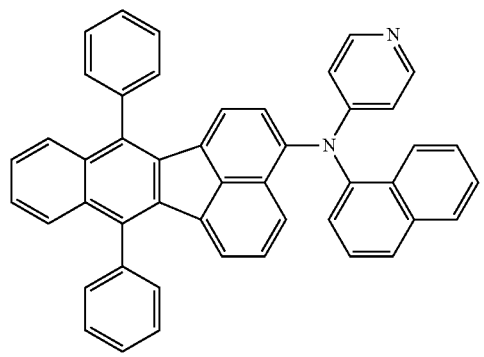
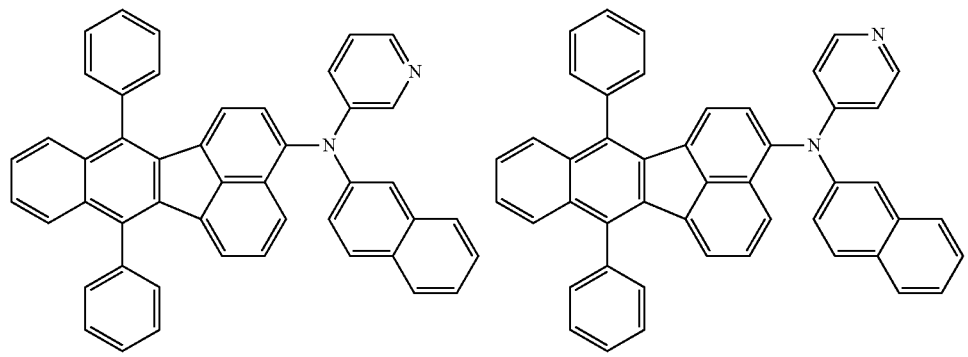
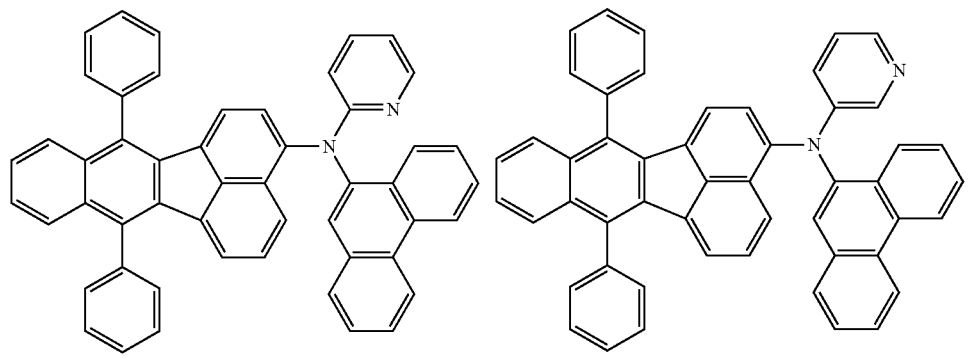
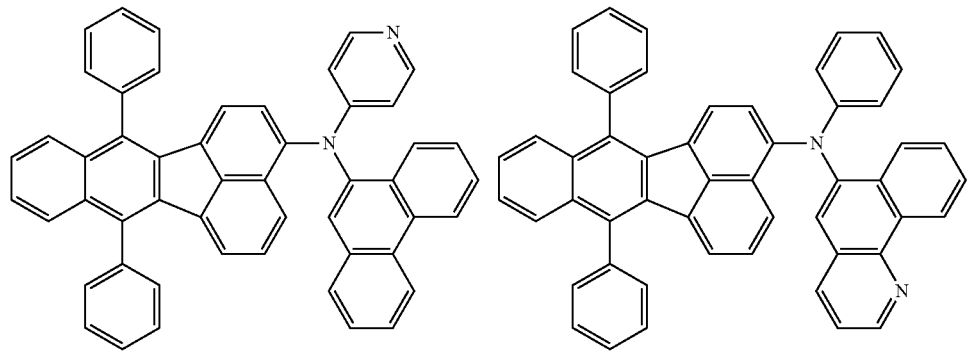

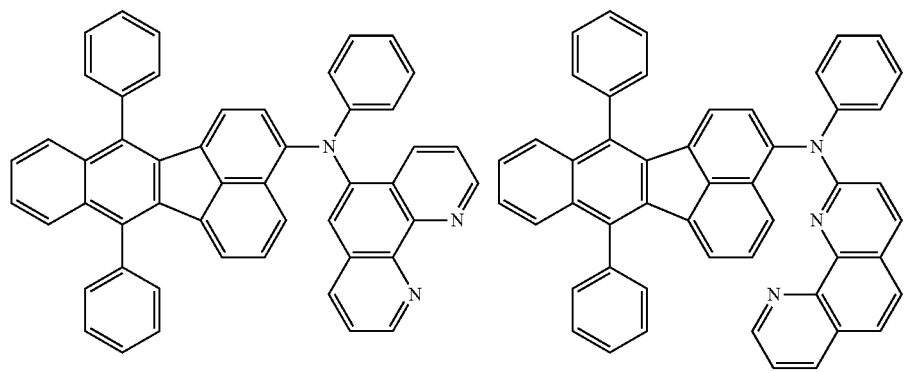
[Chemical Formula 32]
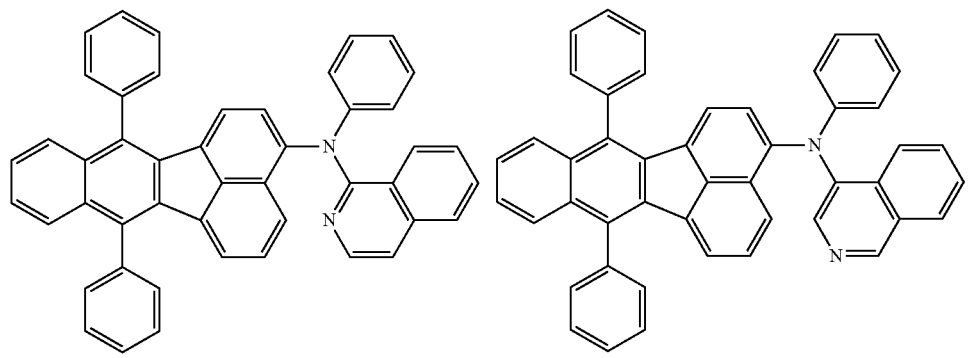
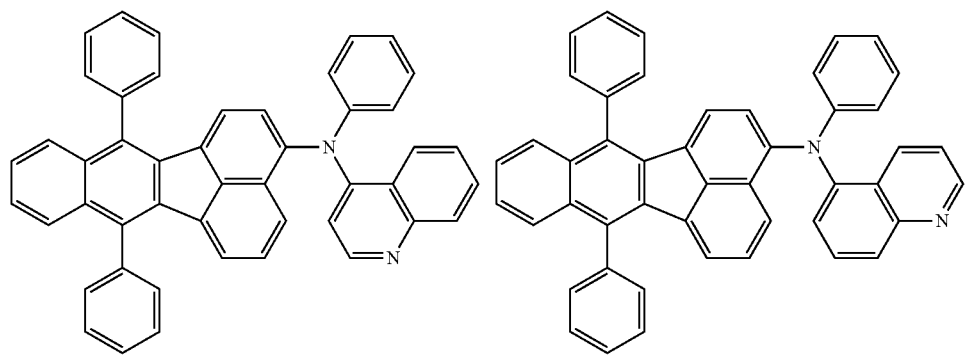
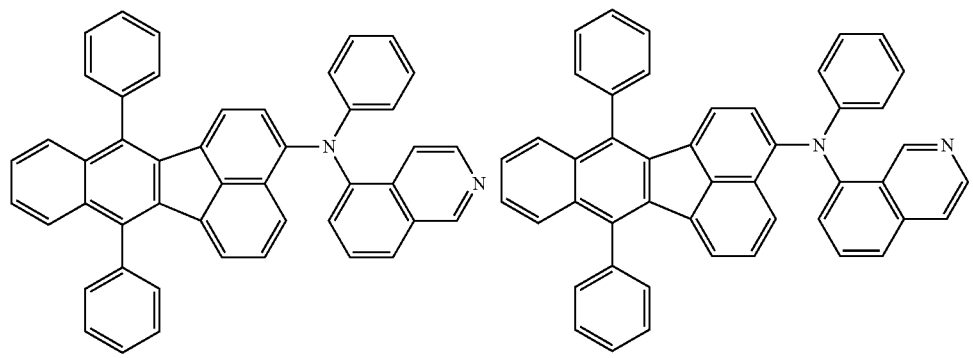

-continued
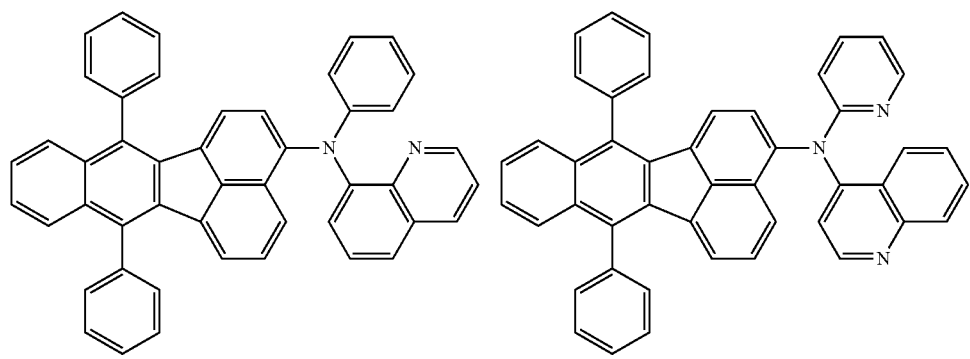
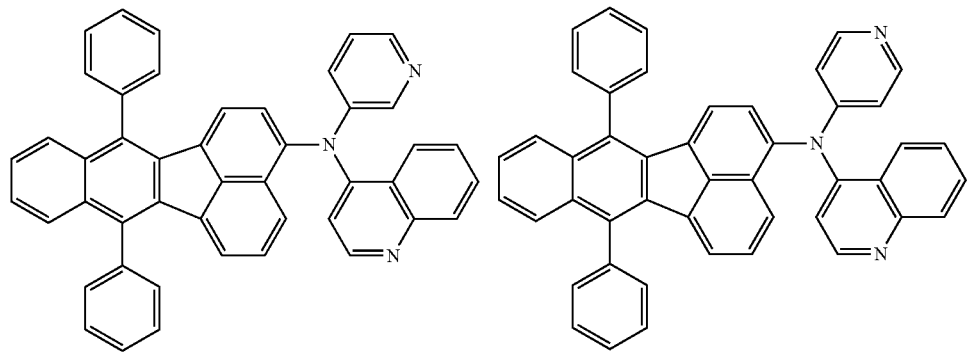
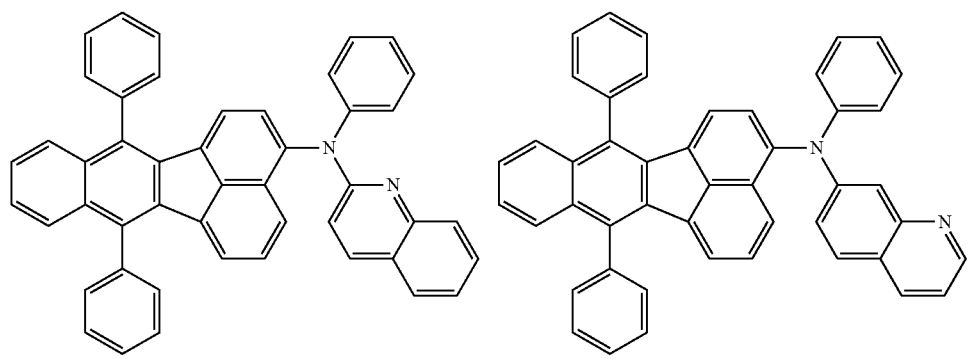
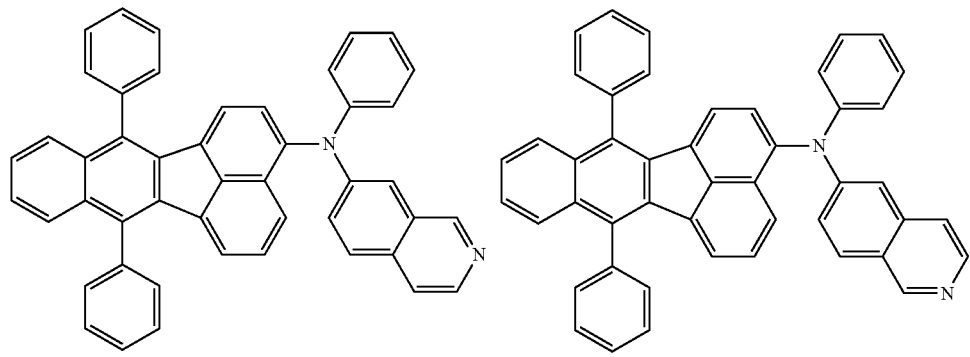

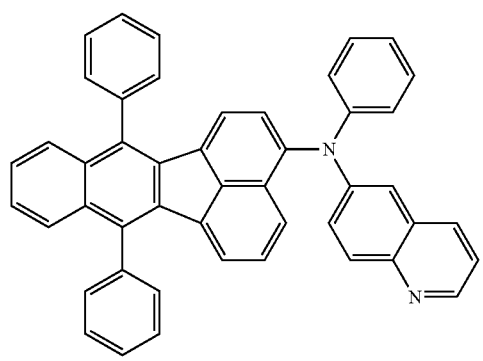
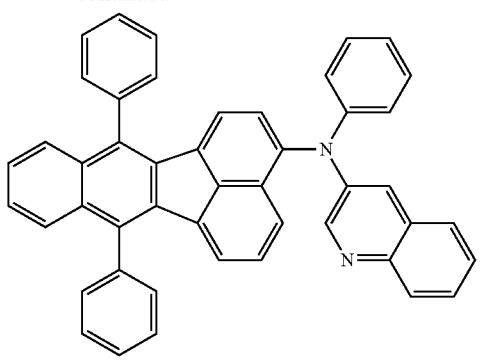
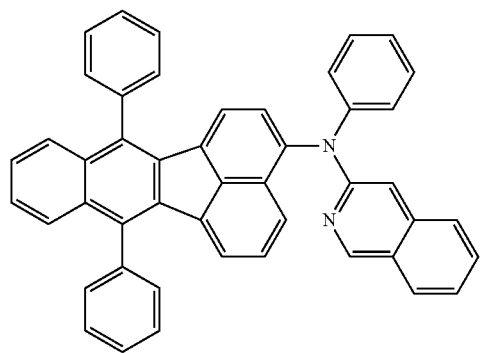
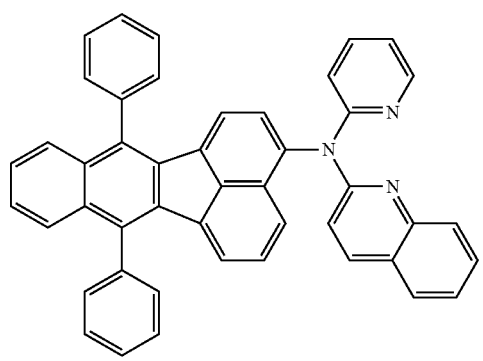
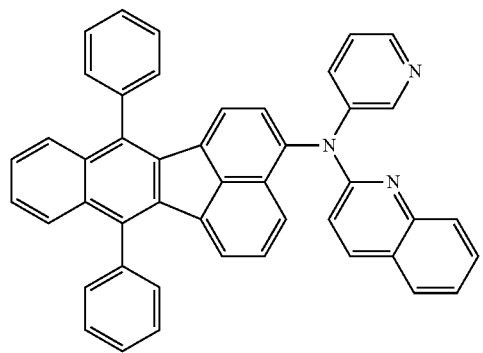
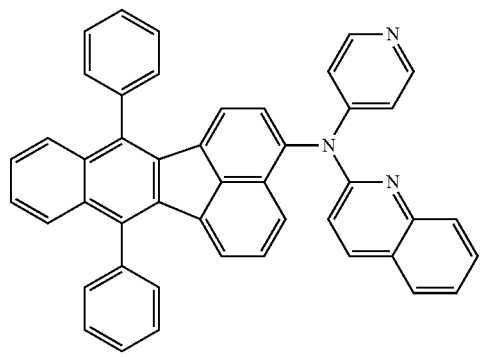
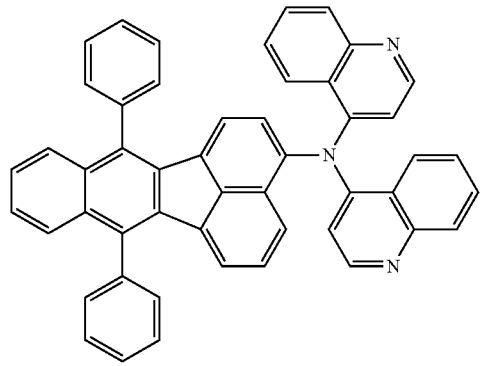
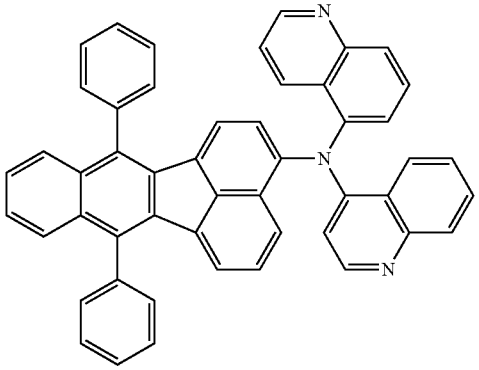

-continued
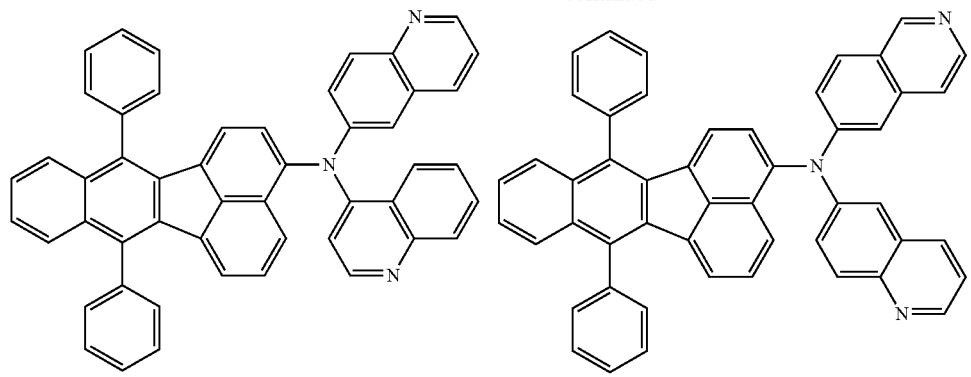
[Chemical Formula 33]
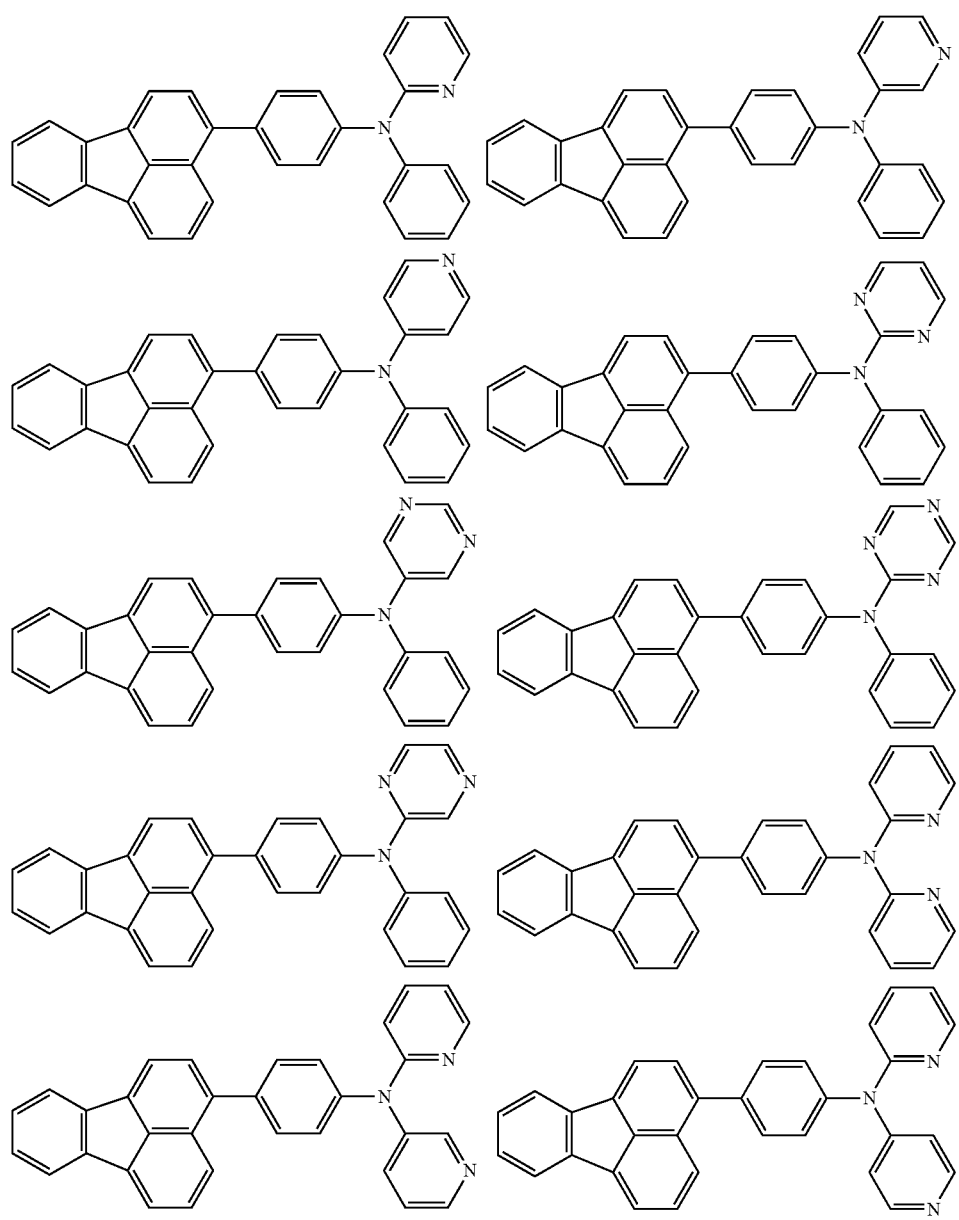

-continued
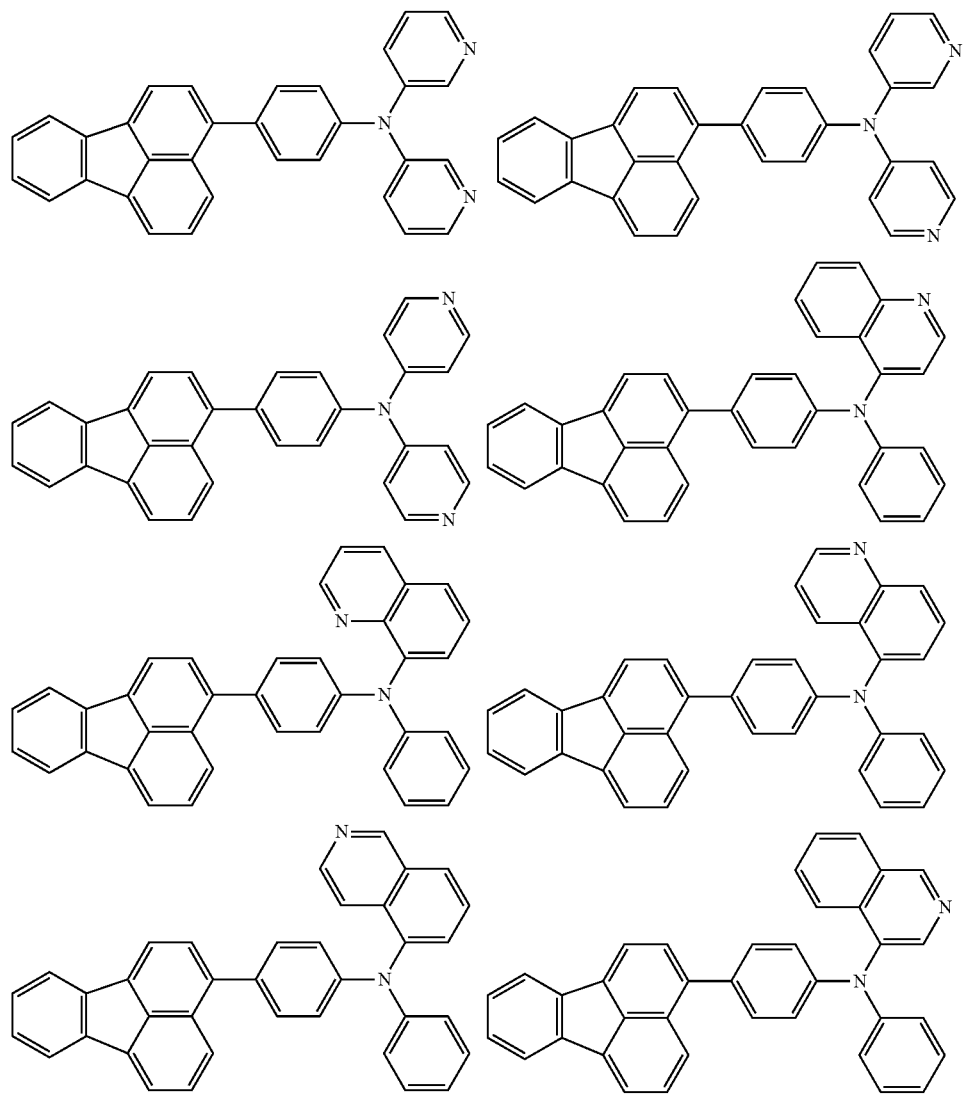
[Chemical Formula 34]
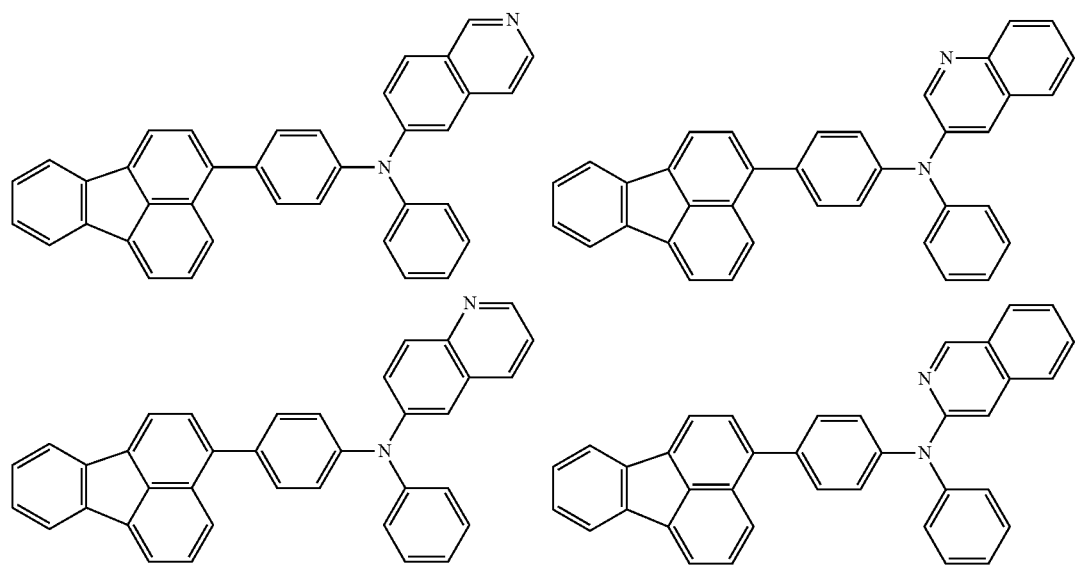

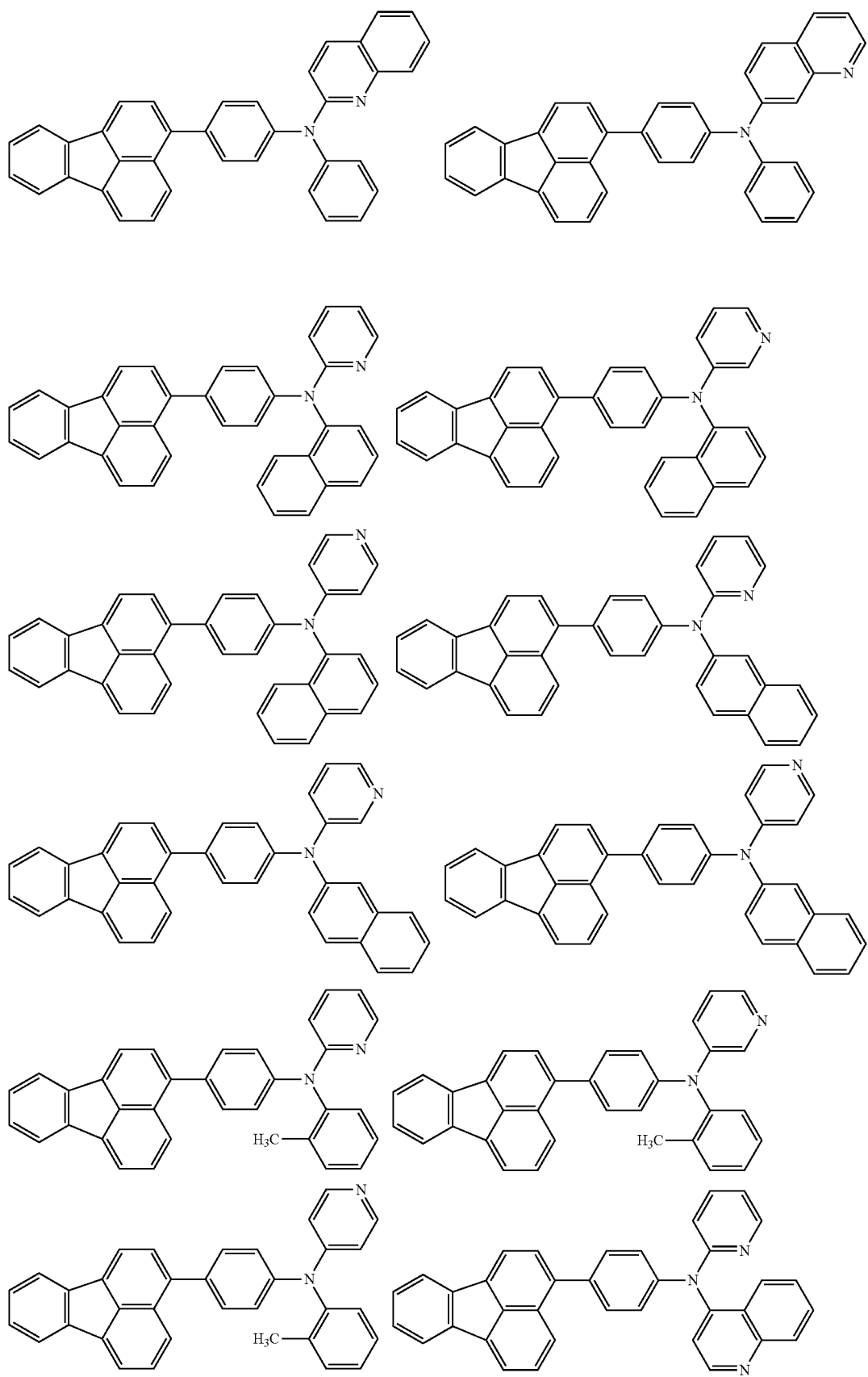

-continued
123
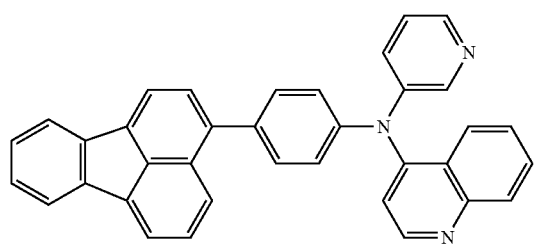
124
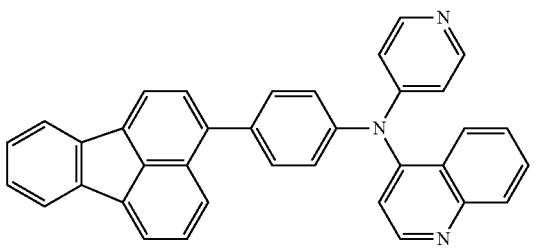
[Chemical Formula 35]
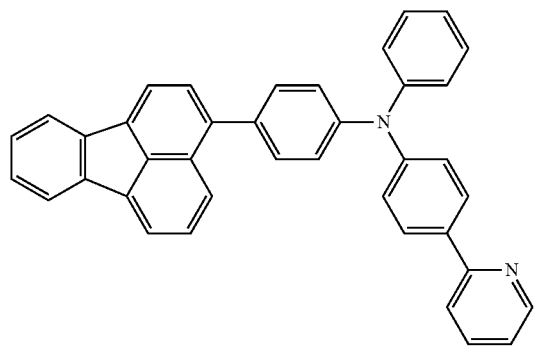
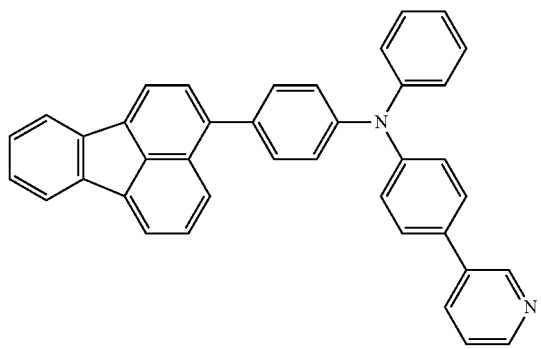
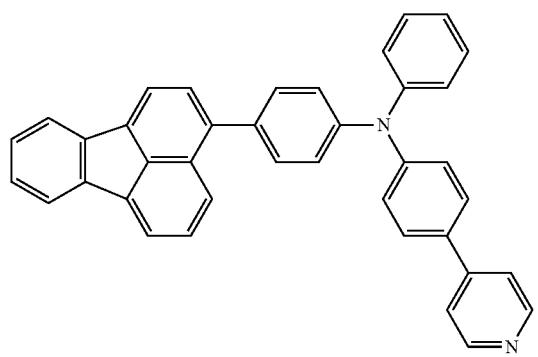
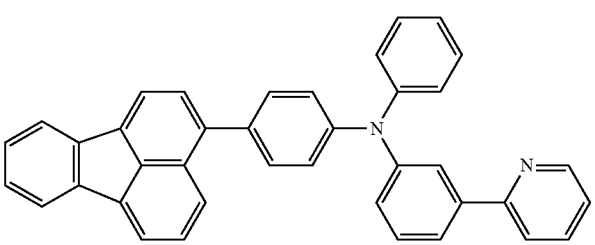
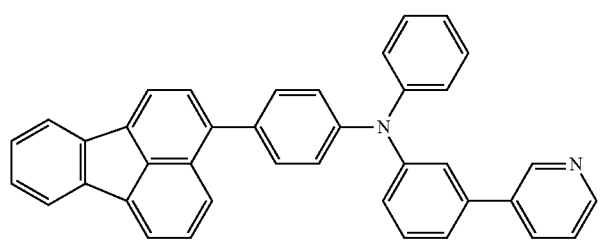
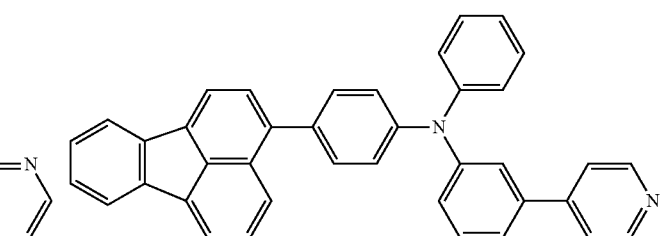
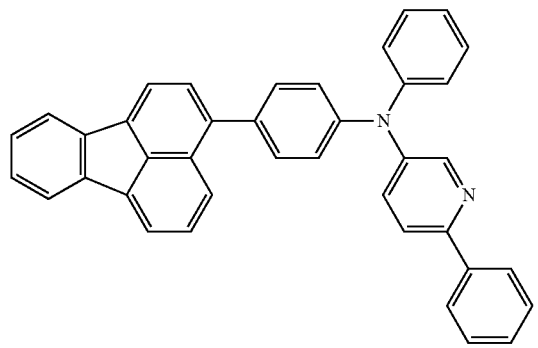
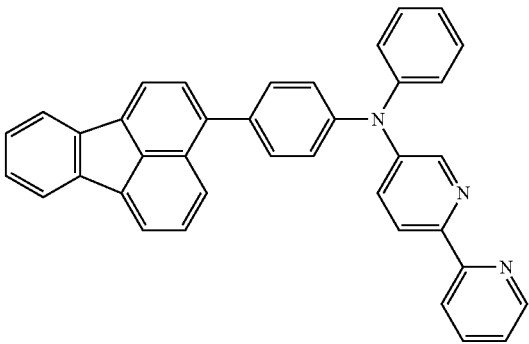

125
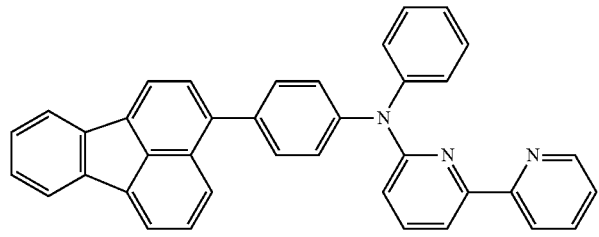
126
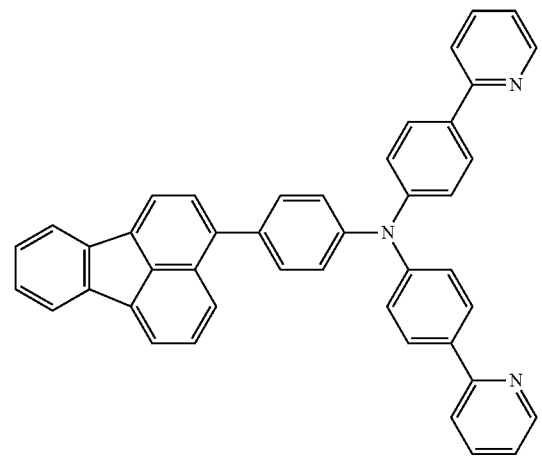
-continued
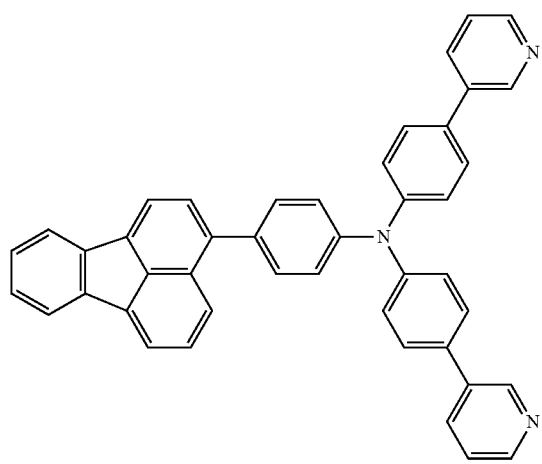
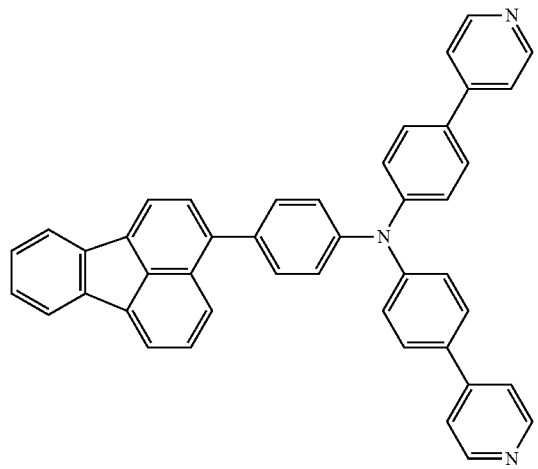
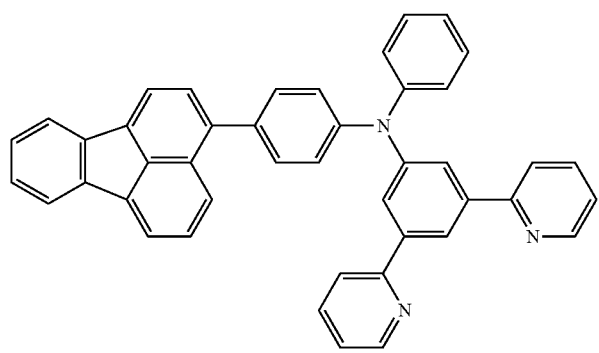
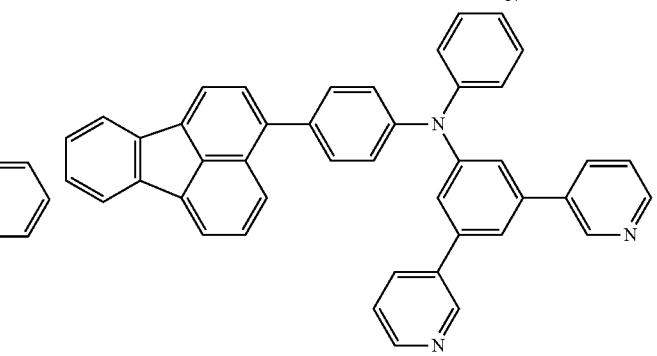
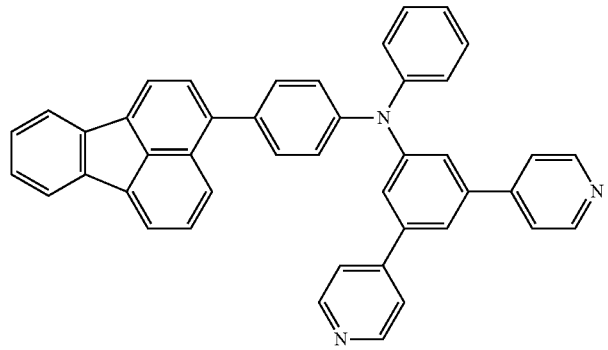
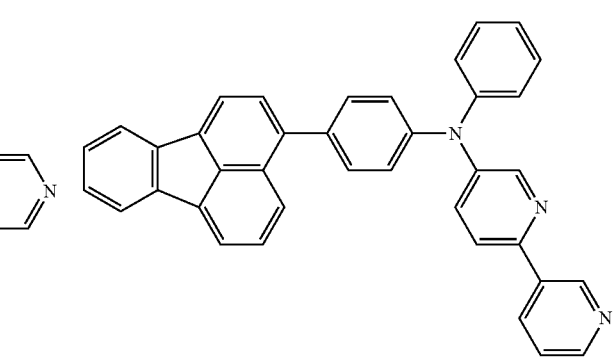

-continued
127 128
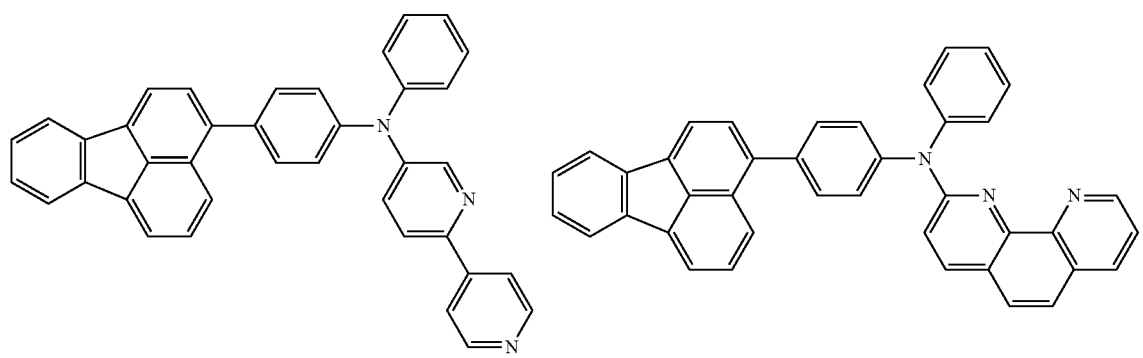 [SMILES: c1ccc(N(c2ccc(-c3ccc4c5c(cccc35)-c3ccccc3-4)cc2)c2ccc(-c3ccncc3)nc2)cc1 ; c1ccc(N(c2ccc(-c3ccc4c5c(cccc35)-c3ccccc3-4)cc2)c2ccc3ccc4cccnc4c3n2)cc1]
[Chemical Formula 36]
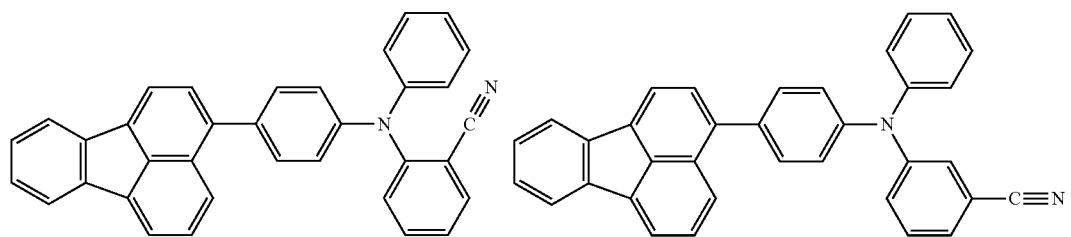
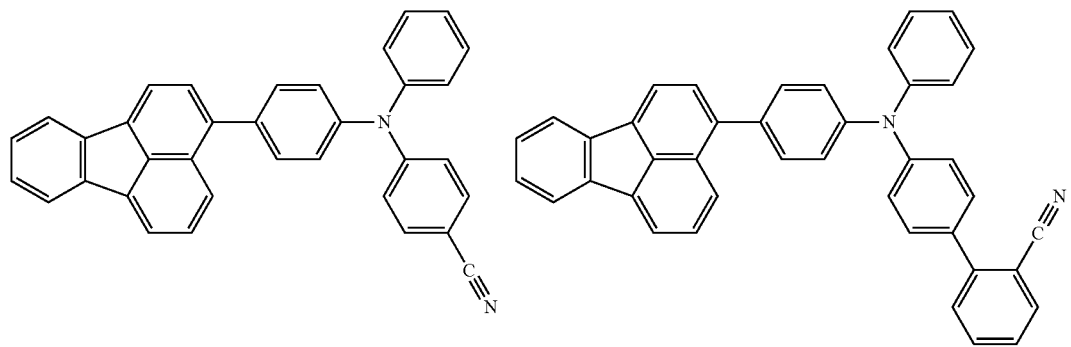
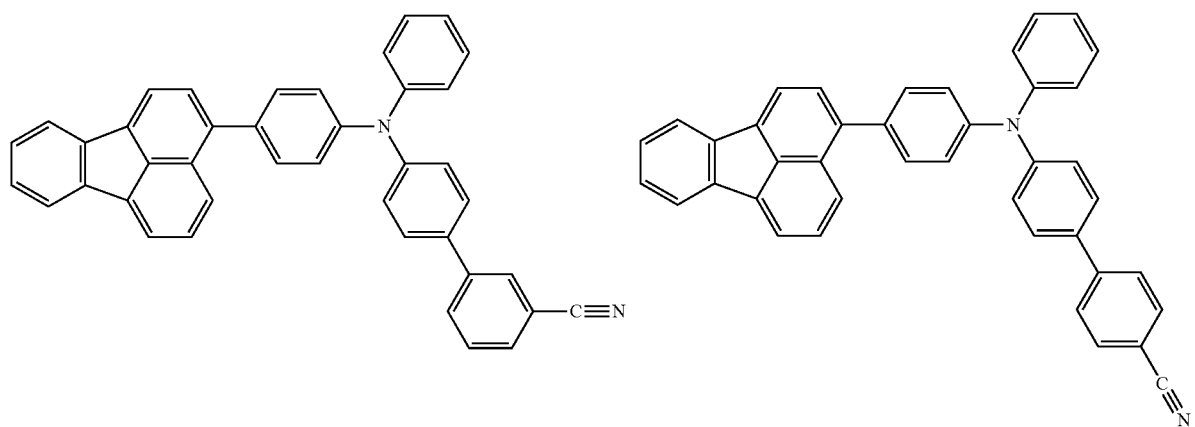

-continued
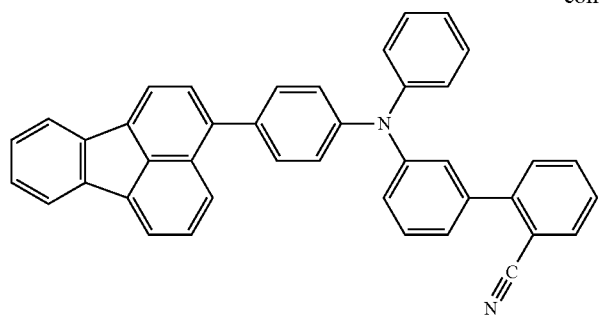
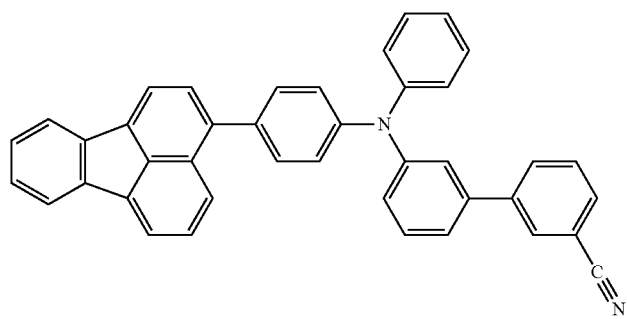
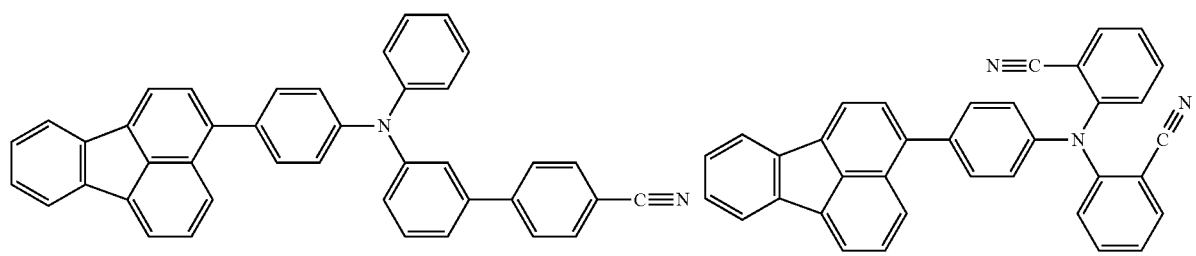
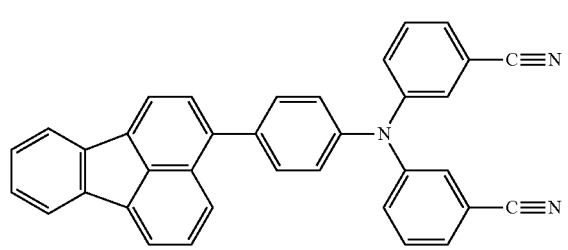
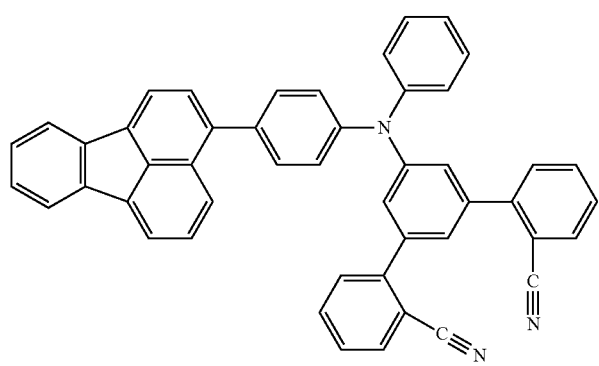

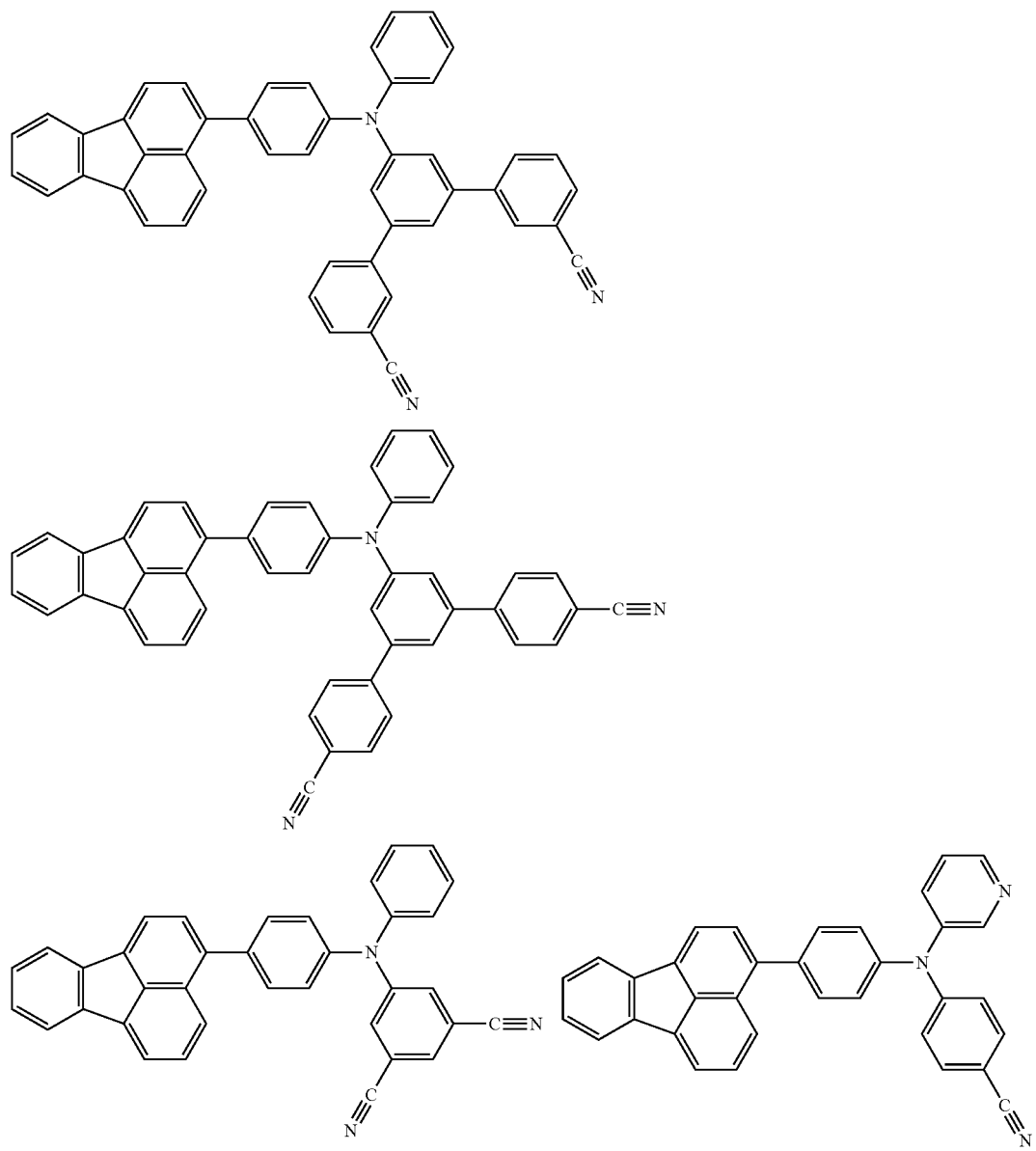
[Chemical Formula 37]
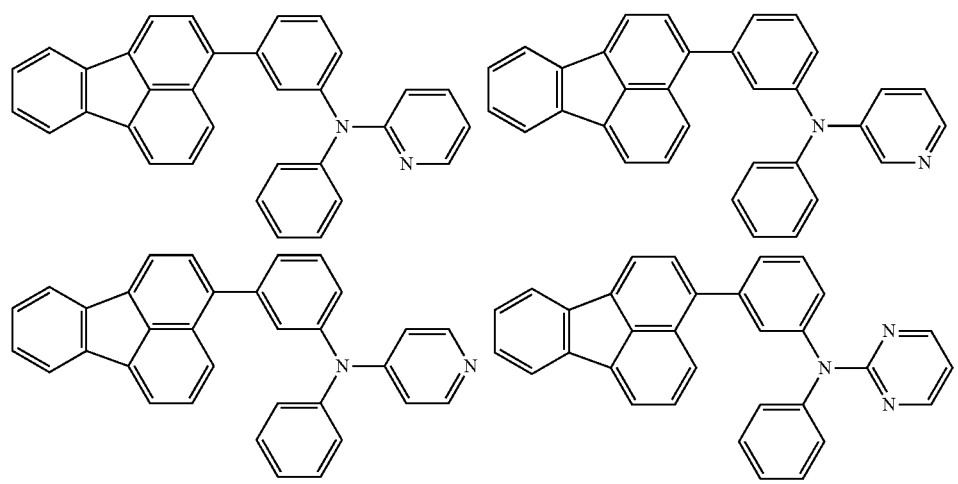

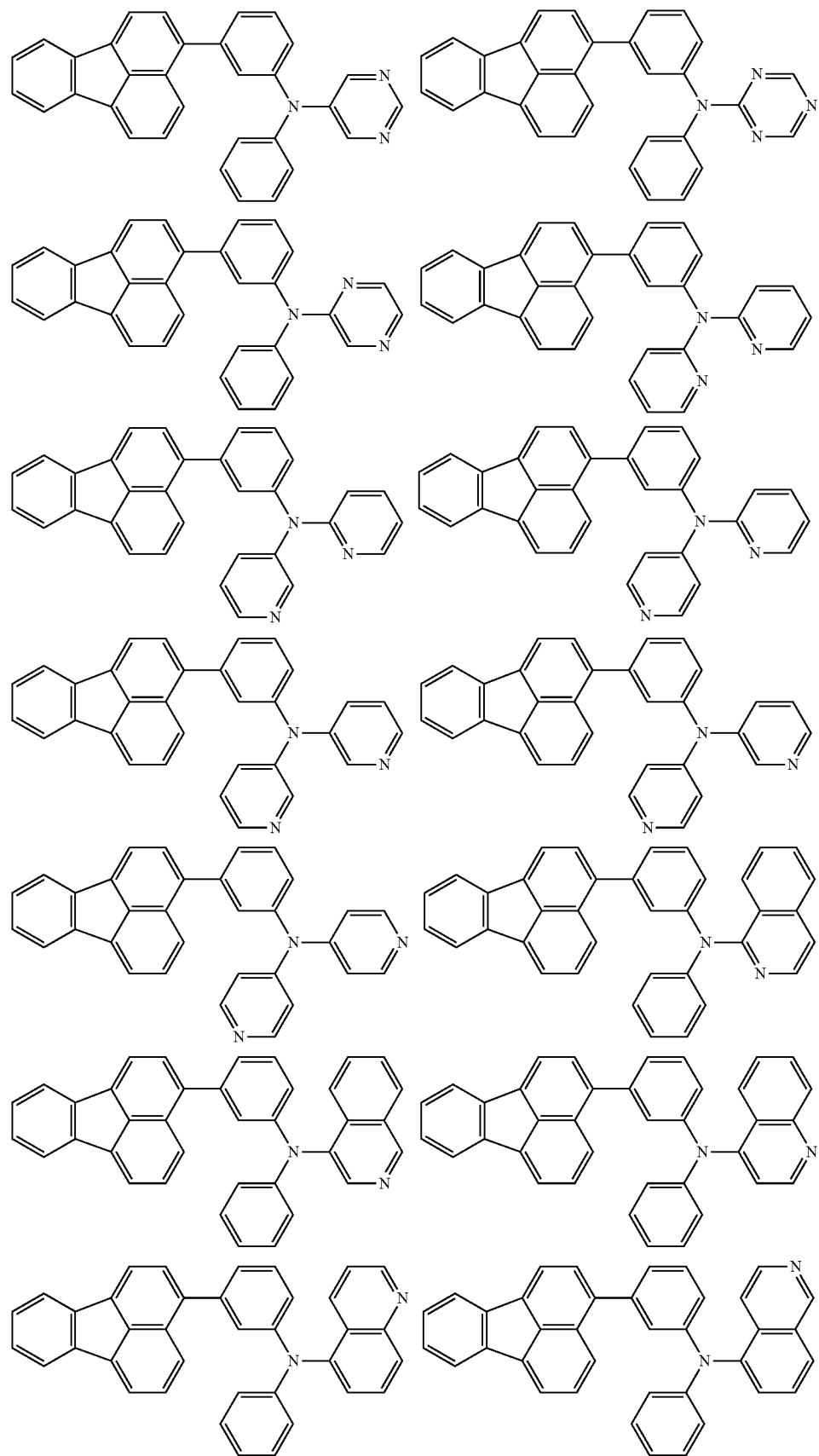

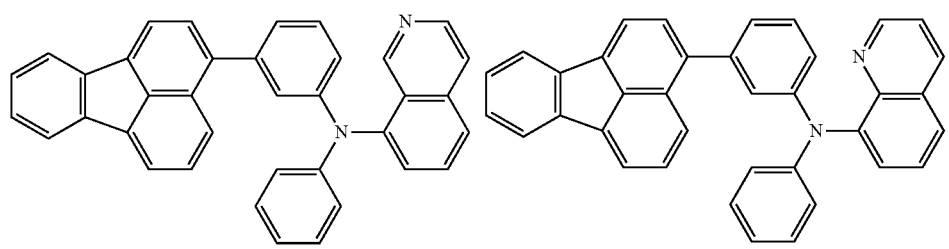
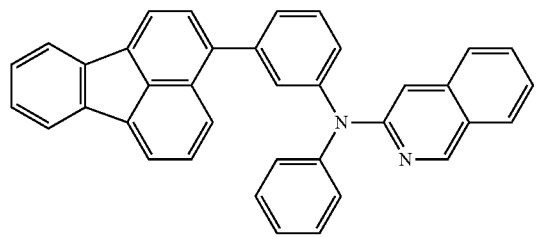
[Chemical Formula 38]
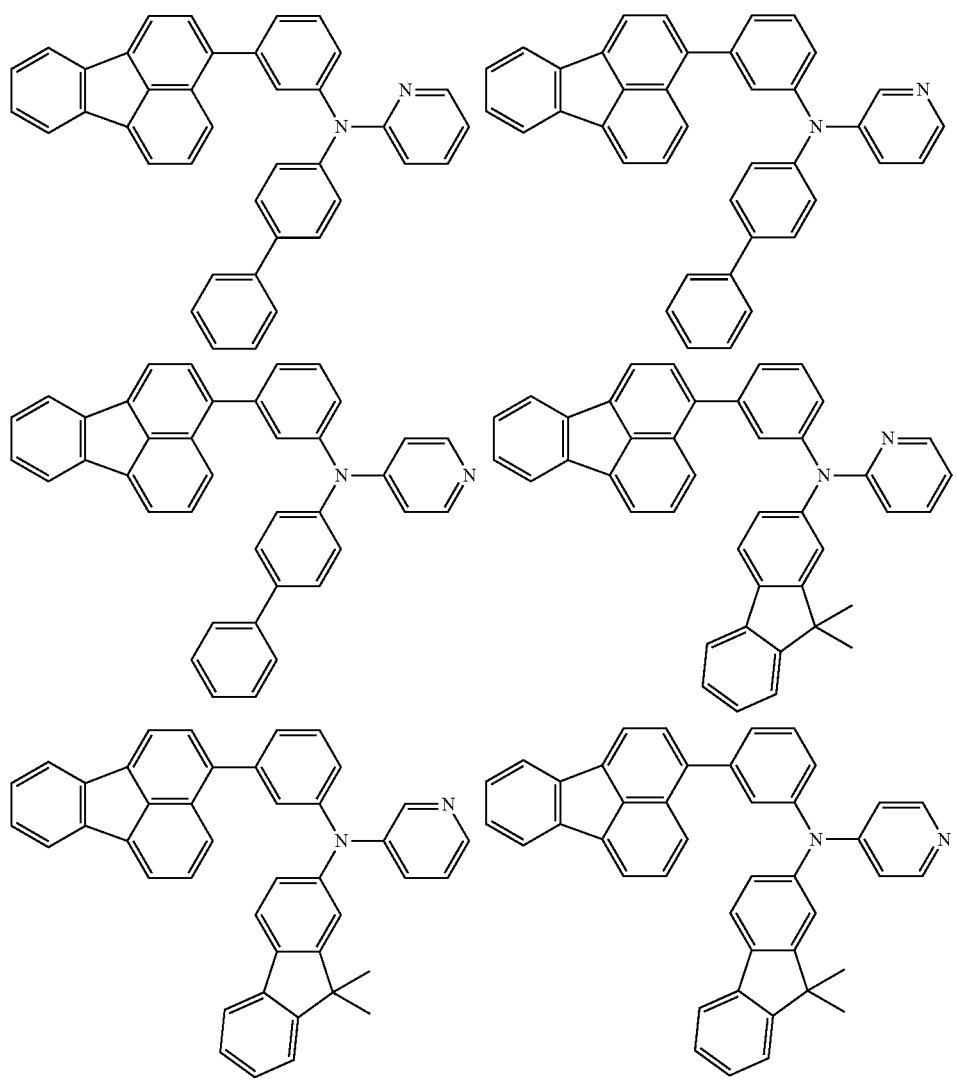

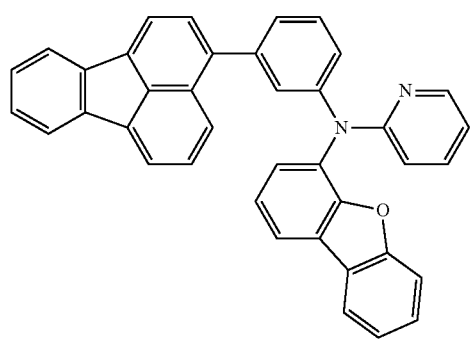
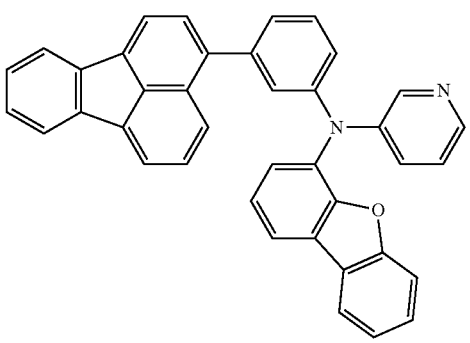
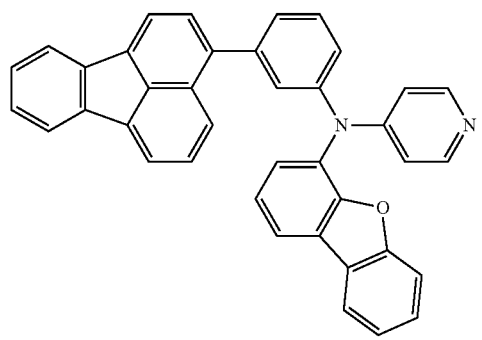
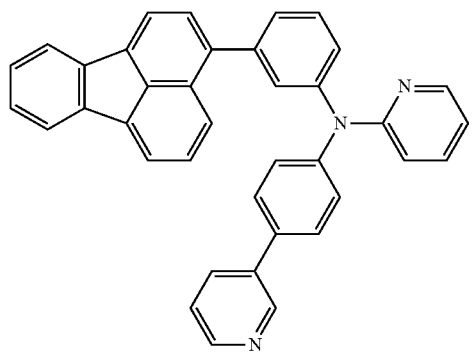
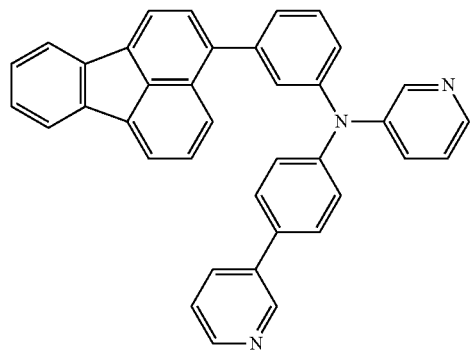
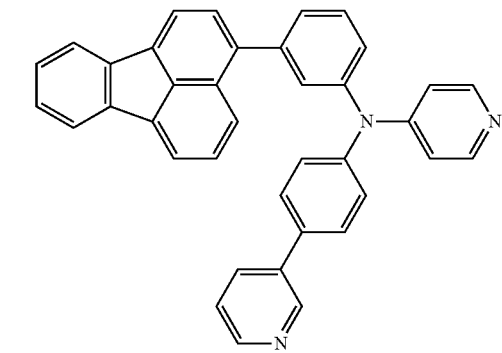
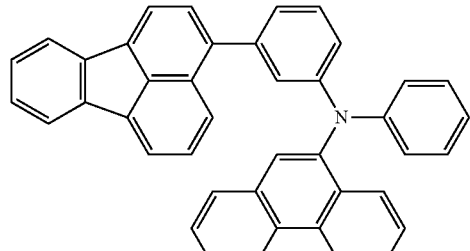
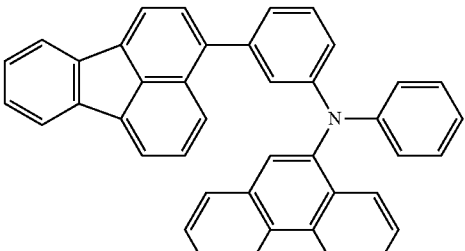
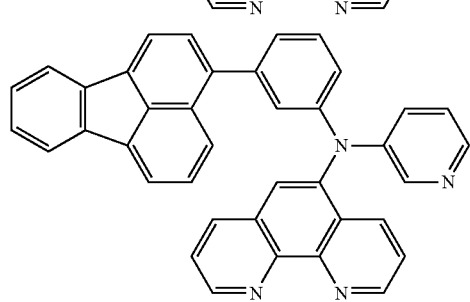

[Chemical Formula 39]
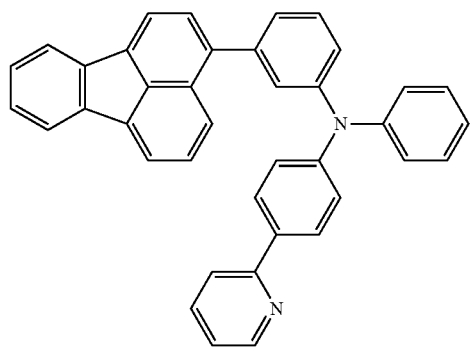
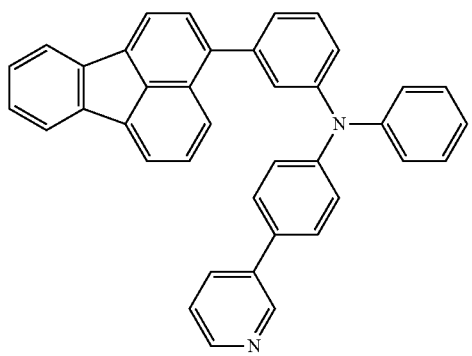
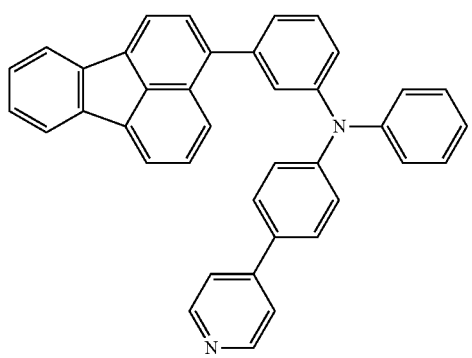
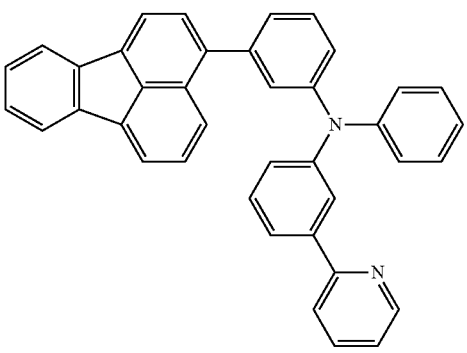
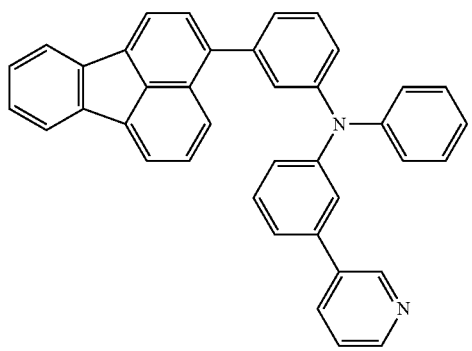
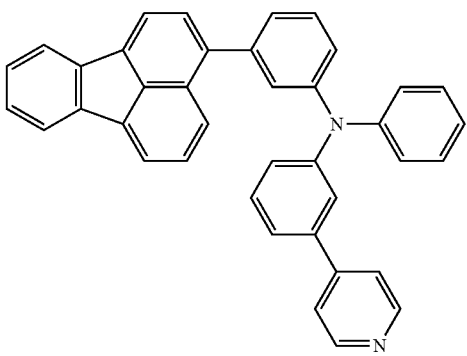
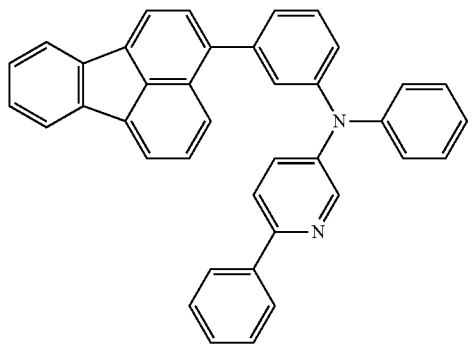
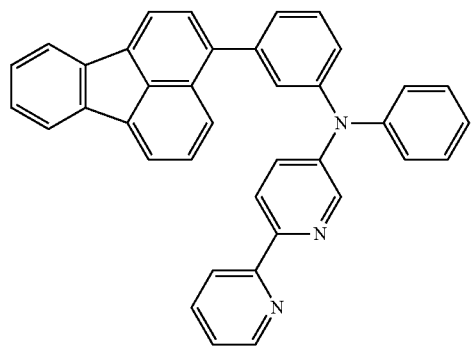

141
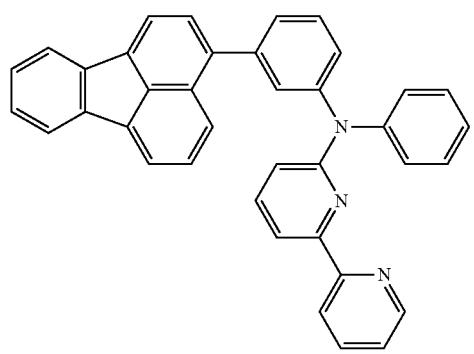
142
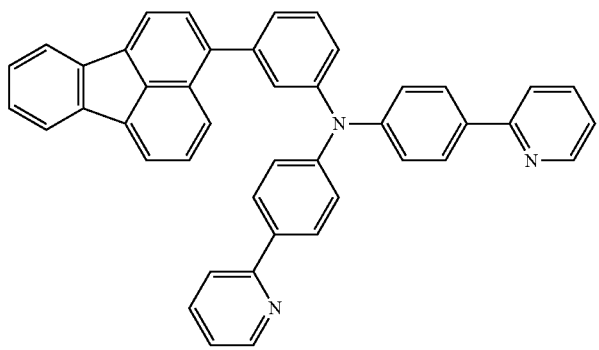
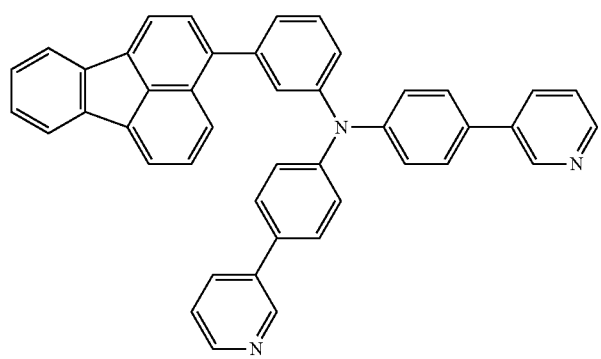
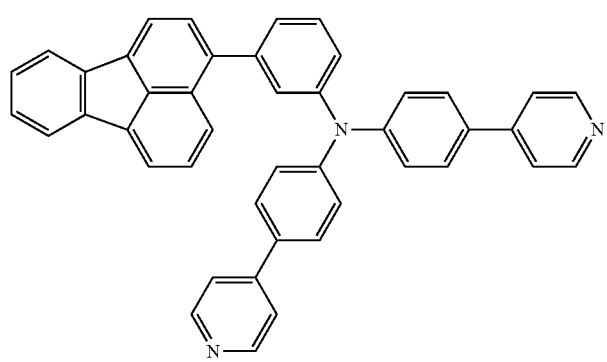
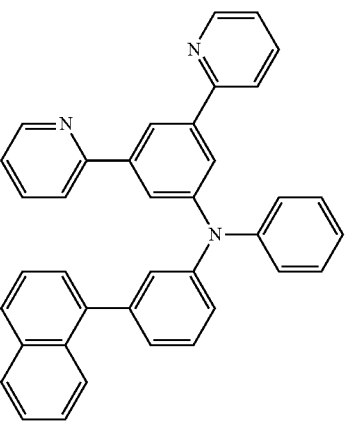
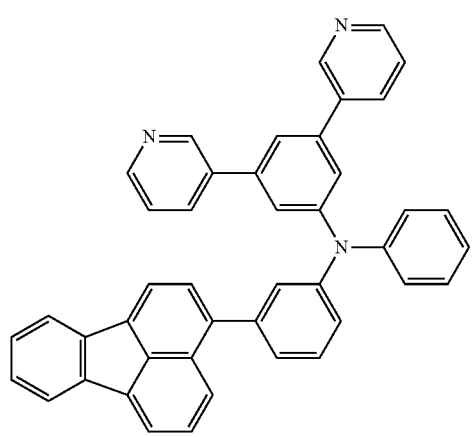
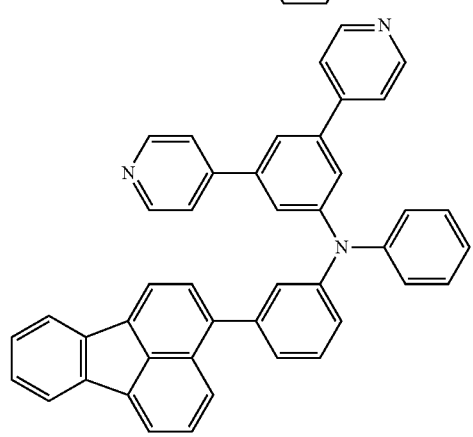

143
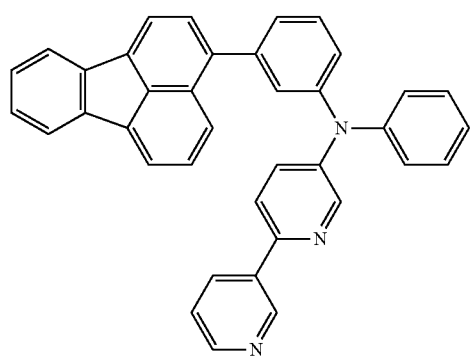
144
-continued
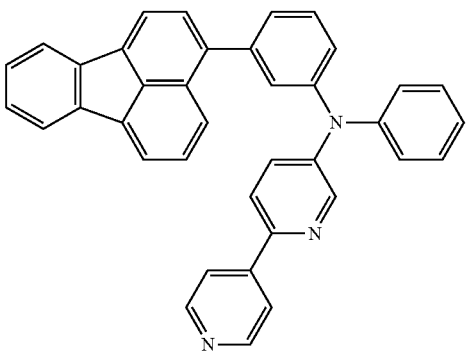
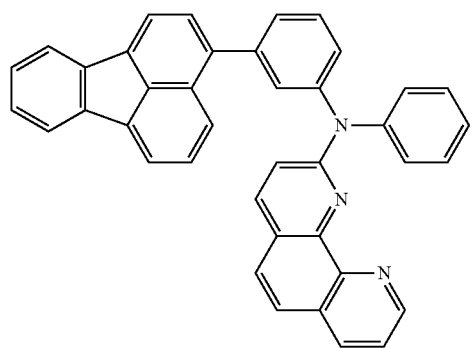
[Chemical Formula 40]
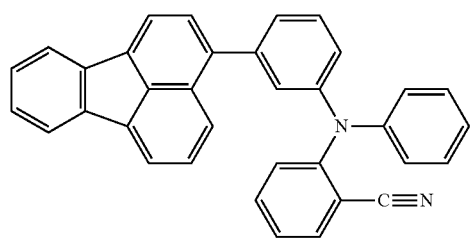
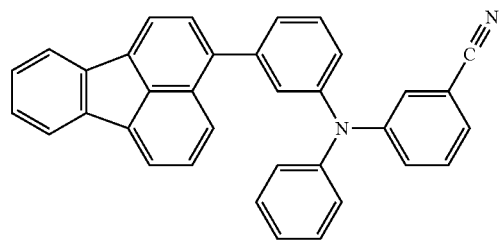
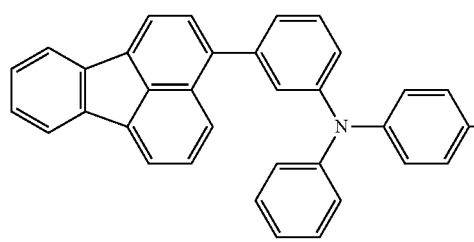
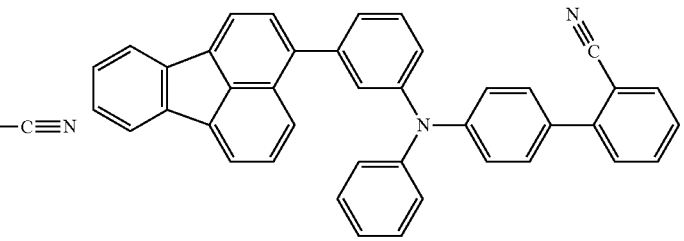
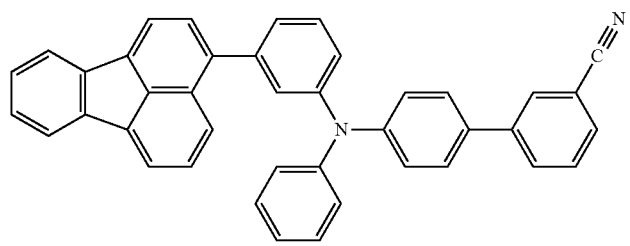
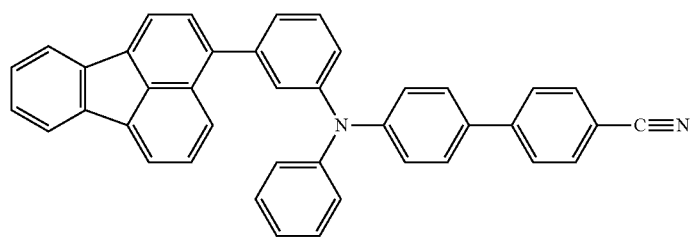

145
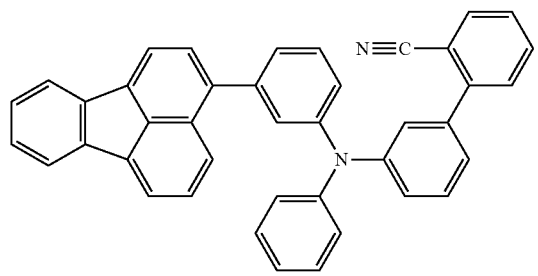
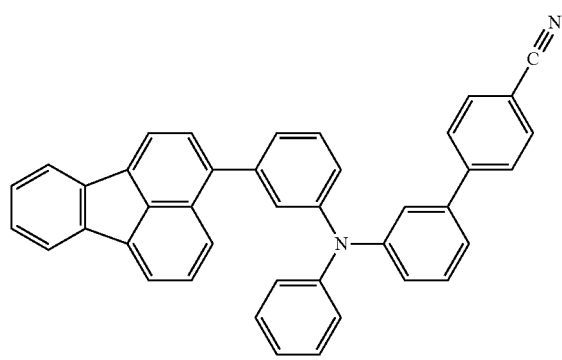
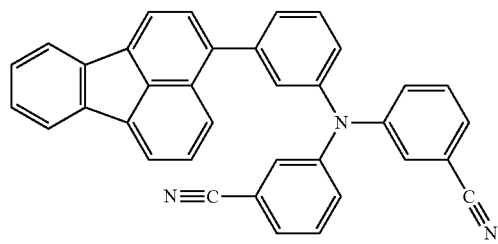
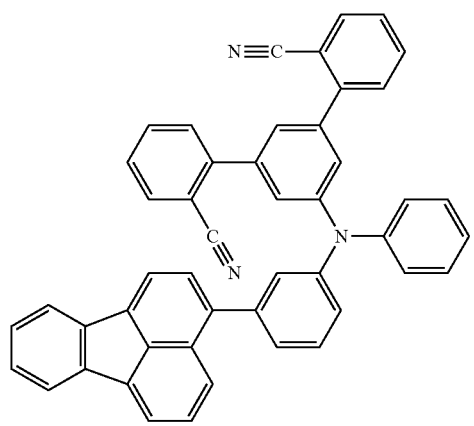
146
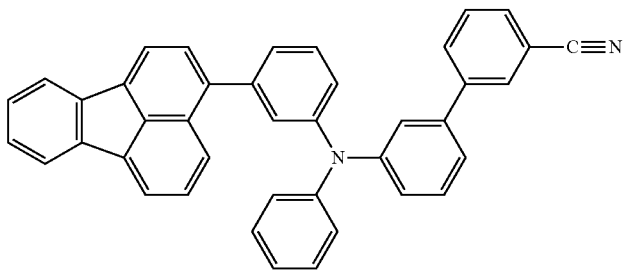
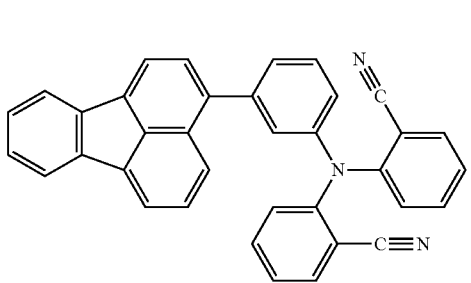
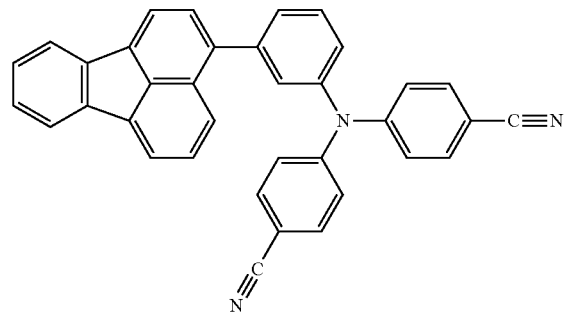
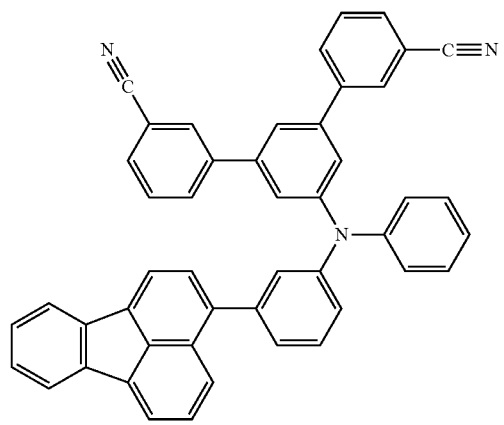

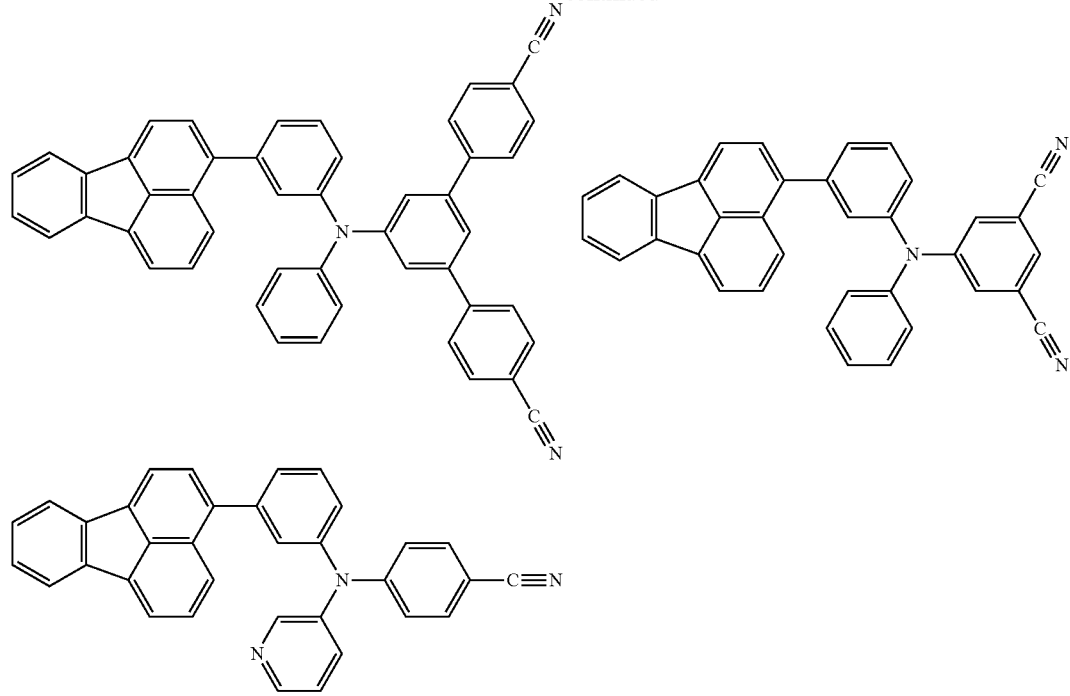
[Chemical Formula 41]
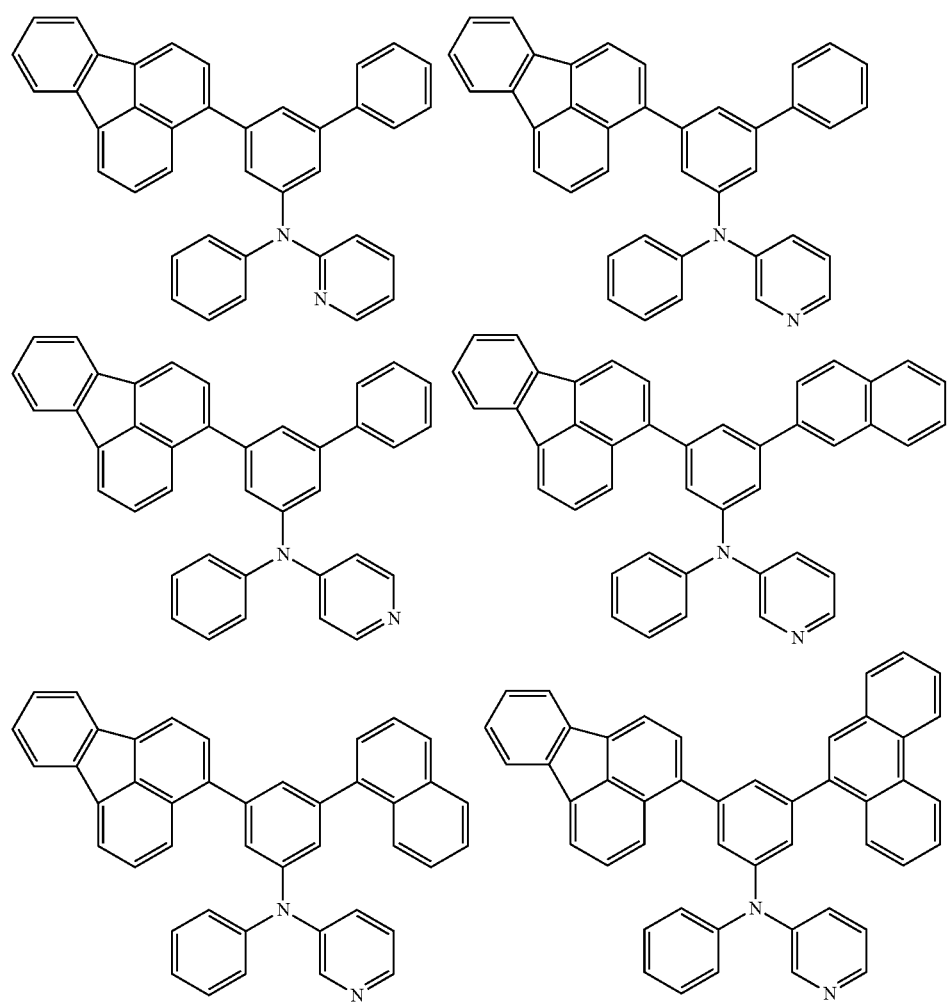

-continued
149
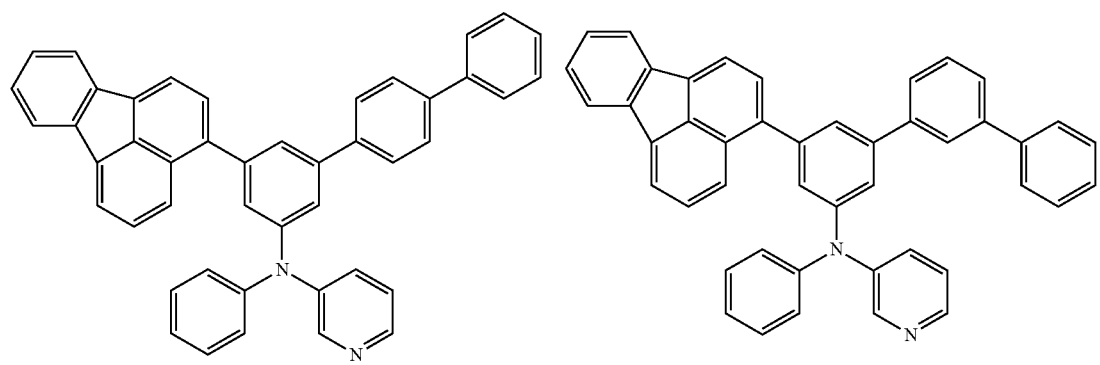
150
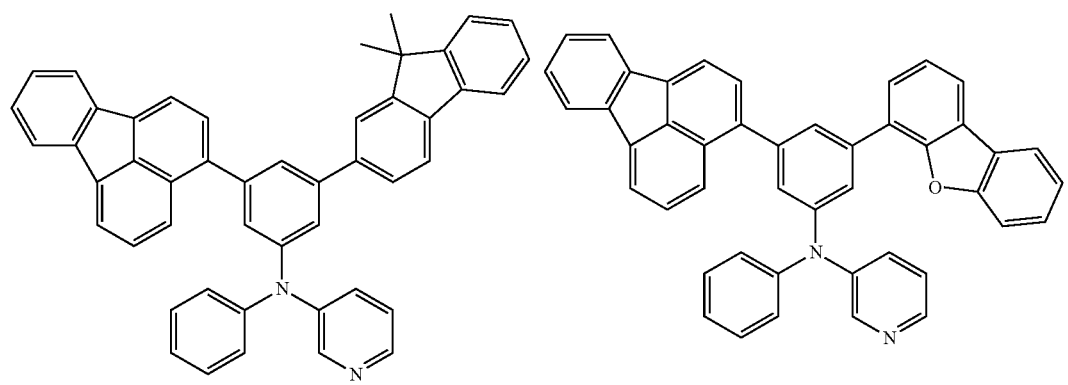
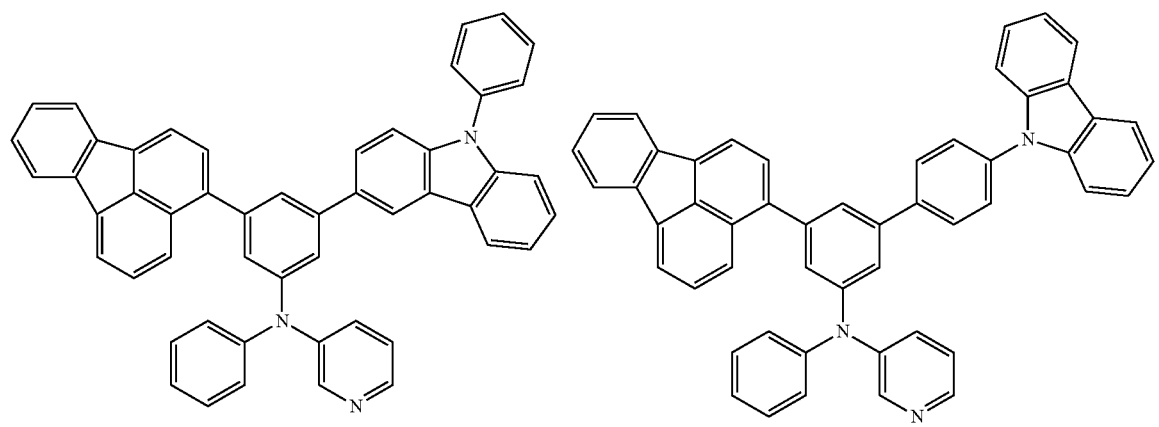
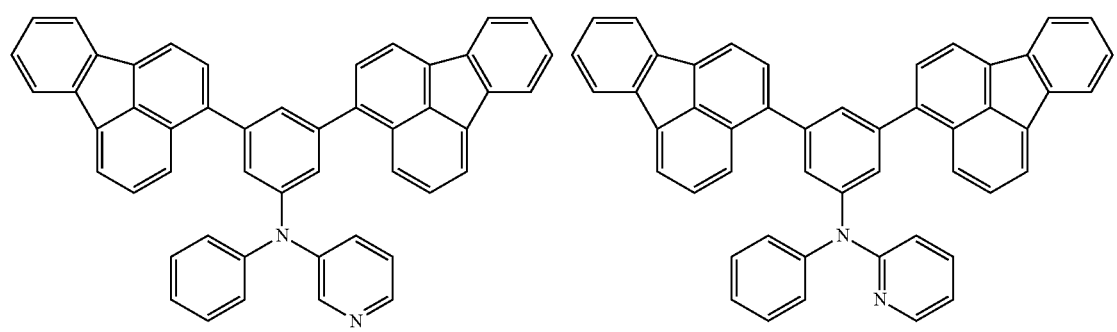

151    152
-continued
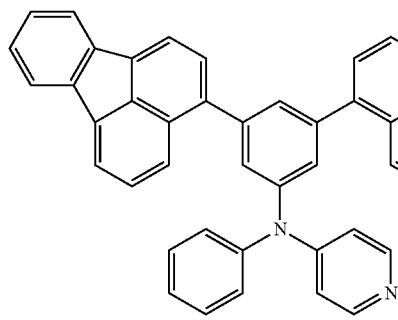
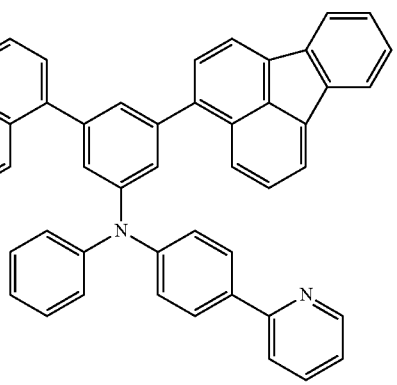
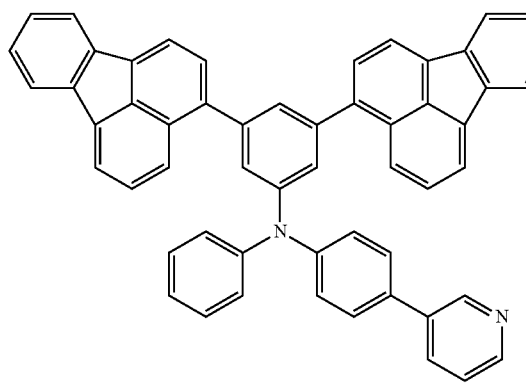
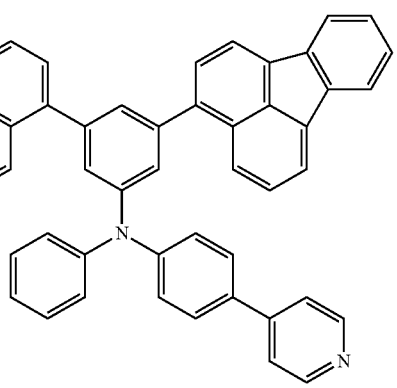
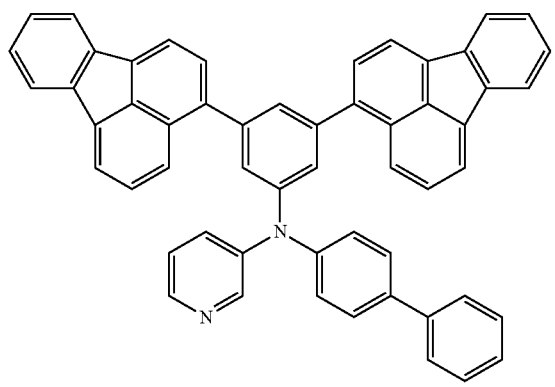
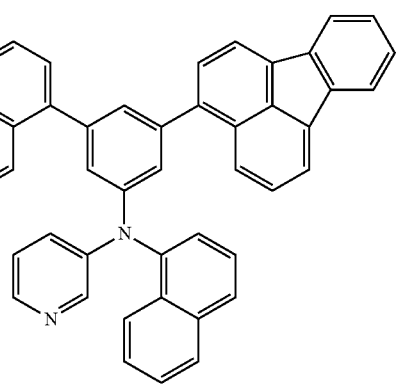
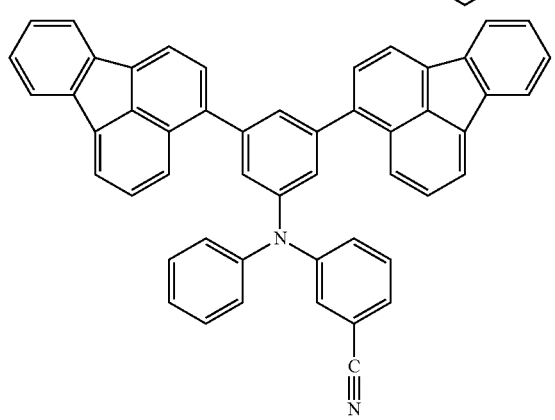

[Chemical Formula 42]
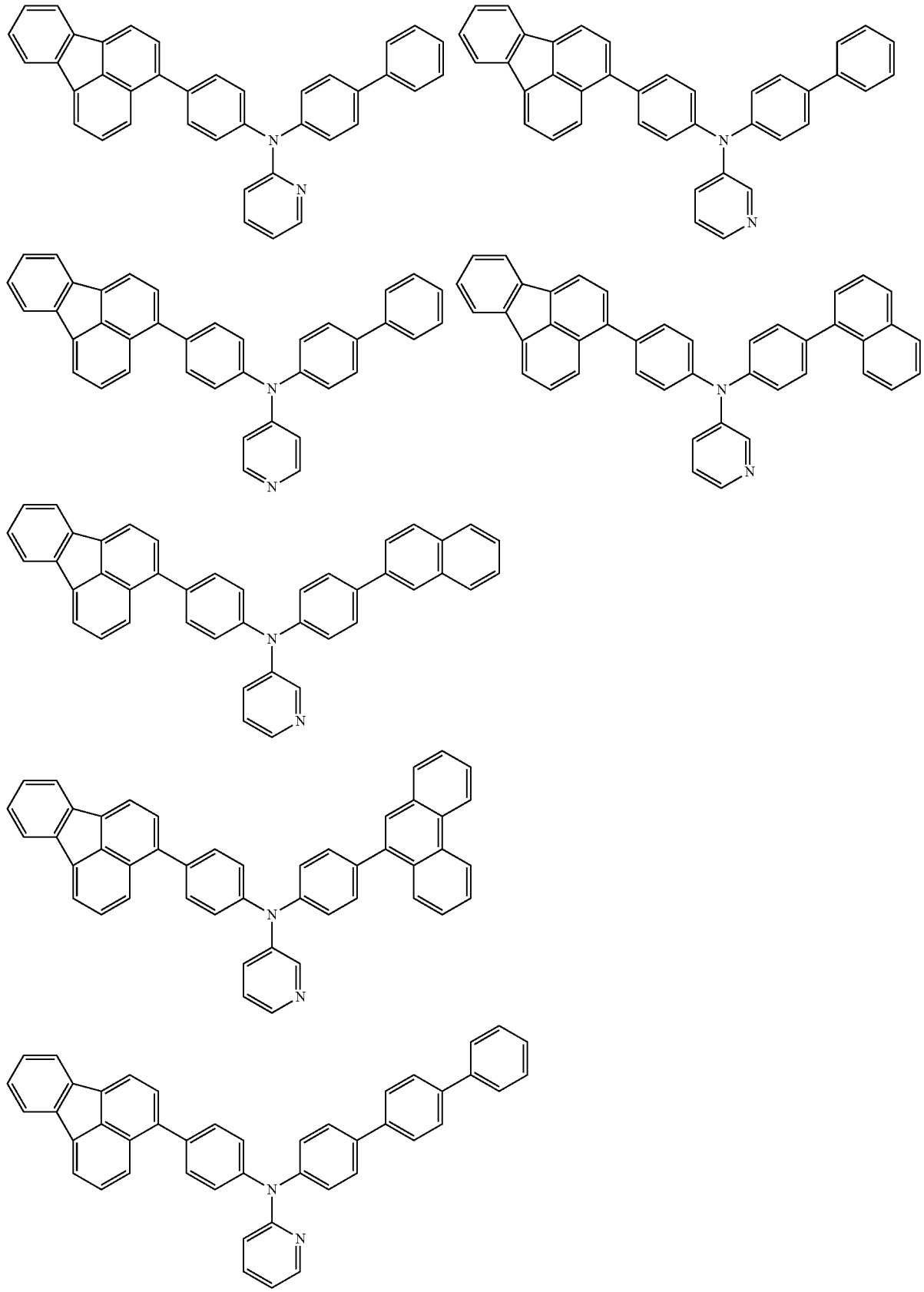

-continued
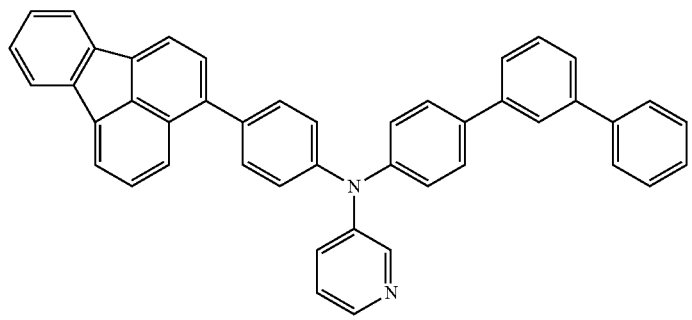
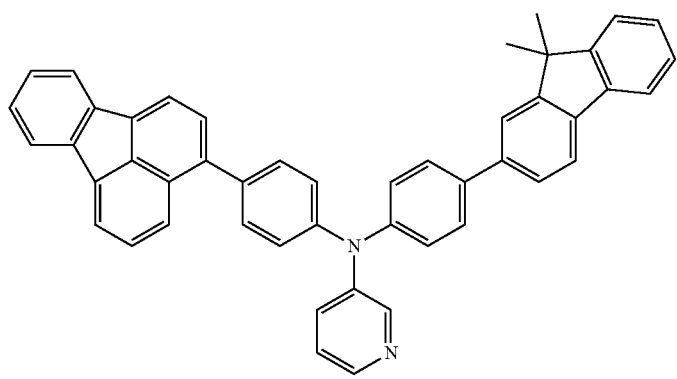
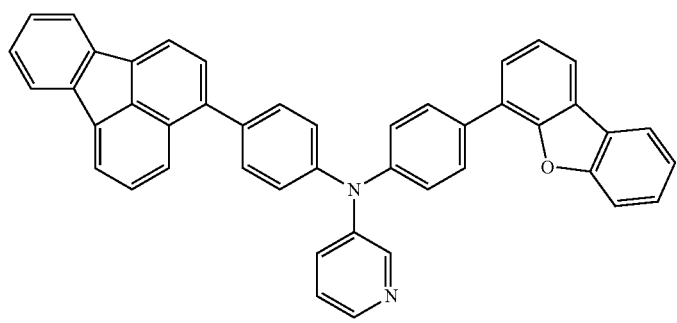
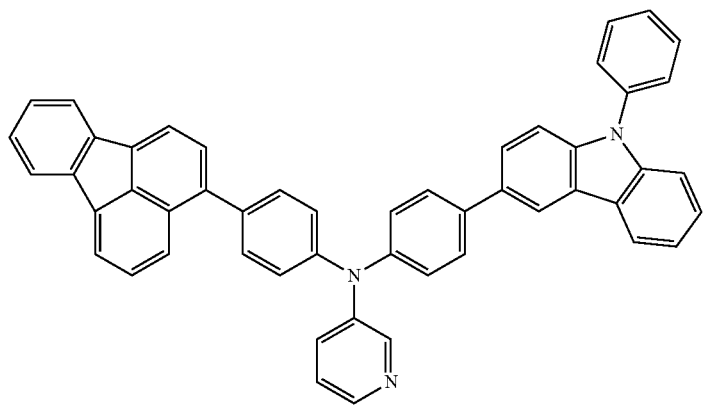

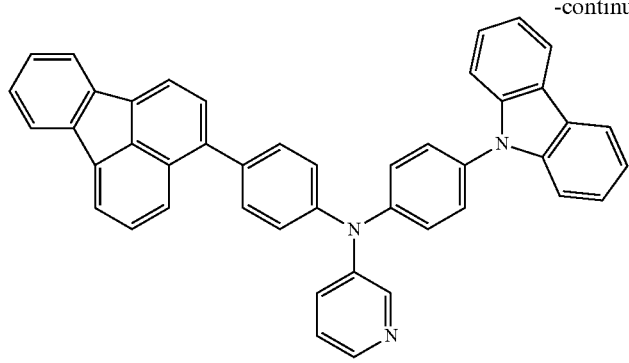
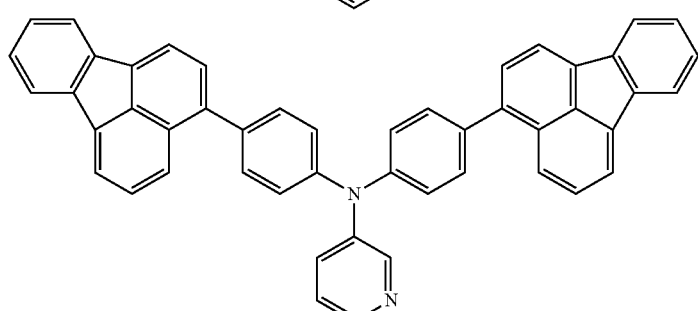
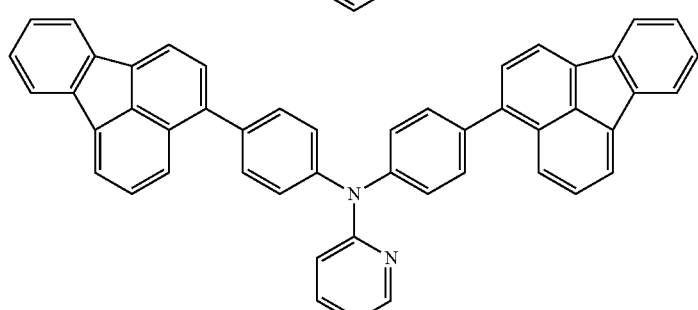
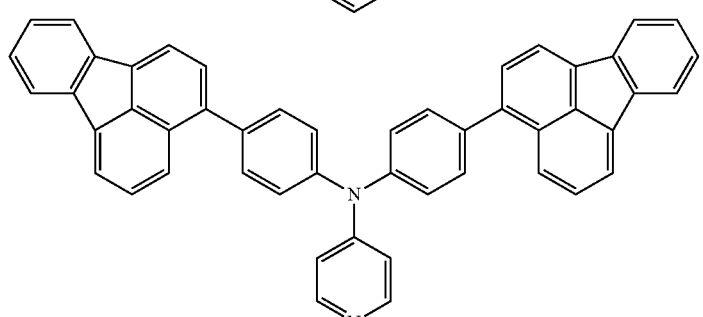
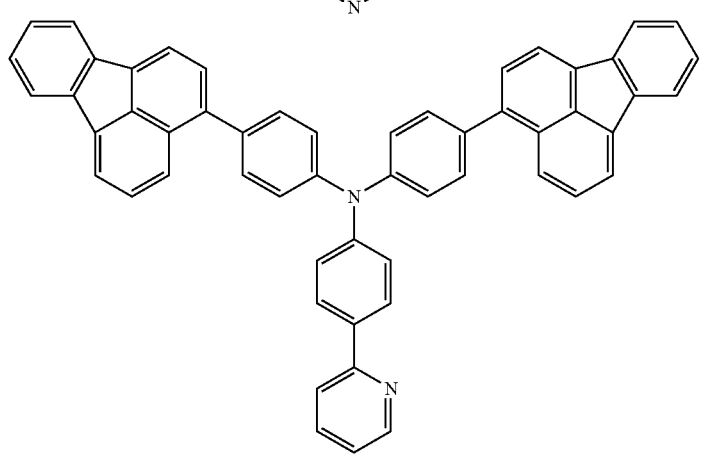

-continued
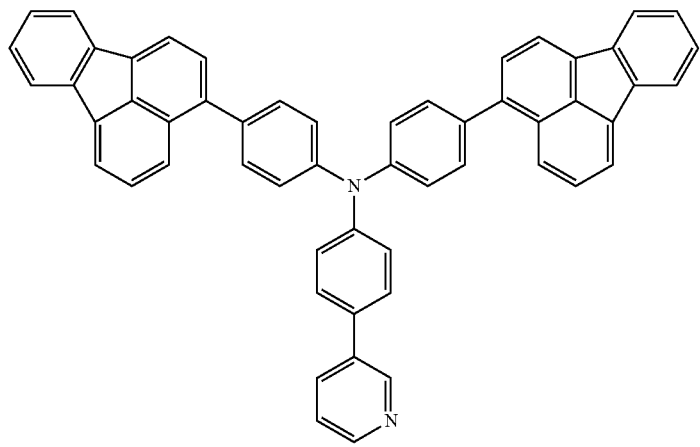
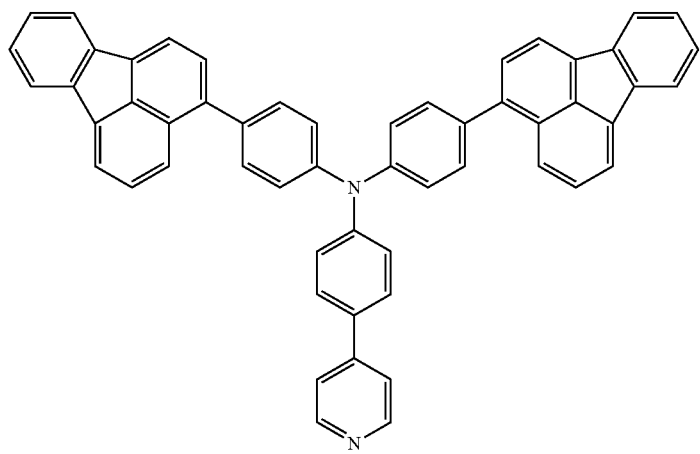
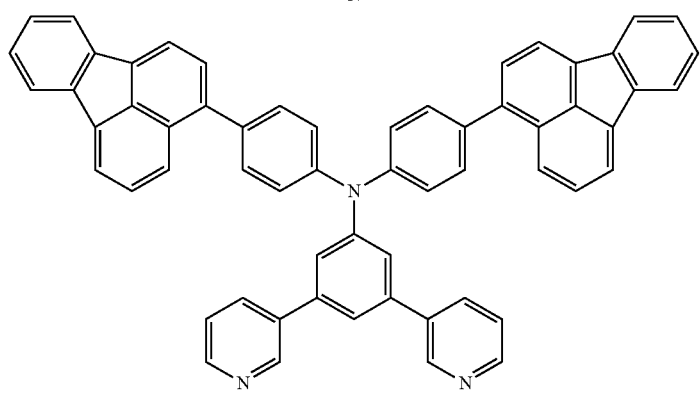
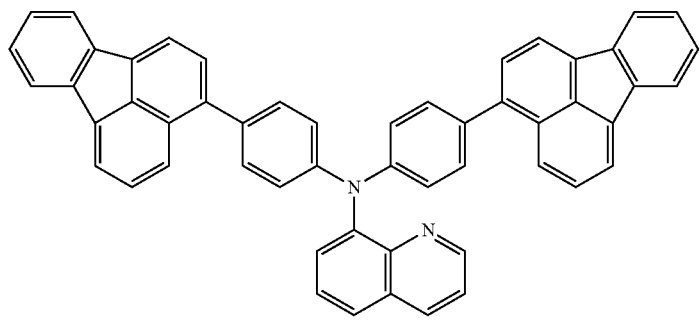

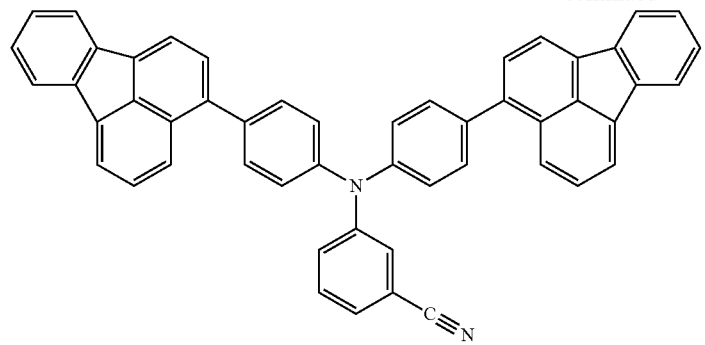
[Chemical Formula 43]
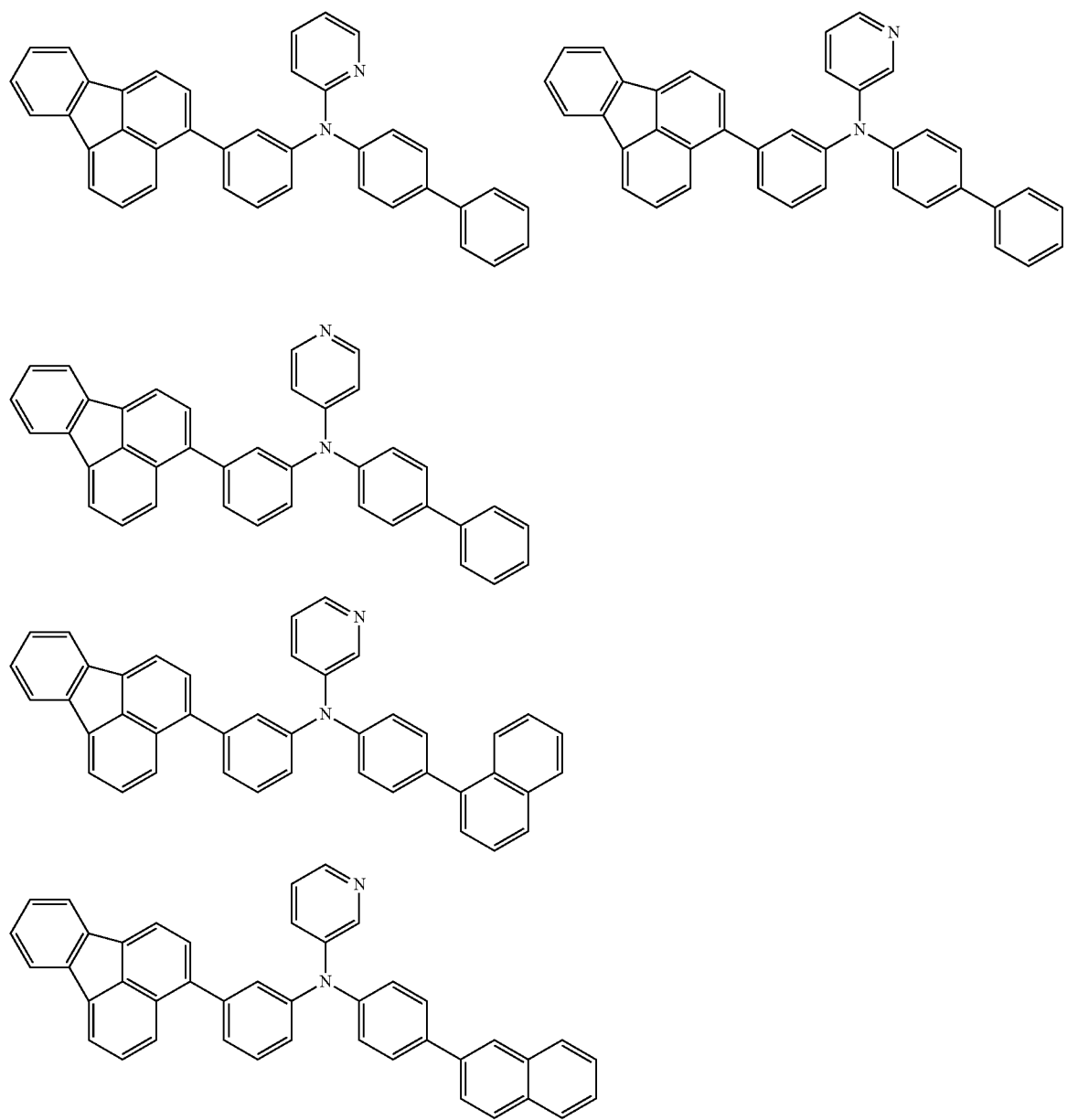

-continued
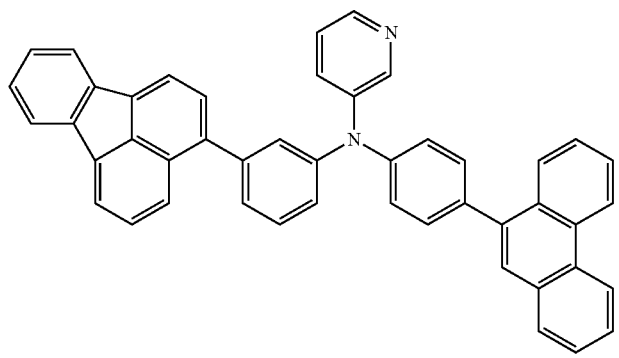
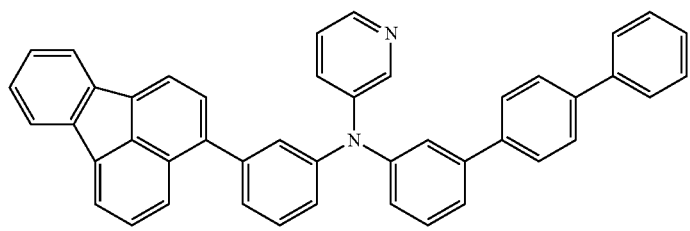
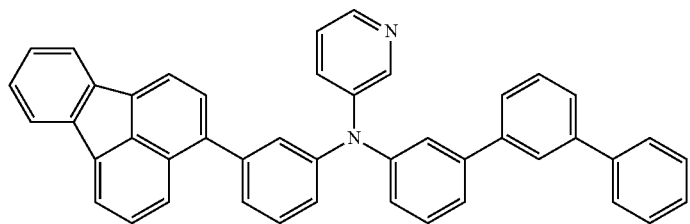
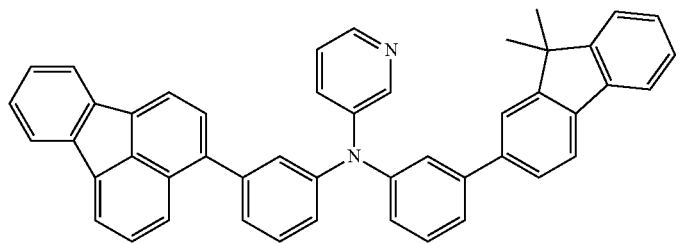
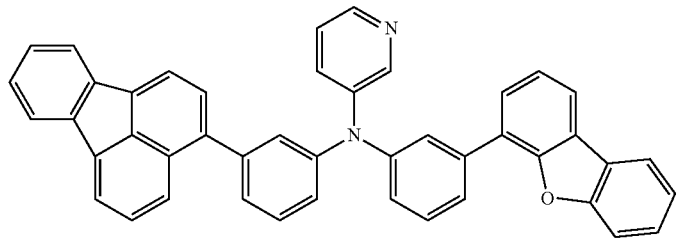
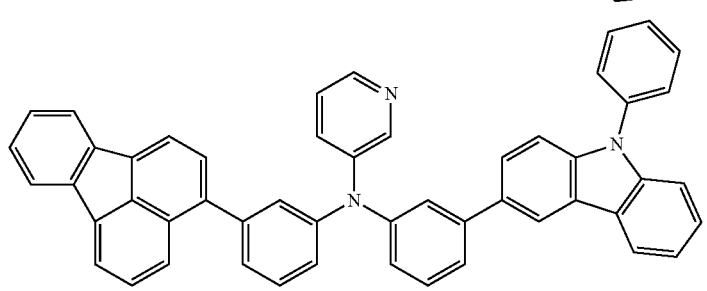

-continued
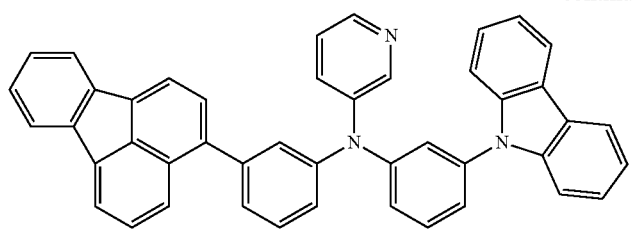
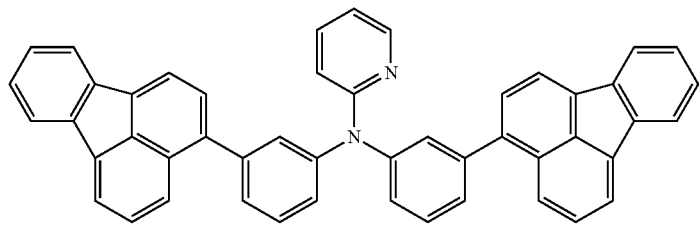
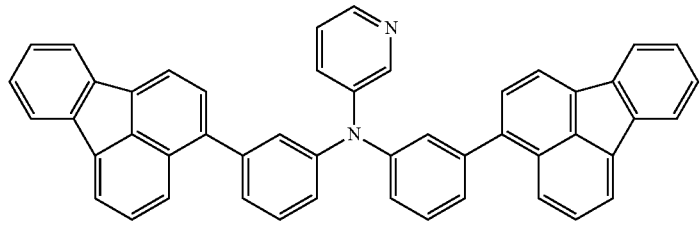
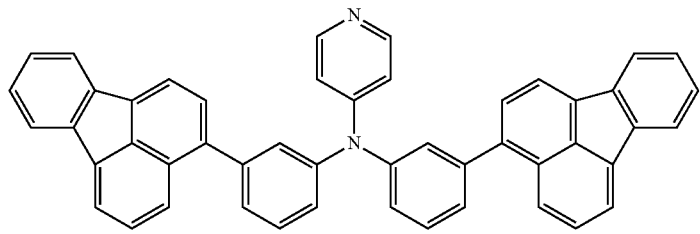
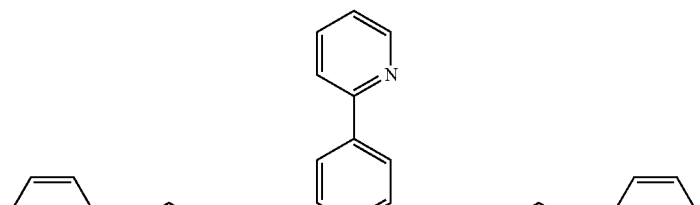
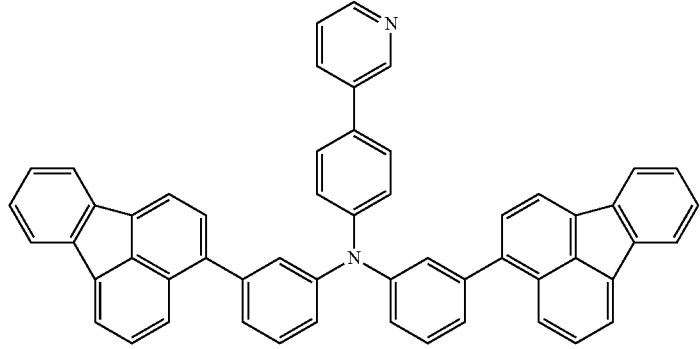

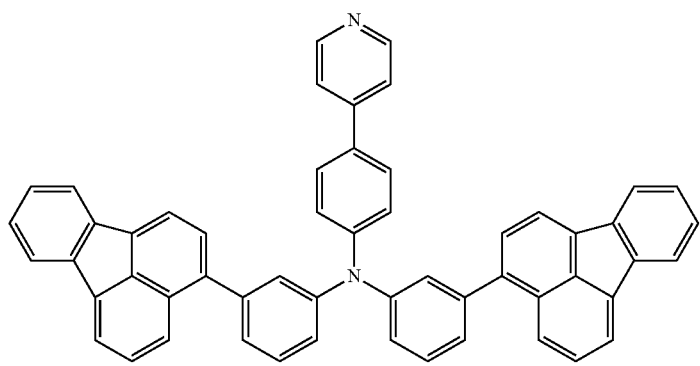
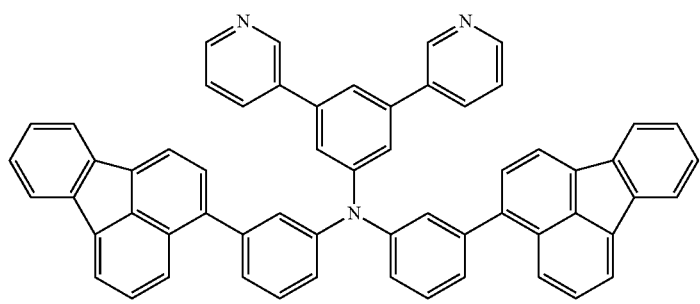
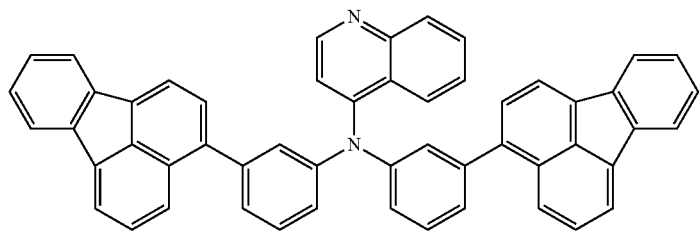
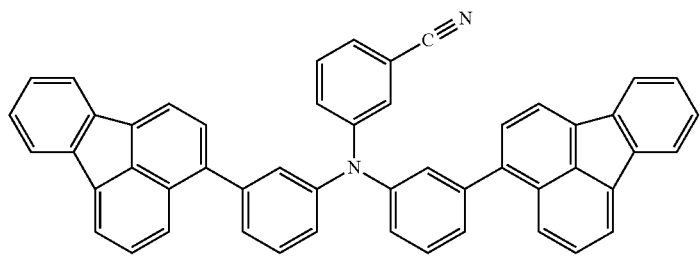
[Chemical Formula 44]
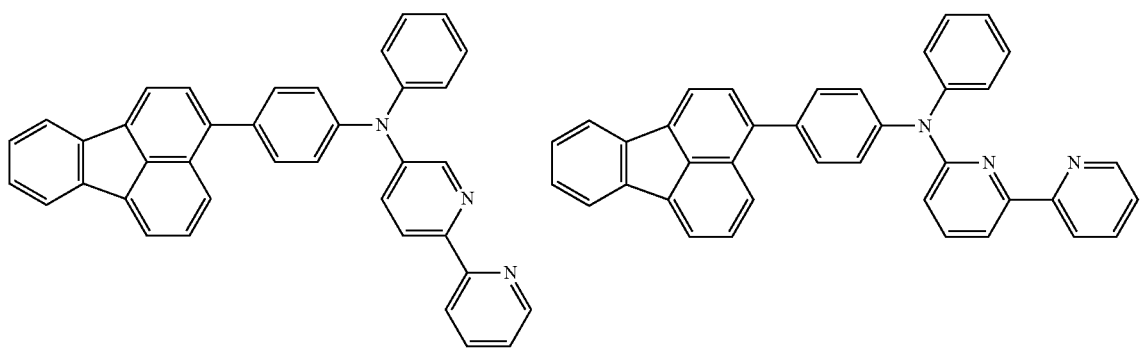

-continued
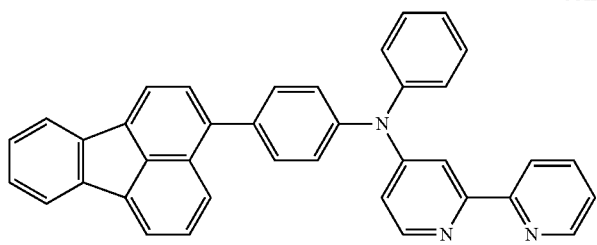
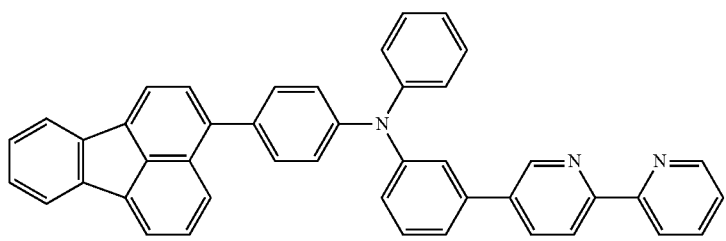
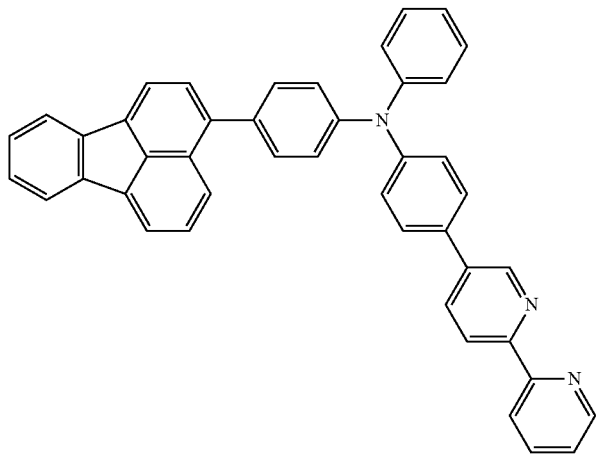
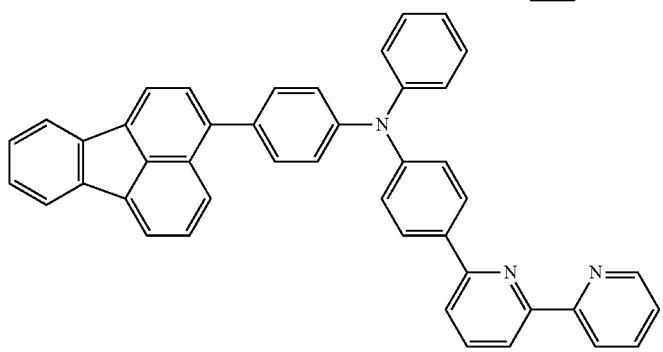
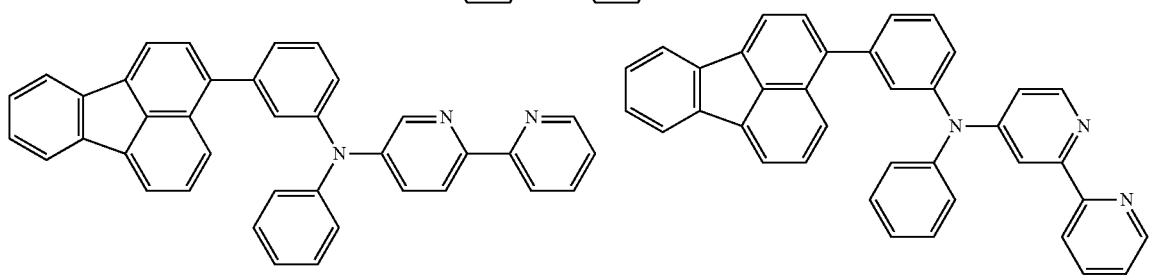

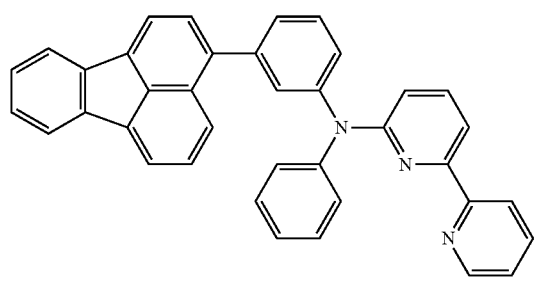
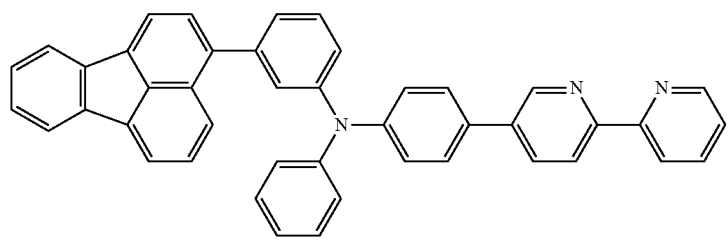
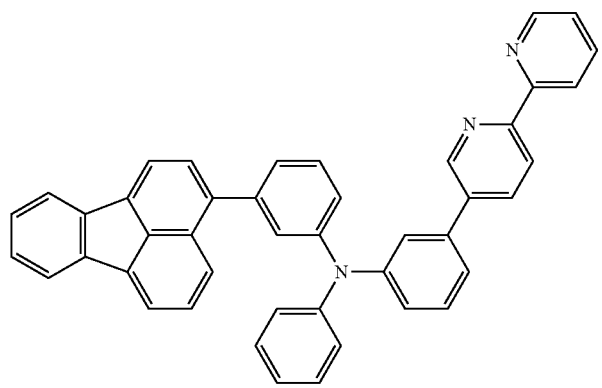
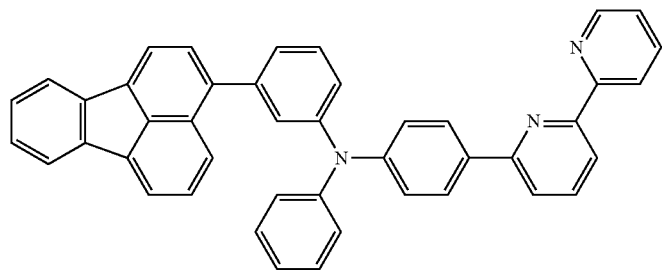
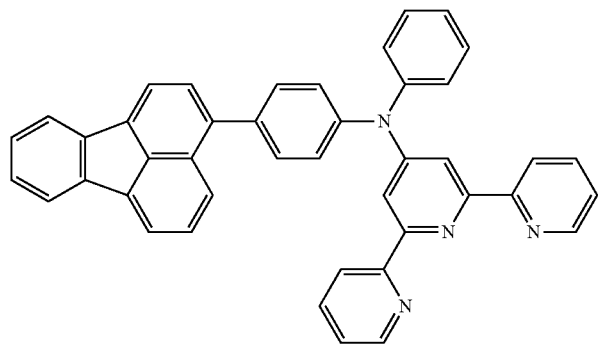

-continued
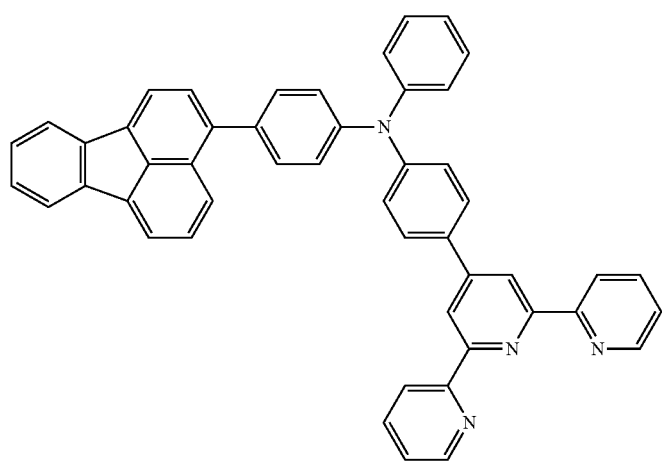
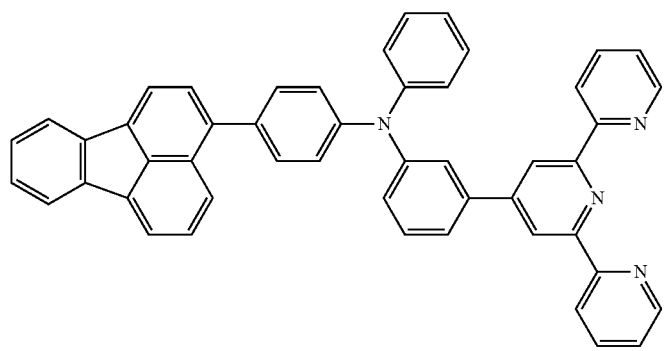
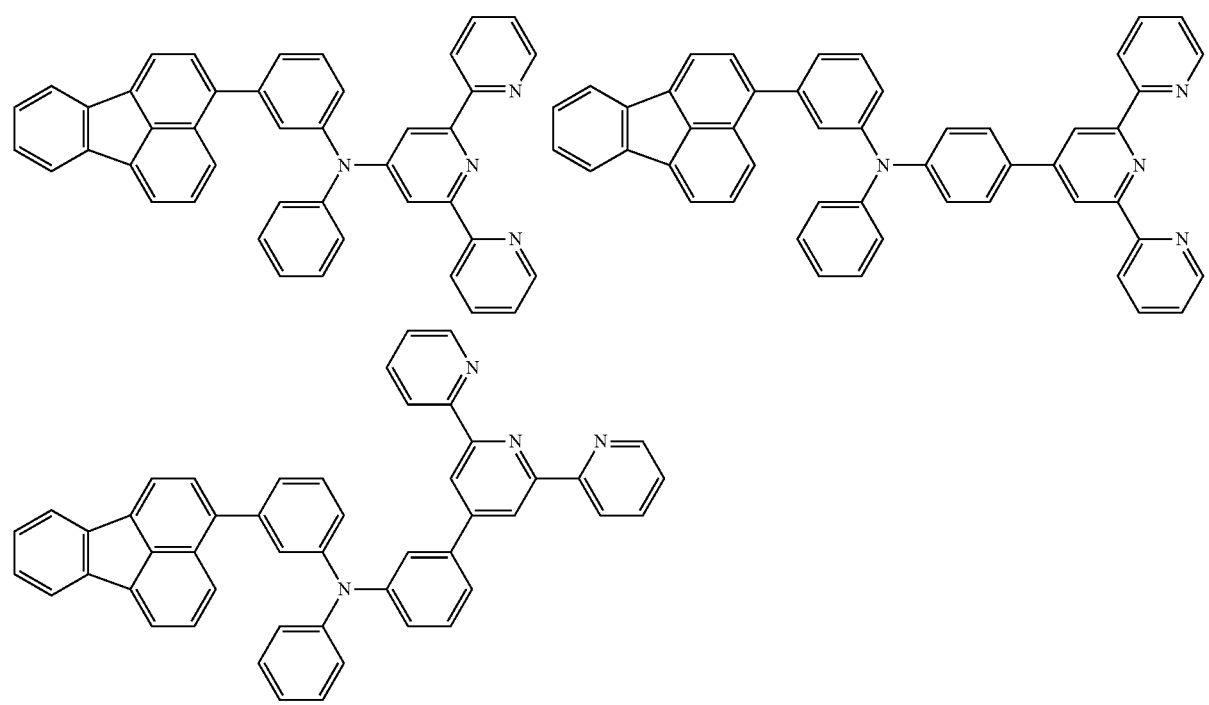

[Chemical Formula 45]
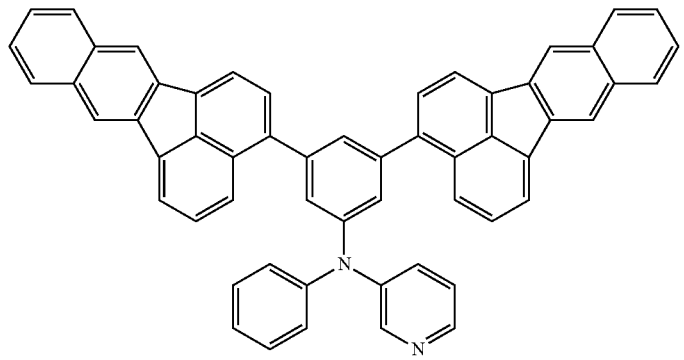
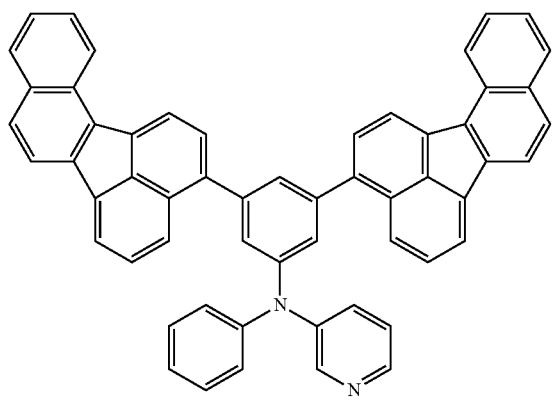
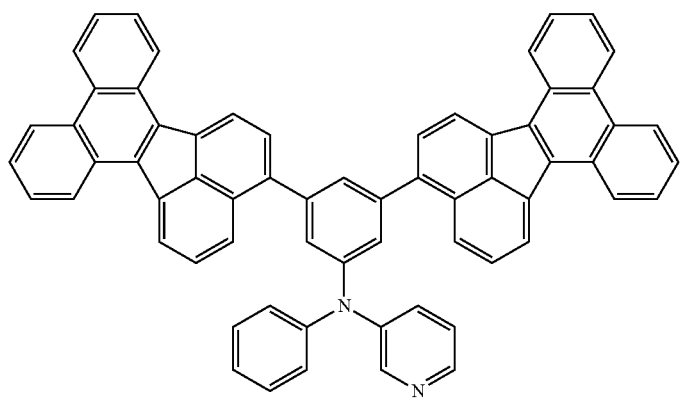
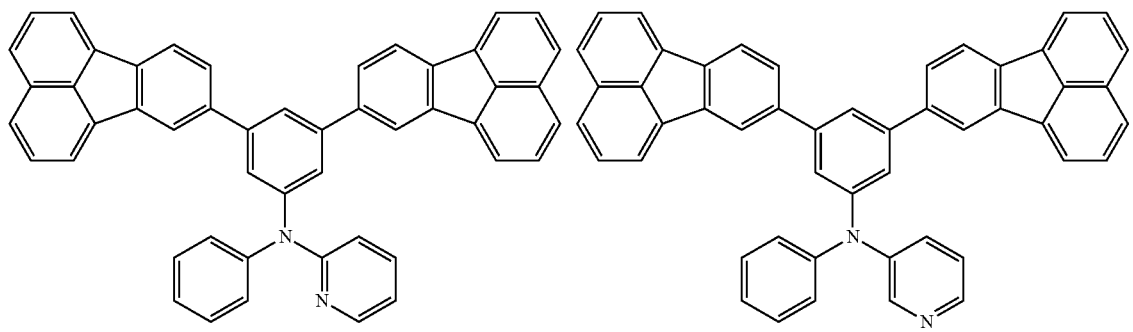

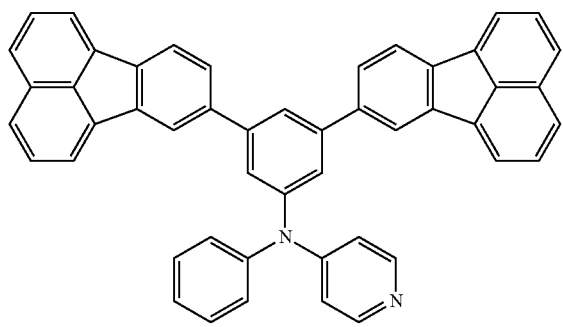
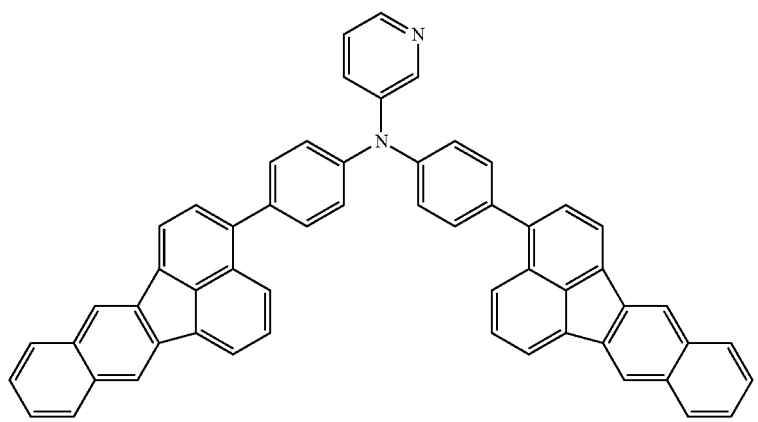
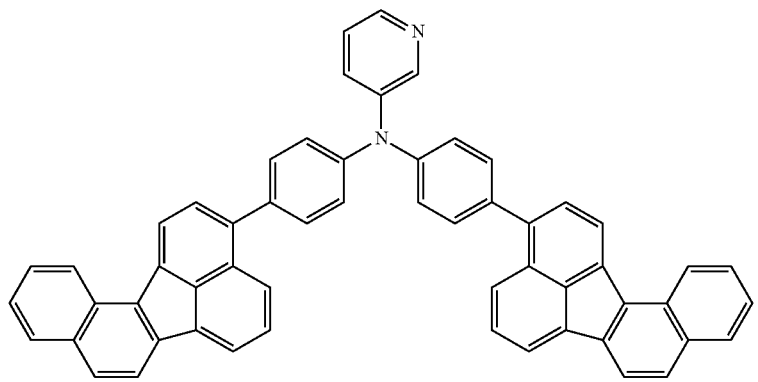
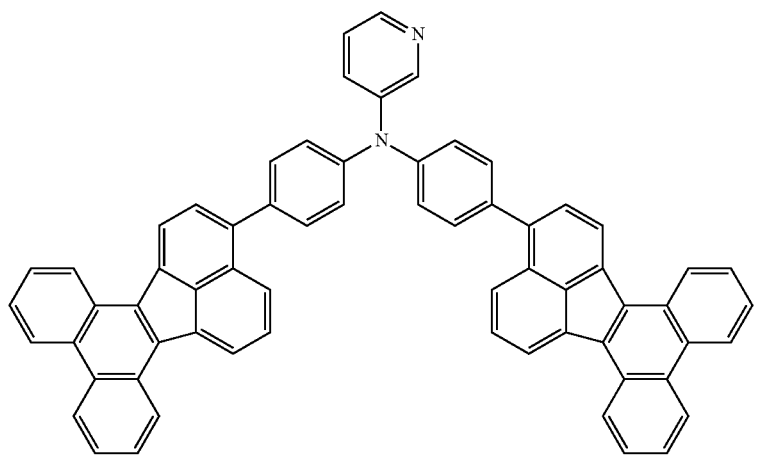

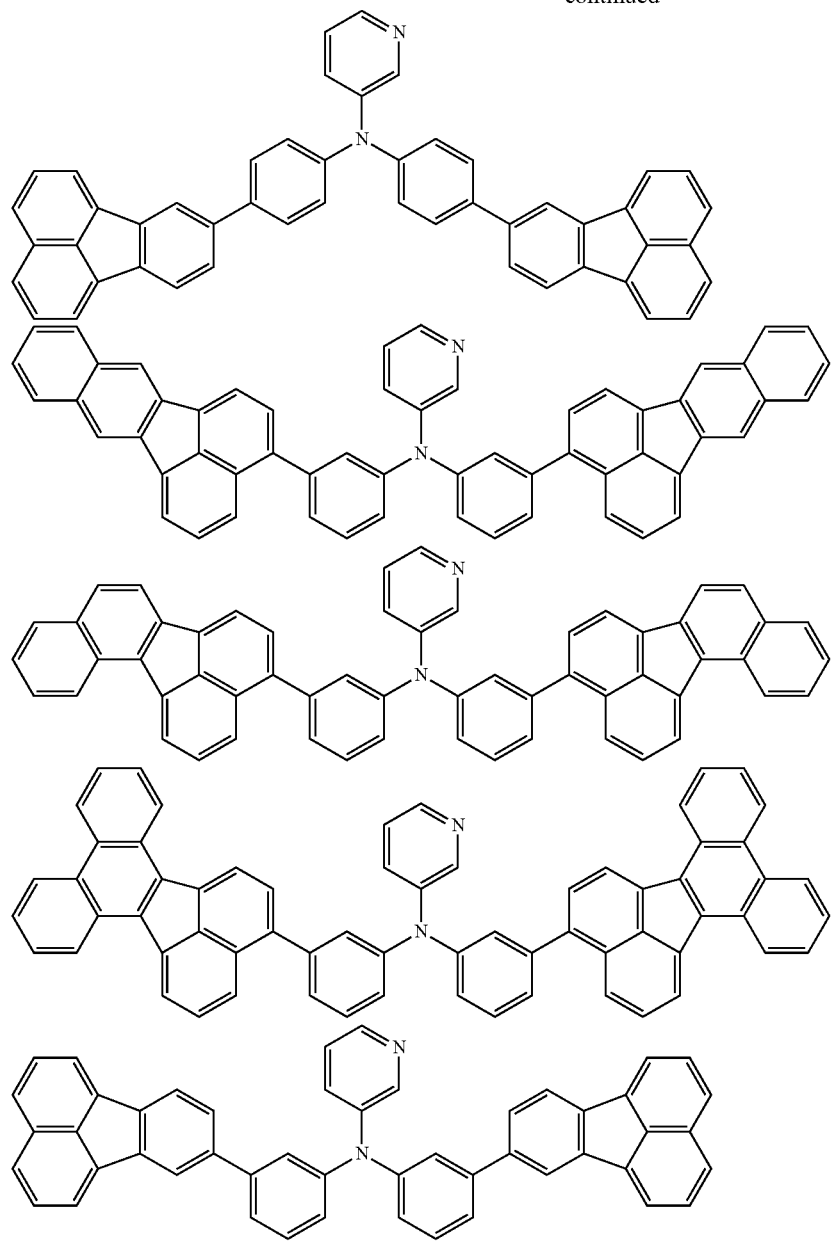

A known method can be used for synthesis of the fluoranthene derivative of the present invention. Examples of the method for introducing $L^2$-N($A^1$)($A^2$) into the fluoranthene skeleton include, but are not limited to, a method using a coupling reaction of a substituted or unsubstituted halogenated fluoranthene derivative and substituted or unsubstituted $L^2$-N($A^1$)($A^2$) under a palladium catalyst or a nickel catalyst. When $L^2$-N($A^1$)($A^2$) is introduced into the fluoranthene skeleton via an arylene group or a heteroarylene group, an arylboronic acid or heteroarylboronic acid substituted with $L^2$-N($A^1$)($A^2$) may be used, or a fluoranthene derivative substituted by an aryl halide may be used. A boronic acid ester may be used in place of the above-mentioned boronic acid.

Preferably, the fluoranthene derivative of the present invention is used as a light-emitting device material. Here, the light-emitting device material of the present invention denotes a material to be used in any layer of a light-emitting device and includes a material to be used in a protective film of a cathode, in addition to materials to be used in one of a hole transporting layer, an emissive layer and an electron transporting layer as described later. Use of the fluoranthene derivative of the present invention in any layer of a light-emitting device can afford high luminous efficiency and also can afford a light-emitting device having a low driving voltage and high durability.

Next, embodiments of the light-emitting device of the present invention will be described in detail. The light-emitting device of the present invention has an anode and a cathode, and an organic layer interposed between the anode and the cathode, the organic layer includes at least an emissive layer and an electron transporting layer, and the emissive layer emits light by electric energy.

Examples of the laminated configuration of the organic layer include, besides a configuration made up of only emissive layer/electron transporting layer, laminated configurations such as 1) hole transporting layer/emissive layer/electron transporting layer, 2) hole transporting layer/emissive layer/electron transporting layer/electron injection layer, and 3) hole injection layer/hole transporting layer/emissive layer/electron transporting layer/electron injection layer. Each of the layers may be in the form of a single layer or a plurality of layers.

The fluoranthene derivative of the present invention may be used for any layer in the above-mentioned device configuration, but is preferably used for the emissive layer or electron transporting layer of the light-emitting device because it has high electron injection/transporting abilities, a high fluorescence quantum yield and high thin-film stability. Particularly, the fluoranthene derivative has excellent electron injection/transporting abilities, and is therefore more preferably used for the electron transporting layer.

In the light-emitting device of the present invention, the anode and the cathode have a role for supplying a sufficient current for light emission of the device, and it is preferred that at least one of them is transparent or translucent in order to take out light. Usually, the anode formed on a substrate is made to be a transparent electrode.

While the material to be used for an anode is not particularly limited and may be electroconductive metal oxides, such as tin oxide, indium oxide, indium tin oxide (ITO), and indium zinc oxide (IZO), metals, such as gold, silver, and chromium, inorganic electroconductive substances, such as copper iodide and copper sulfide, or electroconductive polymers, such as polythiophene, polypyrrole, and polyaniline as long as being a material that is capable of injecting holes into an organic layer efficiently and that is transparent or translucent in order to take out light, use of ITO glass or NESA glass is particularly preferable. These electrode materials may be used alone, or a plurality of materials may be used in lamination or in admixture. Since it is favorable that a sufficient current for light emission of the device can be supplied, the resistance of a transparent electrode is not limited, but from the viewpoint of the power consumption of the device, a low resistance is desirable. For example, an ITO substrate having a resistance of 300Ω☐ or lower functions as a device electrode, but since it is currently possible to supply a substrate having a resistance of about 10Ω☐, it is particularly preferable to use a substrate having a low resistance of 20Ω☐ or lower. The thickness of ITO can be arbitrarily selected according to a resistance value, but ITO is usually used at a thickness of between 100 to 300 nm in many cases.

In addition, in order to retain the mechanical strength of the light-emitting device, it is preferred to form the light-emitting device on a substrate. As the substrate, a glass substrate such as soda glass or alkali-free glass is suitably used. Since it is favorable that the thickness of a glass substrate has a sufficient thickness for retaining the mechanical strength, a thickness of 0.5 mm or more is sufficient. Regarding the material of glass, since it is preferred that the amount of ions eluted from glass is small, alkali-free glass is more preferable. Alternatively, since soda lime glass provided with a barrier coating such as $SiO_2$ is commercially available, it can also be used. Further, as far as the first electrode stably functions, it is not necessary that the substrate is glass and, for example, the anode may be formed on a plastic substrate. Examples of a method of forming an ITO film include, but are not particularly limited to, an electron beam method, a sputtering method, and a chemical reaction method.

A material, to be used in the cathode is not particularly limited, as far as it is a substance which can efficiently inject electrons into the emissive layer. Generally, metals such as platinum, gold, silver, copper, iron, tin, aluminum, and indium, or alloys or multilayer lamination of these metals with metals having a low work function such as lithium, sodium, potassium, calcium and magnesium are preferred. Among them, as a main component, aluminum, silver, and magnesium are preferred from the viewpoints of electric resistance value, easiness of making a film, stability of a film, and luminous efficiency. In particular, it is preferred that the material is constituted by magnesium and silver because electron injection into the electron transporting layer and the electron injection layer in the present invention becomes easy, and low voltage driving becomes possible.

Further, preferable examples include lamination of metals such as platinum, gold, silver, copper, iron, tin, aluminum, and indium, or alloys using these metals, inorganic substances such as silica, titania, and silicon nitride, and organic polymer compounds such as polyvinyl alcohol, polyvinyl chloride, and a hydrocarbon-based polymer compound as a protective film layer on the cathode for protecting the cathode. The fluoranthene derivative of the present invention can also be used as the protective film layer. However, in the case of a device structure for taking out light from the cathode side (top emission structure), the protective film layer is selected from materials having light permeability in a visible light region. Examples of a method for preparation of these electrodes include, but are not particularly limited to, resistance heating, electron beam, sputtering, ion plating and coating.

The hole transporting layer is formed by a method in which one or more hole transporting materials are laminated or mixed, or a method using a mixture of a hole transporting material and a polymer binder. The hole transporting material is required to efficiently transport holes from a positive electrode between electrodes given an electric field, and preferably has high hole injection efficiency and efficiently transports injected holes. For this purpose, the hole transporting material is required to be a substance having an appropriate ionization potential and, moreover, great hole mobility and, further, excellent stability, and generating impurities that become a trap with difficulty at the time of production and at the time of use. The substance satisfying the above-mentioned requirements is not particularly limited, and, for example, benzidine derivatives such as 4,4'-bis(N-(3-methylphenyl)-N-phenylamino)biphenyl (TPD), 4,4'-bis(N-(1-naphthyl)-N-phenylamino)biphenyl (NPD), 4,4'-bis(N,N-bis(4-biphenylyl)amino)biphenyl (TBDB) and bis(N,N'-diphenyl-4-aminophenyl)-N,N-diphenyl-4,4'-diamino-1,1'-biphenyl (TPD232); materials called starburst arylamines, such as 4,4',4"-tris(3-methylphenyl(phenyl)amino)triphenylamine (m-MTDATA) and 4,4',4"-tris(1-naphthyl(phenyl)amino)triphenylamine (1-TNATA); materials having a carbazole skeleton, particularly carbazole polymers, specifically derivatives of a carbazole dimer such as bis(N-arylcarbazole) or bis(N-alkylcarbazole), derivatives of a carbazole trimer and derivatives of a carbazole tetramer; triphenylene compounds; pyrazoline derivatives; stilbene-based compounds; hydrazone-based compounds; benzofuran derivatives; heterocyclic compounds such as thiophene derivatives, oxadiazole derivatives, phthalocyanine derivatives and porphyrin derivatives; fullerene derivatives; and such polymers as polycarbonates and styrene derivatives having the aforementioned monomers on their side chains, polythiophene, polyaniline, polyfluorene, polyvinylcarbazole and polysilane are preferred. Further, inorganic compounds such as p-type Si and p-type SiC can also be used.

The fluoranthene derivative of the present invention can also be used as a hole transporting material because it has great hole mobility and, further, excellent electrochemical stability. The fluoranthene derivative of the present invention may be used as a hole injection material, but is suitably used as a hole transporting material because it has high hole mobility.

The fluoranthene derivative of the present invention has excellent electron injection/transporting properties, and therefore when the light-emitting device material is used for the electron transporting layer, there is the possibility that electrons are not recombined in the emissive layer, and are partially leaked to the hole transporting layer. Therefore, it is preferred that a compound excellent in electron blocking property is used for the hole transporting layer. Particularly, a compound containing a carbazole skeleton is preferred because it is excellent in electron blocking property, and can contribute to an increase in efficiency of the light-emitting device. Further, it is preferred that the compound containing a carbazole skeleton contains a carbazole dimer, carbazole trimer or carbazole tetramer skeleton. This is because they have both a proper electron blocking property and proper hole injection/transporting properties. Further, when the compound containing a carbazole skeleton is used for the hole transporting layer, it is more preferable that an emissive layer to be combined contains the later-described phosphorescence emitting material. This is because the compound having a carbazole skeleton has a high triplet exciton blocking function, so that luminous efficiency can be increased when the compound is combined with a phosphorescence emitting material. Use of a triphenylene skeleton-containing compound, excellent in that it has high hole mobility, for the hole transporting layer is preferred because a carrier balance is improved, so that the effects of improving luminous efficiency and improving durable life can be obtained. It is further preferable that the compound containing a triphenylene skeleton has two or more diarylamino groups. The compound containing a carbazole skeleton and the compound containing a triphenylene skeleton may be each used alone as a hole transporting layer, or may be mixed and used. Other materials may be mixed as long as the effects of the present invention are not impaired. When the hole transporting layer includes a plurality of layers, any one layer should contain the compound containing a carbazole skeleton or the compound containing a triphenylene skeleton.

A hole injection layer may be provided between an anode and a hole transporting layer. When a hole injection layer is provided, the light-emitting device has a reduced driving voltage, and durable life is improved. A material having an ionization potential smaller than that of a material which is usually used for the hole transporting layer is preferably used for the hole injection layer. Specific examples include benzidine derivatives such as TPD232, and starburst arylamine materials, and besides, phthalocyanine derivatives can also be used. It is preferred that the hole-injection layer is formed of an acceptor compound alone, or used with another hole transporting material doped with an acceptor compound. Examples of the acceptor compound include metal chlorides such as iron(III) chloride, aluminum chloride, gallium chloride, indium chloride, and antimony chloride, metal oxides such as molybdenum oxide, vanadium oxide, tungsten oxide, and ruthenium oxide, and charge transfer complexes such as tris(4-bromophenyl) aminium hexachloroantimonate (TBPAH). Moreover, organic compounds having a nitro group, a cyano group, halogen, or a trifluoromethyl group in the molecule, quinone-based compounds, acid anhydride-based compounds, and fullerene can also be used suitably. Specific examples of such compounds include hexacyanobutadiene, hexacyanobenzene, tetracyanoethylene, tetracyanoquinodimethane (TCNQ), tetrafluorotetracyanoquinodimethane (F4-TCNQ), 2,3,6,7,10,11-hexacyano-1,4,5,8,9,12-hexaazatriphenylene (HAT-CN6), p-fluoranil, p-chloranil, p-bromanil, p-benzoquinone, 2,6-dichlorobenzoquinone, 2,5-dichlorobenzoquinone, tetramethylbenzoquinone, 1,2,4,5-tetracyanobenzene, o-dicyanobenzene, p-dicyanobenzene, 1,4-dicyanotetrafluorobenzene, 2,3-dichloro-5,6-dicyanobenzoquinone, p-dinitrobenzene, m-dinitrobenzene, o-dinitrobenzene, p-cyanonitrobenzene, m-cyanonitrobenzene, o-cyanonitrobenzene, 1,4-naphthoquinone, 2,3-dichloronaphthoquinone, 1-nitronaphthalene, 2-nitronaphthalene, 1,3-dinitronaphthalene, 1,5-dinitronaphthalene, 9-cyanoanthracene, 9-nitroanthracene, 9,10-anthraquinone, 1,3,6,8-tetranitrocarbazole, 2,4,7-trinitro-9-fluorenone, 2,3,5,6-tetracyanopyridine, maleic anhydride, phthalic anhydride, C60, and C70.

Of these, metal oxides and cyano group-Containing compounds are preferred because they can be easily handled and deposited, and therefore the above-described effects can be obtained easily. Examples of the preferred metal oxide include molybdenum oxide, vanadium oxide and ruthenium oxide. Among cyano group-containing compounds, (a) a compound having in the molecule at least one electron-accepting nitrogen atom in addition to the nitrogen atom of the cyano group, (b) a compound having both halogen and a cyano group in the molecule, (c) a compound having both a carbonyl group and a cyano group in the molecule, or (d) a compound having in the molecule both halogen and a cyano group and further, at least one electron-accepting nitrogen atom in addition to the nitrogen atom of the cyano group is more preferable because it serves as a strong electron acceptor. Specific examples of the above-mentioned compound include the following compounds.

[Chemical Formula 46]

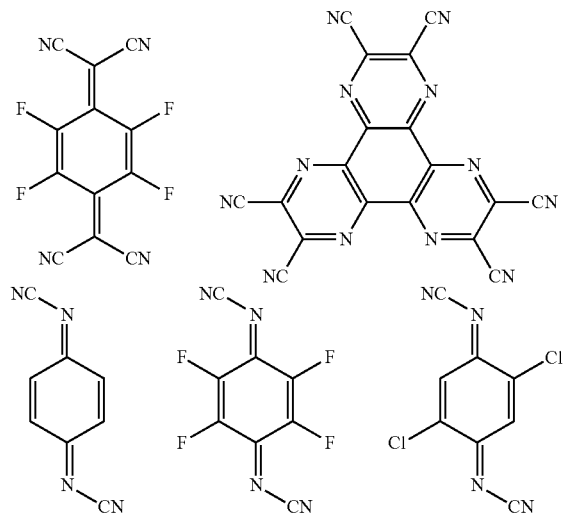

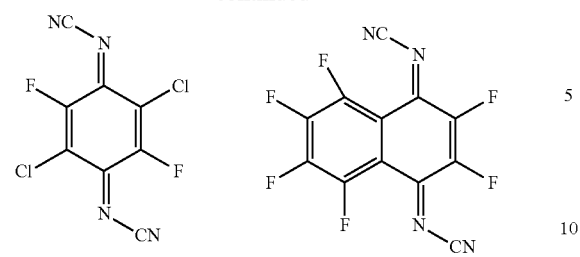
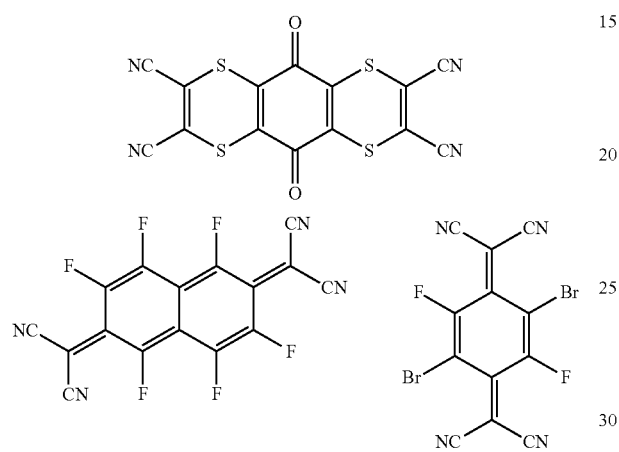
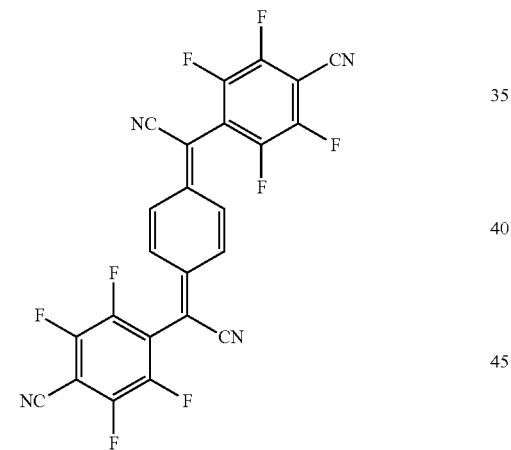
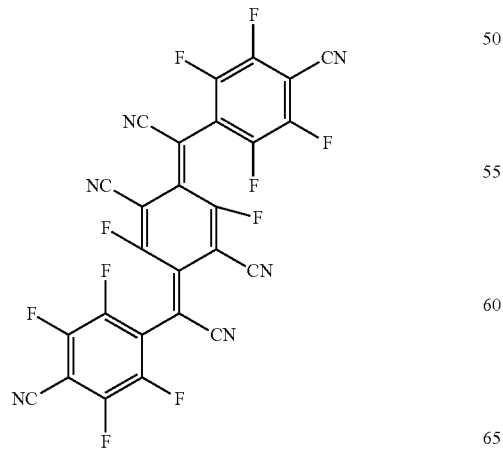
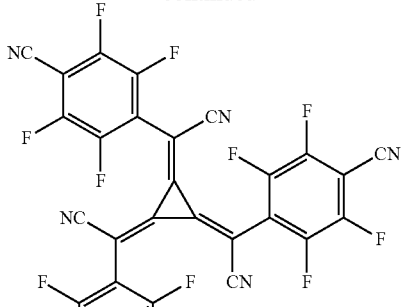
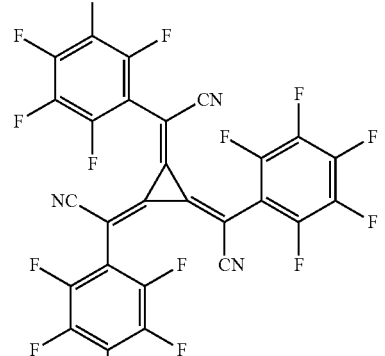
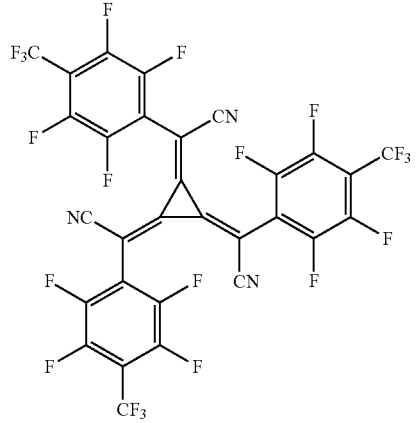
[Chemical Formula 47]
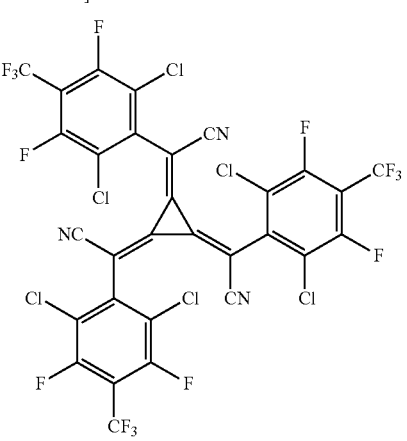

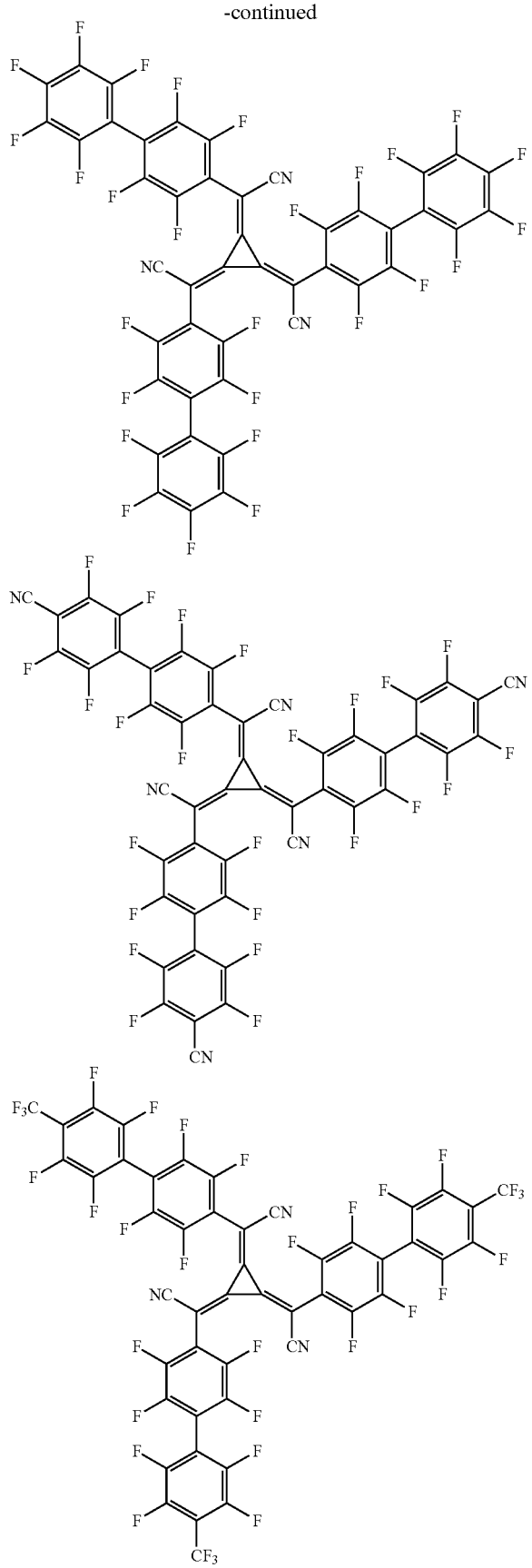

In either of the case where a hole injection layer is formed of an acceptor compound alone or the case where a hole injection layer is doped with an acceptor compound, the hole injection layer may be a single layer or may be a laminate of a plurality of layers. The hole injection material to be used in combination when the hole injection layer is doped with an acceptor compound is preferably the same compound as the compound to be used for the hole transporting layer because a barrier to injection of holes into the hole transporting layer can be mitigated.

The emissive layers may be in the form of a single layer or a plurality of layers, each of which is formed of an emissive material (host material, dopant material), and this may be a mixture of the host material and the dopant material, or the host material alone. That is, in the light-emitting device of the present invention, only the host material or the dopant material may emit light, or both of the host material and the dopant material may emit light, in each emissive layer. From the viewpoints that electric energy is efficiently utilized and light emission at high color purity is obtained, it is preferred that the emissive layer includes a mixture of the host material and the dopant material. In addition, the host material and the dopant material may be one kind or a combination of a plurality of kinds, respectively. The dopant material may be contained in a whole host material, or may be partially contained therein. The dopant material may be laminated, or may be dispersed. The dopant material can control an emitted color. When the amount of the dopant material is too large, concentration quenching occurs, and therefore the dopant material is preferably used in an amount of 20% by weight or less, further preferably 10% by weight or less based on the host material. As a doping method, the dopant material can be co-deposited with the host material, or the dopant material may be mixed with the host material in advance to be deposited simultaneously.

Specific examples of the emissive material that can be used include, but are not particularly limited to, fused ring derivatives such as anthracene and pyrene, metal chelated oxinoid compounds including tris(8-quinolinolato)aluminum, bisstyryl derivatives such as bisstyrylanthracene derivatives and distyrylbenzene derivatives, tetraphenylbutadiene derivatives, indene derivatives, coumarin derivatives; oxadiazole derivatives, pyrrolopyridine derivatives, perinone derivatives, cyclopentadiene derivatives, oxadiazole derivatives, thiadiazolopyridine derivatives, dibenzofuran derivatives, carbazole derivatives, and indolocarbazole derivatives and, as a polymer series, polyphenylenevinylene derivatives, polyparaphenylene derivatives, and polythiophene derivatives, which have hitherto been known as a light emitting body.

The host material contained in the emissive material is not particularly limited, and examples of the host material which can be used include, but are not particularly limited to, compounds having a fused aryl ring such as naphthalene, anthracene, phenanthrene, pyrene, chrysene, naphthacene, triphenylene, perylene, fluoranthene, fluorene and indene, and derivatives thereof, aromatic amine derivatives such as N,N'-dinaphthyl-N,N'-diphenyl-4,4'-diphenyl-1,1'-diamine, metal chelated oxinoid compounds including tris(8-quinolinato)aluminum (III), bisstyryl derivatives such as distyrylbenzene derivatives, tetraphenylbutadiene derivatives, indene derivatives, coumarin derivatives, oxadiazole derivatives, pyrrolopyridine derivatives, perinone derivatives, cyclopentadiene derivatives, pyrrolopyrrole derivatives, thiadiazolopyridine derivatives, dibenzofuran derivatives, carbazole derivatives, indolocarbazole derivatives and triazine derivatives and, as a polymer series, polyphenylenevinylene derivatives, polyparaphenylene derivatives, polyfluorene derivatives, polyvinylcarbazole derivatives, and polythiophene derivatives. The dopant material is not particularly limited, and examples of the dopant material that can be used include compounds having a fused aryl ring such as naphthalene, anthracene, phenanthrene, pyrene, chrysene, triphenylene, perylene, fluoranthene, fluorene and indene, and derivatives thereof (e.g., 2-(benzothiazol-2-yl)-9,10-diphenylanthracene and 5,6,11,12-tetraphenylnaphthacene); compounds having a heteroaryl ring such as furan, pyrrole, thiophene, silole, 9-silafluorene, 9,9'-spirobisilafluorene, benzothiophene, benzofuran, indole, dibenzothiophene, dibenzofuran, imidazopyridine, phenanthroline, pyridine, pyrazine, naphthyridine, quinoxaline, pyrrolopyridine and thioxanthene, and derivatives thereof; borane derivatives; distyrylbenzene derivatives; aminostyryl derivatives such as 4,4'-bis(2-(4-diphenylaminophenyl)ethenyl)biphenyl and 4,4'-bis(N-(stilben-4-yl)-N-phenylamino)stilbene; aromatic acetylene derivatives; tetraphenylbutadiene derivatives; stilbene derivatives; aldazine derivatives; pyrromethene derivatives; diketopyrrolo[3,4-c] pyrrole derivatives; coumarin derivatives such as 2,3,5,6-1H,4H-tetrahydro-9-(2'-benzothiazolyl)quinolizino[9,9a,1-gh] coumarin; azole derivatives such as imidazole, thiazole, thiadiazole, carbazole, oxazole, oxadiazole and triazole, and metal complexes thereof; and aromatic amine derivatives typified by N,N'-diphenyl-N,N'-di(3-methylphenyl)-4,4'-diphenyl-1,1'-di amine.

The emissive layer may contain a phosphorescence emitting material. The phosphorescence emitting material is a material that emits phosphorescence at room temperature. When a phosphorescence emitting material is used as a dopant, basically it is required to obtain phosphorescence emission at room temperature, and the phosphorescence emitting material is not particularly limited, and is preferably an organic metal complex compound containing at least one metal selected from the group consisting of iridium (Ir), ruthenium (Ru), rhodium (Rh), palladium (Pd), platinum (Pt), osmium (Os), and rhenium (Re). Among them, an organic metal complex having iridium or platinum is more preferred because it has a high phosphorescence emission yield at room temperature. As the host to be used in combination with a phosphorescence emitting dopant, aromatic hydrocarbon compound derivatives such as indole derivatives, carbazole derivatives, indolocarbazole derivatives, nitrogen-containing aromatic compound derivatives having a pyridine, pyrimidine or triazine skeleton, polyarylbenzene derivatives, spirofluorene derivatives, truxene derivatives and triphenylene derivatives; compounds containing a chalcogen element, such as dibenzofuran derivatives and dibenzothiophene derivatives; organic metal complexes such as beryllium quinolinol complexes; and the like are suitably used, but the host is not limited thereto as long as basically it has higher triplet energy than a dopant used, and electrons and holes are smoothly injected and transported from the respective transporting layers. Two or more triplet emissive dopants may be contained, and two or more host materials may be contained. Further, one or more triplet emissive dopants and one or more fluorescence emitting dopants may be contained.

The preferable phosphorescence emitting host or dopant is not particularly limited, and specific examples thereof include the following.

[Chemical Formula 48]

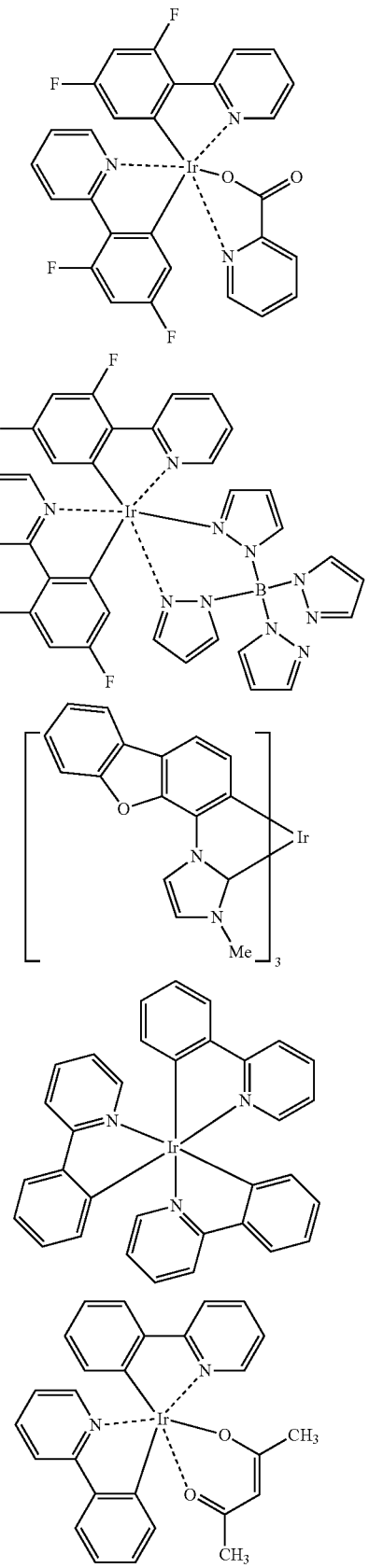

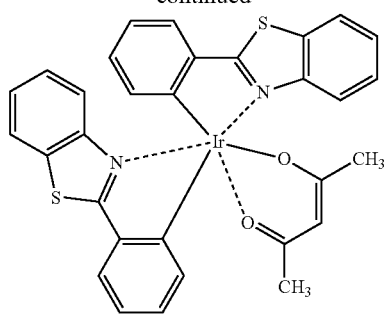
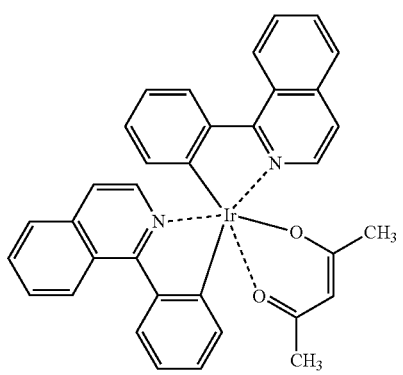
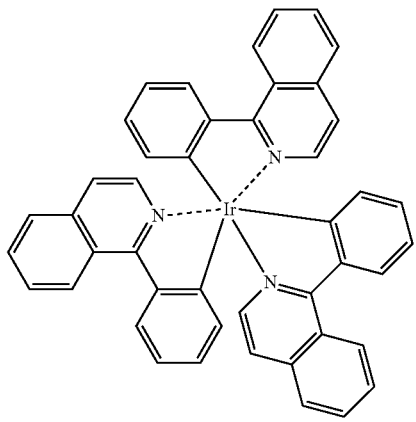
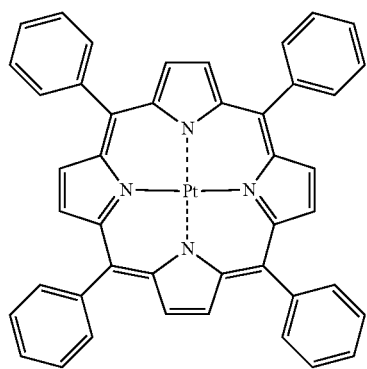
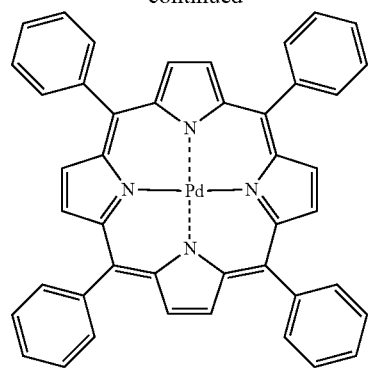
[Chemical Formula 49]
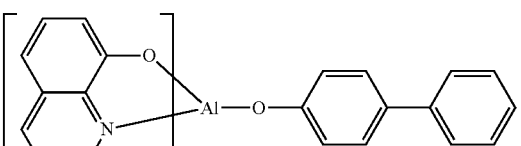
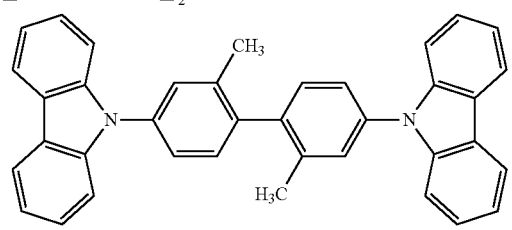
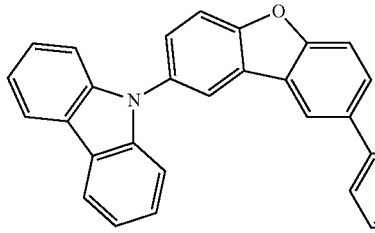
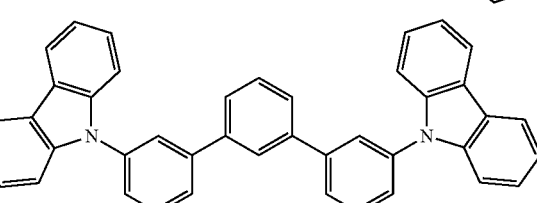
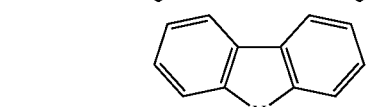
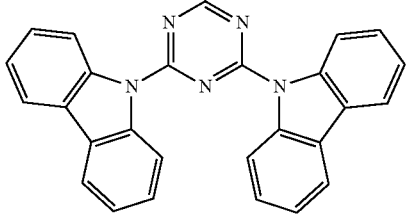

-continued

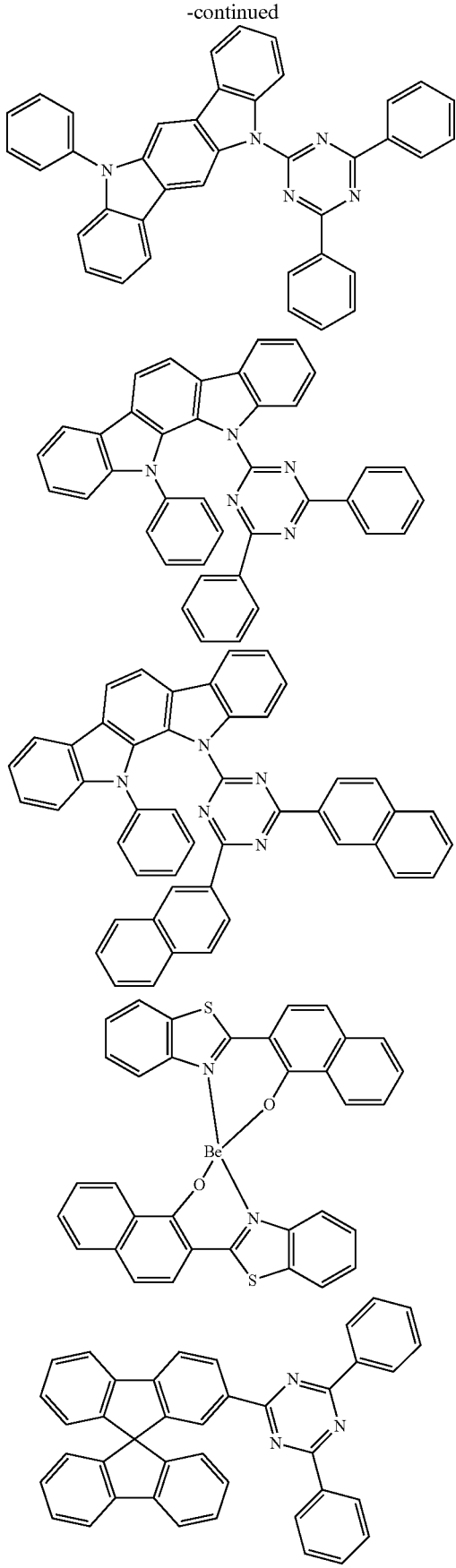

-continued

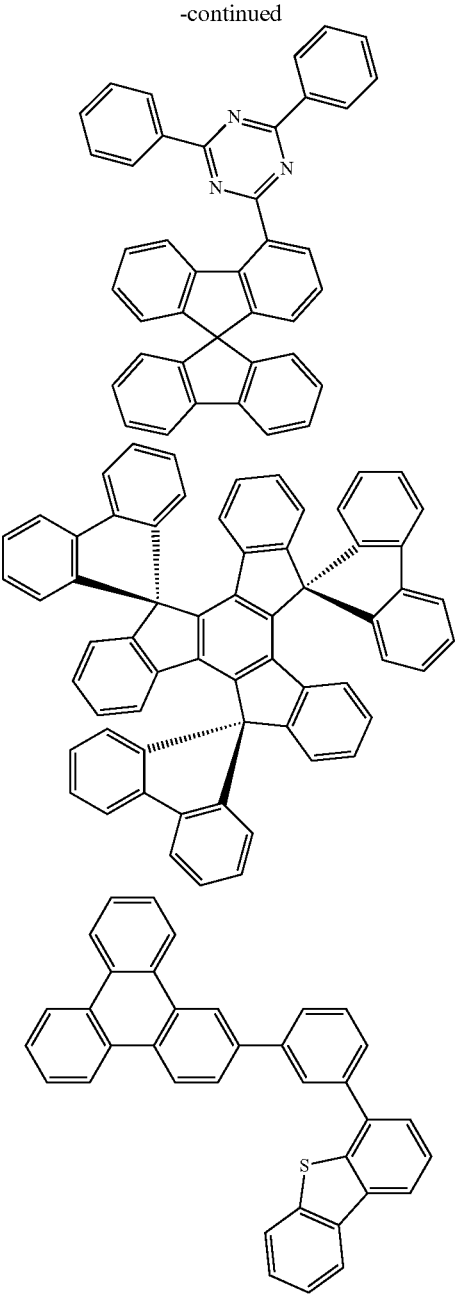

The fluoranthene derivative of the present invention can also be used as an emissive material because it has high light emitting performance. The fluoranthene derivative of the present invention can be suitably used as a blue and green light emitting material because it shows intensive luminescence in a blue to green region (400 to 600 nm region). The fluoranthene derivative of the present invention may be used as a host material, but is suitably used as a dopant material because it has a high fluorescence quantum yield.

In the present invention, the electron transporting layer is a layer in which electrons are injected from the cathode and, further, which transports the electrons. It is desired that the electron transporting layer has a high electron injection efficiency, and efficiently transports injected electrons. For this reason, it is preferred that the electron transporting layer is formed of a substance having great electron affinity and, moreover, great electron mobility and, further, excellent stability, and generating impurities that become a trap with difficulty at the time of production and at the time of use. However, when transportation balance between holes and electrons is considered, if the electron transporting layer mainly plays a role of being able to efficiently inhibiting holes from the anode from flowing to the cathode side without recombination, even when the layer is constituted by a material having not so high electron transporting ability, the effect of improving luminous efficiency becomes equivalent to that when the layer is constituted by a material having a high electron transporting ability. Therefore, the electron transporting layer in the present invention also includes a hole inhibition layer which can efficiently inhibit the transfer of holes as the same meaning.

Examples of the electron transporting material to be used for the electron transporting layer include fused polycyclic aromatic derivatives, such as naphthalene and anthracene, styryl-based aromatic ring derivatives typified by 4,4'-bis(diphenylethenyl)biphenyl, quinone derivatives, such as anthraquinone and diphenoquinone, phosphorus oxide derivatives, and various types of metal complexes, such as quinolinol complexes, e.g., tris(8-quinolinolato)aluminum (III), benzoquinolinol complexes, hydroxyazole complexes, azomethine complexes, tropolone metal complexes, and flavonol metal complexes. It is preferred to use a compound that includes an element selected from carbon, hydrogen, nitrogen, oxygen, silicon and phosphorus, and has a heteroaryl ring structure containing electron-accepting nitrogen because it can reduce a driving voltage and a highly efficient light emission can be obtained.

An aromatic heterocyclic ring containing electron-accepting nitrogen has high electron affinity. An electron transporting material having electron-accepting nitrogen makes easier acceptance of electrons from a cathode having higher electron affinity, and lower voltage driving becomes possible. In addition, since supply of electrons to an emissive layer is increased and a recombining probability is increased, luminous efficiency is improved.

Examples of the heteroaryl ring containing electron-accepting nitrogen include a pyridine ring, a pyrazine ring, a pyrimidine ring, a quinoline ring, a quinoxaline ring, a naphthyridine ring, a pyrimidopyrimidine ring, a benzoquinoline ring, a phenanthroline ring, an imidazole ring, an oxazole ring, an oxadiazole ring, a triazole ring, a thiazole ring, a thiadiazole ring, a benzoxazole ring, a benzothiazole ring, a benzimidazole ring, and a phenanthroimidazole ring.

Examples of preferred compounds having such a heteroaryl ring structure include benzimidazole derivatives, benzoxazole derivatives, benzothiazole derivatives, oxadiazole derivatives, thiadiazole derivatives, triazole derivatives, pyrazine derivatives, phenanthroline derivatives, quinoxaline derivatives, quinoline derivatives, benzoquinoline derivatives, oligopyridine derivatives such as bipyridine and terpyridine, quinoxaline derivatives and naphthyridine derivatives. Among them, imidazole derivatives such as tris(N-phenylbenzimidazol-2-yl)benzene; oxadiazole derivatives such as 1,3-bis[(4-tert-butylphenyl)1,3,4-oxadiazolyl]phenylene; triazole derivatives such as N-naphthyl-2,5-diphenyl-1,3,4-triazole; phenanthroline derivatives such as bathocuproine and 1,3-bis(1,10-phenanthrolin-9-yl)benzene; benzoquinoline derivatives such as 2,2'-bis(benzo[h]quinolin-2-yl)-9,9'-spirobifluorene; bipyridine derivatives such as 2,5-bis(6'-(2',2''-bipyridyl))-1,1-dimethyl-3,4-diphenylsilole; terpyridine derivatives such as 1,3-bis(4'-(2,2': 6'2''-terpyridinyl))benzene; and naphthyridine derivatives such as bis(1-naphthyl)-4-(1,8-naphthyridin-2-yl)phenylphosphine oxide are suitably used in view of an electron transporting ability. It is more preferable that such a derivative has a fused polycyclic aromatic skeleton because if so, then the glass transition temperature will increase and an effect of reducing the voltage of a light-emitting device is great due to increased electron mobility. Moreover, considering the improvement in durable life of a device, the easiness of synthesis, and easy availability of raw materials, it is particularly preferable that the fused polycyclic aromatic skeleton is an anthracene skeleton, a pyrene skeleton, or a phenanthroline skeleton. While the electron transporting material may be used alone, two or more kinds of the electron transporting materials may be used in combination, or one or more kinds of other electron transporting materials may be used in a combination with the electron transporting material.

Preferable electron transporting materials are not particularly limited, and specific examples thereof include the following.

[Chemical Formula 50]

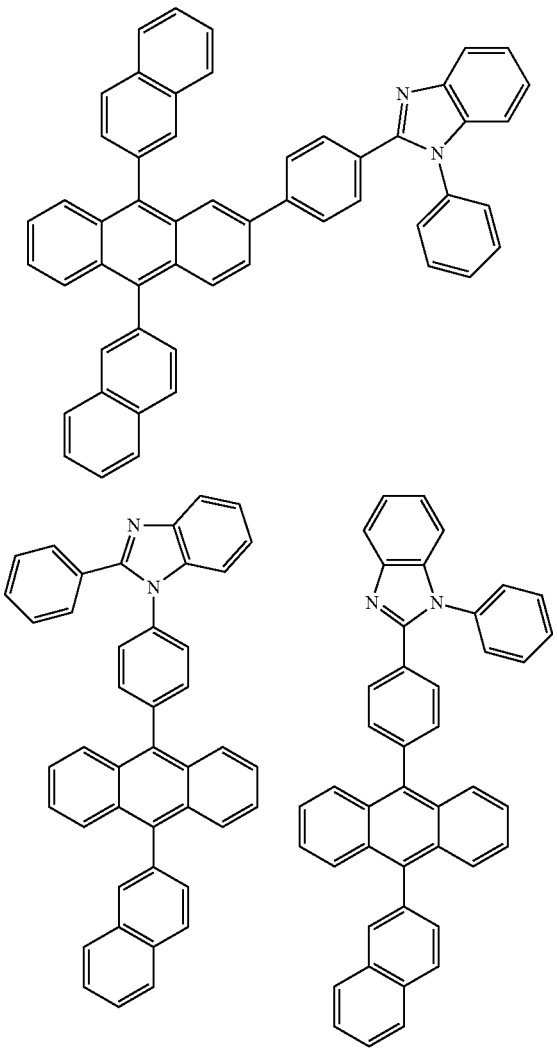

197
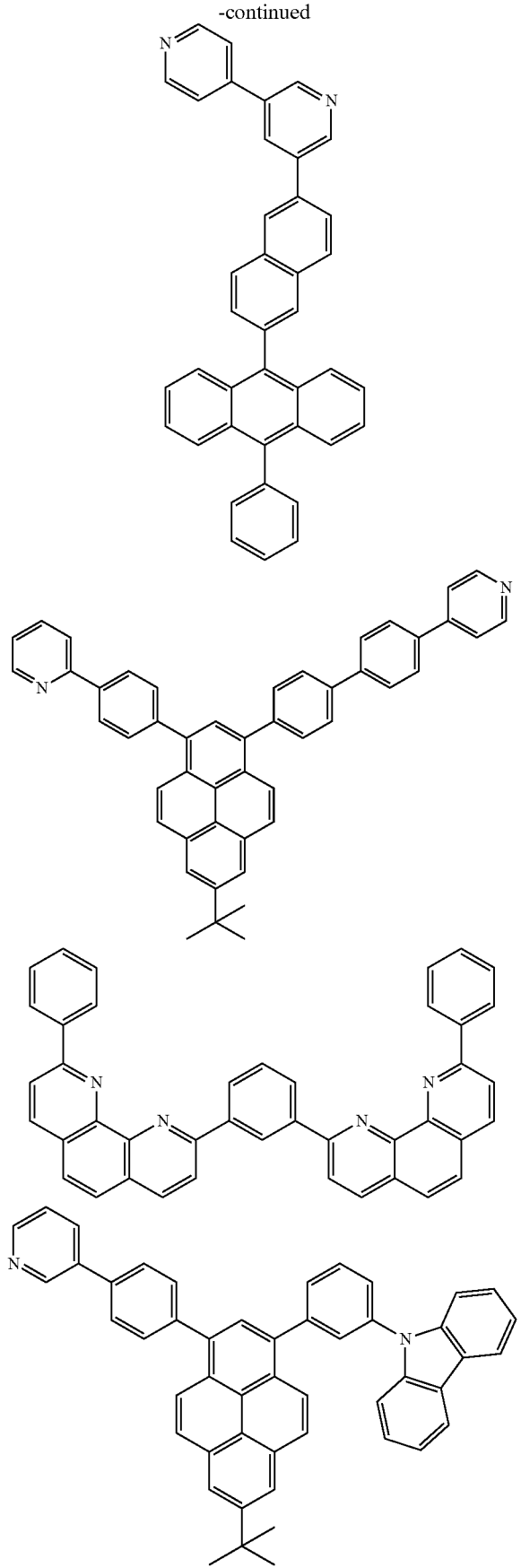
198
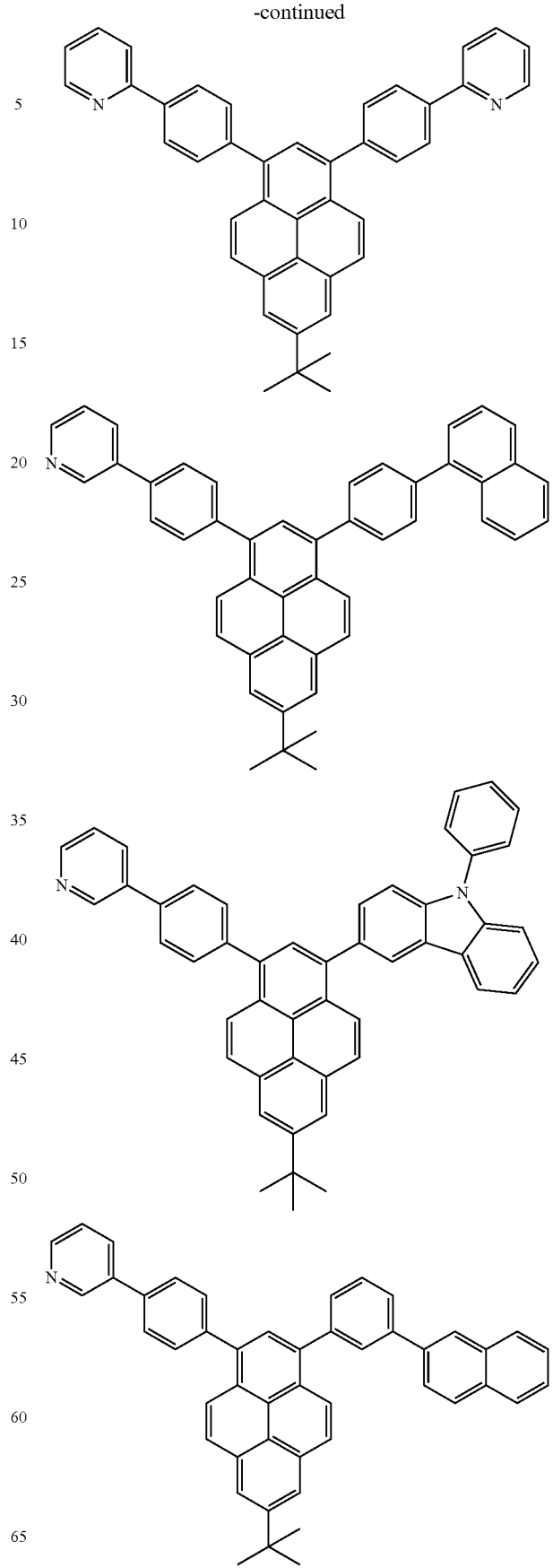

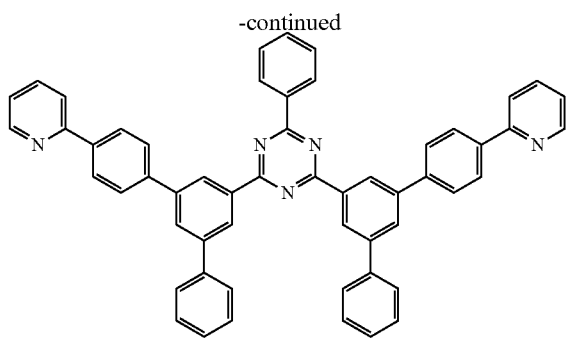

Besides these electron transporting materials, those disclosed in WO 200463159, WO 200360956, Appl. Phys. Lett. 74, 865 (1999), Org. Electron. 4, 113 (2003), WO 2010113743 and WO 20101817 can be used.

The fluoranthene derivative of the present invention can also be suitably used as an electron transporting material because it has high electron injection/transporting abilities.

When the fluoranthene derivative of the present invention is used, it does not need to be restricted to each one type, and a plurality of fluoranthene compounds according to the present invention may be used in admixture, or one or more of other electron transporting materials may be used in admixture with the fluoranthene compound according to the present invention as long as the effects of the present invention are not impaired. The electron transporting material that can be mixed is not particularly limited, and examples thereof include compounds having a fused aryl ring, such as naphthalene, anthracene and pyrene, and derivatives thereof, styryl-based aromatic ring derivatives typified by 4,4'-bis(diphenylethenyl)biphenyl, perylene derivatives, perinone derivatives, coumarin derivatives, naphthalimide derivatives, quinone derivatives such as anthraquinone and diphenoquinone, phosphorus oxide derivatives, carbazole derivatives and indole derivatives, quinolinol complexes such as tris(8-quinolinolato)aluminum(III), hydroxyazole complexes such as hydroxyphenyloxazole complexes, azomethine complexes, tropolone metal complexes, and flavonol metal complexes.

While the electron transporting material may be used alone, two or more kinds of the electron transporting materials may be used in combination, or one or more kinds of other electron transporting materials may be used in a combination with the electron transporting material. Moreover, a donor material may be contained. The donor material denotes a compound which makes easy electron injection into the electron transporting layer from the cathode or the electron injection layer and, moreover, improves the electric conductivity of the electron transporting layer, by improving an electron injection barrier.

Preferable examples of the donor material in the present invention include an alkali metal, an inorganic salt containing an alkali metal, a complex of an alkali metal and an organic substance, an alkaline earth metal, an inorganic salt containing an alkaline earth metal, or a complex of an alkaline earth metal and an organic substance. Examples of the preferable kind of the alkali metal and the alkaline earth metal include alkali metals such as lithium, sodium and cesium, and alkaline earth metals such as magnesium and calcium which have a low work function and have a great effect of improving electron transporting ability.

In addition, since deposition in vacuum is easy and handling is excellent, the donor material is preferably in the state of an inorganic salt or a complex with an organic substance rather than a metal single substance. Moreover, from the viewpoints of improvement in easiness in handling in the atmospheric air and easiness in control of the concentration to be added, the donor material is more preferably in the state of a complex with an organic substance. Examples of the inorganic salt include oxides such as LiO and $Li_2O$, nitrides, fluorides such as LiF, NaF and KF, and carbonates such as $Li_2CO_3$, $Na_2CO_3$, $K_2CO_3$, $Rb_2CO_3$ and $Cs_2CO_3$. Preferable examples of the alkali metal or alkaline earth metal include lithium from the viewpoints of an inexpensive raw material and ease of synthesis. In addition, preferable examples of the organic substance in complexes with an organic substance include quinolinol, benzoquinolinol, flavonol, hydroxyimidazopyridine, hydroxybenzazole, and hydroxytriazole. Particularly, a complex of an alkali metal and an organic substance is preferred, a complex of lithium and an organic substance is more preferred, and lithium quinolinol is especially preferred. Two or more of these donor materials may be used in admixture.

The preferred doping concentration varies depending on a material and a film thickness of the doping region, but for example when the donor material is an inorganic material such as an alkali metal or an alkaline earth metal, it is preferred that an electron transporting layer is formed by performing co-deposition so that the deposition rate ratio of an electron transporting material and a donor material is within the range of 10000:1 to 2:1. The deposition rate ratio is more preferably 100:1 to 5:1, further preferably 100:1 to 10:1. When the donor material is a complex of a metal and an organic substance, it is preferred that an electron transporting layer is formed by performing co-deposition so that the deposition rate ratio of an electron transporting material and the donor material is within the range of 100:1 to 1:100. The deposition rate ratio is more preferably 10:1 to 1:10, further preferably 7:3 to 3:7.

An electron transporting layer with the fluoranthene derivative of the invention doped with a donor material as described above may be used as a charge generation layer in a tandem structure type device in which a plurality of light-emitting devices are coupled.

The method in which an electron transporting layer is doped with a donor material to improve an electron transporting ability exhibits an effect particularly when the film thickness of a thin-film layer is large. The method is particularly preferably used when the total film thickness of the electron transporting layer and the emissive layer is 50 nm or more. For example, there is a method in which an interference effect is used for improving luminous efficiency, and the method is intended to improve light extraction efficiency by matching the phases of light emitted directly from an emissive layer and light reflected at a cathode. The optimum conditions thereof vary depending on a light emitting wavelength, and the total film thickness of the electron transporting layer and the emissive layer becomes 50 nm or more, and may become a large film thickness close to 100 nm in the case of emission of light having a long wavelength, such as red light.

The film thickness of the electron transporting layer, which is doped, may be a part or the whole of the electron transporting layer. When a part of the electron transporting layer is doped, it is desirable to provide a doped-region at least at an electron transporting layer/cathode interface, and the effect of reducing a voltage is obtained by merely doping the vicinity of the cathode interface. On the other hand, when the donor material is in direct contact with the emissive layer, an adverse effect of reducing luminous efficiency may be caused, and in this case, it is preferred to provide a non-doped-region at an emissive layer/electron transporting layer interface.

In the present invention, an electron injection layer may be provided between a cathode and an electron transporting layer. Generally, the electron injection layer is inserted for the purpose of helping injection of electrons from the cathode into the electron transporting layer, and when the electron injection layer is inserted, a compound having a heteroaryl ring structure containing electron-accepting nitrogen may be used, or a layer containing the above-mentioned donor material may be used. The fluoranthene derivative of the present invention may be contained in the electron injection layer. An inorganic substance such as an insulator or a semiconductor can also be used for the electron injection layer. Use of such a material is preferred because a short-circuit of the light-emitting device can be effectively prevented, and electron injection property can be improved. It is preferred that at least one metal compound selected from the group consisting of an alkali metal chalcogenide, an alkaline earth metal chalcogenide, a halide of an alkali metal and a halide of an alkaline earth metal is used as the insulator. It is preferred that the electron injection layer is formed of the above-mentioned alkali metal chalcogenide and the like because electron injection property can be further improved. Specifically, examples of the preferable alkali metal chalcogenide include $Li_2O$, $Na_2S$ and $Na_2Se$, and examples of the preferable alkaline earth metal chalcogenide include CaO, BaO, SrO, BeO, BaS and CaSe. Examples of the preferable halide of an alkali metal include LiF, NaF, KF, LiCl, KCl and NaCl. Examples of the preferable halide of an alkaline earth metal include fluorides such as $CaF_2$, $BaF_2$, $SrF_2$, $MgF_2$ and $BeF_2$, and halides other than fluorides. Further, a complex of an organic substance and a metal is suitably used. Use of a complex of an organic substance and a metal for the electron injection layer is preferred because the film thickness is easily adjusted. As examples of the above-mentioned organic metal complex, preferable examples of the organic substance in complexes with an organic substance include quinolinol, benzoquinolinol, pyridylphenol, flavonol, hydroxyimidazopyridine, hydroxybenzazole, and hydroxytriazole. Particularly, a complex of an alkali metal and an organic substance is preferred, a complex of lithium and an organic substance is more preferred, and lithium quinolinol is especially preferred.

Examples of a method of forming each of the aforementioned layers constituting the light-emitting device include, but are not particularly limited to, resistance heating deposition, electron beam deposition, sputtering, a molecular lamination method, and a coating method, but usually, resistance heating deposition or electron beam deposition is preferable from the viewpoint of device property.

The thickness of the organic layer depends on the resistance value of an emissive substance and, therefore, it cannot be limited, but it is preferably 1 to 1000 nm. The film thickness of each of the emissive layer, the electron transporting layer and the hole transporting layer is preferably 1 nm or more and 200 nm or less, more preferably 5 nm or more and 100 nm or less.

The light-emitting device of the present invention has a function of being able to convert electric energy into light. Herein, a direct current is mainly used as the electric energy, but a pulse current or an alternate current can also be used. A current value and a voltage value are not particularly limited, but when the power consumed and life of the device are considered, they should be selected so that the maximum luminance is obtained by energy as low as possible.

The light-emitting device of the present invention is used suitably as a display that displays in a matrix and/or segment system.

In the matrix system, pixels for display are arranged two-dimensionally such as lattice-like arrangement or mosaic-like arrangement, and the collection of pixels displays letters and images. The shape and size of the pixel are determined depending on utility. For example, for displaying images and letters on personal computers, monitors and televisions, a square pixel being 300 µm or less at each side is usually used and, in the case of a large display such as a display panel, a pixel being millimeter order at each side is used. In the case of a monochromatic display, pixels having the same color may be arranged, and in the case of a color display, pixels having red, green and blue colors are arranged to perform display. In this case, typically, there are a delta type and a stripe type. A method of driving this matrix may be either a passive matrix driving method or an active matrix. The passive matrix driving has a simple structure, but when operation property is considered, the active matrix is more excellent in some cases, and it is necessary to use them properly depending on utility.

The segment system in the present invention is a system by which a pattern is formed so as to display predetermined information, and a region determined by arrangement of this pattern is made to emit light. Examples thereof include time and temperature displays in digital watches and thermometers, operating-state displays in audio equipment, IH cookers and so on, and panel displays of automobiles. The above-mentioned matrix display and segment display may exist together in the same panel.

The light-emitting device of the present invention can also be preferably used as backlight of various instruments. Backlight is used mainly for the purpose of improving the visibility of display apparatuses which do not emit light by themselves, and is used in liquid crystal display equipment, clocks, audio equipment, automobile panels, display panels, signs, and the like. In particular, the light-emitting device of the present invention is preferably used in backlight for liquid crystal display apparatuses, inter alia, for personal computers which are studied to be thinned, and can provide backlight thinner and lighter than conventional products.

EXAMPLES

The present invention will be described by way of Examples, but the present invention is not limited thereto.

Synthesis Example 1

Synthesis of Compound [1]

Mixed were 26.0 g of bromofluoranthene, 35.2 g of bis(pinacolato)diboron, 27.2 g of potassium acetate and 462 mL of dimethylformamide, and the mixture was purged with nitrogen. To this mixed solution were added 0.75 g of a [1,1'-bis(diphenylphosphino)ferrocene]palladium (II) dichloride-dichloromethane complex, and the mixture was heated to 100° C. After 1 hour, the mixture was cooled to room temperature, 250 mL of ethyl acetate, 250 mL of toluene and 250 mL of water were then added, and the liquid was separated. The aqueous layer was extracted with 200 mL of ethyl acetate and 200 mL of toluene, and then combined with the foregoing organic layer, and the mixture was washed with 500 mL of water three times. The organic layer was dried over magnesium sulfate, and the solvent was distilled off. The resultant was purified by silica gel column chromatography, the eluate was evaporated, and vacuum-drying was performed to obtain 16.4 g of an intermediate A.

Next, 16.4 g of the intermediate A, 11.9 g of chloroiodobenzene, 251 mL of dimethoxy ethane and 67 ml of a 1.5 M aqueous sodium carbonate solution were mixed, and the mixture was purged with nitrogen. To this mixed solution was added 352 mg of bis(triphenylphosphine)palladium dichloride, and the mixture was heated and refluxed. After 3 hours, the mixture was cooled to room temperature, 250 ml of water was then added, and the precipitate was filtered, and dried by a vacuum drier. The product filtered was dissolved in toluene, activated carbon and QuadraSil (registered trademark) were then added, and the mixture was filtered with a silica pad. The solvent of the filtrate was distilled off, methanol was then added, and the precipitated solid was filtered, and dried. The resultant solid was re-crystallized with 100 mL of butyl acetate, filtered, and then vacuum-dried to obtain 8.4 g of a yellowish green solid of an intermediate B.

Next, 15.0 g of 3-aminopyridine, 35.8 g of iodobenzene, 21.5 g of sodium-t-butoxide and 400 mL of toluene were mixed, and the mixture was purged with nitrogen. To this mixed solution were added 1.83 g of bis(dibenzylideneacetone)palladium (0) and 1.77 g of bis(diphenylphosphino)ferrocene, and the mixture was heated and refluxed. After 4 hours, the mixture was cooled to room temperature, and then filtered with celite, 250 ml of water was added, and the organic layer was washed. The organic layer was dried over magnesium sulfate, activated carbon was added, the resultant was then filtered with celite, and the solvent was distilled off. The product thus obtained was purified by silica gel column chromatography, the eluate was evaporated, heptane was added, and the mixture was filtered. The resultant solid was vacuum-dried to obtain 4.85 g of an intermediate C.

Next, 3.0 g of the intermediate B, 1.8 g of the intermediate C, 1.3 g of sodium-t-butoxide and 49 mL of o-xylene were mixed, and the mixture was purged with nitrogen. To this mixed solution were added 56 mg of bis(dibenzylideneacetone)palladium (0) and 68 mg of XPhos, and the mixture was heated and refluxed. After 40 minutes, the mixture was cooled to room temperature, and then filtered with celite, and the solvent was distilled off. The product filtered was purified by silica gel column chromatography, and the eluate was evaporated. The product thus obtained was re-crystallized with butyl acetate, then filtered, and vacuum-dried to obtain 3.6 g of a yellowish green solid of a compound [1] (yield: 83%).

$^1$H-NMR analytical results of the resulting yellow solid are as follows, and it was confirmed that the resulting yellowish green solid was the compound [1].

Compound [1]:

$^1$H-NMR (CDCl$_3$ (d=ppm)) δ 7.10-7.25 (m, 6H), 7.32-7.43 (m, 4H), 7.47-7.55 (m, 3H), 7.61-7.67 (m, 2H), 7.90-8.01 (m, 5H), 8.27 (d, 1H), 8.49 (d, 1H).

The compound [1] was used as a light-emitting device material after sublimation purification was performed at about 230° C. under a pressure of 1×10$^{-3}$ Pa using an oil diffusion pump. The HPLC purity (area % at a measurement wavelength of 254 nm) was 99.9% before sublimation purification, and 99.9% after sublimation purification.

[Chemical Formula 51]

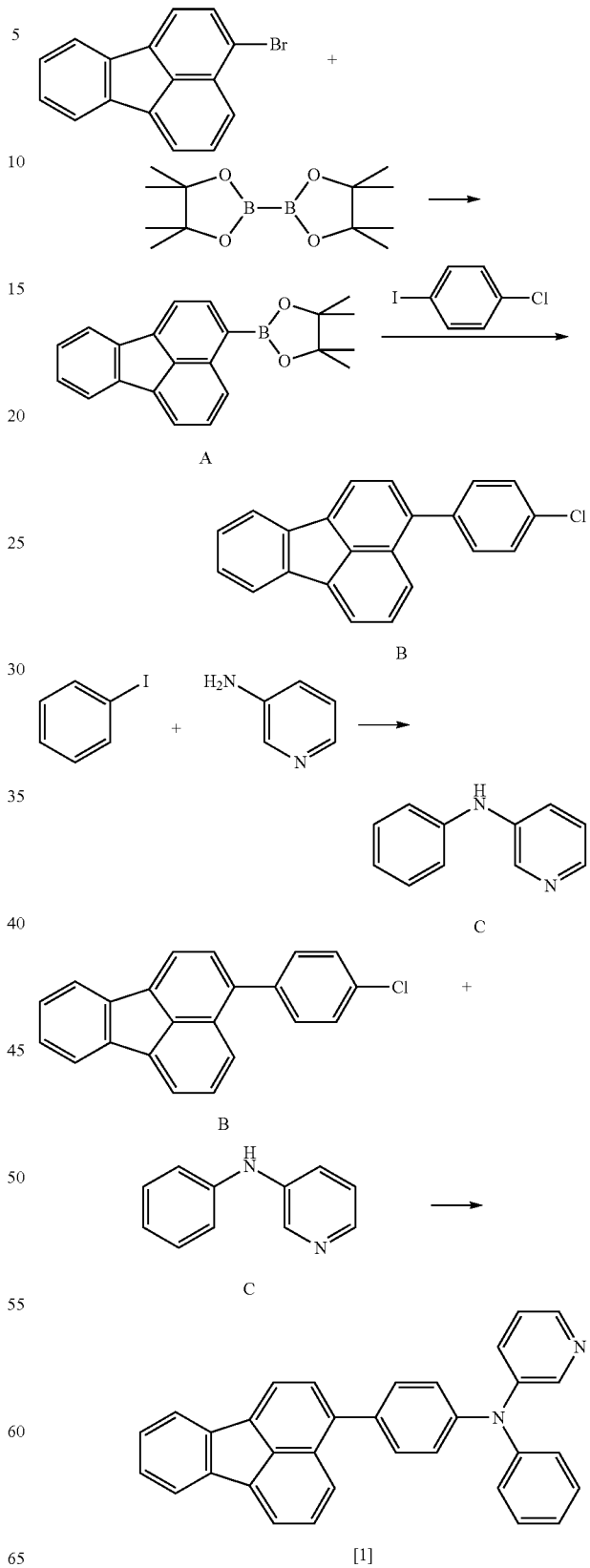

Synthesis Example 2

Synthesis of Compound [2]

Mixed were 14.0 g of acenaphthylene, 25.0 g of diphenylisobenzofuran and 200 ml of o-xylene, and the mixture was heated and refluxed under a nitrogen flow. After 2 hours, the mixture was cooled to room temperature, the solvent was then distilled off, and 300 mL of ether was added. The resultant precipitate was filtered, and vacuum-dried to obtain 27.7 g of an intermediate D (yield: 71%).

Next, 27.7 g of the intermediate D and 200 mL of acetic acid were mixed, 20 mL of 48% aqueous hydrobromic acid was added, and the mixture was heated and refluxed. After 3 hours, the reaction mixture was cooled to room temperature, then filtered, and washed with water and methanol. The resultant solid was vacuum-dried to obtain 25.8 g of an intermediate E (yield: 96%).

Next, 25.8 g of the intermediate E, 11.3 g of N-bromosuccinimide and 318 mL of chloroform were mixed, and the mixture was heated and refluxed. After 1 hour, 3.4 g of N-bromosuccinimide was added, and the mixture was further heated and refluxed. After 2 hours, the mixture was cooled to room temperature, and the chloroform solution was then washed with water and an aqueous sodium thiosulfate solution. The organic layer was dried over magnesium sulfate, 3 g of activated carbon was added, the resultant was then filtered, and the solvent was distilled off. The resultant solid was re-crystallized with 800 mL of butyl acetate, filtered, and then vacuum-dried to obtain 26.9 g of an intermediate F (yield: 87%).

Next, 9.0 g of the intermediate F, 3.2 g of p-chlorophenylboronic acid, 93 mL of dimethoxy ethane and 27 ml of a 1.5 M aqueous sodium carbonate solution were mixed, and purged with nitrogen. To this mixed solution was added 130 mg of bis(triphenylphosphine)palladium dichloride, and the mixture was heated and refluxed. After 3 hours, the mixture was cooled to room temperature, 93 ml of water was then added, and the precipitate was filtered, and dried by a vacuum drier. The product filtered was purified by silica gel column chromatography, and the eluate was evaporated. To the resultant solid was added methanol, and the precipitate was filtered, and then vacuum-dried to obtain 8.4 g of an intermediate C (yield: 87%).

Next, 3.0 g of the intermediate G, 1.2 g of the intermediate C, 0.8 g of sodium-t-butoxide and 29 mL of o-xylene were mixed, and the mixture was purged with nitrogen. To this mixed solution were added 33 mg of bis(dibenzylideneacetone)palladium (0) and 40 mg of XPhos, and the mixture was heated and refluxed. After 2 hours, the mixture was cooled to room temperature, and then filtered with celite, and the solvent of the filtrate was distilled off. The product filtered was purified by silica gel column chromatography, and the eluate was evaporated. The resultant solid was re-crystallized with a mixed solvent of 45 mL of butyl acetate and 40 mL of o-xylene, filtered, and then vacuum-dried to obtain 2.49 g of a yellow solid of a compound [2] (yield: 67%).

$^1$H-NMR analytical results of the resulting yellow solid are as follows, and it was confirmed that the resulting yellow solid was the compound [2].

Compound [2]:

$^1$H-NMR (CDCl$_3$, (d=ppm)) δ 6.63-6.67 (m, 2H), 7.08-7.21 (m, 6H), 7.29-7.48 (m, 9H), 7.56-7.71 (m, 12H), 7.86 (d, 1H), 8.24 (dd, 1H), 8.45 (d, 1H).

The compound [2] was used as a light-emitting device material after sublimation purification was performed at about 320° C. under a pressure of 1×10$^{-3}$ Pa using an oil diffusion pump. The HPLC purity (area % at a measurement wavelength of 254 nm) was 99.9% before sublimation purification, and 99.9% after sublimation purification.

[Chemical Formula 52]

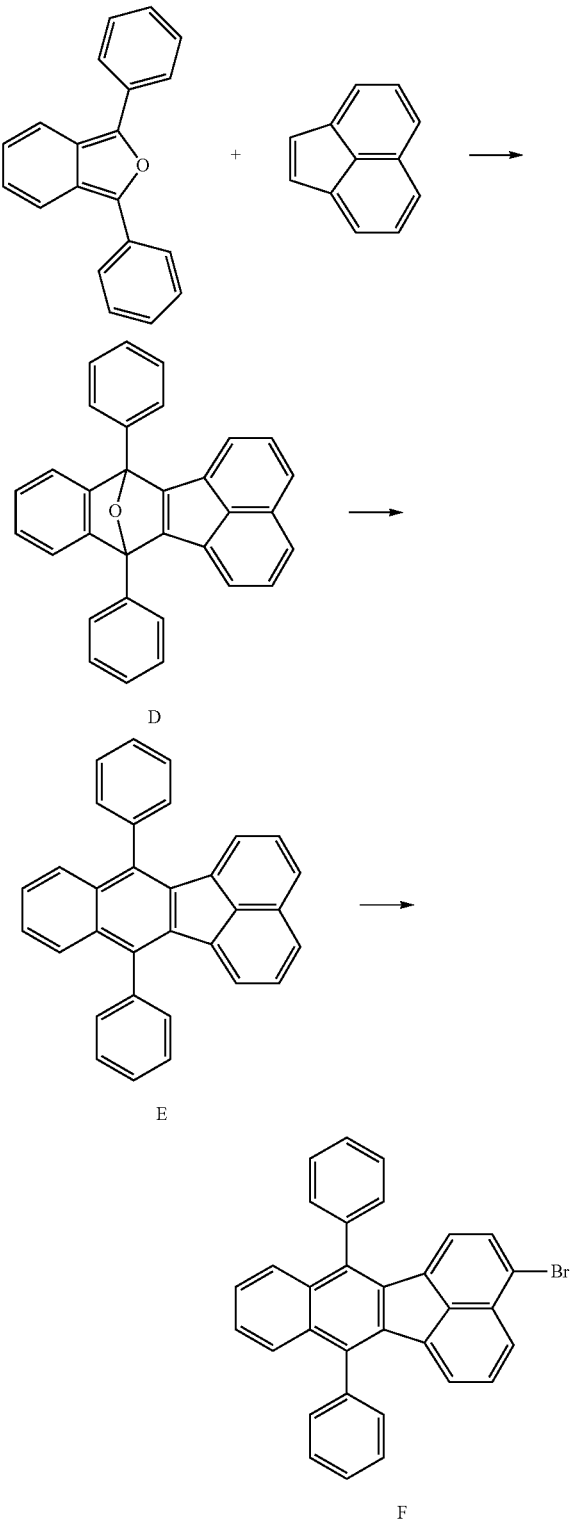

-continued

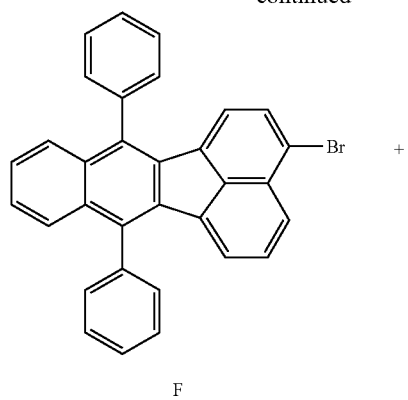

F

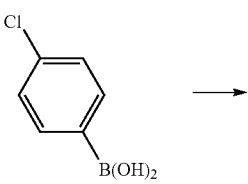

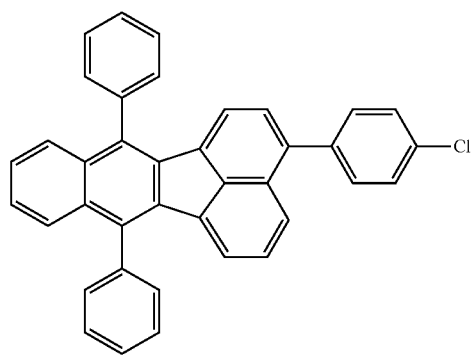

G

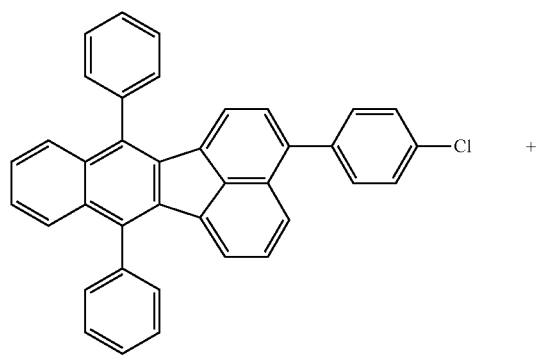

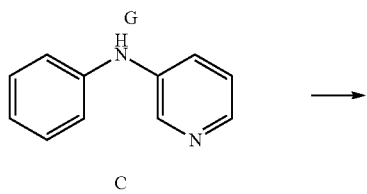

C

-continued

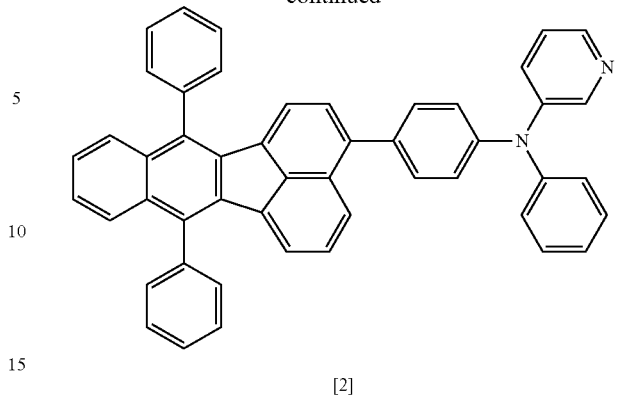

[2]

Synthesis Example 3

Synthesis of Compound [3]

Mixed were 10.0 g of the intermediate F, 7.9 g of bis(pinacolato)diboron, 6.1 g of potassium acetate and 52 mL of dimethylformamide, and the mixture was purged with nitrogen. To this mixed solution was added 0.51 g of a [1,1'-bis(diphenylphosphino)ferrocene]palladium (II) dichloride-dichloromethane complex, and the mixture was heated to 100° C. After 1 hour, the mixture was cooled to room temperature, 200 mL of water was then added, and the precipitated solid was filtered. The resultant solid was dissolved in toluene, activated carbon and QuadraSil (registered trademark) were then added, and the mixture was filtered with a silica pad. The solvent of the filtrate was distilled off, methanol was then added, and the precipitated solid was filtered, and vacuum-dried to obtain 10.8 g of an intermediate H.

Next, 10.8 g of the intermediate H, 5.0 g of bromocarbazole, 101 mL of dimethoxy ethane and 22 ml of a 2.0 M aqueous potassium carbonate solution were mixed, and the mixture was purged with nitrogen. To this mixed solution were added 91 mg of bis-palladium acetate and 308 mg of tri(orthotolyl)phosphine, and the mixture was heated and refluxed. After 1.5 hours, the mixture was cooled to room temperature, 500 mL of toluene and 250 mL of water were then added, and the liquid was separated. The organic layer was washed with water three times, and dried over magnesium sulfate, activated carbon was added, the resultant was then filtered with celite, and the solvent was distilled off. The resultant solid was re-crystallized with 150 mL of o-xylene, filtered, and then vacuum-dried to obtain 7.1 g of a yellowish green solid of an intermediate I.

Next, 3.0 g of the intermediate I, 0.92 g of 3=bromopyridine, 0.71 g of sodium-t-butoxide and 27 mL of o-xylene were mixed, and the mixture was purged with nitrogen. To this mixed solution were added 61 mg of bis(dibenzylideneacetone)palladium (0) and 83 mg of bis(diphenylphosphino)ferrocene, and the mixture was heated and refluxed. After 2 hours, the mixture was cooled to room temperature, and then filtered with celite, and the solvent was distilled off. The product thus obtained was purified by silica gel column chromatography, the eluate was evaporated, methanol was added, and the mixture was heated and refluxed. After 3 hours, the mixture was cooled to room temperature, and filtered. The resultant solid was vacuum-dried to obtain 3.31 g of a compound [3] (yield: 97%).

209

$^1$H-NMR analytical results of the resulting yellow solid are as follows, and it was confirmed that the resulting yellowish green solid was the compound [3].

Compound [3]:

$^1$H-NMR (DMSO-d6 (d-ppm)) δ 6.57-6.66 (m, 2H), 7.33 (t, 1H), 7.40-7.63 (m, 14H), 7.69-7.80 (m, 7H), 7.88 (d, 1H), 8.19 (dt, 1H), 8.32 (d, 1H), 8.43 (s, 1H), 8.77 (dd, 1H), 8.94 (d, 1H).

The compound [3] was used as a light-emitting device material after sublimation purification was performed at about 320° C. under a pressure of $1\times10^{-3}$ Pa using an oil diffusion pump. The HPLC purity (area % at a measurement wavelength of 254 nm) was 99.9% before sublimation purification, and 99.9% after sublimation purification.

[Chemical Formula 53]

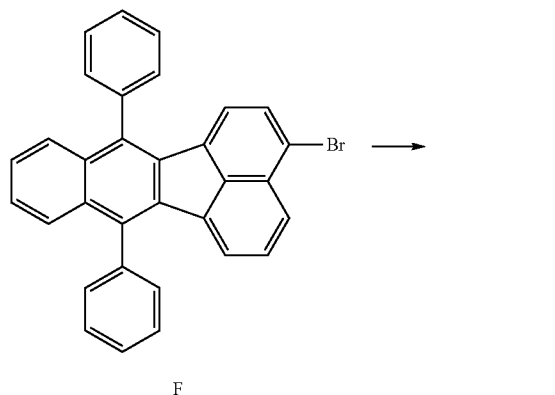

F

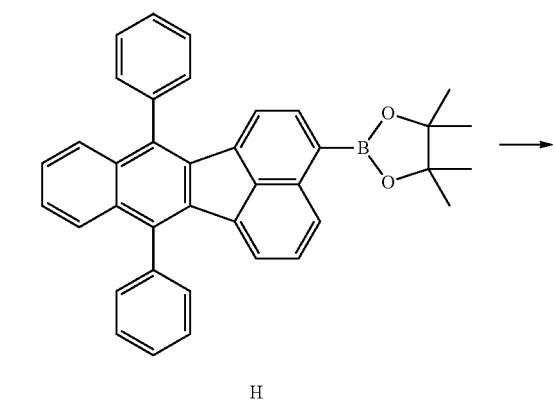

H

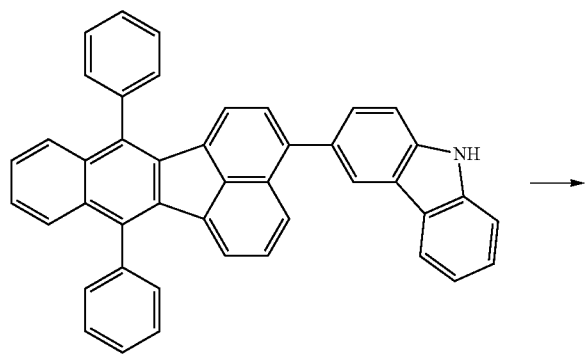

I

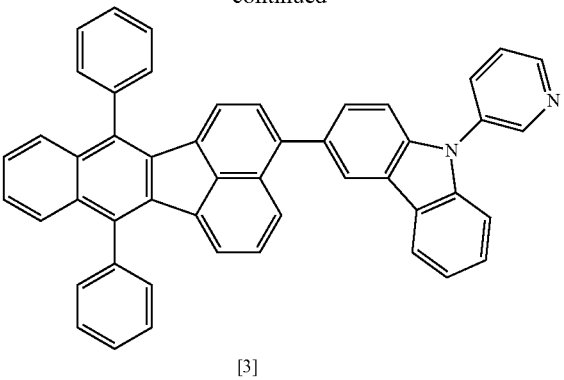

[3]

Example 1

A glass substrate with an ITO transparent electroconductive film deposited thereon in a thickness of 165 nm (manufactured by GEOMATEC Co., Ltd., 11Ω□, sputtered product) was cut into 38×46 mm, and etched. The resulting substrate was ultrasonically washed with "SEMICOCLEAN 56" (trade name, manufactured by Furuuchi Chemical Corporation) for 15 minutes, and then washed with ultrapure water. This substrate was treated with UV-ozone for 1 hour immediately before preparation of a device, and placed in a vacuum deposition apparatus, and the air was evacuated until the degree of vacuum in the apparatus was $5\times10^{-4}$ Pa or lower. By a resistance heating method, first, HAT-CN6 was deposited as a hole injection layer in a thickness of 5 nm, and HT-1 was deposited as a hole transporting layer in a thickness of 50 nm. Next, as an emissive layer, a host material H-1 and a dopant material D-1 were deposited in a thickness of 20 nm so that the doping concentration was 5% by weight. Next, as an electron transporting layer, the compound [1] was deposited and laminated in a thickness of 30 nm. Next, lithium fluoride was deposited in a thickness of 0.5 nm, and aluminum was then deposited in a thickness of 1000 nm to form a cathode, so that a 5×5 mm square device was prepared. The film thickness referred to herein is an indicated value on a crystal oscillation film thickness monitor. The properties of the light-emitting device at 1000 cd/m$^2$ included a driving voltage of 3.7 V and an external quantum efficiency of 4.5%. When the light-emitting device was driven at a constant current with the initial luminance set to 1000 cd/m$^2$, the luminance half-time at which the luminance decreased by 50% was 1600 hours. Compounds HAT-CN6, HT-1, H-1 and D-1 are the compounds shown below.

[Chemical Formula 54]

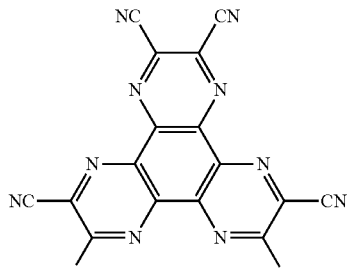

HAT-CN6

-continued
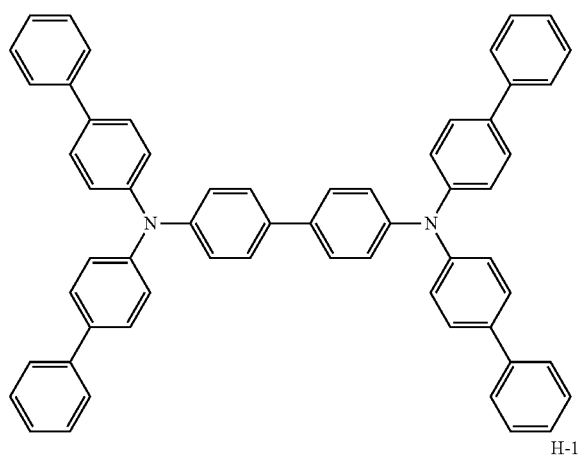
HT-1
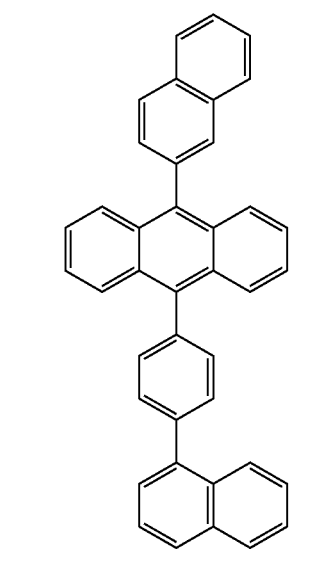
H-1
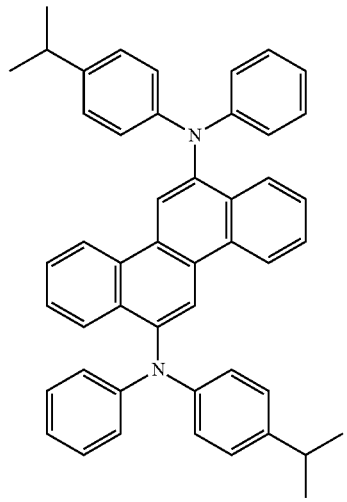
D-1
Examples 2 to 30
In the same manner as in Example 1 except that compounds described in Table 1 were used for the electron transporting layer, light-emitting devices were prepared and evaluated. The results are shown in Table 1. Compounds [4] to [30] are the compounds shown below.
[Chemical Formula 55]
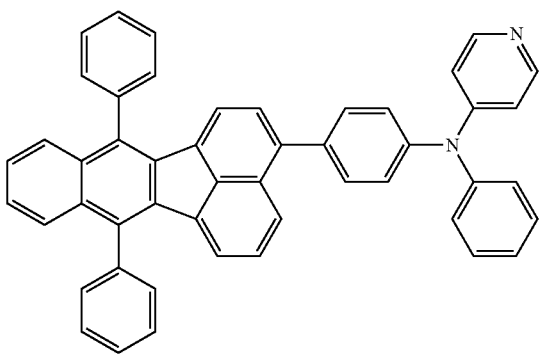
[4]
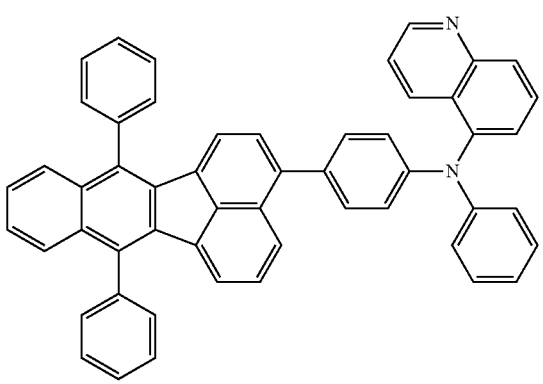
[5]
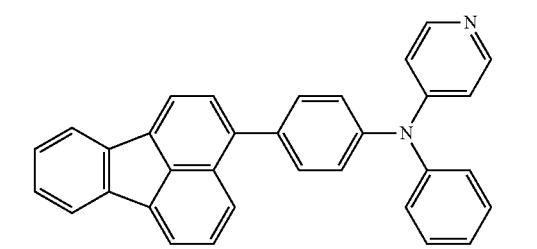
[6]
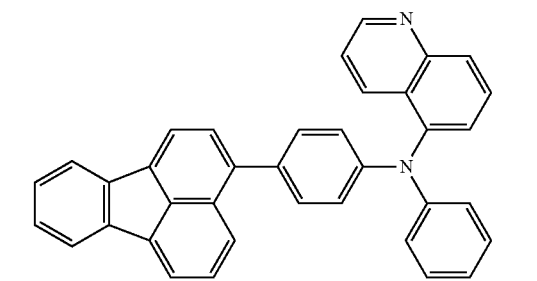
[7]

[8]
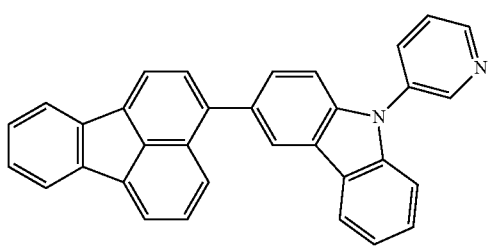
[9]
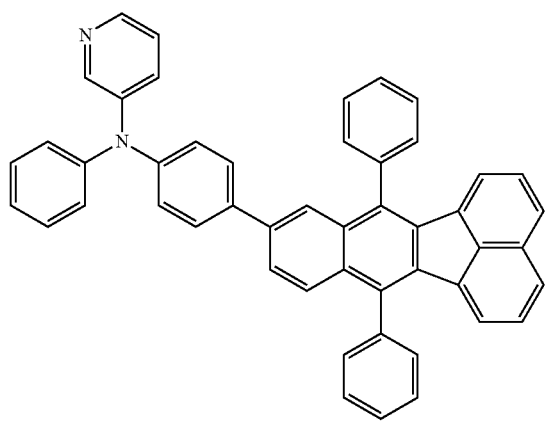
[10]
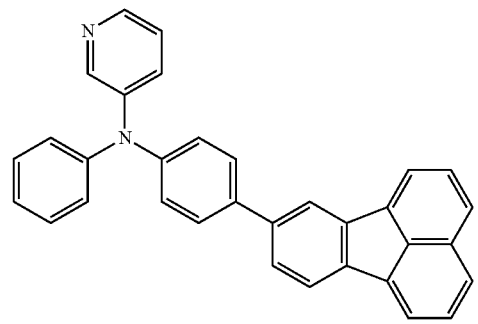
[11]
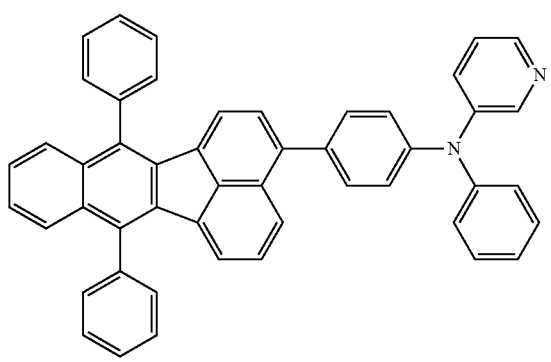
[12]
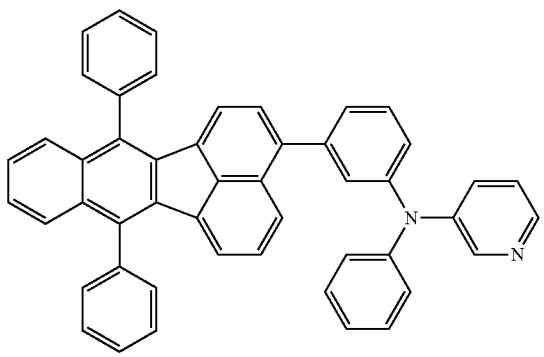
[13]
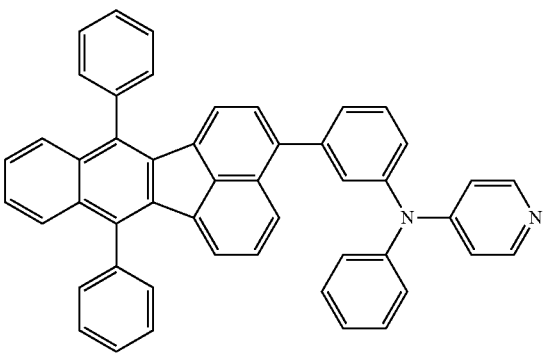
[14]
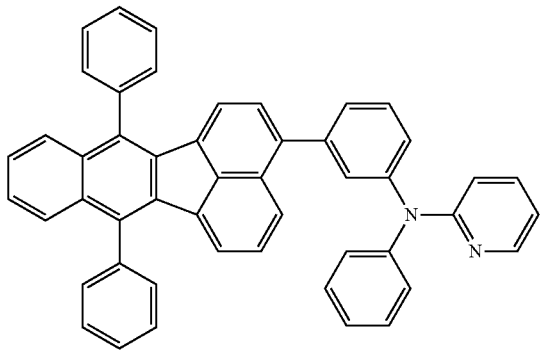
[15]
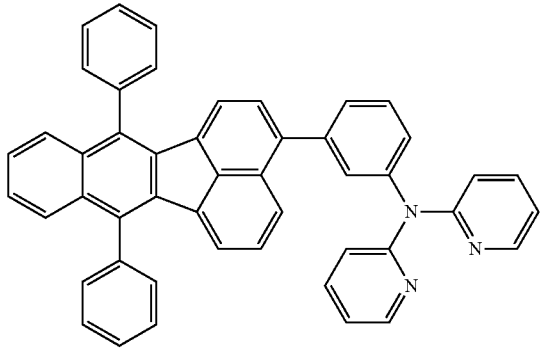

[Chemical Formula 56]
[16]
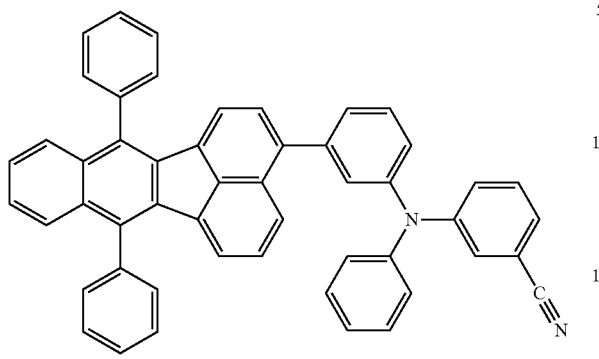
[17]
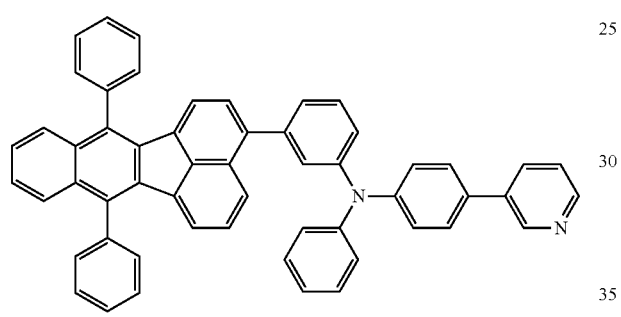
[18]
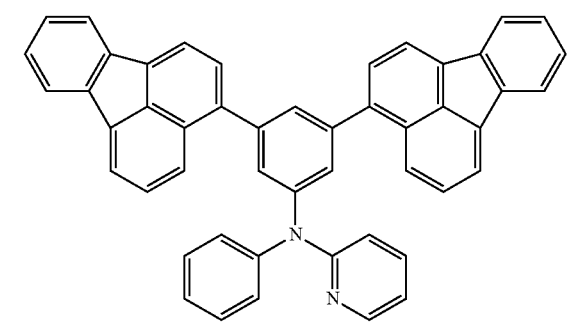
[19]
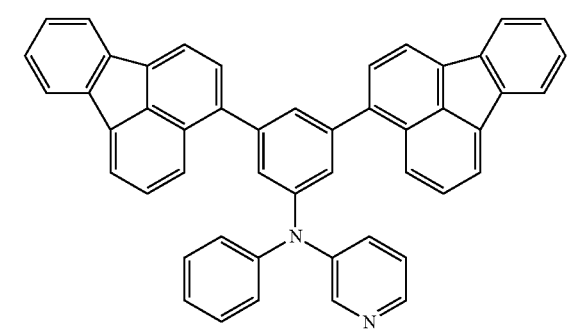
[20]
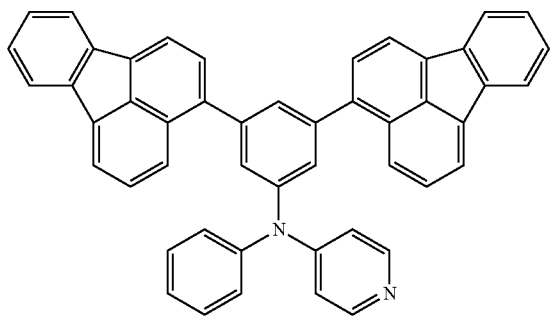
[21]
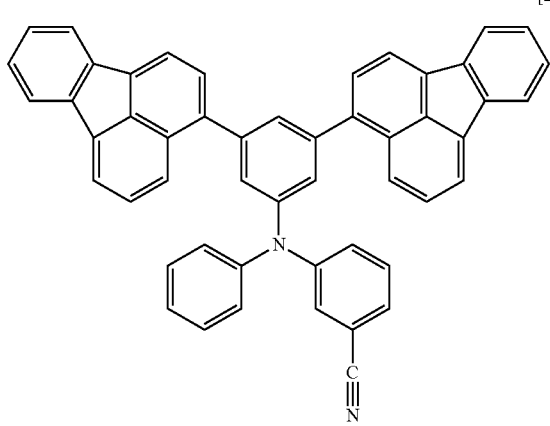
[22]
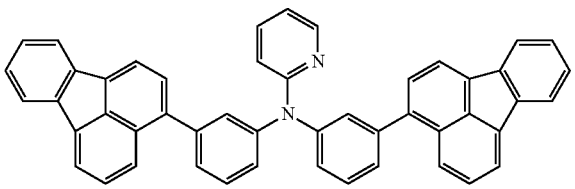
[23]
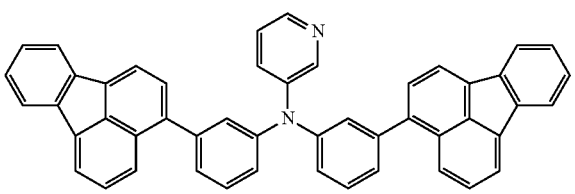
[Chemical Formula 57]
[24]
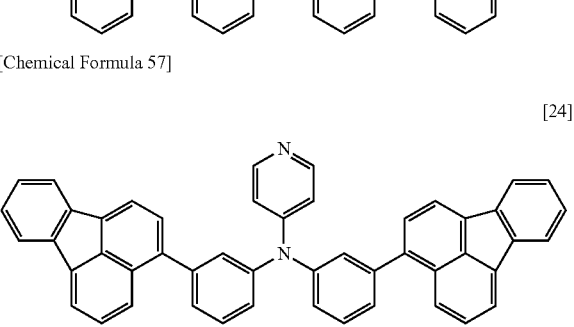

[25] 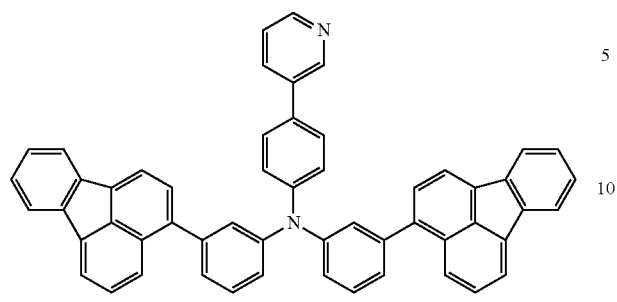
[26] 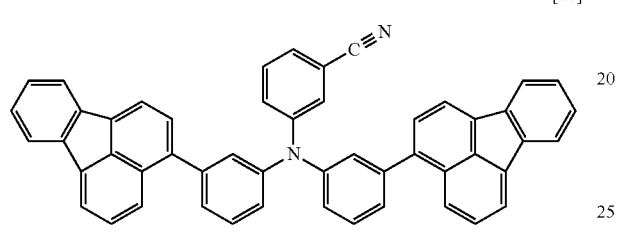
[27] 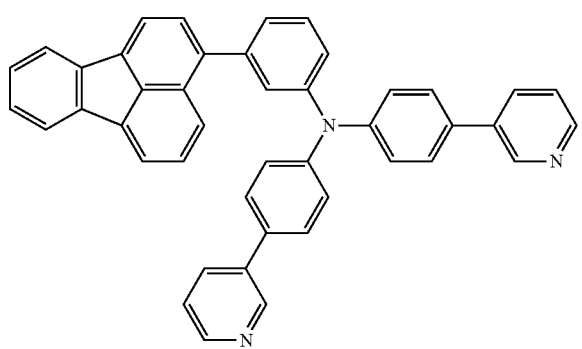
[28] 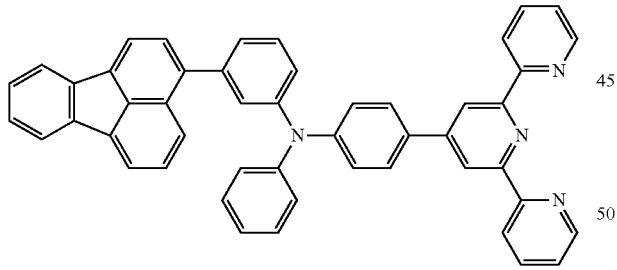
[29] 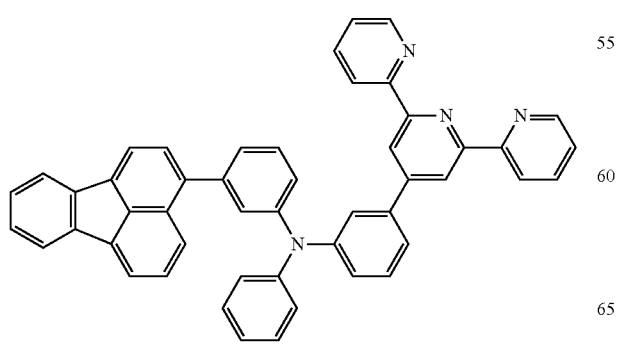
[30] 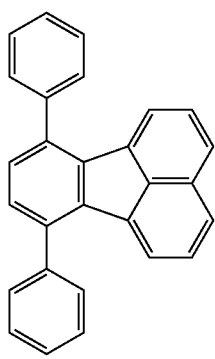
Comparative Examples 1 to 5
In the same manner as in Example 1 except that compounds described in Table 1 were used for the electron transporting layer, light-emitting devices were prepared and evaluated. The results are shown in Table 1. E-1 to E-5 are the compounds shown below.
[Chemical Formula 58]
E-1
E-2
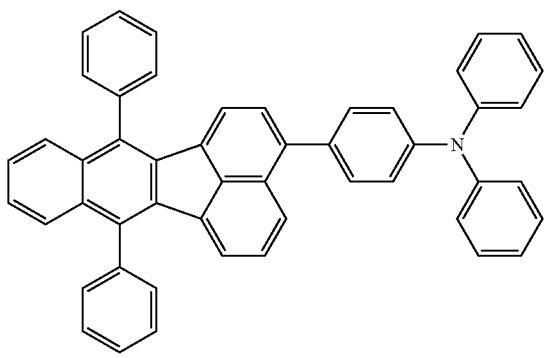

-continued

E-3
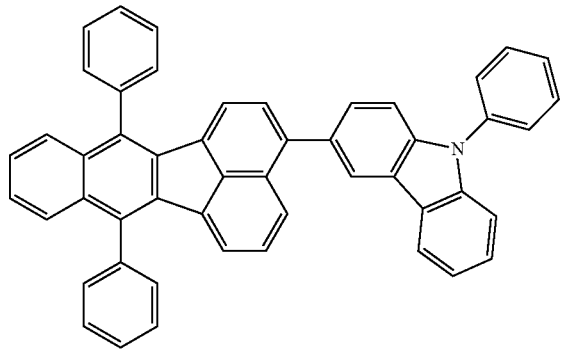

E-4
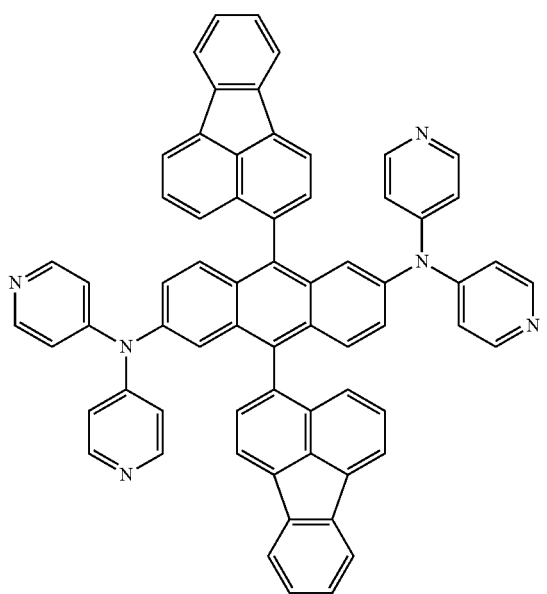

E-5
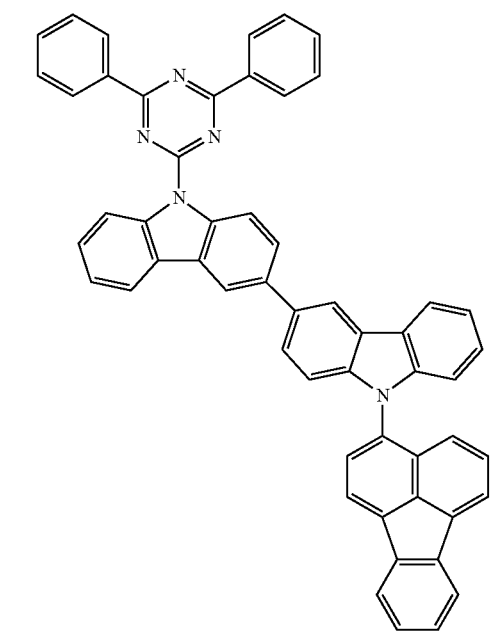

Example 31

A glass substrate with an ITO transparent electroconductive film deposited thereon in a thickness of 165 nm (manufactured by GEOMATEC Co., Ltd., 11Ω☐, sputtered product) was cut into 38×46 mm, and etched. The resulting substrate was ultrasonically washed with "SEMICOCLEAN 56" (trade name, manufactured by Furuuchi Chemical Corporation) for 15 minutes, and then washed with ultrapure water. This substrate was treated with UV-ozone for 1 hour immediately before preparation of a device, and placed in a vacuum deposition apparatus, and the air was evacuated until the degree of vacuum in the apparatus was $5 \times 10^{-4}$ Pa or lower. By a resistance heating method, first, HAT-CN6 was deposited as a hole injection layer in a thickness of 5 nm, and HT-1 was deposited as a hole transporting layer in a thickness of 50 nm. Next, as an emissive layer, a host material H-1 and a dopant material D-1 were deposited in a thickness of 20 nm so that the doping concentration was 5% by weight. Next, as a first electron transporting layer, the compound [1] was deposited and laminated in a thickness of 20 nm. Further as a second electron transporting layer, the compound [1] used as an electron transporting material and lithium used as a donor material were laminated in a thickness of 10 nm so that the deposition rate ratio of the compound [1] and lithium was 20:1. Next, lithium fluoride was deposited in a thickness of 0.5 nm, and aluminum was then deposited in a thickness of 1000 nm to form a cathode, so that a 5×5 mm square device was prepared. The properties of the light-emitting device at 1000 cd/m² included a driving voltage of 3.5 V and an external quantum efficiency of 5.1%. When the light-emitting device was driven at a constant current with the initial luminance set to 1000 cd/m², the luminance half-time at which the luminance decreased by 50% was 2200 hours.

Examples 32 to 60

In the same manner as in Example 31 except that compounds described in Table 2 were used for the electron transporting layer, light-emitting devices were prepared and evaluated. The results are shown in Table 2.

Comparative Examples 6 to 10

In the same manner as in Example 31 except that compounds described in Table 2 were used for the electron transporting layer, light-emitting devices were prepared and evaluated. The results are shown in Table 2.

Example 61

A glass substrate with an ITO transparent electroconductive film deposited thereon in a thickness of 165 nm (manufactured by GEOMATEC Co., Ltd., 11Ω☐, sputtered product) was cut into 38×46 mm, and etched. The resulting substrate was ultrasonically washed with "SEMICOCLEAN 56" (trade name, manufactured by Furuuchi Chemical Corporation) for 15 minutes, and then washed with ultrapure water. This substrate was treated with UV-ozone for 1 hour immediately before preparation of a device, and placed in a vacuum deposition apparatus, and the air was evacuated until the degree of vacuum in the apparatus was 5×10⁻⁴ Pa or lower. By a resistance heating method, first, HAT-CN6 was deposited as a hole injection layer in a thickness of 5 nm, and HT-1 was deposited as a hole transporting layer in a thickness of 50 nm. Next, as an emissive layer, a host material H-1 and a dopant material D-1 were deposited in a thickness of 20 nm so that the doping concentration was 5% by weight. Further as an electron transporting layer, the compound [1] used as an electron transporting material and 2E-1 used as a donor material were laminated in a thickness of 30 nm so that the deposition rate ratio of the compound [1] and 2E-1 was 1:1. This electron transporting layer is shown as a second electron transporting layer in Table 2. Next, lithium fluoride was deposited in a thickness of 0.5 nm, and aluminum was then deposited in a thickness of 1000 nm to form a cathode, so that a 5×5 mm square device was prepared. The properties of the light-emitting device at 1000 cd/m² included a driving voltage of 3.3 V and an external quantum efficiency of 5.8%. When the light-emitting device was driven at a constant current with the initial luminance set to 1000 cd/m², the luminance half-time at which the luminance decreased by 50% was 2800 hours.

Examples 62 to 90

In the same manner as in Example 61 except that compounds described in Table 3 were used for the electron transporting layer and the donor material, light-emitting devices were prepared and evaluated. The results are shown in Table 3. 2E-1 is the compound shown below.

[Chemical Formula 59]

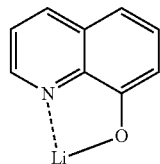

2E-1

Comparative Examples 11 to 15

In the same manner as in Example 61 except that compounds described in Table 3 were used for the electron transporting layer and the donor material, light-emitting devices were prepared and evaluated. The results are shown in Table 3.

Example 91

A glass substrate with an ITO transparent electroconductive film deposited thereon in a thickness of 165 nm (manufactured by GEOMATEC Co., Ltd., 11Ω□, sputtered product) was cut into 38×46 mm, and etched. The resulting substrate was ultrasonically washed with "SEMICOCLEAN 56" (trade name, manufactured by Furuuchi Chemical Corporation) for 15 minutes, and then washed with ultrapure water. This substrate was treated with UV-ozone for 1 hour immediately before preparation of a device, and placed in a vacuum deposition apparatus, and air was evacuated until the degree of vacuum in the apparatus was 5×10⁻⁴ Pa or lower. By a resistance heating method, first, HAT-CN6 was deposited as a hole injection layer in a thickness of 5 nm, and HT-1 was deposited as a hole transporting layer in a thickness of 50 nm. This hole transporting layer is shown as a first hole transporting layer in Table 3. Next, as an emissive layer, a host material H-2 and a dopant material D-2 were deposited in a thickness of 20 nm so that the doping concentration was 10% by weight. Next, as an electron transporting layer, the compound [1] was deposited and laminated in a thickness of 30 nm. Next, lithium fluoride was deposited in a thickness of 0.5 nm, and aluminum was then deposited in a thickness of 1000 nm to form a cathode, so that a 5×5 mm square device was prepared. The film thickness referred to herein is an indicated value on a crystal oscillation film thickness monitor. The properties of the light-emitting device at 4000 cd/m² included a driving voltage of 4.0 V and an external quantum efficiency of 10.8%. When the light-emitting device was driven at a constant current with the initial luminance set to 4000 cd/m², the luminance half-time was 1200 hours. H-2 and D-2 are the compounds shown below.

[Chemical Formula 60]

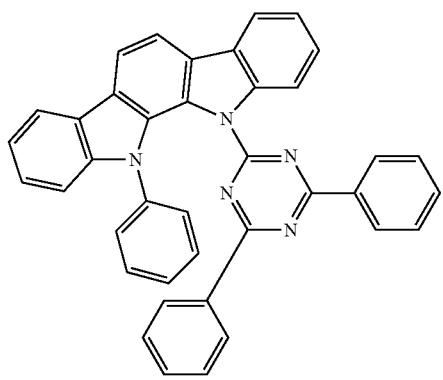

H-2

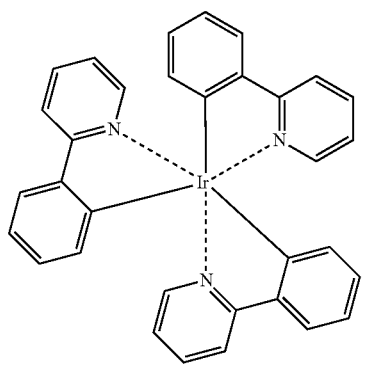

D-2

Example 92

A glass substrate with an ITO transparent electroconductive film deposited thereon in a thickness of 165 nm (manufactured by GEOMATEC Co., Ltd., 11Ω□, sputtered product) was cut into 38×46 mm, and etched. The resulting substrate was ultrasonically washed with "SEMICOCLEAN 56" (trade name, manufactured by Furuuchi Chemical Corporation) for 15 minutes, and then washed with ultrapure water. This substrate was treated with UV-ozone for 1 hour immediately before preparation of a device, and placed in a vacuum deposition apparatus, and the air was evacuated until the degree of vacuum in the apparatus was 5×10⁻⁴ Pa or lower. By a resistance heating method, first, HAT-CN6 was deposited as a hole injection layer in a thickness of 5 nm, and HT-1 was deposited as a first hole transporting layer in a thickness of 40 nm. Further, HT-2 was deposited as a second hole transporting layer in a thickness of 10 nm. Next, as an emissive layer, a host material H-2 and a dopant material D-2 were deposited in a thickness of 20 nm so that the doping concentration was 10% by weight. Next, as an electron transporting layer, the compound [4] was deposited and laminated in a thickness of 30 nm. Next, lithium fluoride was deposited in a thickness of 0.5 nm, and aluminum was then deposited in a thickness of 1000 nm to form a cathode, so that a 5×5 mm square device was prepared. The film thickness referred to herein is an indicated value on a crystal oscillation film thickness monitor. The properties of the light-emitting device at 4000 cd/m² included a driving voltage of 3.9 V and an external quantum efficiency of 13.8%. When the light-emitting device was driven at a constant current with the initial luminance set to 4000 cd/m², the luminance half-time was 1900 hours. HT-2 is the compound shown below.

[Chemical Formula 61]

HT-2

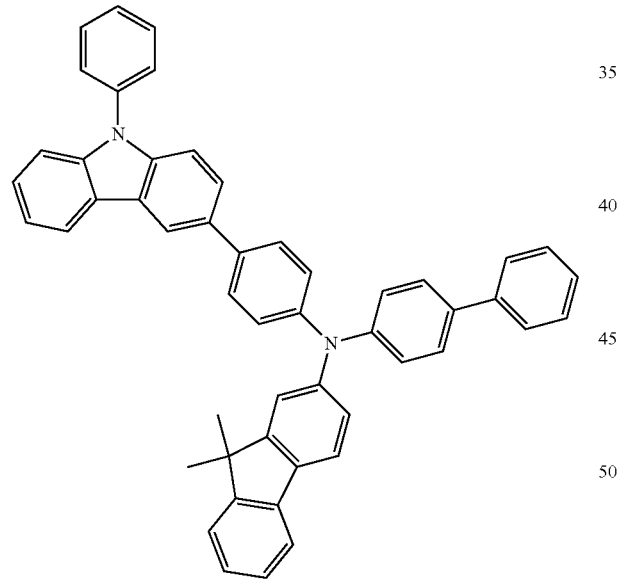

Examples 95, 99 and 103

In the same manner as in Example 91 except that compounds described in Table 4 were used for the electron transporting layer, devices were prepared and evaluated. The results are shown in Table 4.

Comparative Examples 16 and 20

In the same manner as in Example 91 except that compounds described in Table 4 were used for the electron transporting layer, light-emitting devices were prepared and evaluated. The results are shown in Table 4.

Examples 93 to 94, 96 to 98, 100 to 102 and 104 to 106

In the same manner as in Example 92 except that compounds described in Table 4 were used for the second hole transporting layer and the electron transporting layer, devices were prepared and evaluated. The results are shown in Table 4. HT-3 and HT-4 are the compounds shown below.

[Chemical Formula 62]

HT-3

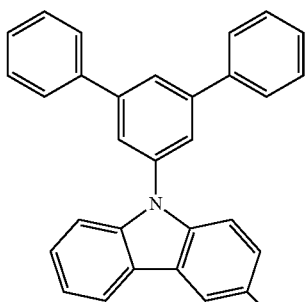

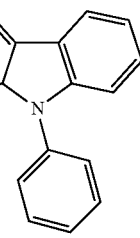

HT-4

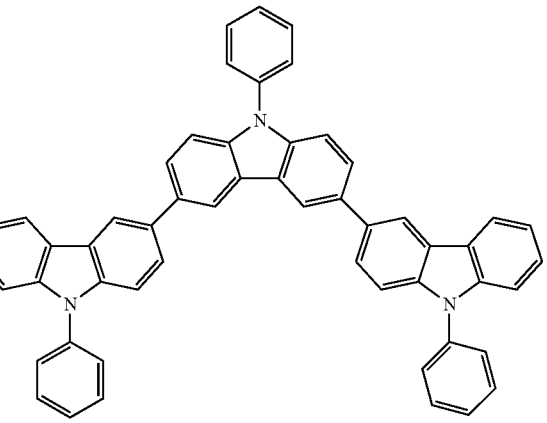

Comparative Examples 17 to 19 and 21 to 23

In the same manner as in Example 32 except that compounds described in Table 4 were used for the second hole transporting layer and the electron transporting layer, devices were prepared and evaluated. The results are shown in Table 4.

TABLE 1

|  | Emissive material | | | Electron transporting layer Compound | Cathode Metal | External quantum efficiency (%) | Driving voltage (V) | Luminance half-time (h) |
| --- | --- | --- | --- | --- | --- | --- | --- | --- |
|  | Host material | Dopant material | Emitted color |  |  |  |  |  |
| Example 1 | H-1 | D-1 | Blue | [1] | Al | 4.5 | 3.7 | 1600 |
| Example 2 |  |  | Blue | [2] | Al | 4.5 | 3.6 | 1800 |
| Example 3 |  |  | Blue | [3] | Al | 4.4 | 3.7 | 1800 |
| Example 4 |  |  | Blue | [4] | Al | 4.5 | 3.7 | 1800 |
| Example 5 |  |  | Blue | [5] | Al | 4.4 | 3.8 | 1700 |
| Example 6 |  |  | Blue | [6] | Al | 4.4 | 3.8 | 1700 |
| Example 7 |  |  | Blue | [7] | Al | 4.5 | 3.9 | 1800 |
| Example 8 |  |  | Blue | [8] | Al | 4.4 | 3.8 | 1600 |
| Example 9 |  |  | Blue | [9] | Al | 3.9 | 4.1 | 1200 |
| Example 10 |  |  | Blue | [10] | Al | 3.8 | 4.2 | 1300 |
| Example 11 |  |  | Blue | [11] | Al | 4.5 | 3.6 | 1300 |
| Example 12 |  |  | Blue | [12] | Al | 4.6 | 3.6 | 1800 |
| Example 13 |  |  | Blue | [13] | Al | 4.5 | 3.7 | 1700 |
| Example 14 |  |  | Blue | [14] | Al | 4.6 | 3.7 | 1600 |
| Example 15 |  |  | Blue | [15] | Al | 4.4 | 3.7 | 1600 |
| Example 16 |  |  | Blue | [16] | Al | 4.6 | 3.6 | 1700 |
| Example 17 |  |  | Blue | [17] | Al | 4.5 | 3.6 | 1700 |
| Example 18 |  |  | Blue | [18] | Al | 4.7 | 3.8 | 1800 |
| Example 19 |  |  | Blue | [19] | Al | 4.7 | 3.7 | 1900 |
| Example 20 |  |  | Blue | [20] | Al | 4.6 | 3.8 | 1800 |
| Example 21 |  |  | Blue | [21] | Al | 4.7 | 3.8 | 1800 |
| Example 22 |  |  | Blue | [22] | Al | 4.7 | 3.7 | 1700 |
| Example 23 |  |  | Blue | [23] | Al | 4.8 | 3.7 | 1900 |
| Example 24 |  |  | Blue | [24] | Al | 4.7 | 3.8 | 1800 |
| Example 25 |  |  | Blue | [25] | Al | 4.6 | 3.8 | 1900 |
| Example 26 |  |  | Blue | [26] | Al | 4.6 | 3.7 | 1800 |
| Example 27 |  |  | Blue | [27] | Al | 4.5 | 3.8 | 1800 |
| Example 28 |  |  | Blue | [28] | Al | 4.5 | 3.8 | 1700 |
| Example 29 |  |  | Blue | [29] | Al | 4.6 | 3.7 | 1800 |
| Example 30 |  |  | Blue | [30] | Al | 4.5 | 3.8 | 1700 |
| Comparative Example 1 | H-1 | D-1 | Blue | E-1 | Al | 1.5 | 8.0 | 300 |
| Comparative Example 2 |  |  | Blue | E-2 | Al | 1.8 | 8.1 | 300 |
| Comparative Example 3 |  |  | Blue | E-3 | Al | 1.7 | 8.2 | 300 |
| Comparative Example 4 |  |  | Blue | E-4 | Al | 1.8 | 6.2 | 300 |
| Comparative Example 5 |  |  | Blue | E-5 | Al | 1.9 | 7.8 | 300 |

TABLE 2

|  | Emissive material | | | First electron transporting layer Compound | Second electron transporting layer | | External quantum efficiency (%) | Driving voltage (V) | Luminance half-time (h) |
| --- | --- | --- | --- | --- | --- | --- | --- | --- | --- |
|  | Host material | Dopant material | Emitted color |  | Compound | Donor compound | Cathode Metal |  |  |
| Example 31 | H-1 | D-1 | Blue | [1] | [1] | Li | Al | 5.1 | 3.5 | 2200 |
| Example 32 |  |  | Blue | [2] | [2] | Li | Al | 5.1 | 3.5 | 2100 |
| Example 33 |  |  | Blue | [3] | [3] | Li | Al | 5.2 | 3.6 | 2300 |
| Example 34 |  |  | Blue | [4] | [4] | Li | Al | 5.3 | 3.6 | 2200 |
| Example 35 |  |  | Blue | [5] | [5] | Li | Al | 5.3 | 3.5 | 2200 |
| Example 36 |  |  | Blue | [6] | [6] | Li | Al | 5.1 | 3.5 | 2100 |
| Example 37 |  |  | Blue | [7] | [7] | Li | Al | 5.4 | 3.5 | 2300 |
| Example 38 |  |  | Blue | [8] | [8] | Li | Al | 5.1 | 3.6 | 2300 |
| Example 39 |  |  | Blue | [9] | [9] | Li | Al | 4.5 | 3.9 | 1600 |
| Example 40 |  |  | Blue | [10] | [10] | Li | Al | 4.6 | 3.9 | 1500 |
| Example 41 |  |  | Blue | [11] | [11] | Li | Al | 5.0 | 3.5 | 2000 |
| Example 42 |  |  | Blue | [12] | [12] | Li | Al | 5.1 | 3.5 | 2000 |
| Example 43 |  |  | Blue | [13] | [13] | Li | Al | 5.4 | 3.5 | 2300 |
| Example 44 |  |  | Blue | [14] | [14] | Li | Al | 5.0 | 3.7 | 2100 |
| Example 45 |  |  | Blue | [15] | [15] | Li | Al | 5.1 | 3.6 | 2100 |
| Example 46 |  |  | Blue | [16] | [16] | Li | Al | 5.0 | 3.6 | 2200 |
| Example 47 |  |  | Blue | [17] | [17] | Li | Al | 5.1 | 3.6 | 2100 |
| Example 48 |  |  | Blue | [18] | [18] | Li | Al | 5.2 | 3.6 | 2000 |
| Example 49 |  |  | Blue | [19] | [19] | Li | Al | 5.2 | 3.5 | 2400 |
| Example 50 |  |  | Blue | [20] | [20] | Li | Al | 5.1 | 3.6 | 2300 |
| Example 51 |  |  | Blue | [21] | [21] | Li | Al | 5.0 | 3.7 | 2200 |
| Example 52 |  |  | Blue | [22] | [22] | Li | Al | 5.2 | 3.5 | 2100 |

TABLE 2-continued

| | Emissive material | | | First electron transporting layer Compound | Second electron transporting layer | | Cathode Metal | External quantum efficiency (%) | Driving voltage (V) | Luminance half-time (h) |
|---|---|---|---|---|---|---|---|---|---|---|
| | Host material | Dopant material | Emitted color | | Compound | Donor compound | | | | |
| Example 53 | | | Blue | [23] | [23] | Li | Al | 5.4 | 3.5 | 2300 |
| Example 54 | | | Blue | [24] | [24] | Li | Al | 5.1 | 3.7 | 2400 |
| Example 55 | | | Blue | [25] | [25] | Li | Al | 5.2 | 3.7 | 2300 |
| Example 56 | | | Blue | [26] | [26] | Li | Al | 5.0 | 3.6 | 2100 |
| Example 57 | | | Blue | [27] | [27] | Li | Al | 5.1 | 3.7 | 2400 |
| Example 58 | | | Blue | [28] | [28] | Li | Al | 5.0 | 3.7 | 2500 |
| Example 59 | | | Blue | [29] | [29] | Li | Al | 5.1 | 3.6 | 2500 |
| Example 60 | | | Blue | [30] | [30] | Li | Al | 5.0 | 3.8 | 2200 |
| Comparative Example 6 | H-1 | D-1 | Blue | E-1 | E-1 | Li | Al | 2.4 | 6.5 | 500 |
| Comparative Example 7 | | | Blue | E-2 | E-2 | Li | Al | 2.3 | 6.3 | 600 |
| Comparative Example 8 | | | Blue | E-3 | E-3 | Li | Al | 2.4 | 6.4 | 500 |
| Comparative Example 9 | | | Blue | E-4 | E-4 | Li | Al | 2.5 | 5.8 | 600 |
| Comparative Example 10 | | | Blue | E-5 | E-5 | Li | Al | 2.5 | 5.9 | 500 |

TABLE 3

| | Emissive material | | | First electron transporting layer compound | Second electron transporting layer | | Cathode Metal | External quantum efficiency (%) | Driving voltage (V) | Luminance half-time (h) |
|---|---|---|---|---|---|---|---|---|---|---|
| | Host material | Dopant material | Emitted color | | compound | Donor compound | | | | |
| Example 61 | H-1 | D-1 | Blue | None | [1] | 2E-1 | Al | 5.8 | 3.3 | 2800 |
| Example 62 | | | Blue | None | [2] | 2E-1 | Al | 5.7 | 3.4 | 2900 |
| Example 63 | | | Blue | None | [3] | 2E-1 | Al | 5.7 | 3.4 | 3100 |
| Example 64 | | | Blue | None | [4] | 2E-1 | Al | 5.9 | 3.3 | 3000 |
| Example 65 | | | Blue | None | [5] | 2E-1 | Al | 5.8 | 3.5 | 2800 |
| Example 66 | | | Blue | None | [6] | 2E-1 | Al | 5.9 | 3.4 | 3100 |
| Example 67 | | | Blue | None | [7] | 2E-1 | Al | 5.7 | 3.3 | 2900 |
| Example 68 | | | Blue | None | [8] | 2E-1 | Al | 5.7 | 3.4 | 3000 |
| Example 69 | | | Blue | None | [9] | 2E-1 | Al | 4.7 | 3.7 | 2100 |
| Example 70 | | | Blue | None | [10] | 2E-1 | Al | 4.8 | 3.7 | 2100 |
| Example 71 | | | Blue | None | [11] | 2E-1 | Al | 4.7 | 3.7 | 2800 |
| Example 72 | | | Blue | None | [12] | 2E-1 | Al | 4.8 | 3.7 | 2900 |
| Example 73 | | | Blue | None | [13] | 2E-1 | Al | 4.7 | 3.7 | 3200 |
| Example 74 | | | Blue | None | [14] | 2E-1 | Al | 4.8 | 3.7 | 2800 |
| Example 75 | | | Blue | None | [15] | 2E-1 | Al | 4.7 | 3.7 | 2900 |
| Example 76 | | | Blue | None | [16] | 2E-1 | Al | 4.8 | 3.7 | 3000 |
| Example 77 | | | Blue | None | [17] | 2E-1 | Al | 4.7 | 3.7 | 2900 |
| Example 78 | | | Blue | None | [18] | 2E-1 | Al | 4.8 | 3.7 | 2900 |
| Example 79 | | | Blue | None | [19] | 2E-1 | Al | 4.7 | 3.7 | 3300 |
| Example 80 | | | Blue | None | [20] | 2E-1 | Al | 4.8 | 3.7 | 3100 |
| Example 81 | | | Blue | None | [21] | 2E-1 | Al | 4.7 | 3.7 | 3100 |
| Example 82 | | | Blue | None | [22] | 2E-1 | Al | 4.8 | 3.7 | 3000 |
| Example 83 | | | Blue | None | [23] | 2E-1 | Al | 4.8 | 3.7 | 3300 |
| Example 84 | | | Blue | None | [24] | 2E-1 | Al | 4.7 | 3.7 | 3200 |
| Example 85 | | | Blue | None | [25] | 2E-1 | Al | 4.8 | 3.7 | 3200 |
| Example 86 | | | Blue | None | [26] | 2E-1 | Al | 4.7 | 3.7 | 3000 |
| Example 87 | | | Blue | None | [27] | 2E-1 | Al | 4.8 | 3.7 | 3400 |
| Example 88 | | | Blue | None | [28] | 2E-1 | Al | 4.7 | 3.7 | 3300 |
| Example 89 | | | Blue | None | [29] | 2E-1 | Al | 4.7 | 3.7 | 3200 |
| Example 90 | | | Blue | None | [30] | 2E-1 | Al | 4.8 | 3.7 | 3200 |
| Comparative Example 11 | H-1 | D-1 | Blue | None | E-1 | 2E-1 | Al | 3.0 | 6.4 | 900 |
| Comparative Example 12 | | | Blue | None | E-2 | 2E-1 | Al | 2.9 | 6.4 | 900 |
| Comparative Example 13 | | | Blue | None | E-3 | 2E-1 | Al | 2.9 | 6.3 | 800 |
| Comparative Example 14 | | | Blue | None | E-4 | 2E-1 | Al | 3.0 | 5.7 | 900 |
| Comparative Example 15 | | | Blue | None | E-5 | 2E-1 | Al | 3.1 | 5.7 | 800 |

TABLE 4

| | Hole injection layer | First hole transporting layer | Second hole transporting layer | Emissive layer Host material | Emissive layer Dopant material | Electron transporting layer | External quantum efficiency (%) | Driving voltage (V) | Luminance half-time (h) |
|---|---|---|---|---|---|---|---|---|---|
| Example 91 | HAT-CN6 | HT-1 | None | H-2 | D-2 | [1] | 10.8 | 4.0 | 1200 |
| Example 92 | | | HT-2 | | | | 13.8 | 3.9 | 1900 |
| Example 93 | | | HT-3 | | | | 17.1 | 4.1 | 2800 |
| Example 94 | | | HT-4 | | | | 17.5 | 4.0 | 2800 |
| Example 95 | | | None | | | [2] | 11.5 | 4.0 | 1100 |
| Example 96 | | | HT-2 | | | | 14.9 | 4.1 | 1800 |
| Example 97 | | | HT-3 | | | | 17.5 | 3.9 | 2700 |
| Example 98 | | | HT-4 | | | | 18.0 | 4.1 | 2800 |
| Example 99 | | | None | | | [3] | 10.1 | 3.9 | 1200 |
| Example 100 | | | HT-2 | | | | 14.1 | 3.8 | 1900 |
| Example 101 | | | HT-3 | | | | 17.2 | 4.1 | 2700 |
| Example 102 | | | HT-4 | | | | 18.1 | 4.0 | 3000 |
| Example 103 | | | None | | | [8] | 9.8 | 4.1 | 1100 |
| Example 104 | | | HT-2 | | | | 13.5 | 4.1 | 1800 |
| Example 105 | | | HT-3 | | | | 17.2 | 4.2 | 2600 |
| Example 106 | | | HT-4 | | | | 17.9 | 4.0 | 2700 |
| Comparative Example 16 | HAT-CN6 | HT-1 | None | H-2 | D-2 | E-1 | 5.9 | 7.6 | 400 |
| Comparative Example 17 | | | HT-2 | | | | 6.2 | 7.6 | 600 |
| Comparative Example 18 | | | HT-3 | | | | 6.6 | 7.5 | 800 |
| Comparative Example 19 | | | HT-4 | | | | 6.5 | 1.6 | 800 |
| Comparative Example 20 | | | None | | | E-2 | 6.1 | 1.1 | 300 |
| Comparative Example 21 | | | HT-2 | | | | 7.2 | 7.5 | 400 |
| Comparative Example 22 | | | HT-3 | | | | 8.0 | 7.6 | 700 |
| Comparative Example 23 | | | HT-4 | | | | 8.1 | 7.5 | 800 |

The invention claimed is:

1. A fluoranthene derivative represented by the following general formula (3):

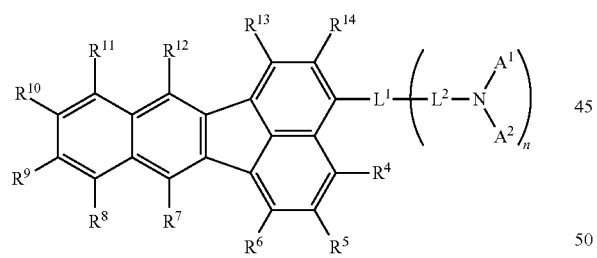

(3)

wherein
R$^4$ to R$^{14}$ may be the same or different, and are each selected from the group consisting of hydrogen, an alkyl group, a cycloalkyl group, a heterocyclic group, an alkenyl group, a cycloalkenyl group, an alkynyl group, an alkoxy group, an alkylthio group, an aryl ether group, an aryl thioether group, an aryl group, a heteroaryl group, halogen, a carbonyl group, a carboxyl group, an oxycarbonyl group and a carbamoyl group; and R$^4$ to R$^{14}$ may form a ring by adjacent substituents;
L$^1$ represents a substituted or unsubstituted arylene group,
L$^2$ represents a single bond, a substituted or unsubstituted arylene group, or a substituted or unsubstituted heteroarylene group;
A$^1$ and A$^2$ each represent a substituted or unsubstituted benzene ring having 6 to 40 carbon atoms, a substituted or unsubstituted fused aromatic hydrocarbon ring having 6 to 40 carbon atoms, a substituted or unsubstituted monocyclic aromatic heterocyclic ring having 1 to 40 carbon atoms, or a substituted or unsubstituted fused aromatic heterocyclic ring having 1 to 40 carbon atoms, with the proviso that at least one of atoms that form rings A$^1$ and A$^2$ is an electron-accepting nitrogen atom;
L$^2$ and A$^2$ may form a ring when L$^2$ is a substituted or unsubstituted arylene group, and A$^2$ is a substituted or unsubstituted benzene ring having 6 to 40 carbon atoms, or a substituted or unsubstituted fused aromatic hydrocarbon ring having 6 to 40 carbon atoms;
substituents that L$^1$, L$^2$, A$^1$ and A$^2$ optionally have are each selected from the group consisting of an alkyl group, a cycloalkyl group, a heterocyclic group, an alkenyl group, a cycloalkenyl group, an alkynyl group, an alkoxy group, an alkylthio group, an aryl ether group, an aryl thioether group, an aryl group, a heteroaryl group, a halogen, a cyano group, a carbonyl group, a carboxyl group, an oxycarbonyl group, a carbamoyl group and —P(=O)R$^1$R$^2$;
R$^1$ and R$^2$ each represent an aryl group or a heteroaryl group;
R$^1$ and R$^2$ may be fused to form a ring; and
n is 1 or 2; and when n is 2, two L$^2$-N(A$^1$)(A$^2$)s may be the same or different, with the proviso that a carbazolylene group is not included as a heteroarylene group, and when n is 2 and L$^2$ is a single bond, L$^1$ is not an acene having three or more rings.

2. The fluoranthene derivative according to claim 1, wherein n is 1.

3. The fluoranthene derivative according to claim 1, wherein $R^7$ and $R^{12}$ are each a substituted or unsubstituted aryl group.

4. The fluoranthene derivative according to claim 1, wherein $R^7$ and $R^{12}$ are each a phenyl group.

5. The fluoranthene derivative according to claim 1, wherein $A^1$ has a structure represented by any one of the following general formulae (10) to (12):

wherein $B^1$ to $B^{19}$ each represent CH, a substituted carbon atom or a nitrogen atom, with

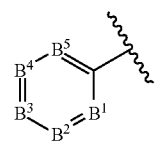
(10)

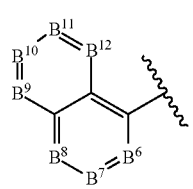
(11)

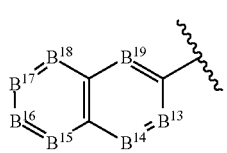
(12)

the proviso that when $B^1$ to $B^{19}$ do not contain nitrogen atoms, $A^2$ is a substituted or unsubstituted monocyclic aromatic heterocyclic ring containing electron-accepting nitrogen, or a substituted or unsubstituted fused aromatic heterocyclic ring containing electron-accepting nitrogen, and when $L^2\text{-}N(A^1)(A^2)$ has a structure represented by any one of the general formulae (6) to (9), any one of $B^1$ to $B^{19}$ is a nitrogen atom; and a substituent that $B^1$ to $B^{19}$ optionally have is the same as in the general formula (1).

6. The fluoranthene derivative according to claim 1, wherein $A^2$ has a structure represented by any one of the following general formulae (13) to (15):

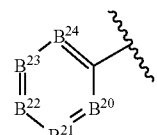
(13)

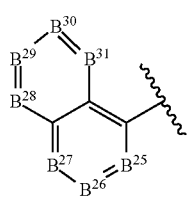
(14)

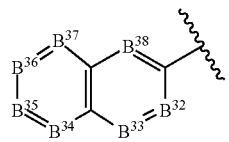
(15)

wherein $B^{20}$ to $B^{38}$ each represent CH, a substituted carbon atom or a nitrogen atom, with the proviso that when the $B^1$ to $B^{19}$ do not contain nitrogen atoms, at least one of $B^{20}$ to $B^{38}$ is a nitrogen atom, and when $L^2\text{-}N(A^1)(A^2)$ has a structure represented by any one of the general formulae (6) to (9), $B^{20}$ to $B^{38}$ do not contain nitrogen atoms; and a substituent that $B^{20}$ to $B^{38}$ optionally have is the same as in the general formula (1).

7. A light-emitting device material comprising the fluoranthene derivative according to claim 1.

8. A light-emitting device which has an organic layer between an anode and a cathode and emits light by means of electric energy, wherein the organic layer contains the fluoranthene derivative according claim 1.

9. A light-emitting device which has an organic layer between an anode and a cathode and emits light by means of electric energy, wherein the organic layer comprises an electron transporting layer, and the electron transporting layer contains the fluoranthene derivative according to claim 1.

10. The light-emitting device according to claim 8, wherein the organic layer comprises a hole transporting layer, and the hole transporting layer contains a material having a carbazole skeleton.

11. The fluoranthene derivative according to claim 1, wherein $L^2\text{-}N(A^1)(A^2)$ has a structure represented by any one of the following general formulae (6) to (9):

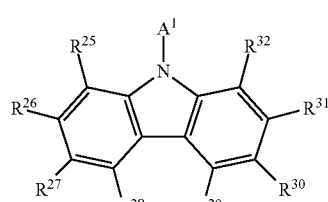
(6)

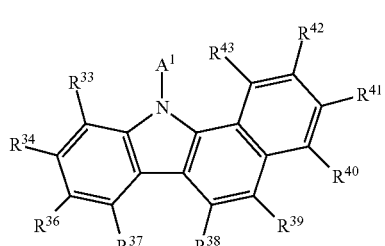
(7)

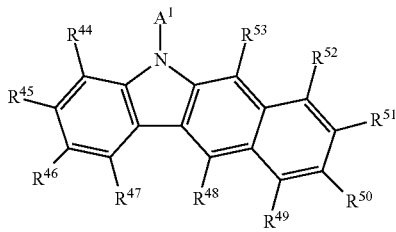
(8)

(9)

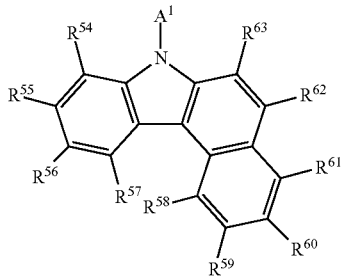

wherein $A^1$ is a substituted or unsubstituted monocyclic aromatic heterocyclic ring having 1 to 40 carbon atoms, or a substituted or unsubstituted fused aromatic heterocyclic ring having 1 to 40 carbon atoms, with the proviso that at least one of atoms that form $A^1$ is an electron-accepting nitrogen atom; $R^{25}$ to $R^{63}$ may be the same or different, and are each selected from the group consisting of hydrogen, an alkyl group, a cycloalkyl group, a heterocyclic group, an alkenyl group, a cycloalkenyl group, an alkynyl group, an alkoxy group, an alkylthio group, an aryl ether group, an aryl thioether group, an aryl group, a heteroaryl group, halogen, a carbonyl group, a carboxyl group, an oxycarbonyl group and a carbamoyl group; and $R^{25}$ to $R^{63}$ may form a ring by adjacent substituents, with the proviso that the group is coupled to $L^1$ at the position of any one of $R^{25}$ to $R^{63}$.

12. A fluoranthene derivative represented by the following general formula (5):

(5)

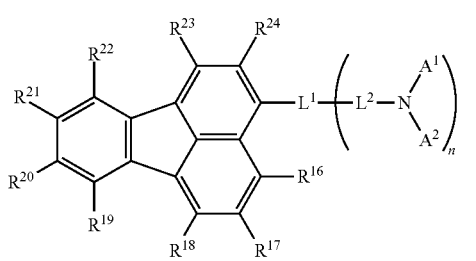

wherein
$R^{16}$ to $R^{24}$ may be the same or different, and are each selected from the group consisting of hydrogen, an alkyl group, a cycloalkyl group, a heterocyclic group, an alkenyl group, a cycloalkenyl group, an alkynyl group, an alkoxy group, an alkylthio group, an aryl ether group, an aryl thioether group, an aryl group, a heteroaryl group, halogen, a carbonyl group, a carboxyl group, an oxycarbonyl group and a carbamoyl group; $R^{16}$ to $R^{24}$ may form a ring by adjacent substituents;
$L^1$ represents a substituted or unsubstituted arylene group,
$L^2$ represents a single bond, a substituted or unsubstituted arylene group, or a substituted or unsubstituted heteroarylene group;
$A^1$ and $A^2$ each represent a substituted or unsubstituted benzene ring having 6 to 40 carbon atoms, a substituted or unsubstituted fused aromatic hydrocarbon ring having 6 to 40 carbon atoms, a substituted or unsubstituted monocyclic aromatic heterocyclic ring having 1 to 40 carbon atoms, or a substituted or unsubstituted fused aromatic heterocyclic ring having 1 to 40 carbon atoms, with the proviso that at least one of atoms that form rings $A^1$ and $A^2$ is an electron-accepting nitrogen atom;

$L^2$ and $A^2$ may form a ring when $L^2$ is a substituted or unsubstituted arylene group, and $A^2$ is a substituted or unsubstituted benzene ring having 6 to 40 carbon atoms, or a substituted or unsubstituted fused aromatic hydrocarbon ring having 6 to 40 carbon atoms;

substituents that $L^1$, $L^2$, $A^1$ and $A^2$ optionally have are each selected from the group consisting of an alkyl group, a cycloalkyl group, a heterocyclic group, an alkenyl group, a cycloalkenyl group, an alkynyl group, an alkoxy group, an alkylthio group, an aryl ether group, an aryl thioether group, an aryl group, a heteroaryl group, a halogen, a cyano group, a carbonyl group, a carboxyl group, an oxycarbonyl group, a carbamoyl group and —P(=O)$R^1R^2$;

$R^1$ and $R^2$ each represent an aryl group or a heteroaryl group;

$R^1$ and $R^2$ may be fused to form a ring; and n is 1 or 2; and when n is 2, two $L^2$-N($A^1$)($A^2$)s may be the same or different, with the proviso that a carbazolylene group is not included as a heteroarylene group, and when n is 2 and $L^2$ is a single bond, $L^1$ is not an acene having three or more rings.

13. The fluoranthene derivative according to claim 12, wherein $L^2$-N($A^1$)($A^2$) has a structure represented by any one of the following general formulae (6) to (9):

(6)

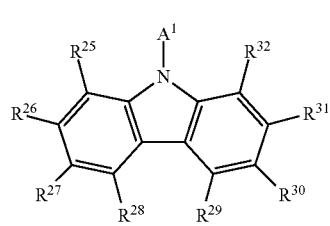

(7)

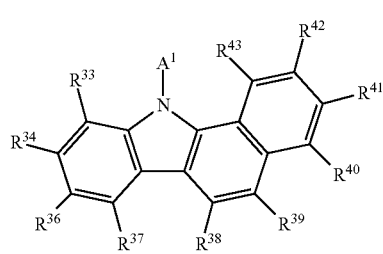

(8)

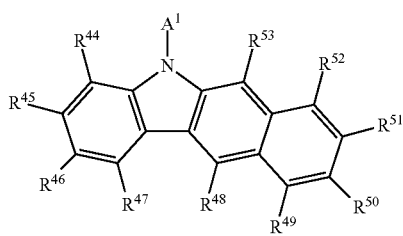

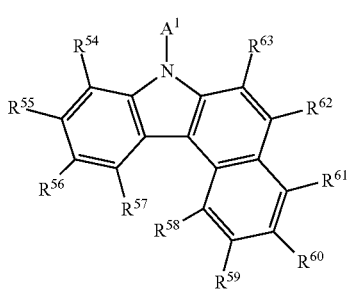

(9)

wherein $A^1$ is a substituted or unsubstituted monocyclic aromatic heterocyclic ring having 1 to 40 carbon atoms, or a substituted or unsubstituted fused aromatic heterocyclic ring having 1 to 40 carbon atoms, with the proviso that at least one of atoms that form $A^1$ is an electron-accepting nitrogen atom; $R^{25}$ to $R^{63}$ may be the same or different, and are each selected from the group consisting of hydrogen, an alkyl group, a cycloalkyl group, a heterocyclic group, an alkenyl group, a cycloalkenyl group, an alkynyl group, an alkoxy group, an alkylthio group, an aryl ether group, an aryl thioether group, an aryl group, a heteroaryl group, halogen, a carbonyl group, a carboxyl group, an oxycarbonyl group and a carbamoyl group; and $R^{25}$ to $R^{63}$ may form a ring by adjacent substituents, with the proviso that the group is coupled to $L^1$ at the position of any one of $R^{25}$ to $R^{63}$.

* * * * *